US012295397B2

(12) United States Patent
Stagsted et al.

(10) Patent No.: US 12,295,397 B2
(45) Date of Patent: May 13, 2025

(54) DIETARY PEPTIDES

(71) Applicant: Diet4Life APS, Hammel (DK)

(72) Inventors: Jan Stagsted, Hammel (DK); Jiehui Zhou, Braband (DK); Randi Jessen, Trige (DK); Johan Palmfeldt, Hjortshøj (DK); Erik Torngaard Hansen, Nivaa (DK)

(73) Assignee: Diet4life ApS, Hammel (DK)

( * ) Notice: Subject to any disclaimer, the term of this patent is extended or adjusted under 35 U.S.C. 154(b) by 0 days.

(21) Appl. No.: 17/678,574

(22) Filed: Feb. 23, 2022

(65) Prior Publication Data

US 2022/0248736 A1   Aug. 11, 2022

Related U.S. Application Data

(62) Division of application No. 16/062,429, filed as application No. PCT/EP2016/081572 on Dec. 16, 2016, now Pat. No. 11,259,554.

(30) Foreign Application Priority Data

Dec. 16, 2015   (EP) .................................. 15200440

(51) Int. Cl.
| | |
|---|---|
| *A23L 33/17* | (2016.01) |
| *A23L 29/00* | (2016.01) |
| *A61K 38/00* | (2006.01) |
| *A61K 38/04* | (2006.01) |
| *C07K 7/06* | (2006.01) |
| *C07K 7/08* | (2006.01) |
| *C07K 14/575* | (2006.01) |

(52) U.S. Cl.
CPC .............. *A23L 33/17* (2016.08); *A23L 29/03* (2016.08); *A61K 38/04* (2013.01); *C07K 7/06* (2013.01); *C07K 7/08* (2013.01); *C07K 14/57509* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,846,940 A | 12/1998 | Okamoto et al. | |
| 2007/0044171 A1 | 2/2007 | Kovalic et al. | |
| 2009/0082265 A1 | 3/2009 | Bartel et al. | |
| 2009/0117578 A1 | 5/2009 | Metz et al. | |
| 2022/0315632 A1* | 10/2022 | Stagsted | ............. C07K 14/4716 |
| 2023/0042729 A1* | 2/2023 | Stagsted | ................ A23L 33/18 |

FOREIGN PATENT DOCUMENTS

| | | |
|---|---|---|
| KR | 10-2009-0112270 A | 10/2009 |
| RU | 2012136530 A | 3/2014 |
| RU | 2016110800 A | 10/2017 |
| WO | WO 2008/001045 A1 | 1/2008 |
| WO | WO 2008/001045 A8 | 1/2008 |
| WO | WO 2008/074329 A3 | 6/2008 |
| WO | WO-2008074329 A2 * | 6/2008 ............. A61K 38/07 |
| WO | WO-2010063124 A1 * | 6/2010 ......... A61K 38/2264 |
| WO | WO 2011/005893 A2 | 1/2011 |
| WO | WO 2011/092473 A1 | 8/2011 |
| WO | WO 2011/119484 A1 | 9/2011 |
| WO | WO 2015/048342 A2 | 4/2015 |
| WO | WO 2017/100700 A2 | 6/2017 |

OTHER PUBLICATIONS

Christos et al. "Stable Isosteres of Neurotensin C-terminal Pentapeptides Derived By Modification of the Amide Function" Bioorganic & Medicinal Chemistry Letters 3:1035-1040. (Year: 1993).*
Cusack et al. "Pharmacological and Biochemical Profiles of Unique Neurotensins 8-13 Analogs Exhibiting Species Selectivity, Stereoselectivity, and Superagonism" J. Biol. Chem. 280:18359-18366. (Year: 1995).*
Cain et al. "Identification of Simpler Analogs of Neurotensin(9-13) Which Retain Antinocioceptive Activity" Bioorganic & Medicinal Chemistry Letters:1767-1772 (Year: 1993).*
Abiko, et anan., "Syntheses of Neurotensin (NT) Analogues and Their Comparative Anorectic Effect on Food Intake in Rats," *Protein and Peptide Letters*, 2001, vol. 8(6), pp. 461-468.
Cain, G., et al., "Identification of Simpler Analogs of Neurotensin(9-13) Which Retain Antinociceptive Activity," *Bioorganic & Medicinal Chemistry Letters*, 1993, vol. 3(8), pp. 1767-1772.
Christos, T., et al., "Stable Isosteres of Neurotensin C-Terminal Pentapeptides Derived by Modification of the Amide Function," *Bioorganic & Medicinal Chemistry Letters*, 1993, vol. 3(6), pp. 1035-1040.
Cusack, B., et al., "Pharmacological and Biochemical Profiles of Unique Neurotensins 8-13 Analogs Exhibiting Species Selectivity, Stereoselectivity, and Superagonism," *The Journal of Biological Chemistry*, 1995, vol. 280(31), pp. 18359-18366.
Einsiedel, J., et al., "Peptide backbone modifications on the C-terminal hexapeptide of neurotensin," *Bioorganic & Medicinal Chemistry Letters*, 2008, vol. 18, pp. 2013-2018.
Einsiedel, J., et al., "Discovery of Highly Potent and Neurotensin Receptor 2 Selective Neurotensin Mimetics," *Journal of Medicinal Chemistry*, 2011, vol. 54, pp. 2915-2923.
Nguyen, T., et al., Accession No. 2010:399801, Study on characterization of angiotensin converting enzyme inhibitory peptides (ACEIPS) recovered from food proteins by fermentation and enzymatic hydrolysis, 2010, 1 page.

(Continued)

*Primary Examiner* — Sudhakar Katakam
*Assistant Examiner* — Zachary J Miknis
(74) *Attorney, Agent, or Firm* — Womble Bond Dickinson

(57) ABSTRACT

The present invention relates to novel peptides, composition comprising such peptides including nutritional supplements and methods for inducing satiation and satiety, for weight management and preventing or reducing the incidence of obesity, or for preventing or reducing cardiovascular diseases, atherosclerosis, hypertension, hepatosteatosis, cancer and/or diabetes.

21 Claims, 20 Drawing Sheets

Figure 1:
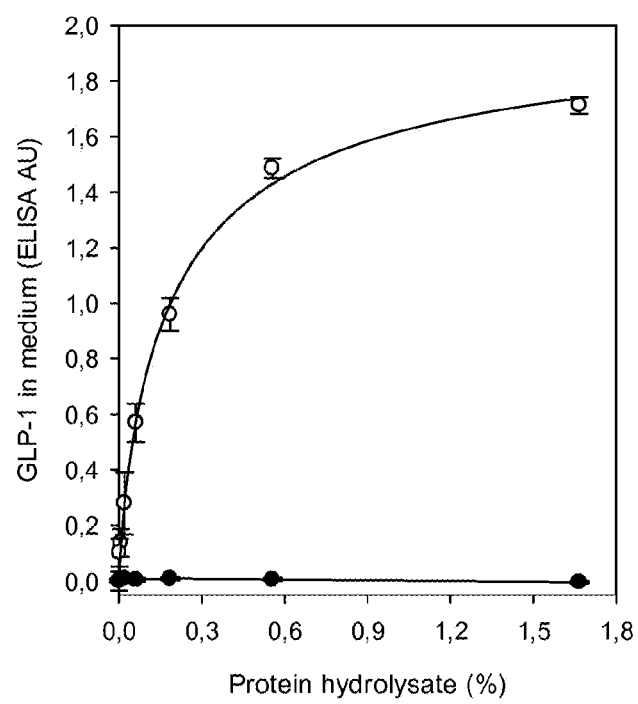

Specification includes a Sequence Listing.

(56) References Cited

OTHER PUBLICATIONS

Samson, W., et al., "A 35 Amino Acid Fragment of Leptin Inhibits Feeding in the Rat," *Endocrinology*, 1996, vol. 137(11), pp. 5182-5185.
Zhao, J., et al., "Facile Synthesis of Peptidyl Salicylaldehyde Esters and Its Use in Cyclic Peptide Synthesis," *Organic Letters*, 2013, vol. 15(20), pp. 5182-5185.
Neurotensin (8-13). Anaspec. Catalog #AS-22964 (2015), pp. 1-6.
Food energy—methods of analysis and conversion factors, Chapter 3—Calculation of the energy content of foods—energy conversion factors, Food and Agriculture Organization of the United Nations, Rome, 2003, 19 pages.

* cited by examiner

● ASDKPYIL
○ RRPYIL
▼ DKPYIL
△ $A_D$SDKPYIL
■ $AA_D$DKPYIL

Figure 10

Neurotensin (NT)/Neuromedin N (NN) precursor

MRGMNLQLVCLTLLAFSSWSLCSDSEEDVRALEADLLTNMHTSKISKASPPSWKMTLLNVCSLINNVNSPAEEAGDMHDDLVGK
RKLPLVLDGFSLEAMLTIFQLQKICRSRAFQHWEIIQEDILDNVNDKNEKEEVIKRKIPYILKRQLYENKPRRPYILKRGSYYY

MLTKFETKSARVKGLSFHPKRPWIL  ASDKPYIL    ASDKPYIL    DC7-2
                                                   Xenin

```
HsACTN1  AGDKNYIT
HsACTN4  AGDKNFIT
HsACTN2  ASDKPYIL
HsACTN3  AGDKNYIT
DmACTN   AADKPYIL
CeACTN   ASGKTFIT
DdACTN   AEDKDFIT
SpACTN   ADGKSYVT
DrACTN   AADKPYIL
```

Effect of repeated DC7-2 administration on accumulated feed intake in mice

SEQUENCE LISTING

<160> NUMBER OF SEQ ID NOS: 1029

<210> SEQ ID NO 1
<211> LENGTH: 8
<212> TYPE: PRT
<213> ORGANISM: Artificial Sequence
<220> FEATURE:
<223> OTHER INFORMATION: Artificial peptide sequence

```
<220> FEATURE:
<221> NAME/KEY: MISC_FEATURE
<222> LOCATION: (1)..(1)
<223> OTHER INFORMATION: Xaa in position 1 is A, L, I, or V
<220> FEATURE:
<221> NAME/KEY: MISC_FEATURE
<222> LOCATION: (2)..(2)
<223> OTHER INFORMATION: Xaa in position 2 is S, T, G, A, N, E or D
<220> FEATURE:
<221> NAME/KEY: MISC_FEATURE
<222> LOCATION: (3)..(3)
<223> OTHER INFORMATION: Xaa in position 3 is D, E, or G
<220> FEATURE:
<221> NAME/KEY: MISC_FEATURE
<222> LOCATION: (5)..(5)
<223> OTHER INFORMATION: Xaa in position 5 is P, N, S, D, A, T, K, or G
<220> FEATURE:
<221> NAME/KEY: MISC_FEATURE
<222> LOCATION: (6)..(6)
<223> OTHER INFORMATION: Xaa in position 6 is Y, N, I, W, or F
<220> FEATURE:
<221> NAME/KEY: MISC_FEATURE
<222> LOCATION: (7)..(7)
<223> OTHER INFORMATION: Xaa in position 7 is I, L, R, or V
<220> FEATURE:
<221> NAME/KEY: MISC_FEATURE
<222> LOCATION: (8)..(8)
<223> OTHER INFORMATION: Xaa in position 8 is L, I, V, S, M, or T

<400> SEQUENCE: 1

Xaa Xaa Xaa Lys Xaa Xaa Xaa Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: Recombinant peptide
<220> FEATURE:
<221> NAME/KEY: MISC_FEATURE
<222> LOCATION: (1)..(1)
<223> OTHER INFORMATION: Xaa in position 1 is N-term (-NH2) A, L, I, or
      V
<220> FEATURE:
<221> NAME/KEY: MISC_FEATURE
<222> LOCATION: (2)..(2)
<223> OTHER INFORMATION: Xaa in position 2 is S, T, G, A, N, E or D
<220> FEATURE:
<221> NAME/KEY: MISC_FEATURE
<222> LOCATION: (3)..(3)
<223> OTHER INFORMATION: Xaa in position 3 is D, E, or G
<220> FEATURE:
<221> NAME/KEY: MISC_FEATURE
<222> LOCATION: (5)..(5)
<223> OTHER INFORMATION: Xaa in position 5 is P, N, S, D, A, T, K, or G
<220> FEATURE:
<221> NAME/KEY: MISC_FEATURE
<222> LOCATION: (6)..(6)
<223> OTHER INFORMATION: Xaa in position 6 is Y, N, I, W, or F
<220> FEATURE:
<221> NAME/KEY: MISC_FEATURE
<222> LOCATION: (7)..(7)
<223> OTHER INFORMATION: Xaa in position 7 is I, L, R, or V
<220> FEATURE:
<221> NAME/KEY: MISC_FEATURE
<222> LOCATION: (8)..(8)
<223> OTHER INFORMATION: Xaa in position 8 is a C-term L, I, V, S, M, or
      T

<400> SEQUENCE: 2

Xaa Xaa Xaa Lys Xaa Xaa Xaa Xaa
1               5

<210> SEQ ID NO 3
```

```
<211> LENGTH: 8
<212> TYPE: PRT
<213> ORGANISM: Artificial Sequence
<220> FEATURE:
<223> OTHER INFORMATION: Recombinant peptide
<220> FEATURE:
<221> NAME/KEY: MISC_FEATURE
<222> LOCATION: (1)..(1)
<223> OTHER INFORMATION: Xaa in position 1 is A, L, I, or V
<220> FEATURE:
<221> NAME/KEY: MISC_FEATURE
<222> LOCATION: (2)..(2)
<223> OTHER INFORMATION: Xaa in position 2 is S, T, G, A, N, E or D
<220> FEATURE:
<221> NAME/KEY: MISC_FEATURE
<222> LOCATION: (3)..(3)
<223> OTHER INFORMATION: Xaa in position 3 is D, R, K, E, or G
<220> FEATURE:
<221> NAME/KEY: MISC_FEATURE
<222> LOCATION: (4)..(4)
<223> OTHER INFORMATION: Xaa in position 4 is K or R
<220> FEATURE:
<221> NAME/KEY: MISC_FEATURE
<222> LOCATION: (5)..(5)
<223> OTHER INFORMATION: Xaa in position 5 is P, N, S, D, A, T, K, or G
<220> FEATURE:
<221> NAME/KEY: MISC_FEATURE
<222> LOCATION: (6)..(6)
<223> OTHER INFORMATION: Xaa in position 6 is Y, N, I, W, or F
<220> FEATURE:
<221> NAME/KEY: MISC_FEATURE
<222> LOCATION: (7)..(7)
<223> OTHER INFORMATION: Xaa in position 7 is I, L, R, or V
<220> FEATURE:
<221> NAME/KEY: MISC_FEATURE
<222> LOCATION: (8)..(8)
<223> OTHER INFORMATION: Xaa in position 8 is L, I, V, S, M, or T

<400> SEQUENCE: 3

Xaa Xaa Xaa Xaa Xaa Xaa Xaa Xaa
1               5

<210> SEQ ID NO 4
<211> LENGTH: 4
<212> TYPE: PRT
<213> ORGANISM: Artificial Sequence
<220> FEATURE:
<223> OTHER INFORMATION: Recombinant peptide

<400> SEQUENCE: 4

Pro Tyr Ile Leu
1

<210> SEQ ID NO 5
<211> LENGTH: 16
<212> TYPE: PRT
<213> ORGANISM: Artificial Sequence
<220> FEATURE:
<223> OTHER INFORMATION: Recombinant peptide

<400> SEQUENCE: 5

Ala Val Thr Glu Lys Lys Tyr Ile Leu Tyr Asp Phe Ser Val Thr Ser
1               5                   10                  15

<210> SEQ ID NO 6
<211> LENGTH: 8
<212> TYPE: PRT
<213> ORGANISM: Artificial Sequence
<220> FEATURE:
<223> OTHER INFORMATION: Recombinant peptide

<400> SEQUENCE: 6
```

```
Ala Ser Asp Lys Pro Tyr Ile Leu
1               5

<210> SEQ ID NO 7
<211> LENGTH: 7
<212> TYPE: PRT
<213> ORGANISM: Artificial Sequence
<220> FEATURE:
<223> OTHER INFORMATION: Recombinant peptide

<400> SEQUENCE: 7

Ser Asp Lys Pro Tyr Ile Leu
1               5

<210> SEQ ID NO 8
<211> LENGTH: 6
<212> TYPE: PRT
<213> ORGANISM: Artificial Sequence
<220> FEATURE:
<223> OTHER INFORMATION: Recombinant peptide

<400> SEQUENCE: 8

Asp Lys Pro Tyr Ile Leu
1               5

<210> SEQ ID NO 9
<211> LENGTH: 5
<212> TYPE: PRT
<213> ORGANISM: Artificial Sequence
<220> FEATURE:
<223> OTHER INFORMATION: Recombinant peptide

<400> SEQUENCE: 9

Lys Pro Tyr Ile Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Recombinant peptide

<400> SEQUENCE: 10

Ala Gly Asp Lys Asn Tyr Ile Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Recombinant peptide

<400> SEQUENCE: 11

Ala Gly Asp Lys Asn Tyr Ile Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Recombinant peptide

<400> SEQUENCE: 12

Ala Gly Asp Lys Ser Tyr Ile Thr
```

1               5

<210> SEQ ID NO 13
<211> LENGTH: 8
<212> TYPE: PRT
<213> ORGANISM: Artificial Sequence
<220> FEATURE:
<223> OTHER INFORMATION: Recombinant peptide

<400> SEQUENCE: 13

Ala Asp Gly Lys Pro Tyr Ile Val
1               5

<210> SEQ ID NO 14
<211> LENGTH: 8
<212> TYPE: PRT
<213> ORGANISM: Artificial Sequence
<220> FEATURE:
<223> OTHER INFORMATION: Recombinant peptide

<400> SEQUENCE: 14

Ala Glu Asp Lys Asp Phe Ile Thr
1               5

<210> SEQ ID NO 15
<211> LENGTH: 8
<212> TYPE: PRT
<213> ORGANISM: Artificial Sequence
<220> FEATURE:
<223> OTHER INFORMATION: Recombinant peptide

<400> SEQUENCE: 15

Ala Ala Asp Lys Pro Tyr Ile Leu
1               5

<210> SEQ ID NO 16
<211> LENGTH: 8
<212> TYPE: PRT
<213> ORGANISM: Artificial Sequence
<220> FEATURE:
<223> OTHER INFORMATION: Recombinant peptide

<400> SEQUENCE: 16

Ala Thr Asp Lys Pro Tyr Ile Leu
1               5

<210> SEQ ID NO 17
<211> LENGTH: 8
<212> TYPE: PRT
<213> ORGANISM: Artificial Sequence
<220> FEATURE:
<223> OTHER INFORMATION: Recombinant peptide

<400> SEQUENCE: 17

Ala Gly Asp Lys Pro Tyr Ile Thr
1               5

<210> SEQ ID NO 18
<211> LENGTH: 8
<212> TYPE: PRT
<213> ORGANISM: Artificial Sequence
<220> FEATURE:
<223> OTHER INFORMATION: Recombinant peptide

<400> SEQUENCE: 18

Ala Ser Glu Lys Pro Tyr Ile Leu
1               5

```
<210> SEQ ID NO 19
<211> LENGTH: 8
<212> TYPE: PRT
<213> ORGANISM: Artificial Sequence
<220> FEATURE:
<223> OTHER INFORMATION: Recombinant peptide

<400> SEQUENCE: 19

Ala Asp Gly Lys Pro Tyr Val Thr
1               5

<210> SEQ ID NO 20
<211> LENGTH: 8
<212> TYPE: PRT
<213> ORGANISM: Artificial Sequence
<220> FEATURE:
<223> OTHER INFORMATION: Recombinant peptide

<400> SEQUENCE: 20

Ala Gly Asp Lys Pro Tyr Ile Leu
1               5

<210> SEQ ID NO 21
<211> LENGTH: 8
<212> TYPE: PRT
<213> ORGANISM: Artificial Sequence
<220> FEATURE:
<223> OTHER INFORMATION: Recombinant peptide

<400> SEQUENCE: 21

Ala Ser Asp Lys Pro Asn Ile Leu
1               5

<210> SEQ ID NO 22
<211> LENGTH: 8
<212> TYPE: PRT
<213> ORGANISM: Artificial Sequence
<220> FEATURE:
<223> OTHER INFORMATION: Recombinant peptide

<400> SEQUENCE: 22

Ala Ser Asp Lys Pro Tyr Ile Thr
1               5

<210> SEQ ID NO 23
<211> LENGTH: 8
<212> TYPE: PRT
<213> ORGANISM: Artificial Sequence
<220> FEATURE:
<223> OTHER INFORMATION: Recombinant peptide

<400> SEQUENCE: 23

Ala Ala Asp Lys Pro Phe Ile Leu
1               5

<210> SEQ ID NO 24
<211> LENGTH: 8
<212> TYPE: PRT
<213> ORGANISM: Artificial Sequence
<220> FEATURE:
<223> OTHER INFORMATION: Recombinant peptide

<400> SEQUENCE: 24

Ala Ser Asp Lys Ala Tyr Ile Thr
1               5
```

```
<210> SEQ ID NO 25
<211> LENGTH: 8
<212> TYPE: PRT
<213> ORGANISM: Artificial Sequence
<220> FEATURE:
<223> OTHER INFORMATION: Recombinant peptide

<400> SEQUENCE: 25

Ala Gly Asp Lys Ala Tyr Ile Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Recombinant peptide

<400> SEQUENCE: 26

Ala Asn Gly Lys Pro Phe Ile Thr
1               5

<210> SEQ ID NO 27
<211> LENGTH: 8
<212> TYPE: PRT
<213> ORGANISM: Artificial Sequence
<220> FEATURE:
<223> OTHER INFORMATION: Recombinant peptide

<400> SEQUENCE: 27

Ala Gly Asp Lys Asn Phe Ile Thr
1               5

<210> SEQ ID NO 28
<211> LENGTH: 8
<212> TYPE: PRT
<213> ORGANISM: Artificial Sequence
<220> FEATURE:
<223> OTHER INFORMATION: Recombinant peptide

<400> SEQUENCE: 28

Ala Ser Asp Lys Ser Tyr Ile Thr
1               5

<210> SEQ ID NO 29
<211> LENGTH: 8
<212> TYPE: PRT
<213> ORGANISM: Artificial Sequence
<220> FEATURE:
<223> OTHER INFORMATION: Recombinant peptide

<400> SEQUENCE: 29

Ala Ser Asp Lys Thr Tyr Ile Thr
1               5

<210> SEQ ID NO 30
<211> LENGTH: 8
<212> TYPE: PRT
<213> ORGANISM: Artificial Sequence
<220> FEATURE:
<223> OTHER INFORMATION: Recombinant peptide

<400> SEQUENCE: 30

Ala Ser Asp Lys Asn Tyr Ile Thr
1               5
```

```
<210> SEQ ID NO 31
<211> LENGTH: 8
<212> TYPE: PRT
<213> ORGANISM: Artificial Sequence
<220> FEATURE:
<223> OTHER INFORMATION: Recombinant peptide

<400> SEQUENCE: 31

Ala Gly Asp Lys Lys Tyr Ile Thr
1               5

<210> SEQ ID NO 32
<211> LENGTH: 8
<212> TYPE: PRT
<213> ORGANISM: Artificial Sequence
<220> FEATURE:
<223> OTHER INFORMATION: Recombinant peptide

<400> SEQUENCE: 32

Ala Gly Asp Lys Asn Tyr Ile Ser
1               5

<210> SEQ ID NO 33
<211> LENGTH: 8
<212> TYPE: PRT
<213> ORGANISM: Artificial Sequence
<220> FEATURE:
<223> OTHER INFORMATION: Recombinant peptide

<400> SEQUENCE: 33

Ala Ala Asp Lys Asn Tyr Ile Thr
1               5

<210> SEQ ID NO 34
<211> LENGTH: 8
<212> TYPE: PRT
<213> ORGANISM: Artificial Sequence
<220> FEATURE:
<223> OTHER INFORMATION: Recombinant peptide

<400> SEQUENCE: 34

Ala Gly Asp Lys Asn Tyr Ile Met
1               5

<210> SEQ ID NO 35
<211> LENGTH: 8
<212> TYPE: PRT
<213> ORGANISM: Artificial Sequence
<220> FEATURE:
<223> OTHER INFORMATION: Recombinant peptide

<400> SEQUENCE: 35

Ala Ala Asp Lys Asn Phe Ile Met
1               5

<210> SEQ ID NO 36
<211> LENGTH: 8
<212> TYPE: PRT
<213> ORGANISM: Artificial Sequence
<220> FEATURE:
<223> OTHER INFORMATION: Recombinant peptide

<400> SEQUENCE: 36

Ala Ala Asp Lys Asn Phe Ile Thr
1               5

<210> SEQ ID NO 37
```

```
<211> LENGTH: 8
<212> TYPE: PRT
<213> ORGANISM: Artificial Sequence
<220> FEATURE:
<223> OTHER INFORMATION: Recombinant peptide

<400> SEQUENCE: 37

Ala Gly Asp Lys Gly Ile Arg Ser
1               5

<210> SEQ ID NO 38
<211> LENGTH: 7
<212> TYPE: PRT
<213> ORGANISM: Artificial Sequence
<220> FEATURE:
<223> OTHER INFORMATION: Recombinant peptide

<400> SEQUENCE: 38

Pro Arg Arg Pro Tyr Ile Leu
1               5

<210> SEQ ID NO 39
<211> LENGTH: 6
<212> TYPE: PRT
<213> ORGANISM: Artificial Sequence
<220> FEATURE:
<223> OTHER INFORMATION: Recombinant peptide

<400> SEQUENCE: 39

Arg Arg Pro Tyr Ile Leu
1               5

<210> SEQ ID NO 40
<211> LENGTH: 5
<212> TYPE: PRT
<213> ORGANISM: Artificial Sequence
<220> FEATURE:
<223> OTHER INFORMATION: Recombinant peptide

<400> SEQUENCE: 40

Arg Pro Tyr Ile Leu
1               5

<210> SEQ ID NO 41
<211> LENGTH: 6
<212> TYPE: PRT
<213> ORGANISM: Artificial Sequence
<220> FEATURE:
<223> OTHER INFORMATION: Recombinant peptide

<400> SEQUENCE: 41

Arg Arg Pro Trp Ile Leu
1               5

<210> SEQ ID NO 42
<211> LENGTH: 6
<212> TYPE: PRT
<213> ORGANISM: Artificial Sequence
<220> FEATURE:
<223> OTHER INFORMATION: Recombinant peptide

<400> SEQUENCE: 42

Lys Arg Pro Tyr Ile Leu
1               5

<210> SEQ ID NO 43
<211> LENGTH: 6
```

```
<212> TYPE: PRT
<213> ORGANISM: Artificial Sequence
<220> FEATURE:
<223> OTHER INFORMATION: Recombinant peptide

<400> SEQUENCE: 43

Lys Lys Pro Tyr Ile Leu
1               5

<210> SEQ ID NO 44
<211> LENGTH: 6
<212> TYPE: PRT
<213> ORGANISM: Artificial Sequence
<220> FEATURE:
<223> OTHER INFORMATION: Recombinant peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 44

Lys Xaa Pro Tyr Ile Leu
1               5

<210> SEQ ID NO 45
<211> LENGTH: 5
<212> TYPE: PRT
<213> ORGANISM: Artificial Sequence
<220> FEATURE:
<223> OTHER INFORMATION: Recombinant peptide

<400> SEQUENCE: 45

Lys Pro Tyr Ile Ile
1               5

<210> SEQ ID NO 46
<211> LENGTH: 5
<212> TYPE: PRT
<213> ORGANISM: Artificial Sequence
<220> FEATURE:
<223> OTHER INFORMATION: Recombinant peptide

<400> SEQUENCE: 46

Lys Pro Tyr Ile Val
1               5

<210> SEQ ID NO 47
<211> LENGTH: 5
<212> TYPE: PRT
<213> ORGANISM: Artificial Sequence
<220> FEATURE:
<223> OTHER INFORMATION: Recombinant peptide

<400> SEQUENCE: 47

Lys Pro Tyr Leu Leu
1               5

<210> SEQ ID NO 48
<211> LENGTH: 5
<212> TYPE: PRT
<213> ORGANISM: Artificial Sequence
<220> FEATURE:
<223> OTHER INFORMATION: Recombinant peptide

<400> SEQUENCE: 48

Lys Pro Tyr Leu Ile
1               5
```

```
<210> SEQ ID NO 49
<211> LENGTH: 5
<212> TYPE: PRT
<213> ORGANISM: Artificial Sequence
<220> FEATURE:
<223> OTHER INFORMATION: Recombinant peptide

<400> SEQUENCE: 49

Lys Pro Tyr Leu Val
1               5

<210> SEQ ID NO 50
<211> LENGTH: 5
<212> TYPE: PRT
<213> ORGANISM: Artificial Sequence
<220> FEATURE:
<223> OTHER INFORMATION: Recombinant peptide

<400> SEQUENCE: 50

Lys Pro Tyr Val Leu
1               5

<210> SEQ ID NO 51
<211> LENGTH: 5
<212> TYPE: PRT
<213> ORGANISM: Artificial Sequence
<220> FEATURE:
<223> OTHER INFORMATION: Recombinant peptide

<400> SEQUENCE: 51

Lys Pro Tyr Val Ile
1               5

<210> SEQ ID NO 52
<211> LENGTH: 5
<212> TYPE: PRT
<213> ORGANISM: Artificial Sequence
<220> FEATURE:
<223> OTHER INFORMATION: Recombinant peptide

<400> SEQUENCE: 52

Lys Pro Tyr Val Val
1               5

<210> SEQ ID NO 53
<211> LENGTH: 5
<212> TYPE: PRT
<213> ORGANISM: Artificial Sequence
<220> FEATURE:
<223> OTHER INFORMATION: Recombinant peptide

<400> SEQUENCE: 53

Lys Pro Trp Ile Leu
1               5

<210> SEQ ID NO 54
<211> LENGTH: 5
<212> TYPE: PRT
<213> ORGANISM: Artificial Sequence
<220> FEATURE:
<223> OTHER INFORMATION: Recombinant peptide

<400> SEQUENCE: 54

Lys Pro Trp Ile Ile
1               5
```

```
<210> SEQ ID NO 55
<211> LENGTH: 5
<212> TYPE: PRT
<213> ORGANISM: Artificial Sequence
<220> FEATURE:
<223> OTHER INFORMATION: Recombinant peptide

<400> SEQUENCE: 55

Lys Pro Trp Ile Val
1               5

<210> SEQ ID NO 56
<211> LENGTH: 5
<212> TYPE: PRT
<213> ORGANISM: Artificial Sequence
<220> FEATURE:
<223> OTHER INFORMATION: Recombinant peptide

<400> SEQUENCE: 56

Lys Pro Trp Leu Leu
1               5

<210> SEQ ID NO 57
<211> LENGTH: 5
<212> TYPE: PRT
<213> ORGANISM: Artificial Sequence
<220> FEATURE:
<223> OTHER INFORMATION: Recombinant peptide

<400> SEQUENCE: 57

Lys Pro Trp Leu Ile
1               5

<210> SEQ ID NO 58
<211> LENGTH: 5
<212> TYPE: PRT
<213> ORGANISM: Artificial Sequence
<220> FEATURE:
<223> OTHER INFORMATION: Recombinant peptide

<400> SEQUENCE: 58

Lys Pro Trp Leu Val
1               5

<210> SEQ ID NO 59
<211> LENGTH: 5
<212> TYPE: PRT
<213> ORGANISM: Artificial Sequence
<220> FEATURE:
<223> OTHER INFORMATION: Recombinant peptide

<400> SEQUENCE: 59

Lys Pro Trp Val Leu
1               5

<210> SEQ ID NO 60
<211> LENGTH: 5
<212> TYPE: PRT
<213> ORGANISM: Artificial Sequence
<220> FEATURE:
<223> OTHER INFORMATION: Recombinant peptide

<400> SEQUENCE: 60

Lys Pro Trp Val Ile
1               5

<210> SEQ ID NO 61
```

```
<211> LENGTH: 5
<212> TYPE: PRT
<213> ORGANISM: Artificial Sequence
<220> FEATURE:
<223> OTHER INFORMATION: Recombinant peptide

<400> SEQUENCE: 61

Lys Pro Trp Val Val
1               5

<210> SEQ ID NO 62
<211> LENGTH: 5
<212> TYPE: PRT
<213> ORGANISM: Artificial Sequence
<220> FEATURE:
<223> OTHER INFORMATION: Recombinant peptide

<400> SEQUENCE: 62

Arg Pro Tyr Ile Ile
1               5

<210> SEQ ID NO 63
<211> LENGTH: 5
<212> TYPE: PRT
<213> ORGANISM: Artificial Sequence
<220> FEATURE:
<223> OTHER INFORMATION: Recombinant peptide

<400> SEQUENCE: 63

Arg Pro Tyr Ile Val
1               5

<210> SEQ ID NO 64
<211> LENGTH: 5
<212> TYPE: PRT
<213> ORGANISM: Artificial Sequence
<220> FEATURE:
<223> OTHER INFORMATION: Recombinant peptide

<400> SEQUENCE: 64

Arg Pro Tyr Leu Leu
1               5

<210> SEQ ID NO 65
<211> LENGTH: 5
<212> TYPE: PRT
<213> ORGANISM: Artificial Sequence
<220> FEATURE:
<223> OTHER INFORMATION: Recombinant peptide

<400> SEQUENCE: 65

Arg Pro Tyr Leu Ile
1               5

<210> SEQ ID NO 66
<211> LENGTH: 5
<212> TYPE: PRT
<213> ORGANISM: Artificial Sequence
<220> FEATURE:
<223> OTHER INFORMATION: Recombinant peptide

<400> SEQUENCE: 66

Arg Pro Tyr Leu Val
1               5

<210> SEQ ID NO 67
<211> LENGTH: 5
```

```
<212> TYPE: PRT
<213> ORGANISM: Artificial Sequence
<220> FEATURE:
<223> OTHER INFORMATION: Recombinant peptide

<400> SEQUENCE: 67

Arg Pro Tyr Val Leu
1               5

<210> SEQ ID NO 68
<211> LENGTH: 5
<212> TYPE: PRT
<213> ORGANISM: Artificial Sequence
<220> FEATURE:
<223> OTHER INFORMATION: Recombinant peptide

<400> SEQUENCE: 68

Arg Pro Tyr Val Ile
1               5

<210> SEQ ID NO 69
<211> LENGTH: 5
<212> TYPE: PRT
<213> ORGANISM: Artificial Sequence
<220> FEATURE:
<223> OTHER INFORMATION: Recombinant peptide

<400> SEQUENCE: 69

Arg Pro Tyr Val Val
1               5

<210> SEQ ID NO 70
<211> LENGTH: 5
<212> TYPE: PRT
<213> ORGANISM: Artificial Sequence
<220> FEATURE:
<223> OTHER INFORMATION: Recombinant peptide

<400> SEQUENCE: 70

Arg Pro Trp Ile Leu
1               5

<210> SEQ ID NO 71
<211> LENGTH: 5
<212> TYPE: PRT
<213> ORGANISM: Artificial Sequence
<220> FEATURE:
<223> OTHER INFORMATION: Recombinant peptide

<400> SEQUENCE: 71

Arg Pro Trp Ile Ile
1               5

<210> SEQ ID NO 72
<211> LENGTH: 5
<212> TYPE: PRT
<213> ORGANISM: Artificial Sequence
<220> FEATURE:
<223> OTHER INFORMATION: Recombinant peptide

<400> SEQUENCE: 72

Arg Pro Trp Ile Val
1               5

<210> SEQ ID NO 73
<211> LENGTH: 5
<212> TYPE: PRT
```

```
<213> ORGANISM: Artificial Sequence
<220> FEATURE:
<223> OTHER INFORMATION: Recombinant peptide

<400> SEQUENCE: 73

Arg Pro Trp Leu Leu
1               5

<210> SEQ ID NO 74
<211> LENGTH: 5
<212> TYPE: PRT
<213> ORGANISM: Artificial Sequence
<220> FEATURE:
<223> OTHER INFORMATION: Recombinant peptide

<400> SEQUENCE: 74

Arg Pro Trp Leu Ile
1               5

<210> SEQ ID NO 75
<211> LENGTH: 5
<212> TYPE: PRT
<213> ORGANISM: Artificial Sequence
<220> FEATURE:
<223> OTHER INFORMATION: Recombinant peptide

<400> SEQUENCE: 75

Arg Pro Trp Leu Val
1               5

<210> SEQ ID NO 76
<211> LENGTH: 5
<212> TYPE: PRT
<213> ORGANISM: Artificial Sequence
<220> FEATURE:
<223> OTHER INFORMATION: Recombinant peptide

<400> SEQUENCE: 76

Arg Pro Trp Val Leu
1               5

<210> SEQ ID NO 77
<211> LENGTH: 5
<212> TYPE: PRT
<213> ORGANISM: Artificial Sequence
<220> FEATURE:
<223> OTHER INFORMATION: Recombinant peptide

<400> SEQUENCE: 77

Arg Pro Trp Val Ile
1               5

<210> SEQ ID NO 78
<211> LENGTH: 5
<212> TYPE: PRT
<213> ORGANISM: Artificial Sequence
<220> FEATURE:
<223> OTHER INFORMATION: Recombinant peptide

<400> SEQUENCE: 78

Arg Pro Trp Val Val
1               5

<210> SEQ ID NO 79
<211> LENGTH: 6
<212> TYPE: PRT
<213> ORGANISM: Artificial Sequence
```

```
<220> FEATURE:
<223> OTHER INFORMATION: Recombinant peptide

<400> SEQUENCE: 79

Asp Lys Pro Tyr Ile Ile
1               5

<210> SEQ ID NO 80
<211> LENGTH: 6
<212> TYPE: PRT
<213> ORGANISM: Artificial Sequence
<220> FEATURE:
<223> OTHER INFORMATION: Recombinant peptide

<400> SEQUENCE: 80

Asp Lys Pro Tyr Ile Val
1               5

<210> SEQ ID NO 81
<211> LENGTH: 6
<212> TYPE: PRT
<213> ORGANISM: Artificial Sequence
<220> FEATURE:
<223> OTHER INFORMATION: Recombinant peptide

<400> SEQUENCE: 81

Asp Lys Pro Tyr Leu Leu
1               5

<210> SEQ ID NO 82
<211> LENGTH: 6
<212> TYPE: PRT
<213> ORGANISM: Artificial Sequence
<220> FEATURE:
<223> OTHER INFORMATION: Recombinant peptide

<400> SEQUENCE: 82

Asp Lys Pro Tyr Leu Ile
1               5

<210> SEQ ID NO 83
<211> LENGTH: 6
<212> TYPE: PRT
<213> ORGANISM: Artificial Sequence
<220> FEATURE:
<223> OTHER INFORMATION: Recombinant peptide

<400> SEQUENCE: 83

Asp Lys Pro Tyr Leu Val
1               5

<210> SEQ ID NO 84
<211> LENGTH: 6
<212> TYPE: PRT
<213> ORGANISM: Artificial Sequence
<220> FEATURE:
<223> OTHER INFORMATION: Recombinant peptide

<400> SEQUENCE: 84

Asp Lys Pro Tyr Val Leu
1               5

<210> SEQ ID NO 85
<211> LENGTH: 6
<212> TYPE: PRT
<213> ORGANISM: Artificial Sequence
<220> FEATURE:
```

```
<223> OTHER INFORMATION: Recombinant peptide

<400> SEQUENCE: 85

Asp Lys Pro Tyr Val Ile
1               5

<210> SEQ ID NO 86
<211> LENGTH: 6
<212> TYPE: PRT
<213> ORGANISM: Artificial Sequence
<220> FEATURE:
<223> OTHER INFORMATION: Recombinant peptide

<400> SEQUENCE: 86

Asp Lys Pro Tyr Val Val
1               5

<210> SEQ ID NO 87
<211> LENGTH: 6
<212> TYPE: PRT
<213> ORGANISM: Artificial Sequence
<220> FEATURE:
<223> OTHER INFORMATION: Recombinant peptide

<400> SEQUENCE: 87

Asp Lys Pro Trp Ile Leu
1               5

<210> SEQ ID NO 88
<211> LENGTH: 6
<212> TYPE: PRT
<213> ORGANISM: Artificial Sequence
<220> FEATURE:
<223> OTHER INFORMATION: Recombinant peptide

<400> SEQUENCE: 88

Asp Lys Pro Trp Ile Ile
1               5

<210> SEQ ID NO 89
<211> LENGTH: 6
<212> TYPE: PRT
<213> ORGANISM: Artificial Sequence
<220> FEATURE:
<223> OTHER INFORMATION: Recombinant peptide

<400> SEQUENCE: 89

Asp Lys Pro Trp Ile Val
1               5

<210> SEQ ID NO 90
<211> LENGTH: 6
<212> TYPE: PRT
<213> ORGANISM: Artificial Sequence
<220> FEATURE:
<223> OTHER INFORMATION: Recombinant peptide

<400> SEQUENCE: 90

Asp Lys Pro Trp Leu Leu
1               5

<210> SEQ ID NO 91
<211> LENGTH: 6
<212> TYPE: PRT
<213> ORGANISM: Artificial Sequence
<220> FEATURE:
<223> OTHER INFORMATION: Recombinant peptide
```

<400> SEQUENCE: 91

Asp Lys Pro Trp Leu Ile
1               5

<210> SEQ ID NO 92
<211> LENGTH: 6
<212> TYPE: PRT
<213> ORGANISM: Artificial Sequence
<220> FEATURE:
<223> OTHER INFORMATION: Recombinant peptide

<400> SEQUENCE: 92

Asp Lys Pro Trp Leu Val
1               5

<210> SEQ ID NO 93
<211> LENGTH: 6
<212> TYPE: PRT
<213> ORGANISM: Artificial Sequence
<220> FEATURE:
<223> OTHER INFORMATION: Recombinant peptide

<400> SEQUENCE: 93

Asp Lys Pro Trp Val Leu
1               5

<210> SEQ ID NO 94
<211> LENGTH: 6
<212> TYPE: PRT
<213> ORGANISM: Artificial Sequence
<220> FEATURE:
<223> OTHER INFORMATION: Recombinant peptide

<400> SEQUENCE: 94

Asp Lys Pro Trp Val Ile
1               5

<210> SEQ ID NO 95
<211> LENGTH: 6
<212> TYPE: PRT
<213> ORGANISM: Artificial Sequence
<220> FEATURE:
<223> OTHER INFORMATION: Recombinant peptide

<400> SEQUENCE: 95

Asp Lys Pro Trp Val Val
1               5

<210> SEQ ID NO 96
<211> LENGTH: 6
<212> TYPE: PRT
<213> ORGANISM: Artificial Sequence
<220> FEATURE:
<223> OTHER INFORMATION: Recombinant peptide

<400> SEQUENCE: 96

Asp Arg Pro Tyr Ile Leu
1               5

<210> SEQ ID NO 97
<211> LENGTH: 6
<212> TYPE: PRT
<213> ORGANISM: Artificial Sequence
<220> FEATURE:
<223> OTHER INFORMATION: Recombinant peptide

<400> SEQUENCE: 97

Asp Arg Pro Tyr Ile Ile
1               5

<210> SEQ ID NO 98
<211> LENGTH: 6
<212> TYPE: PRT
<213> ORGANISM: Artificial Sequence
<220> FEATURE:
<223> OTHER INFORMATION: Recombinant peptide

<400> SEQUENCE: 98

Asp Arg Pro Tyr Ile Val
1               5

<210> SEQ ID NO 99
<211> LENGTH: 6
<212> TYPE: PRT
<213> ORGANISM: Artificial Sequence
<220> FEATURE:
<223> OTHER INFORMATION: Recombinant peptide

<400> SEQUENCE: 99

Asp Arg Pro Tyr Leu Leu
1               5

<210> SEQ ID NO 100
<211> LENGTH: 6
<212> TYPE: PRT
<213> ORGANISM: Artificial Sequence
<220> FEATURE:
<223> OTHER INFORMATION: Recombinant peptide

<400> SEQUENCE: 100

Asp Arg Pro Tyr Leu Ile
1               5

<210> SEQ ID NO 101
<211> LENGTH: 6
<212> TYPE: PRT
<213> ORGANISM: Artificial Sequence
<220> FEATURE:
<223> OTHER INFORMATION: Recombinant peptide

<400> SEQUENCE: 101

Asp Arg Pro Tyr Leu Val
1               5

<210> SEQ ID NO 102
<211> LENGTH: 6
<212> TYPE: PRT
<213> ORGANISM: Artificial Sequence
<220> FEATURE:
<223> OTHER INFORMATION: Recombinant peptide

<400> SEQUENCE: 102

Asp Arg Pro Tyr Val Leu
1               5

<210> SEQ ID NO 103
<211> LENGTH: 6
<212> TYPE: PRT
<213> ORGANISM: Artificial Sequence
<220> FEATURE:
<223> OTHER INFORMATION: Recombinant peptide

<400> SEQUENCE: 103

Asp Arg Pro Tyr Val Ile
1               5

<210> SEQ ID NO 104
<211> LENGTH: 6
<212> TYPE: PRT
<213> ORGANISM: Artificial Sequence
<220> FEATURE:
<223> OTHER INFORMATION: Recombinant peptide

<400> SEQUENCE: 104

Asp Arg Pro Tyr Val Val
1               5

<210> SEQ ID NO 105
<211> LENGTH: 6
<212> TYPE: PRT
<213> ORGANISM: Artificial Sequence
<220> FEATURE:
<223> OTHER INFORMATION: Recombinant peptide

<400> SEQUENCE: 105

Asp Arg Pro Trp Ile Leu
1               5

<210> SEQ ID NO 106
<211> LENGTH: 6
<212> TYPE: PRT
<213> ORGANISM: Artificial Sequence
<220> FEATURE:
<223> OTHER INFORMATION: Recombinant peptide

<400> SEQUENCE: 106

Asp Arg Pro Trp Ile Ile
1               5

<210> SEQ ID NO 107
<211> LENGTH: 6
<212> TYPE: PRT
<213> ORGANISM: Artificial Sequence
<220> FEATURE:
<223> OTHER INFORMATION: Recombinant peptide

<400> SEQUENCE: 107

Asp Arg Pro Trp Ile Val
1               5

<210> SEQ ID NO 108
<211> LENGTH: 6
<212> TYPE: PRT
<213> ORGANISM: Artificial Sequence
<220> FEATURE:
<223> OTHER INFORMATION: Recombinant peptide

<400> SEQUENCE: 108

Asp Arg Pro Trp Leu Leu
1               5

<210> SEQ ID NO 109
<211> LENGTH: 6
<212> TYPE: PRT
<213> ORGANISM: Artificial Sequence
<220> FEATURE:
<223> OTHER INFORMATION: Recombinant peptide

<400> SEQUENCE: 109

```
Asp Arg Pro Trp Leu Ile
1               5

<210> SEQ ID NO 110
<211> LENGTH: 6
<212> TYPE: PRT
<213> ORGANISM: Artificial Sequence
<220> FEATURE:
<223> OTHER INFORMATION: Recombinant peptide

<400> SEQUENCE: 110

Asp Arg Pro Trp Leu Val
1               5

<210> SEQ ID NO 111
<211> LENGTH: 6
<212> TYPE: PRT
<213> ORGANISM: Artificial Sequence
<220> FEATURE:
<223> OTHER INFORMATION: Recombinant peptide

<400> SEQUENCE: 111

Asp Arg Pro Trp Val Leu
1               5

<210> SEQ ID NO 112
<211> LENGTH: 6
<212> TYPE: PRT
<213> ORGANISM: Artificial Sequence
<220> FEATURE:
<223> OTHER INFORMATION: Recombinant peptide

<400> SEQUENCE: 112

Asp Arg Pro Trp Val Ile
1               5

<210> SEQ ID NO 113
<211> LENGTH: 6
<212> TYPE: PRT
<213> ORGANISM: Artificial Sequence
<220> FEATURE:
<223> OTHER INFORMATION: Recombinant peptide

<400> SEQUENCE: 113

Asp Arg Pro Trp Val Val
1               5

<210> SEQ ID NO 114
<211> LENGTH: 6
<212> TYPE: PRT
<213> ORGANISM: Artificial Sequence
<220> FEATURE:
<223> OTHER INFORMATION: Recombinant peptide

<400> SEQUENCE: 114

Glu Lys Pro Tyr Ile Leu
1               5

<210> SEQ ID NO 115
<211> LENGTH: 6
<212> TYPE: PRT
<213> ORGANISM: Artificial Sequence
<220> FEATURE:
<223> OTHER INFORMATION: Recombinant peptide

<400> SEQUENCE: 115

Glu Lys Pro Tyr Ile Ile
```

```
1               5

<210> SEQ ID NO 116
<211> LENGTH: 6
<212> TYPE: PRT
<213> ORGANISM: Artificial Sequence
<220> FEATURE:
<223> OTHER INFORMATION: Recombinant peptide

<400> SEQUENCE: 116

Glu Lys Pro Tyr Ile Val
1               5

<210> SEQ ID NO 117
<211> LENGTH: 6
<212> TYPE: PRT
<213> ORGANISM: Artificial Sequence
<220> FEATURE:
<223> OTHER INFORMATION: Recombinant peptide

<400> SEQUENCE: 117

Glu Lys Pro Tyr Leu Leu
1               5

<210> SEQ ID NO 118
<211> LENGTH: 6
<212> TYPE: PRT
<213> ORGANISM: Artificial Sequence
<220> FEATURE:
<223> OTHER INFORMATION: Recombinant peptide

<400> SEQUENCE: 118

Glu Lys Pro Tyr Leu Ile
1               5

<210> SEQ ID NO 119
<211> LENGTH: 6
<212> TYPE: PRT
<213> ORGANISM: Artificial Sequence
<220> FEATURE:
<223> OTHER INFORMATION: Recombinant peptide

<400> SEQUENCE: 119

Glu Lys Pro Tyr Leu Val
1               5

<210> SEQ ID NO 120
<211> LENGTH: 6
<212> TYPE: PRT
<213> ORGANISM: Artificial Sequence
<220> FEATURE:
<223> OTHER INFORMATION: Recombinant peptide

<400> SEQUENCE: 120

Glu Lys Pro Tyr Val Leu
1               5

<210> SEQ ID NO 121
<211> LENGTH: 6
<212> TYPE: PRT
<213> ORGANISM: Artificial Sequence
<220> FEATURE:
<223> OTHER INFORMATION: Recombinant peptide

<400> SEQUENCE: 121

Glu Lys Pro Tyr Val Ile
1               5
```

```
<210> SEQ ID NO 122
<211> LENGTH: 6
<212> TYPE: PRT
<213> ORGANISM: Artificial Sequence
<220> FEATURE:
<223> OTHER INFORMATION: Recombinant peptide

<400> SEQUENCE: 122

Glu Lys Pro Tyr Val Val
1               5

<210> SEQ ID NO 123
<211> LENGTH: 6
<212> TYPE: PRT
<213> ORGANISM: Artificial Sequence
<220> FEATURE:
<223> OTHER INFORMATION: Recombinant peptide

<400> SEQUENCE: 123

Glu Lys Pro Trp Ile Leu
1               5

<210> SEQ ID NO 124
<211> LENGTH: 6
<212> TYPE: PRT
<213> ORGANISM: Artificial Sequence
<220> FEATURE:
<223> OTHER INFORMATION: Recombinant peptide

<400> SEQUENCE: 124

Glu Lys Pro Trp Ile Ile
1               5

<210> SEQ ID NO 125
<211> LENGTH: 6
<212> TYPE: PRT
<213> ORGANISM: Artificial Sequence
<220> FEATURE:
<223> OTHER INFORMATION: Recombinant peptide

<400> SEQUENCE: 125

Glu Lys Pro Trp Ile Val
1               5

<210> SEQ ID NO 126
<211> LENGTH: 6
<212> TYPE: PRT
<213> ORGANISM: Artificial Sequence
<220> FEATURE:
<223> OTHER INFORMATION: Recombinant peptide

<400> SEQUENCE: 126

Glu Lys Pro Trp Leu Leu
1               5

<210> SEQ ID NO 127
<211> LENGTH: 6
<212> TYPE: PRT
<213> ORGANISM: Artificial Sequence
<220> FEATURE:
<223> OTHER INFORMATION: Recombinant peptide

<400> SEQUENCE: 127

Glu Lys Pro Trp Leu Ile
1               5
```

```
<210> SEQ ID NO 128
<211> LENGTH: 6
<212> TYPE: PRT
<213> ORGANISM: Artificial Sequence
<220> FEATURE:
<223> OTHER INFORMATION: Recombinant peptide

<400> SEQUENCE: 128

Glu Lys Pro Trp Leu Val
1               5

<210> SEQ ID NO 129
<211> LENGTH: 6
<212> TYPE: PRT
<213> ORGANISM: Artificial Sequence
<220> FEATURE:
<223> OTHER INFORMATION: Recombinant peptide

<400> SEQUENCE: 129

Glu Lys Pro Trp Val Leu
1               5

<210> SEQ ID NO 130
<211> LENGTH: 6
<212> TYPE: PRT
<213> ORGANISM: Artificial Sequence
<220> FEATURE:
<223> OTHER INFORMATION: Recombinant peptide

<400> SEQUENCE: 130

Glu Lys Pro Trp Val Ile
1               5

<210> SEQ ID NO 131
<211> LENGTH: 6
<212> TYPE: PRT
<213> ORGANISM: Artificial Sequence
<220> FEATURE:
<223> OTHER INFORMATION: Recombinant peptide

<400> SEQUENCE: 131

Glu Lys Pro Trp Val Val
1               5

<210> SEQ ID NO 132
<211> LENGTH: 6
<212> TYPE: PRT
<213> ORGANISM: Artificial Sequence
<220> FEATURE:
<223> OTHER INFORMATION: Recombinant peptide

<400> SEQUENCE: 132

Glu Arg Pro Tyr Ile Leu
1               5

<210> SEQ ID NO 133
<211> LENGTH: 6
<212> TYPE: PRT
<213> ORGANISM: Artificial Sequence
<220> FEATURE:
<223> OTHER INFORMATION: Recombinant peptide

<400> SEQUENCE: 133

Glu Arg Pro Tyr Ile Ile
1               5
```

```
<210> SEQ ID NO 134
<211> LENGTH: 6
<212> TYPE: PRT
<213> ORGANISM: Artificial Sequence
<220> FEATURE:
<223> OTHER INFORMATION: Recombinant peptide

<400> SEQUENCE: 134

Glu Arg Pro Tyr Ile Val
1               5

<210> SEQ ID NO 135
<211> LENGTH: 6
<212> TYPE: PRT
<213> ORGANISM: Artificial Sequence
<220> FEATURE:
<223> OTHER INFORMATION: Recombinant peptide

<400> SEQUENCE: 135

Glu Arg Pro Tyr Leu Leu
1               5

<210> SEQ ID NO 136
<211> LENGTH: 6
<212> TYPE: PRT
<213> ORGANISM: Artificial Sequence
<220> FEATURE:
<223> OTHER INFORMATION: Recombinant peptide

<400> SEQUENCE: 136

Glu Arg Pro Tyr Leu Ile
1               5

<210> SEQ ID NO 137
<211> LENGTH: 6
<212> TYPE: PRT
<213> ORGANISM: Artificial Sequence
<220> FEATURE:
<223> OTHER INFORMATION: Recombinant peptide

<400> SEQUENCE: 137

Glu Arg Pro Tyr Leu Val
1               5

<210> SEQ ID NO 138
<211> LENGTH: 6
<212> TYPE: PRT
<213> ORGANISM: Artificial Sequence
<220> FEATURE:
<223> OTHER INFORMATION: Recombinant peptide

<400> SEQUENCE: 138

Glu Arg Pro Tyr Val Leu
1               5

<210> SEQ ID NO 139
<211> LENGTH: 6
<212> TYPE: PRT
<213> ORGANISM: Artificial Sequence
<220> FEATURE:
<223> OTHER INFORMATION: Recombinant peptide

<400> SEQUENCE: 139

Glu Arg Pro Tyr Val Ile
1               5

<210> SEQ ID NO 140
```

```
<211> LENGTH: 6
<212> TYPE: PRT
<213> ORGANISM: Artificial Sequence
<220> FEATURE:
<223> OTHER INFORMATION: Recombinant peptide

<400> SEQUENCE: 140

Glu Arg Pro Tyr Val Val
1               5

<210> SEQ ID NO 141
<211> LENGTH: 6
<212> TYPE: PRT
<213> ORGANISM: Artificial Sequence
<220> FEATURE:
<223> OTHER INFORMATION: Recombinant peptide

<400> SEQUENCE: 141

Glu Arg Pro Trp Ile Leu
1               5

<210> SEQ ID NO 142
<211> LENGTH: 6
<212> TYPE: PRT
<213> ORGANISM: Artificial Sequence
<220> FEATURE:
<223> OTHER INFORMATION: Recombinant peptide

<400> SEQUENCE: 142

Glu Arg Pro Trp Ile Ile
1               5

<210> SEQ ID NO 143
<211> LENGTH: 6
<212> TYPE: PRT
<213> ORGANISM: Artificial Sequence
<220> FEATURE:
<223> OTHER INFORMATION: Recombinant peptide

<400> SEQUENCE: 143

Glu Arg Pro Trp Ile Val
1               5

<210> SEQ ID NO 144
<211> LENGTH: 6
<212> TYPE: PRT
<213> ORGANISM: Artificial Sequence
<220> FEATURE:
<223> OTHER INFORMATION: Recombinant peptide

<400> SEQUENCE: 144

Glu Arg Pro Trp Leu Leu
1               5

<210> SEQ ID NO 145
<211> LENGTH: 6
<212> TYPE: PRT
<213> ORGANISM: Artificial Sequence
<220> FEATURE:
<223> OTHER INFORMATION: Recombinant peptide

<400> SEQUENCE: 145

Glu Arg Pro Trp Leu Ile
1               5

<210> SEQ ID NO 146
<211> LENGTH: 6
```

```
<212> TYPE: PRT
<213> ORGANISM: Artificial Sequence
<220> FEATURE:
<223> OTHER INFORMATION: Recombinant peptide

<400> SEQUENCE: 146

Glu Arg Pro Trp Leu Val
1               5

<210> SEQ ID NO 147
<211> LENGTH: 6
<212> TYPE: PRT
<213> ORGANISM: Artificial Sequence
<220> FEATURE:
<223> OTHER INFORMATION: Recombinant peptide

<400> SEQUENCE: 147

Glu Arg Pro Trp Val Leu
1               5

<210> SEQ ID NO 148
<211> LENGTH: 6
<212> TYPE: PRT
<213> ORGANISM: Artificial Sequence
<220> FEATURE:
<223> OTHER INFORMATION: Recombinant peptide

<400> SEQUENCE: 148

Glu Arg Pro Trp Val Ile
1               5

<210> SEQ ID NO 149
<211> LENGTH: 6
<212> TYPE: PRT
<213> ORGANISM: Artificial Sequence
<220> FEATURE:
<223> OTHER INFORMATION: Recombinant peptide

<400> SEQUENCE: 149

Glu Arg Pro Trp Val Val
1               5

<210> SEQ ID NO 150
<211> LENGTH: 6
<212> TYPE: PRT
<213> ORGANISM: Artificial Sequence
<220> FEATURE:
<223> OTHER INFORMATION: Recombinant peptide

<400> SEQUENCE: 150

Arg Lys Pro Tyr Ile Leu
1               5

<210> SEQ ID NO 151
<211> LENGTH: 6
<212> TYPE: PRT
<213> ORGANISM: Artificial Sequence
<220> FEATURE:
<223> OTHER INFORMATION: Recombinant peptide

<400> SEQUENCE: 151

Arg Lys Pro Tyr Ile Ile
1               5

<210> SEQ ID NO 152
<211> LENGTH: 6
<212> TYPE: PRT
```

```
<213> ORGANISM: Artificial Sequence
<220> FEATURE:
<223> OTHER INFORMATION: Recombinant peptide

<400> SEQUENCE: 152

Arg Lys Pro Tyr Ile Val
1               5

<210> SEQ ID NO 153
<211> LENGTH: 6
<212> TYPE: PRT
<213> ORGANISM: Artificial Sequence
<220> FEATURE:
<223> OTHER INFORMATION: Recombinant peptide

<400> SEQUENCE: 153

Arg Lys Pro Tyr Leu Leu
1               5

<210> SEQ ID NO 154
<211> LENGTH: 6
<212> TYPE: PRT
<213> ORGANISM: Artificial Sequence
<220> FEATURE:
<223> OTHER INFORMATION: Recombinant peptide

<400> SEQUENCE: 154

Arg Lys Pro Tyr Leu Ile
1               5

<210> SEQ ID NO 155
<211> LENGTH: 6
<212> TYPE: PRT
<213> ORGANISM: Artificial Sequence
<220> FEATURE:
<223> OTHER INFORMATION: Recombinant peptide

<400> SEQUENCE: 155

Arg Lys Pro Tyr Leu Val
1               5

<210> SEQ ID NO 156
<211> LENGTH: 6
<212> TYPE: PRT
<213> ORGANISM: Artificial Sequence
<220> FEATURE:
<223> OTHER INFORMATION: Recombinant peptide

<400> SEQUENCE: 156

Arg Lys Pro Tyr Val Leu
1               5

<210> SEQ ID NO 157
<211> LENGTH: 6
<212> TYPE: PRT
<213> ORGANISM: Artificial Sequence
<220> FEATURE:
<223> OTHER INFORMATION: Recombinant peptide

<400> SEQUENCE: 157

Arg Lys Pro Tyr Val Ile
1               5

<210> SEQ ID NO 158
<211> LENGTH: 6
<212> TYPE: PRT
<213> ORGANISM: Artificial Sequence
```

```
<220> FEATURE:
<223> OTHER INFORMATION: Recombinant peptide

<400> SEQUENCE: 158

Arg Lys Pro Tyr Val Val
1               5

<210> SEQ ID NO 159
<211> LENGTH: 6
<212> TYPE: PRT
<213> ORGANISM: Artificial Sequence
<220> FEATURE:
<223> OTHER INFORMATION: Recombinant peptide

<400> SEQUENCE: 159

Arg Lys Pro Trp Ile Leu
1               5

<210> SEQ ID NO 160
<211> LENGTH: 6
<212> TYPE: PRT
<213> ORGANISM: Artificial Sequence
<220> FEATURE:
<223> OTHER INFORMATION: Recombinant peptide

<400> SEQUENCE: 160

Arg Lys Pro Trp Ile Ile
1               5

<210> SEQ ID NO 161
<211> LENGTH: 6
<212> TYPE: PRT
<213> ORGANISM: Artificial Sequence
<220> FEATURE:
<223> OTHER INFORMATION: Recombinant peptide

<400> SEQUENCE: 161

Arg Lys Pro Trp Ile Val
1               5

<210> SEQ ID NO 162
<211> LENGTH: 6
<212> TYPE: PRT
<213> ORGANISM: Artificial Sequence
<220> FEATURE:
<223> OTHER INFORMATION: Recombinant peptide

<400> SEQUENCE: 162

Arg Lys Pro Trp Leu Leu
1               5

<210> SEQ ID NO 163
<211> LENGTH: 6
<212> TYPE: PRT
<213> ORGANISM: Artificial Sequence
<220> FEATURE:
<223> OTHER INFORMATION: Recombinant peptide

<400> SEQUENCE: 163

Arg Lys Pro Trp Leu Ile
1               5

<210> SEQ ID NO 164
<211> LENGTH: 6
<212> TYPE: PRT
<213> ORGANISM: Artificial Sequence
<220> FEATURE:
```

```
<223> OTHER INFORMATION: Recombinant peptide

<400> SEQUENCE: 164

Arg Lys Pro Trp Leu Val
1               5

<210> SEQ ID NO 165
<211> LENGTH: 6
<212> TYPE: PRT
<213> ORGANISM: Artificial Sequence
<220> FEATURE:
<223> OTHER INFORMATION: Recombinant peptide

<400> SEQUENCE: 165

Arg Lys Pro Trp Val Leu
1               5

<210> SEQ ID NO 166
<211> LENGTH: 6
<212> TYPE: PRT
<213> ORGANISM: Artificial Sequence
<220> FEATURE:
<223> OTHER INFORMATION: Recombinant peptide

<400> SEQUENCE: 166

Arg Lys Pro Trp Val Ile
1               5

<210> SEQ ID NO 167
<211> LENGTH: 6
<212> TYPE: PRT
<213> ORGANISM: Artificial Sequence
<220> FEATURE:
<223> OTHER INFORMATION: Recombinant peptide

<400> SEQUENCE: 167

Arg Lys Pro Trp Val Val
1               5

<210> SEQ ID NO 168
<211> LENGTH: 6
<212> TYPE: PRT
<213> ORGANISM: Artificial Sequence
<220> FEATURE:
<223> OTHER INFORMATION: Recombinant peptide

<400> SEQUENCE: 168

Arg Arg Pro Tyr Ile Ile
1               5

<210> SEQ ID NO 169
<211> LENGTH: 6
<212> TYPE: PRT
<213> ORGANISM: Artificial Sequence
<220> FEATURE:
<223> OTHER INFORMATION: Recombinant peptide

<400> SEQUENCE: 169

Arg Arg Pro Tyr Ile Val
1               5

<210> SEQ ID NO 170
<211> LENGTH: 6
<212> TYPE: PRT
<213> ORGANISM: Artificial Sequence
<220> FEATURE:
<223> OTHER INFORMATION: Recombinant peptide
```

<400> SEQUENCE: 170

Arg Arg Pro Tyr Leu Leu
1               5

<210> SEQ ID NO 171
<211> LENGTH: 6
<212> TYPE: PRT
<213> ORGANISM: Artificial Sequence
<220> FEATURE:
<223> OTHER INFORMATION: Recombinant peptide

<400> SEQUENCE: 171

Arg Arg Pro Tyr Leu Ile
1               5

<210> SEQ ID NO 172
<211> LENGTH: 6
<212> TYPE: PRT
<213> ORGANISM: Artificial Sequence
<220> FEATURE:
<223> OTHER INFORMATION: Recombinant peptide

<400> SEQUENCE: 172

Arg Arg Pro Tyr Leu Val
1               5

<210> SEQ ID NO 173
<211> LENGTH: 6
<212> TYPE: PRT
<213> ORGANISM: Artificial Sequence
<220> FEATURE:
<223> OTHER INFORMATION: Recombinant peptide

<400> SEQUENCE: 173

Arg Arg Pro Tyr Val Leu
1               5

<210> SEQ ID NO 174
<211> LENGTH: 6
<212> TYPE: PRT
<213> ORGANISM: Artificial Sequence
<220> FEATURE:
<223> OTHER INFORMATION: Recombinant peptide

<400> SEQUENCE: 174

Arg Arg Pro Tyr Val Ile
1               5

<210> SEQ ID NO 175
<211> LENGTH: 6
<212> TYPE: PRT
<213> ORGANISM: Artificial Sequence
<220> FEATURE:
<223> OTHER INFORMATION: Recombinant peptide

<400> SEQUENCE: 175

Arg Arg Pro Tyr Val Val
1               5

<210> SEQ ID NO 176
<211> LENGTH: 6
<212> TYPE: PRT
<213> ORGANISM: Artificial Sequence
<220> FEATURE:
<223> OTHER INFORMATION: Recombinant peptide

```
<400> SEQUENCE: 176

Arg Arg Pro Trp Ile Ile
1               5

<210> SEQ ID NO 177
<211> LENGTH: 6
<212> TYPE: PRT
<213> ORGANISM: Artificial Sequence
<220> FEATURE:
<223> OTHER INFORMATION: Recombinant peptide

<400> SEQUENCE: 177

Arg Arg Pro Trp Ile Val
1               5

<210> SEQ ID NO 178
<211> LENGTH: 6
<212> TYPE: PRT
<213> ORGANISM: Artificial Sequence
<220> FEATURE:
<223> OTHER INFORMATION: Recombinant peptide

<400> SEQUENCE: 178

Arg Arg Pro Trp Leu Leu
1               5

<210> SEQ ID NO 179
<211> LENGTH: 6
<212> TYPE: PRT
<213> ORGANISM: Artificial Sequence
<220> FEATURE:
<223> OTHER INFORMATION: Recombinant peptide

<400> SEQUENCE: 179

Arg Arg Pro Trp Leu Ile
1               5

<210> SEQ ID NO 180
<211> LENGTH: 6
<212> TYPE: PRT
<213> ORGANISM: Artificial Sequence
<220> FEATURE:
<223> OTHER INFORMATION: Recombinant peptide

<400> SEQUENCE: 180

Arg Arg Pro Trp Leu Val
1               5

<210> SEQ ID NO 181
<211> LENGTH: 6
<212> TYPE: PRT
<213> ORGANISM: Artificial Sequence
<220> FEATURE:
<223> OTHER INFORMATION: Recombinant peptide

<400> SEQUENCE: 181

Arg Arg Pro Trp Val Leu
1               5

<210> SEQ ID NO 182
<211> LENGTH: 6
<212> TYPE: PRT
<213> ORGANISM: Artificial Sequence
<220> FEATURE:
<223> OTHER INFORMATION: Recombinant peptide

<400> SEQUENCE: 182
```

Arg Arg Pro Trp Val Ile
1               5

<210> SEQ ID NO 183
<211> LENGTH: 6
<212> TYPE: PRT
<213> ORGANISM: Artificial Sequence
<220> FEATURE:
<223> OTHER INFORMATION: Recombinant peptide

<400> SEQUENCE: 183

Arg Arg Pro Trp Val Val
1               5

<210> SEQ ID NO 184
<211> LENGTH: 6
<212> TYPE: PRT
<213> ORGANISM: Artificial Sequence
<220> FEATURE:
<223> OTHER INFORMATION: Recombinant peptide

<400> SEQUENCE: 184

Gly Lys Pro Tyr Ile Leu
1               5

<210> SEQ ID NO 185
<211> LENGTH: 6
<212> TYPE: PRT
<213> ORGANISM: Artificial Sequence
<220> FEATURE:
<223> OTHER INFORMATION: Recombinant peptide

<400> SEQUENCE: 185

Gly Lys Pro Tyr Ile Ile
1               5

<210> SEQ ID NO 186
<211> LENGTH: 6
<212> TYPE: PRT
<213> ORGANISM: Artificial Sequence
<220> FEATURE:
<223> OTHER INFORMATION: Recombinant peptide

<400> SEQUENCE: 186

Gly Lys Pro Tyr Ile Val
1               5

<210> SEQ ID NO 187
<211> LENGTH: 6
<212> TYPE: PRT
<213> ORGANISM: Artificial Sequence
<220> FEATURE:
<223> OTHER INFORMATION: Recombinant peptide

<400> SEQUENCE: 187

Gly Lys Pro Tyr Leu Leu
1               5

<210> SEQ ID NO 188
<211> LENGTH: 6
<212> TYPE: PRT
<213> ORGANISM: Artificial Sequence
<220> FEATURE:
<223> OTHER INFORMATION: Recombinant peptide

<400> SEQUENCE: 188

```
Gly Lys Pro Tyr Leu Ile
1               5

<210> SEQ ID NO 189
<211> LENGTH: 6
<212> TYPE: PRT
<213> ORGANISM: Artificial Sequence
<220> FEATURE:
<223> OTHER INFORMATION: Recombinant peptide

<400> SEQUENCE: 189

Gly Lys Pro Tyr Leu Val
1               5

<210> SEQ ID NO 190
<211> LENGTH: 6
<212> TYPE: PRT
<213> ORGANISM: Artificial Sequence
<220> FEATURE:
<223> OTHER INFORMATION: Recombinant peptide

<400> SEQUENCE: 190

Gly Lys Pro Tyr Val Leu
1               5

<210> SEQ ID NO 191
<211> LENGTH: 6
<212> TYPE: PRT
<213> ORGANISM: Artificial Sequence
<220> FEATURE:
<223> OTHER INFORMATION: Recombinant peptide

<400> SEQUENCE: 191

Gly Lys Pro Tyr Val Ile
1               5

<210> SEQ ID NO 192
<211> LENGTH: 6
<212> TYPE: PRT
<213> ORGANISM: Artificial Sequence
<220> FEATURE:
<223> OTHER INFORMATION: Recombinant peptide

<400> SEQUENCE: 192

Gly Lys Pro Tyr Val Val
1               5

<210> SEQ ID NO 193
<211> LENGTH: 6
<212> TYPE: PRT
<213> ORGANISM: Artificial Sequence
<220> FEATURE:
<223> OTHER INFORMATION: Recombinant peptide

<400> SEQUENCE: 193

Gly Lys Pro Trp Ile Leu
1               5

<210> SEQ ID NO 194
<211> LENGTH: 6
<212> TYPE: PRT
<213> ORGANISM: Artificial Sequence
<220> FEATURE:
<223> OTHER INFORMATION: Recombinant peptide

<400> SEQUENCE: 194

Gly Lys Pro Trp Ile Ile
```

```
1               5

<210> SEQ ID NO 195
<211> LENGTH: 6
<212> TYPE: PRT
<213> ORGANISM: Artificial Sequence
<220> FEATURE:
<223> OTHER INFORMATION: Recombinant peptide

<400> SEQUENCE: 195

Gly Lys Pro Trp Ile Val
1               5

<210> SEQ ID NO 196
<211> LENGTH: 6
<212> TYPE: PRT
<213> ORGANISM: Artificial Sequence
<220> FEATURE:
<223> OTHER INFORMATION: Recombinant peptide

<400> SEQUENCE: 196

Gly Lys Pro Trp Leu Leu
1               5

<210> SEQ ID NO 197
<211> LENGTH: 6
<212> TYPE: PRT
<213> ORGANISM: Artificial Sequence
<220> FEATURE:
<223> OTHER INFORMATION: Recombinant peptide

<400> SEQUENCE: 197

Gly Lys Pro Trp Leu Ile
1               5

<210> SEQ ID NO 198
<211> LENGTH: 6
<212> TYPE: PRT
<213> ORGANISM: Artificial Sequence
<220> FEATURE:
<223> OTHER INFORMATION: Recombinant peptide

<400> SEQUENCE: 198

Gly Lys Pro Trp Leu Val
1               5

<210> SEQ ID NO 199
<211> LENGTH: 6
<212> TYPE: PRT
<213> ORGANISM: Artificial Sequence
<220> FEATURE:
<223> OTHER INFORMATION: Recombinant peptide

<400> SEQUENCE: 199

Gly Lys Pro Trp Val Leu
1               5

<210> SEQ ID NO 200
<211> LENGTH: 6
<212> TYPE: PRT
<213> ORGANISM: Artificial Sequence
<220> FEATURE:
<223> OTHER INFORMATION: Recombinant peptide

<400> SEQUENCE: 200

Gly Lys Pro Trp Val Ile
1               5
```

<210> SEQ ID NO 201
<211> LENGTH: 6
<212> TYPE: PRT
<213> ORGANISM: Artificial Sequence
<220> FEATURE:
<223> OTHER INFORMATION: Recombinant peptide

<400> SEQUENCE: 201

Gly Lys Pro Trp Val Val
1               5

<210> SEQ ID NO 202
<211> LENGTH: 6
<212> TYPE: PRT
<213> ORGANISM: Artificial Sequence
<220> FEATURE:
<223> OTHER INFORMATION: Recombinant peptide

<400> SEQUENCE: 202

Gly Arg Pro Tyr Ile Leu
1               5

<210> SEQ ID NO 203
<211> LENGTH: 6
<212> TYPE: PRT
<213> ORGANISM: Artificial Sequence
<220> FEATURE:
<223> OTHER INFORMATION: Recombinant peptide

<400> SEQUENCE: 203

Gly Arg Pro Tyr Ile Ile
1               5

<210> SEQ ID NO 204
<211> LENGTH: 6
<212> TYPE: PRT
<213> ORGANISM: Artificial Sequence
<220> FEATURE:
<223> OTHER INFORMATION: Recombinant peptide

<400> SEQUENCE: 204

Gly Arg Pro Tyr Ile Val
1               5

<210> SEQ ID NO 205
<211> LENGTH: 6
<212> TYPE: PRT
<213> ORGANISM: Artificial Sequence
<220> FEATURE:
<223> OTHER INFORMATION: Recombinant peptide

<400> SEQUENCE: 205

Gly Arg Pro Tyr Leu Leu
1               5

<210> SEQ ID NO 206
<211> LENGTH: 6
<212> TYPE: PRT
<213> ORGANISM: Artificial Sequence
<220> FEATURE:
<223> OTHER INFORMATION: Recombinant peptide

<400> SEQUENCE: 206

Gly Arg Pro Tyr Leu Ile
1               5

```
<210> SEQ ID NO 207
<211> LENGTH: 6
<212> TYPE: PRT
<213> ORGANISM: Artificial Sequence
<220> FEATURE:
<223> OTHER INFORMATION: Recombinant peptide

<400> SEQUENCE: 207

Gly Arg Pro Tyr Leu Val
1               5

<210> SEQ ID NO 208
<211> LENGTH: 6
<212> TYPE: PRT
<213> ORGANISM: Artificial Sequence
<220> FEATURE:
<223> OTHER INFORMATION: Recombinant peptide

<400> SEQUENCE: 208

Gly Arg Pro Tyr Val Leu
1               5

<210> SEQ ID NO 209
<211> LENGTH: 6
<212> TYPE: PRT
<213> ORGANISM: Artificial Sequence
<220> FEATURE:
<223> OTHER INFORMATION: Recombinant peptide

<400> SEQUENCE: 209

Gly Arg Pro Tyr Val Ile
1               5

<210> SEQ ID NO 210
<211> LENGTH: 6
<212> TYPE: PRT
<213> ORGANISM: Artificial Sequence
<220> FEATURE:
<223> OTHER INFORMATION: Recombinant peptide

<400> SEQUENCE: 210

Gly Arg Pro Tyr Val Val
1               5

<210> SEQ ID NO 211
<211> LENGTH: 6
<212> TYPE: PRT
<213> ORGANISM: Artificial Sequence
<220> FEATURE:
<223> OTHER INFORMATION: Recombinant peptide

<400> SEQUENCE: 211

Gly Arg Pro Trp Ile Leu
1               5

<210> SEQ ID NO 212
<211> LENGTH: 6
<212> TYPE: PRT
<213> ORGANISM: Artificial Sequence
<220> FEATURE:
<223> OTHER INFORMATION: Recombinant peptide

<400> SEQUENCE: 212

Gly Arg Pro Trp Ile Ile
1               5
```

```
<210> SEQ ID NO 213
<211> LENGTH: 6
<212> TYPE: PRT
<213> ORGANISM: Artificial Sequence
<220> FEATURE:
<223> OTHER INFORMATION: Recombinant peptide

<400> SEQUENCE: 213

Gly Arg Pro Trp Ile Val
1               5

<210> SEQ ID NO 214
<211> LENGTH: 6
<212> TYPE: PRT
<213> ORGANISM: Artificial Sequence
<220> FEATURE:
<223> OTHER INFORMATION: Recombinant peptide

<400> SEQUENCE: 214

Gly Arg Pro Trp Leu Leu
1               5

<210> SEQ ID NO 215
<211> LENGTH: 6
<212> TYPE: PRT
<213> ORGANISM: Artificial Sequence
<220> FEATURE:
<223> OTHER INFORMATION: Recombinant peptide

<400> SEQUENCE: 215

Gly Arg Pro Trp Leu Ile
1               5

<210> SEQ ID NO 216
<211> LENGTH: 6
<212> TYPE: PRT
<213> ORGANISM: Artificial Sequence
<220> FEATURE:
<223> OTHER INFORMATION: Recombinant peptide

<400> SEQUENCE: 216

Gly Arg Pro Trp Leu Val
1               5

<210> SEQ ID NO 217
<211> LENGTH: 6
<212> TYPE: PRT
<213> ORGANISM: Artificial Sequence
<220> FEATURE:
<223> OTHER INFORMATION: Recombinant peptide

<400> SEQUENCE: 217

Gly Arg Pro Trp Val Leu
1               5

<210> SEQ ID NO 218
<211> LENGTH: 6
<212> TYPE: PRT
<213> ORGANISM: Artificial Sequence
<220> FEATURE:
<223> OTHER INFORMATION: Recombinant peptide

<400> SEQUENCE: 218

Gly Arg Pro Trp Val Ile
1               5

<210> SEQ ID NO 219
```

```
<211> LENGTH: 6
<212> TYPE: PRT
<213> ORGANISM: Artificial Sequence
<220> FEATURE:
<223> OTHER INFORMATION: Recombinant peptide

<400> SEQUENCE: 219

Gly Arg Pro Trp Val Val
1               5

<210> SEQ ID NO 220
<211> LENGTH: 7
<212> TYPE: PRT
<213> ORGANISM: Artificial Sequence
<220> FEATURE:
<223> OTHER INFORMATION: Recombinant peptide

<400> SEQUENCE: 220

Ser Asp Lys Pro Tyr Ile Leu
1               5

<210> SEQ ID NO 221
<211> LENGTH: 7
<212> TYPE: PRT
<213> ORGANISM: Artificial Sequence
<220> FEATURE:
<223> OTHER INFORMATION: Recombinant peptide

<400> SEQUENCE: 221

Ser Asp Lys Pro Tyr Ile Ile
1               5

<210> SEQ ID NO 222
<211> LENGTH: 7
<212> TYPE: PRT
<213> ORGANISM: Artificial Sequence
<220> FEATURE:
<223> OTHER INFORMATION: Recombinant peptide

<400> SEQUENCE: 222

Ser Asp Lys Pro Tyr Ile Val
1               5

<210> SEQ ID NO 223
<211> LENGTH: 7
<212> TYPE: PRT
<213> ORGANISM: Artificial Sequence
<220> FEATURE:
<223> OTHER INFORMATION: Recombinant peptide

<400> SEQUENCE: 223

Ser Asp Lys Pro Tyr Leu Leu
1               5

<210> SEQ ID NO 224
<211> LENGTH: 7
<212> TYPE: PRT
<213> ORGANISM: Artificial Sequence
<220> FEATURE:
<223> OTHER INFORMATION: Recombinant peptide

<400> SEQUENCE: 224

Ser Asp Lys Pro Tyr Leu Ile
1               5

<210> SEQ ID NO 225
<211> LENGTH: 7
```

```
<212> TYPE: PRT
<213> ORGANISM: Artificial Sequence
<220> FEATURE:
<223> OTHER INFORMATION: Recombinant peptide

<400> SEQUENCE: 225

Ser Asp Lys Pro Tyr Leu Val
1               5

<210> SEQ ID NO 226
<211> LENGTH: 7
<212> TYPE: PRT
<213> ORGANISM: Artificial Sequence
<220> FEATURE:
<223> OTHER INFORMATION: Recombinant peptide

<400> SEQUENCE: 226

Ser Asp Lys Pro Tyr Val Leu
1               5

<210> SEQ ID NO 227
<211> LENGTH: 7
<212> TYPE: PRT
<213> ORGANISM: Artificial Sequence
<220> FEATURE:
<223> OTHER INFORMATION: Recombinant peptide

<400> SEQUENCE: 227

Ser Asp Lys Pro Tyr Val Ile
1               5

<210> SEQ ID NO 228
<211> LENGTH: 7
<212> TYPE: PRT
<213> ORGANISM: Artificial Sequence
<220> FEATURE:
<223> OTHER INFORMATION: Recombinant peptide

<400> SEQUENCE: 228

Ser Asp Lys Pro Tyr Val Val
1               5

<210> SEQ ID NO 229
<211> LENGTH: 7
<212> TYPE: PRT
<213> ORGANISM: Artificial Sequence
<220> FEATURE:
<223> OTHER INFORMATION: Recombinant peptide

<400> SEQUENCE: 229

Ser Asp Lys Pro Trp Ile Leu
1               5

<210> SEQ ID NO 230
<211> LENGTH: 7
<212> TYPE: PRT
<213> ORGANISM: Artificial Sequence
<220> FEATURE:
<223> OTHER INFORMATION: Recombinant peptide

<400> SEQUENCE: 230

Ser Asp Lys Pro Trp Ile Ile
1               5

<210> SEQ ID NO 231
<211> LENGTH: 7
<212> TYPE: PRT
```

```
<213> ORGANISM: Artificial Sequence
<220> FEATURE:
<223> OTHER INFORMATION: Recombinant peptide

<400> SEQUENCE: 231

Ser Asp Lys Pro Trp Ile Val
1               5

<210> SEQ ID NO 232
<211> LENGTH: 7
<212> TYPE: PRT
<213> ORGANISM: Artificial Sequence
<220> FEATURE:
<223> OTHER INFORMATION: Recombinant peptide

<400> SEQUENCE: 232

Ser Asp Lys Pro Trp Leu Leu
1               5

<210> SEQ ID NO 233
<211> LENGTH: 7
<212> TYPE: PRT
<213> ORGANISM: Artificial Sequence
<220> FEATURE:
<223> OTHER INFORMATION: Recombinant peptide

<400> SEQUENCE: 233

Ser Asp Lys Pro Trp Leu Ile
1               5

<210> SEQ ID NO 234
<211> LENGTH: 7
<212> TYPE: PRT
<213> ORGANISM: Artificial Sequence
<220> FEATURE:
<223> OTHER INFORMATION: Recombinant peptide

<400> SEQUENCE: 234

Ser Asp Lys Pro Trp Leu Val
1               5

<210> SEQ ID NO 235
<211> LENGTH: 7
<212> TYPE: PRT
<213> ORGANISM: Artificial Sequence
<220> FEATURE:
<223> OTHER INFORMATION: Recombinant peptide

<400> SEQUENCE: 235

Ser Asp Lys Pro Trp Val Leu
1               5

<210> SEQ ID NO 236
<211> LENGTH: 7
<212> TYPE: PRT
<213> ORGANISM: Artificial Sequence
<220> FEATURE:
<223> OTHER INFORMATION: Recombinant peptide

<400> SEQUENCE: 236

Ser Asp Lys Pro Trp Val Ile
1               5

<210> SEQ ID NO 237
<211> LENGTH: 7
<212> TYPE: PRT
<213> ORGANISM: Artificial Sequence
```

```
<220> FEATURE:
<223> OTHER INFORMATION: Recombinant peptide

<400> SEQUENCE: 237

Ser Asp Lys Pro Trp Val Val
1               5

<210> SEQ ID NO 238
<211> LENGTH: 7
<212> TYPE: PRT
<213> ORGANISM: Artificial Sequence
<220> FEATURE:
<223> OTHER INFORMATION: Recombinant peptide

<400> SEQUENCE: 238

Ser Asp Arg Pro Tyr Ile Leu
1               5

<210> SEQ ID NO 239
<211> LENGTH: 7
<212> TYPE: PRT
<213> ORGANISM: Artificial Sequence
<220> FEATURE:
<223> OTHER INFORMATION: Recombinant peptide

<400> SEQUENCE: 239

Ser Asp Arg Pro Tyr Ile Ile
1               5

<210> SEQ ID NO 240
<211> LENGTH: 7
<212> TYPE: PRT
<213> ORGANISM: Artificial Sequence
<220> FEATURE:
<223> OTHER INFORMATION: Recombinant peptide

<400> SEQUENCE: 240

Ser Asp Arg Pro Tyr Ile Val
1               5

<210> SEQ ID NO 241
<211> LENGTH: 7
<212> TYPE: PRT
<213> ORGANISM: Artificial Sequence
<220> FEATURE:
<223> OTHER INFORMATION: Recombinant peptide

<400> SEQUENCE: 241

Ser Asp Arg Pro Tyr Leu Leu
1               5

<210> SEQ ID NO 242
<211> LENGTH: 7
<212> TYPE: PRT
<213> ORGANISM: Artificial Sequence
<220> FEATURE:
<223> OTHER INFORMATION: Recombinant peptide

<400> SEQUENCE: 242

Ser Asp Arg Pro Tyr Leu Ile
1               5

<210> SEQ ID NO 243
<211> LENGTH: 7
<212> TYPE: PRT
<213> ORGANISM: Artificial Sequence
<220> FEATURE:
```

<223> OTHER INFORMATION: Recombinant peptide

<400> SEQUENCE: 243

Ser Asp Arg Pro Tyr Leu Val
1               5

<210> SEQ ID NO 244
<211> LENGTH: 7
<212> TYPE: PRT
<213> ORGANISM: Artificial Sequence
<220> FEATURE:
<223> OTHER INFORMATION: Recombinant peptide

<400> SEQUENCE: 244

Ser Asp Arg Pro Tyr Val Leu
1               5

<210> SEQ ID NO 245
<211> LENGTH: 7
<212> TYPE: PRT
<213> ORGANISM: Artificial Sequence
<220> FEATURE:
<223> OTHER INFORMATION: Recombinant peptide

<400> SEQUENCE: 245

Ser Asp Arg Pro Tyr Val Ile
1               5

<210> SEQ ID NO 246
<211> LENGTH: 7
<212> TYPE: PRT
<213> ORGANISM: Artificial Sequence
<220> FEATURE:
<223> OTHER INFORMATION: Recombinant peptide

<400> SEQUENCE: 246

Ser Asp Arg Pro Tyr Val Val
1               5

<210> SEQ ID NO 247
<211> LENGTH: 7
<212> TYPE: PRT
<213> ORGANISM: Artificial Sequence
<220> FEATURE:
<223> OTHER INFORMATION: Recombinant peptide

<400> SEQUENCE: 247

Ser Asp Arg Pro Trp Ile Leu
1               5

<210> SEQ ID NO 248
<211> LENGTH: 7
<212> TYPE: PRT
<213> ORGANISM: Artificial Sequence
<220> FEATURE:
<223> OTHER INFORMATION: Recombinant peptide

<400> SEQUENCE: 248

Ser Asp Arg Pro Trp Ile Ile
1               5

<210> SEQ ID NO 249
<211> LENGTH: 7
<212> TYPE: PRT
<213> ORGANISM: Artificial Sequence
<220> FEATURE:
<223> OTHER INFORMATION: Recombinant peptide

```
<400> SEQUENCE: 249

Ser Asp Arg Pro Trp Ile Val
1               5

<210> SEQ ID NO 250
<211> LENGTH: 7
<212> TYPE: PRT
<213> ORGANISM: Artificial Sequence
<220> FEATURE:
<223> OTHER INFORMATION: Recombinant peptide

<400> SEQUENCE: 250

Ser Asp Arg Pro Trp Leu Leu
1               5

<210> SEQ ID NO 251
<211> LENGTH: 7
<212> TYPE: PRT
<213> ORGANISM: Artificial Sequence
<220> FEATURE:
<223> OTHER INFORMATION: Recombinant peptide

<400> SEQUENCE: 251

Ser Asp Arg Pro Trp Leu Ile
1               5

<210> SEQ ID NO 252
<211> LENGTH: 7
<212> TYPE: PRT
<213> ORGANISM: Artificial Sequence
<220> FEATURE:
<223> OTHER INFORMATION: Recombinant peptide

<400> SEQUENCE: 252

Ser Asp Arg Pro Trp Leu Val
1               5

<210> SEQ ID NO 253
<211> LENGTH: 7
<212> TYPE: PRT
<213> ORGANISM: Artificial Sequence
<220> FEATURE:
<223> OTHER INFORMATION: Recombinant peptide

<400> SEQUENCE: 253

Ser Asp Arg Pro Trp Val Leu
1               5

<210> SEQ ID NO 254
<211> LENGTH: 7
<212> TYPE: PRT
<213> ORGANISM: Artificial Sequence
<220> FEATURE:
<223> OTHER INFORMATION: Recombinant peptide

<400> SEQUENCE: 254

Ser Asp Arg Pro Trp Val Ile
1               5

<210> SEQ ID NO 255
<211> LENGTH: 7
<212> TYPE: PRT
<213> ORGANISM: Artificial Sequence
<220> FEATURE:
<223> OTHER INFORMATION: Recombinant peptide
```

```
<400> SEQUENCE: 255

Ser Asp Arg Pro Trp Val Val
1               5

<210> SEQ ID NO 256
<211> LENGTH: 7
<212> TYPE: PRT
<213> ORGANISM: Artificial Sequence
<220> FEATURE:
<223> OTHER INFORMATION: Recombinant peptide

<400> SEQUENCE: 256

Ser Glu Lys Pro Tyr Ile Leu
1               5

<210> SEQ ID NO 257
<211> LENGTH: 7
<212> TYPE: PRT
<213> ORGANISM: Artificial Sequence
<220> FEATURE:
<223> OTHER INFORMATION: Recombinant peptide

<400> SEQUENCE: 257

Ser Glu Lys Pro Tyr Ile Ile
1               5

<210> SEQ ID NO 258
<211> LENGTH: 7
<212> TYPE: PRT
<213> ORGANISM: Artificial Sequence
<220> FEATURE:
<223> OTHER INFORMATION: Recombinant peptide

<400> SEQUENCE: 258

Ser Glu Lys Pro Tyr Ile Val
1               5

<210> SEQ ID NO 259
<211> LENGTH: 7
<212> TYPE: PRT
<213> ORGANISM: Artificial Sequence
<220> FEATURE:
<223> OTHER INFORMATION: Recombinant peptide

<400> SEQUENCE: 259

Ser Glu Lys Pro Tyr Leu Leu
1               5

<210> SEQ ID NO 260
<211> LENGTH: 7
<212> TYPE: PRT
<213> ORGANISM: Artificial Sequence
<220> FEATURE:
<223> OTHER INFORMATION: Recombinant peptide

<400> SEQUENCE: 260

Ser Glu Lys Pro Tyr Leu Ile
1               5

<210> SEQ ID NO 261
<211> LENGTH: 7
<212> TYPE: PRT
<213> ORGANISM: Artificial Sequence
<220> FEATURE:
<223> OTHER INFORMATION: Recombinant peptide

<400> SEQUENCE: 261
```

```
Ser Glu Lys Pro Tyr Leu Val
1               5

<210> SEQ ID NO 262
<211> LENGTH: 7
<212> TYPE: PRT
<213> ORGANISM: Artificial Sequence
<220> FEATURE:
<223> OTHER INFORMATION: Recombinant peptide

<400> SEQUENCE: 262

Ser Glu Lys Pro Tyr Val Leu
1               5

<210> SEQ ID NO 263
<211> LENGTH: 7
<212> TYPE: PRT
<213> ORGANISM: Artificial Sequence
<220> FEATURE:
<223> OTHER INFORMATION: Recombinant peptide

<400> SEQUENCE: 263

Ser Glu Lys Pro Tyr Val Ile
1               5

<210> SEQ ID NO 264
<211> LENGTH: 7
<212> TYPE: PRT
<213> ORGANISM: Artificial Sequence
<220> FEATURE:
<223> OTHER INFORMATION: Recombinant peptide

<400> SEQUENCE: 264

Ser Glu Lys Pro Tyr Val Val
1               5

<210> SEQ ID NO 265
<211> LENGTH: 7
<212> TYPE: PRT
<213> ORGANISM: Artificial Sequence
<220> FEATURE:
<223> OTHER INFORMATION: Recombinant peptide

<400> SEQUENCE: 265

Ser Glu Lys Pro Trp Ile Leu
1               5

<210> SEQ ID NO 266
<211> LENGTH: 7
<212> TYPE: PRT
<213> ORGANISM: Artificial Sequence
<220> FEATURE:
<223> OTHER INFORMATION: Recombinant peptide

<400> SEQUENCE: 266

Ser Glu Lys Pro Trp Ile Ile
1               5

<210> SEQ ID NO 267
<211> LENGTH: 7
<212> TYPE: PRT
<213> ORGANISM: Artificial Sequence
<220> FEATURE:
<223> OTHER INFORMATION: Recombinant peptide

<400> SEQUENCE: 267
```

```
Ser Glu Lys Pro Trp Ile Val
1               5

<210> SEQ ID NO 268
<211> LENGTH: 7
<212> TYPE: PRT
<213> ORGANISM: Artificial Sequence
<220> FEATURE:
<223> OTHER INFORMATION: Recombinant peptide

<400> SEQUENCE: 268

Ser Glu Lys Pro Trp Leu Leu
1               5

<210> SEQ ID NO 269
<211> LENGTH: 7
<212> TYPE: PRT
<213> ORGANISM: Artificial Sequence
<220> FEATURE:
<223> OTHER INFORMATION: Recombinant peptide

<400> SEQUENCE: 269

Ser Glu Lys Pro Trp Leu Ile
1               5

<210> SEQ ID NO 270
<211> LENGTH: 7
<212> TYPE: PRT
<213> ORGANISM: Artificial Sequence
<220> FEATURE:
<223> OTHER INFORMATION: Recombinant peptide

<400> SEQUENCE: 270

Ser Glu Lys Pro Trp Leu Val
1               5

<210> SEQ ID NO 271
<211> LENGTH: 7
<212> TYPE: PRT
<213> ORGANISM: Artificial Sequence
<220> FEATURE:
<223> OTHER INFORMATION: Recombinant peptide

<400> SEQUENCE: 271

Ser Glu Lys Pro Trp Val Leu
1               5

<210> SEQ ID NO 272
<211> LENGTH: 7
<212> TYPE: PRT
<213> ORGANISM: Artificial Sequence
<220> FEATURE:
<223> OTHER INFORMATION: Recombinant peptide

<400> SEQUENCE: 272

Ser Glu Lys Pro Trp Val Ile
1               5

<210> SEQ ID NO 273
<211> LENGTH: 7
<212> TYPE: PRT
<213> ORGANISM: Artificial Sequence
<220> FEATURE:
<223> OTHER INFORMATION: Recombinant peptide

<400> SEQUENCE: 273

Ser Glu Lys Pro Trp Val Val
```

-continued

```
1               5

<210> SEQ ID NO 274
<211> LENGTH: 7
<212> TYPE: PRT
<213> ORGANISM: Artificial Sequence
<220> FEATURE:
<223> OTHER INFORMATION: Recombinant peptide

<400> SEQUENCE: 274

Ser Glu Arg Pro Tyr Ile Leu
1               5

<210> SEQ ID NO 275
<211> LENGTH: 7
<212> TYPE: PRT
<213> ORGANISM: Artificial Sequence
<220> FEATURE:
<223> OTHER INFORMATION: Recombinant peptide

<400> SEQUENCE: 275

Ser Glu Arg Pro Tyr Ile Ile
1               5

<210> SEQ ID NO 276
<211> LENGTH: 7
<212> TYPE: PRT
<213> ORGANISM: Artificial Sequence
<220> FEATURE:
<223> OTHER INFORMATION: Recombinant peptide

<400> SEQUENCE: 276

Ser Glu Arg Pro Tyr Ile Val
1               5

<210> SEQ ID NO 277
<211> LENGTH: 7
<212> TYPE: PRT
<213> ORGANISM: Artificial Sequence
<220> FEATURE:
<223> OTHER INFORMATION: Recombinant peptide

<400> SEQUENCE: 277

Ser Glu Arg Pro Tyr Leu Leu
1               5

<210> SEQ ID NO 278
<211> LENGTH: 7
<212> TYPE: PRT
<213> ORGANISM: Artificial Sequence
<220> FEATURE:
<223> OTHER INFORMATION: Recombinant peptide

<400> SEQUENCE: 278

Ser Glu Arg Pro Tyr Leu Ile
1               5

<210> SEQ ID NO 279
<211> LENGTH: 7
<212> TYPE: PRT
<213> ORGANISM: Artificial Sequence
<220> FEATURE:
<223> OTHER INFORMATION: Recombinant peptide

<400> SEQUENCE: 279

Ser Glu Arg Pro Tyr Leu Val
1               5
```

-continued

```
<210> SEQ ID NO 280
<211> LENGTH: 7
<212> TYPE: PRT
<213> ORGANISM: Artificial Sequence
<220> FEATURE:
<223> OTHER INFORMATION: Recombinant peptide

<400> SEQUENCE: 280

Ser Glu Arg Pro Tyr Val Leu
1               5

<210> SEQ ID NO 281
<211> LENGTH: 7
<212> TYPE: PRT
<213> ORGANISM: Artificial Sequence
<220> FEATURE:
<223> OTHER INFORMATION: Recombinant peptide

<400> SEQUENCE: 281

Ser Glu Arg Pro Tyr Val Ile
1               5

<210> SEQ ID NO 282
<211> LENGTH: 7
<212> TYPE: PRT
<213> ORGANISM: Artificial Sequence
<220> FEATURE:
<223> OTHER INFORMATION: Recombinant peptide

<400> SEQUENCE: 282

Ser Glu Arg Pro Tyr Val Val
1               5

<210> SEQ ID NO 283
<211> LENGTH: 7
<212> TYPE: PRT
<213> ORGANISM: Artificial Sequence
<220> FEATURE:
<223> OTHER INFORMATION: Recombinant peptide

<400> SEQUENCE: 283

Ser Glu Arg Pro Trp Ile Leu
1               5

<210> SEQ ID NO 284
<211> LENGTH: 7
<212> TYPE: PRT
<213> ORGANISM: Artificial Sequence
<220> FEATURE:
<223> OTHER INFORMATION: Recombinant peptide

<400> SEQUENCE: 284

Ser Glu Arg Pro Trp Ile Ile
1               5

<210> SEQ ID NO 285
<211> LENGTH: 7
<212> TYPE: PRT
<213> ORGANISM: Artificial Sequence
<220> FEATURE:
<223> OTHER INFORMATION: Recombinant peptide

<400> SEQUENCE: 285

Ser Glu Arg Pro Trp Ile Val
1               5
```

<210> SEQ ID NO 286
<211> LENGTH: 7
<212> TYPE: PRT
<213> ORGANISM: Artificial Sequence
<220> FEATURE:
<223> OTHER INFORMATION: Recombinant peptide

<400> SEQUENCE: 286

Ser Glu Arg Pro Trp Leu Leu
1               5

<210> SEQ ID NO 287
<211> LENGTH: 7
<212> TYPE: PRT
<213> ORGANISM: Artificial Sequence
<220> FEATURE:
<223> OTHER INFORMATION: Recombinant peptide

<400> SEQUENCE: 287

Ser Glu Arg Pro Trp Leu Ile
1               5

<210> SEQ ID NO 288
<211> LENGTH: 7
<212> TYPE: PRT
<213> ORGANISM: Artificial Sequence
<220> FEATURE:
<223> OTHER INFORMATION: Recombinant peptide

<400> SEQUENCE: 288

Ser Glu Arg Pro Trp Leu Val
1               5

<210> SEQ ID NO 289
<211> LENGTH: 7
<212> TYPE: PRT
<213> ORGANISM: Artificial Sequence
<220> FEATURE:
<223> OTHER INFORMATION: Recombinant peptide

<400> SEQUENCE: 289

Ser Glu Arg Pro Trp Val Leu
1               5

<210> SEQ ID NO 290
<211> LENGTH: 7
<212> TYPE: PRT
<213> ORGANISM: Artificial Sequence
<220> FEATURE:
<223> OTHER INFORMATION: Recombinant peptide

<400> SEQUENCE: 290

Ser Glu Arg Pro Trp Val Ile
1               5

<210> SEQ ID NO 291
<211> LENGTH: 7
<212> TYPE: PRT
<213> ORGANISM: Artificial Sequence
<220> FEATURE:
<223> OTHER INFORMATION: Recombinant peptide

<400> SEQUENCE: 291

Ser Glu Arg Pro Trp Val Val
1               5

```
<210> SEQ ID NO 292
<211> LENGTH: 7
<212> TYPE: PRT
<213> ORGANISM: Artificial Sequence
<220> FEATURE:
<223> OTHER INFORMATION: Recombinant peptide

<400> SEQUENCE: 292

Thr Asp Lys Pro Tyr Ile Leu
1               5

<210> SEQ ID NO 293
<211> LENGTH: 7
<212> TYPE: PRT
<213> ORGANISM: Artificial Sequence
<220> FEATURE:
<223> OTHER INFORMATION: Recombinant peptide

<400> SEQUENCE: 293

Thr Asp Lys Pro Tyr Ile Ile
1               5

<210> SEQ ID NO 294
<211> LENGTH: 7
<212> TYPE: PRT
<213> ORGANISM: Artificial Sequence
<220> FEATURE:
<223> OTHER INFORMATION: Recombinant peptide

<400> SEQUENCE: 294

Thr Asp Lys Pro Tyr Ile Val
1               5

<210> SEQ ID NO 295
<211> LENGTH: 7
<212> TYPE: PRT
<213> ORGANISM: Artificial Sequence
<220> FEATURE:
<223> OTHER INFORMATION: Recombinant peptide

<400> SEQUENCE: 295

Thr Asp Lys Pro Tyr Leu Leu
1               5

<210> SEQ ID NO 296
<211> LENGTH: 7
<212> TYPE: PRT
<213> ORGANISM: Artificial Sequence
<220> FEATURE:
<223> OTHER INFORMATION: Recombinant peptide

<400> SEQUENCE: 296

Thr Asp Lys Pro Tyr Leu Ile
1               5

<210> SEQ ID NO 297
<211> LENGTH: 7
<212> TYPE: PRT
<213> ORGANISM: Artificial Sequence
<220> FEATURE:
<223> OTHER INFORMATION: Recombinant peptide

<400> SEQUENCE: 297

Thr Asp Lys Pro Tyr Leu Val
1               5

<210> SEQ ID NO 298
```

```
<211> LENGTH: 7
<212> TYPE: PRT
<213> ORGANISM: Artificial Sequence
<220> FEATURE:
<223> OTHER INFORMATION: Recombinant peptide

<400> SEQUENCE: 298

Thr Asp Lys Pro Tyr Val Leu
1               5

<210> SEQ ID NO 299
<211> LENGTH: 7
<212> TYPE: PRT
<213> ORGANISM: Artificial Sequence
<220> FEATURE:
<223> OTHER INFORMATION: Recombinant peptide

<400> SEQUENCE: 299

Thr Asp Lys Pro Tyr Val Ile
1               5

<210> SEQ ID NO 300
<211> LENGTH: 7
<212> TYPE: PRT
<213> ORGANISM: Artificial Sequence
<220> FEATURE:
<223> OTHER INFORMATION: Recombinant peptide

<400> SEQUENCE: 300

Thr Asp Lys Pro Tyr Val Val
1               5

<210> SEQ ID NO 301
<211> LENGTH: 7
<212> TYPE: PRT
<213> ORGANISM: Artificial Sequence
<220> FEATURE:
<223> OTHER INFORMATION: Recombinant peptide

<400> SEQUENCE: 301

Thr Asp Lys Pro Trp Ile Leu
1               5

<210> SEQ ID NO 302
<211> LENGTH: 7
<212> TYPE: PRT
<213> ORGANISM: Artificial Sequence
<220> FEATURE:
<223> OTHER INFORMATION: Recombinant peptide

<400> SEQUENCE: 302

Thr Asp Lys Pro Trp Ile Ile
1               5

<210> SEQ ID NO 303
<211> LENGTH: 7
<212> TYPE: PRT
<213> ORGANISM: Artificial Sequence
<220> FEATURE:
<223> OTHER INFORMATION: Recombinant peptide

<400> SEQUENCE: 303

Thr Asp Lys Pro Trp Ile Val
1               5

<210> SEQ ID NO 304
<211> LENGTH: 7
```

```
<212> TYPE: PRT
<213> ORGANISM: Artificial Sequence
<220> FEATURE:
<223> OTHER INFORMATION: Recombinant peptide

<400> SEQUENCE: 304

Thr Asp Lys Pro Trp Leu Leu
1               5

<210> SEQ ID NO 305
<211> LENGTH: 7
<212> TYPE: PRT
<213> ORGANISM: Artificial Sequence
<220> FEATURE:
<223> OTHER INFORMATION: Recombinant peptide

<400> SEQUENCE: 305

Thr Asp Lys Pro Trp Leu Ile
1               5

<210> SEQ ID NO 306
<211> LENGTH: 7
<212> TYPE: PRT
<213> ORGANISM: Artificial Sequence
<220> FEATURE:
<223> OTHER INFORMATION: Recombinant peptide

<400> SEQUENCE: 306

Thr Asp Lys Pro Trp Leu Val
1               5

<210> SEQ ID NO 307
<211> LENGTH: 7
<212> TYPE: PRT
<213> ORGANISM: Artificial Sequence
<220> FEATURE:
<223> OTHER INFORMATION: Recombinant peptide

<400> SEQUENCE: 307

Thr Asp Lys Pro Trp Val Leu
1               5

<210> SEQ ID NO 308
<211> LENGTH: 7
<212> TYPE: PRT
<213> ORGANISM: Artificial Sequence
<220> FEATURE:
<223> OTHER INFORMATION: Recombinant peptide

<400> SEQUENCE: 308

Thr Asp Lys Pro Trp Val Ile
1               5

<210> SEQ ID NO 309
<211> LENGTH: 7
<212> TYPE: PRT
<213> ORGANISM: Artificial Sequence
<220> FEATURE:
<223> OTHER INFORMATION: Recombinant peptide

<400> SEQUENCE: 309

Thr Asp Lys Pro Trp Val Val
1               5

<210> SEQ ID NO 310
<211> LENGTH: 7
<212> TYPE: PRT
```

<213> ORGANISM: Artificial Sequence
<220> FEATURE:
<223> OTHER INFORMATION: Recombinant peptide

<400> SEQUENCE: 310

Thr Asp Arg Pro Tyr Ile Leu
1               5

<210> SEQ ID NO 311
<211> LENGTH: 7
<212> TYPE: PRT
<213> ORGANISM: Artificial Sequence
<220> FEATURE:
<223> OTHER INFORMATION: Recombinant peptide

<400> SEQUENCE: 311

Thr Asp Arg Pro Tyr Ile Ile
1               5

<210> SEQ ID NO 312
<211> LENGTH: 7
<212> TYPE: PRT
<213> ORGANISM: Artificial Sequence
<220> FEATURE:
<223> OTHER INFORMATION: Recombinant peptide

<400> SEQUENCE: 312

Thr Asp Arg Pro Tyr Ile Val
1               5

<210> SEQ ID NO 313
<211> LENGTH: 7
<212> TYPE: PRT
<213> ORGANISM: Artificial Sequence
<220> FEATURE:
<223> OTHER INFORMATION: Recombinant peptide

<400> SEQUENCE: 313

Thr Asp Arg Pro Tyr Leu Leu
1               5

<210> SEQ ID NO 314
<211> LENGTH: 7
<212> TYPE: PRT
<213> ORGANISM: Artificial Sequence
<220> FEATURE:
<223> OTHER INFORMATION: Recombinant peptide

<400> SEQUENCE: 314

Thr Asp Arg Pro Tyr Leu Ile
1               5

<210> SEQ ID NO 315
<211> LENGTH: 7
<212> TYPE: PRT
<213> ORGANISM: Artificial Sequence
<220> FEATURE:
<223> OTHER INFORMATION: Recombinant peptide

<400> SEQUENCE: 315

Thr Asp Arg Pro Tyr Leu Val
1               5

<210> SEQ ID NO 316
<211> LENGTH: 7
<212> TYPE: PRT
<213> ORGANISM: Artificial Sequence

```
<220> FEATURE:
<223> OTHER INFORMATION: Recombinant peptide

<400> SEQUENCE: 316

Thr Asp Arg Pro Tyr Val Leu
1               5

<210> SEQ ID NO 317
<211> LENGTH: 7
<212> TYPE: PRT
<213> ORGANISM: Artificial Sequence
<220> FEATURE:
<223> OTHER INFORMATION: Recombinant peptide

<400> SEQUENCE: 317

Thr Asp Arg Pro Tyr Val Ile
1               5

<210> SEQ ID NO 318
<211> LENGTH: 7
<212> TYPE: PRT
<213> ORGANISM: Artificial Sequence
<220> FEATURE:
<223> OTHER INFORMATION: Recombinant peptide

<400> SEQUENCE: 318

Thr Asp Arg Pro Tyr Val Val
1               5

<210> SEQ ID NO 319
<211> LENGTH: 7
<212> TYPE: PRT
<213> ORGANISM: Artificial Sequence
<220> FEATURE:
<223> OTHER INFORMATION: Recombinant peptide

<400> SEQUENCE: 319

Thr Asp Arg Pro Trp Ile Leu
1               5

<210> SEQ ID NO 320
<211> LENGTH: 7
<212> TYPE: PRT
<213> ORGANISM: Artificial Sequence
<220> FEATURE:
<223> OTHER INFORMATION: Recombinant peptide

<400> SEQUENCE: 320

Thr Asp Arg Pro Trp Ile Ile
1               5

<210> SEQ ID NO 321
<211> LENGTH: 7
<212> TYPE: PRT
<213> ORGANISM: Artificial Sequence
<220> FEATURE:
<223> OTHER INFORMATION: Recombinant peptide

<400> SEQUENCE: 321

Thr Asp Arg Pro Trp Ile Val
1               5

<210> SEQ ID NO 322
<211> LENGTH: 7
<212> TYPE: PRT
<213> ORGANISM: Artificial Sequence
<220> FEATURE:
```

```
<223> OTHER INFORMATION: Recombinant peptide

<400> SEQUENCE: 322

Thr Asp Arg Pro Trp Leu Leu
1               5

<210> SEQ ID NO 323
<211> LENGTH: 7
<212> TYPE: PRT
<213> ORGANISM: Artificial Sequence
<220> FEATURE:
<223> OTHER INFORMATION: Recombinant peptide

<400> SEQUENCE: 323

Thr Asp Arg Pro Trp Leu Ile
1               5

<210> SEQ ID NO 324
<211> LENGTH: 7
<212> TYPE: PRT
<213> ORGANISM: Artificial Sequence
<220> FEATURE:
<223> OTHER INFORMATION: Recombinant peptide

<400> SEQUENCE: 324

Thr Asp Arg Pro Trp Leu Val
1               5

<210> SEQ ID NO 325
<211> LENGTH: 7
<212> TYPE: PRT
<213> ORGANISM: Artificial Sequence
<220> FEATURE:
<223> OTHER INFORMATION: Recombinant peptide

<400> SEQUENCE: 325

Thr Asp Arg Pro Trp Val Leu
1               5

<210> SEQ ID NO 326
<211> LENGTH: 7
<212> TYPE: PRT
<213> ORGANISM: Artificial Sequence
<220> FEATURE:
<223> OTHER INFORMATION: Recombinant peptide

<400> SEQUENCE: 326

Thr Asp Arg Pro Trp Val Ile
1               5

<210> SEQ ID NO 327
<211> LENGTH: 7
<212> TYPE: PRT
<213> ORGANISM: Artificial Sequence
<220> FEATURE:
<223> OTHER INFORMATION: Recombinant peptide

<400> SEQUENCE: 327

Thr Asp Arg Pro Trp Val Val
1               5

<210> SEQ ID NO 328
<211> LENGTH: 7
<212> TYPE: PRT
<213> ORGANISM: Artificial Sequence
<220> FEATURE:
<223> OTHER INFORMATION: Recombinant peptide
```

<400> SEQUENCE: 328

Thr Glu Lys Pro Tyr Ile Leu
1               5

<210> SEQ ID NO 329
<211> LENGTH: 7
<212> TYPE: PRT
<213> ORGANISM: Artificial Sequence
<220> FEATURE:
<223> OTHER INFORMATION: Recombinant peptide

<400> SEQUENCE: 329

Thr Glu Lys Pro Tyr Ile Ile
1               5

<210> SEQ ID NO 330
<211> LENGTH: 7
<212> TYPE: PRT
<213> ORGANISM: Artificial Sequence
<220> FEATURE:
<223> OTHER INFORMATION: Recombinant peptide

<400> SEQUENCE: 330

Thr Glu Lys Pro Tyr Ile Val
1               5

<210> SEQ ID NO 331
<211> LENGTH: 7
<212> TYPE: PRT
<213> ORGANISM: Artificial Sequence
<220> FEATURE:
<223> OTHER INFORMATION: Recombinant peptide

<400> SEQUENCE: 331

Thr Glu Lys Pro Tyr Leu Leu
1               5

<210> SEQ ID NO 332
<211> LENGTH: 7
<212> TYPE: PRT
<213> ORGANISM: Artificial Sequence
<220> FEATURE:
<223> OTHER INFORMATION: Recombinant peptide

<400> SEQUENCE: 332

Thr Glu Lys Pro Tyr Leu Ile
1               5

<210> SEQ ID NO 333
<211> LENGTH: 7
<212> TYPE: PRT
<213> ORGANISM: Artificial Sequence
<220> FEATURE:
<223> OTHER INFORMATION: Recombinant peptide

<400> SEQUENCE: 333

Thr Glu Lys Pro Tyr Leu Val
1               5

<210> SEQ ID NO 334
<211> LENGTH: 7
<212> TYPE: PRT
<213> ORGANISM: Artificial Sequence
<220> FEATURE:
<223> OTHER INFORMATION: Recombinant peptide

```
<400> SEQUENCE: 334

Thr Glu Lys Pro Tyr Val Leu
1               5

<210> SEQ ID NO 335
<211> LENGTH: 7
<212> TYPE: PRT
<213> ORGANISM: Artificial Sequence
<220> FEATURE:
<223> OTHER INFORMATION: Recombinant peptide

<400> SEQUENCE: 335

Thr Glu Lys Pro Tyr Val Ile
1               5

<210> SEQ ID NO 336
<211> LENGTH: 7
<212> TYPE: PRT
<213> ORGANISM: Artificial Sequence
<220> FEATURE:
<223> OTHER INFORMATION: Recombinant peptide

<400> SEQUENCE: 336

Thr Glu Lys Pro Tyr Val Val
1               5

<210> SEQ ID NO 337
<211> LENGTH: 7
<212> TYPE: PRT
<213> ORGANISM: Artificial Sequence
<220> FEATURE:
<223> OTHER INFORMATION: Recombinant peptide

<400> SEQUENCE: 337

Thr Glu Lys Pro Trp Ile Leu
1               5

<210> SEQ ID NO 338
<211> LENGTH: 7
<212> TYPE: PRT
<213> ORGANISM: Artificial Sequence
<220> FEATURE:
<223> OTHER INFORMATION: Recombinant peptide

<400> SEQUENCE: 338

Thr Glu Lys Pro Trp Ile Ile
1               5

<210> SEQ ID NO 339
<211> LENGTH: 7
<212> TYPE: PRT
<213> ORGANISM: Artificial Sequence
<220> FEATURE:
<223> OTHER INFORMATION: Recombinant peptide

<400> SEQUENCE: 339

Thr Glu Lys Pro Trp Ile Val
1               5

<210> SEQ ID NO 340
<211> LENGTH: 7
<212> TYPE: PRT
<213> ORGANISM: Artificial Sequence
<220> FEATURE:
<223> OTHER INFORMATION: Recombinant peptide

<400> SEQUENCE: 340
```

Thr Glu Lys Pro Trp Leu Leu
1               5

<210> SEQ ID NO 341
<211> LENGTH: 7
<212> TYPE: PRT
<213> ORGANISM: Artificial Sequence
<220> FEATURE:
<223> OTHER INFORMATION: Recombinant peptide

<400> SEQUENCE: 341

Thr Glu Lys Pro Trp Leu Ile
1               5

<210> SEQ ID NO 342
<211> LENGTH: 7
<212> TYPE: PRT
<213> ORGANISM: Artificial Sequence
<220> FEATURE:
<223> OTHER INFORMATION: Recombinant peptide

<400> SEQUENCE: 342

Thr Glu Lys Pro Trp Leu Val
1               5

<210> SEQ ID NO 343
<211> LENGTH: 7
<212> TYPE: PRT
<213> ORGANISM: Artificial Sequence
<220> FEATURE:
<223> OTHER INFORMATION: Recombinant peptide

<400> SEQUENCE: 343

Thr Glu Lys Pro Trp Val Leu
1               5

<210> SEQ ID NO 344
<211> LENGTH: 7
<212> TYPE: PRT
<213> ORGANISM: Artificial Sequence
<220> FEATURE:
<223> OTHER INFORMATION: Recombinant peptide

<400> SEQUENCE: 344

Thr Glu Lys Pro Trp Val Ile
1               5

<210> SEQ ID NO 345
<211> LENGTH: 7
<212> TYPE: PRT
<213> ORGANISM: Artificial Sequence
<220> FEATURE:
<223> OTHER INFORMATION: Recombinant peptide

<400> SEQUENCE: 345

Thr Glu Lys Pro Trp Val Val
1               5

<210> SEQ ID NO 346
<211> LENGTH: 7
<212> TYPE: PRT
<213> ORGANISM: Artificial Sequence
<220> FEATURE:
<223> OTHER INFORMATION: Recombinant peptide

<400> SEQUENCE: 346

Thr Glu Arg Pro Tyr Ile Leu
1               5

<210> SEQ ID NO 347
<211> LENGTH: 7
<212> TYPE: PRT
<213> ORGANISM: Artificial Sequence
<220> FEATURE:
<223> OTHER INFORMATION: Recombinant peptide

<400> SEQUENCE: 347

Thr Glu Arg Pro Tyr Ile Ile
1               5

<210> SEQ ID NO 348
<211> LENGTH: 7
<212> TYPE: PRT
<213> ORGANISM: Artificial Sequence
<220> FEATURE:
<223> OTHER INFORMATION: Recombinant peptide

<400> SEQUENCE: 348

Thr Glu Arg Pro Tyr Ile Val
1               5

<210> SEQ ID NO 349
<211> LENGTH: 7
<212> TYPE: PRT
<213> ORGANISM: Artificial Sequence
<220> FEATURE:
<223> OTHER INFORMATION: Recombinant peptide

<400> SEQUENCE: 349

Thr Glu Arg Pro Tyr Leu Leu
1               5

<210> SEQ ID NO 350
<211> LENGTH: 7
<212> TYPE: PRT
<213> ORGANISM: Artificial Sequence
<220> FEATURE:
<223> OTHER INFORMATION: Recombinant peptide

<400> SEQUENCE: 350

Thr Glu Arg Pro Tyr Leu Ile
1               5

<210> SEQ ID NO 351
<211> LENGTH: 7
<212> TYPE: PRT
<213> ORGANISM: Artificial Sequence
<220> FEATURE:
<223> OTHER INFORMATION: Recombinant peptide

<400> SEQUENCE: 351

Thr Glu Arg Pro Tyr Leu Val
1               5

<210> SEQ ID NO 352
<211> LENGTH: 7
<212> TYPE: PRT
<213> ORGANISM: Artificial Sequence
<220> FEATURE:
<223> OTHER INFORMATION: Recombinant peptide

<400> SEQUENCE: 352

Thr Glu Arg Pro Tyr Val Leu

```
1               5

<210> SEQ ID NO 353
<211> LENGTH: 7
<212> TYPE: PRT
<213> ORGANISM: Artificial Sequence
<220> FEATURE:
<223> OTHER INFORMATION: Recombinant peptide

<400> SEQUENCE: 353

Thr Glu Arg Pro Tyr Val Ile
1               5

<210> SEQ ID NO 354
<211> LENGTH: 7
<212> TYPE: PRT
<213> ORGANISM: Artificial Sequence
<220> FEATURE:
<223> OTHER INFORMATION: Recombinant peptide

<400> SEQUENCE: 354

Thr Glu Arg Pro Tyr Val Val
1               5

<210> SEQ ID NO 355
<211> LENGTH: 7
<212> TYPE: PRT
<213> ORGANISM: Artificial Sequence
<220> FEATURE:
<223> OTHER INFORMATION: Recombinant peptide

<400> SEQUENCE: 355

Thr Glu Arg Pro Trp Ile Leu
1               5

<210> SEQ ID NO 356
<211> LENGTH: 7
<212> TYPE: PRT
<213> ORGANISM: Artificial Sequence
<220> FEATURE:
<223> OTHER INFORMATION: Recombinant peptide

<400> SEQUENCE: 356

Thr Glu Arg Pro Trp Ile Ile
1               5

<210> SEQ ID NO 357
<211> LENGTH: 7
<212> TYPE: PRT
<213> ORGANISM: Artificial Sequence
<220> FEATURE:
<223> OTHER INFORMATION: Recombinant peptide

<400> SEQUENCE: 357

Thr Glu Arg Pro Trp Ile Val
1               5

<210> SEQ ID NO 358
<211> LENGTH: 7
<212> TYPE: PRT
<213> ORGANISM: Artificial Sequence
<220> FEATURE:
<223> OTHER INFORMATION: Recombinant peptide

<400> SEQUENCE: 358

Thr Glu Arg Pro Trp Leu Leu
1               5
```

<210> SEQ ID NO 359
<211> LENGTH: 7
<212> TYPE: PRT
<213> ORGANISM: Artificial Sequence
<220> FEATURE:
<223> OTHER INFORMATION: Recombinant peptide

<400> SEQUENCE: 359

Thr Glu Arg Pro Trp Leu Ile
1               5

<210> SEQ ID NO 360
<211> LENGTH: 7
<212> TYPE: PRT
<213> ORGANISM: Artificial Sequence
<220> FEATURE:
<223> OTHER INFORMATION: Recombinant peptide

<400> SEQUENCE: 360

Thr Glu Arg Pro Trp Leu Val
1               5

<210> SEQ ID NO 361
<211> LENGTH: 7
<212> TYPE: PRT
<213> ORGANISM: Artificial Sequence
<220> FEATURE:
<223> OTHER INFORMATION: Recombinant peptide

<400> SEQUENCE: 361

Thr Glu Arg Pro Trp Val Leu
1               5

<210> SEQ ID NO 362
<211> LENGTH: 7
<212> TYPE: PRT
<213> ORGANISM: Artificial Sequence
<220> FEATURE:
<223> OTHER INFORMATION: Recombinant peptide

<400> SEQUENCE: 362

Thr Glu Arg Pro Trp Val Ile
1               5

<210> SEQ ID NO 363
<211> LENGTH: 7
<212> TYPE: PRT
<213> ORGANISM: Artificial Sequence
<220> FEATURE:
<223> OTHER INFORMATION: Recombinant peptide

<400> SEQUENCE: 363

Thr Glu Arg Pro Trp Val Val
1               5

<210> SEQ ID NO 364
<211> LENGTH: 8
<212> TYPE: PRT
<213> ORGANISM: Artificial Sequence
<220> FEATURE:
<223> OTHER INFORMATION: Recombinant peptide

<400> SEQUENCE: 364

Ala Ser Asp Lys Pro Tyr Ile Ile
1               5

```
<210> SEQ ID NO 365
<211> LENGTH: 8
<212> TYPE: PRT
<213> ORGANISM: Artificial Sequence
<220> FEATURE:
<223> OTHER INFORMATION: Recombinant peptide

<400> SEQUENCE: 365

Ala Ser Asp Lys Pro Tyr Ile Val
1               5

<210> SEQ ID NO 366
<211> LENGTH: 8
<212> TYPE: PRT
<213> ORGANISM: Artificial Sequence
<220> FEATURE:
<223> OTHER INFORMATION: Recombinant peptide

<400> SEQUENCE: 366

Ala Ser Asp Lys Pro Tyr Leu Leu
1               5

<210> SEQ ID NO 367
<211> LENGTH: 8
<212> TYPE: PRT
<213> ORGANISM: Artificial Sequence
<220> FEATURE:
<223> OTHER INFORMATION: Recombinant peptide

<400> SEQUENCE: 367

Ala Ser Asp Lys Pro Tyr Leu Ile
1               5

<210> SEQ ID NO 368
<211> LENGTH: 8
<212> TYPE: PRT
<213> ORGANISM: Artificial Sequence
<220> FEATURE:
<223> OTHER INFORMATION: Recombinant peptide

<400> SEQUENCE: 368

Ala Ser Asp Lys Pro Tyr Leu Val
1               5

<210> SEQ ID NO 369
<211> LENGTH: 8
<212> TYPE: PRT
<213> ORGANISM: Artificial Sequence
<220> FEATURE:
<223> OTHER INFORMATION: Recombinant peptide

<400> SEQUENCE: 369

Ala Ser Asp Lys Pro Tyr Val Leu
1               5

<210> SEQ ID NO 370
<211> LENGTH: 8
<212> TYPE: PRT
<213> ORGANISM: Artificial Sequence
<220> FEATURE:
<223> OTHER INFORMATION: Recombinant peptide

<400> SEQUENCE: 370

Ala Ser Asp Lys Pro Tyr Val Ile
1               5
```

```
<210> SEQ ID NO 371
<211> LENGTH: 8
<212> TYPE: PRT
<213> ORGANISM: Artificial Sequence
<220> FEATURE:
<223> OTHER INFORMATION: Recombinant peptide

<400> SEQUENCE: 371

Ala Ser Asp Lys Pro Tyr Val Val
1               5

<210> SEQ ID NO 372
<211> LENGTH: 8
<212> TYPE: PRT
<213> ORGANISM: Artificial Sequence
<220> FEATURE:
<223> OTHER INFORMATION: Recombinant peptide

<400> SEQUENCE: 372

Ala Ser Asp Lys Pro Trp Ile Leu
1               5

<210> SEQ ID NO 373
<211> LENGTH: 8
<212> TYPE: PRT
<213> ORGANISM: Artificial Sequence
<220> FEATURE:
<223> OTHER INFORMATION: Recombinant peptide

<400> SEQUENCE: 373

Ala Ser Asp Lys Pro Trp Ile Ile
1               5

<210> SEQ ID NO 374
<211> LENGTH: 8
<212> TYPE: PRT
<213> ORGANISM: Artificial Sequence
<220> FEATURE:
<223> OTHER INFORMATION: Recombinant peptide

<400> SEQUENCE: 374

Ala Ser Asp Lys Pro Trp Ile Val
1               5

<210> SEQ ID NO 375
<211> LENGTH: 8
<212> TYPE: PRT
<213> ORGANISM: Artificial Sequence
<220> FEATURE:
<223> OTHER INFORMATION: Recombinant peptide

<400> SEQUENCE: 375

Ala Ser Asp Lys Pro Trp Leu Leu
1               5

<210> SEQ ID NO 376
<211> LENGTH: 8
<212> TYPE: PRT
<213> ORGANISM: Artificial Sequence
<220> FEATURE:
<223> OTHER INFORMATION: Recombinant peptide

<400> SEQUENCE: 376

Ala Ser Asp Lys Pro Trp Leu Ile
1               5

<210> SEQ ID NO 377
```

```
<211> LENGTH: 8
<212> TYPE: PRT
<213> ORGANISM: Artificial Sequence
<220> FEATURE:
<223> OTHER INFORMATION: Recombinant peptide

<400> SEQUENCE: 377

Ala Ser Asp Lys Pro Trp Leu Val
1               5

<210> SEQ ID NO 378
<211> LENGTH: 8
<212> TYPE: PRT
<213> ORGANISM: Artificial Sequence
<220> FEATURE:
<223> OTHER INFORMATION: Recombinant peptide

<400> SEQUENCE: 378

Ala Ser Asp Lys Pro Trp Val Leu
1               5

<210> SEQ ID NO 379
<211> LENGTH: 8
<212> TYPE: PRT
<213> ORGANISM: Artificial Sequence
<220> FEATURE:
<223> OTHER INFORMATION: Recombinant peptide

<400> SEQUENCE: 379

Ala Ser Asp Lys Pro Trp Val Ile
1               5

<210> SEQ ID NO 380
<211> LENGTH: 8
<212> TYPE: PRT
<213> ORGANISM: Artificial Sequence
<220> FEATURE:
<223> OTHER INFORMATION: Recombinant peptide

<400> SEQUENCE: 380

Ala Ser Asp Lys Pro Trp Val Val
1               5

<210> SEQ ID NO 381
<211> LENGTH: 8
<212> TYPE: PRT
<213> ORGANISM: Artificial Sequence
<220> FEATURE:
<223> OTHER INFORMATION: Recombinant peptide

<400> SEQUENCE: 381

Ala Ser Asp Arg Pro Tyr Ile Leu
1               5

<210> SEQ ID NO 382
<211> LENGTH: 8
<212> TYPE: PRT
<213> ORGANISM: Artificial Sequence
<220> FEATURE:
<223> OTHER INFORMATION: Recombinant peptide

<400> SEQUENCE: 382

Ala Ser Asp Arg Pro Tyr Ile Ile
1               5

<210> SEQ ID NO 383
<211> LENGTH: 8
```

```
<212> TYPE: PRT
<213> ORGANISM: Artificial Sequence
<220> FEATURE:
<223> OTHER INFORMATION: Recombinant peptide

<400> SEQUENCE: 383

Ala Ser Asp Arg Pro Tyr Ile Val
1               5

<210> SEQ ID NO 384
<211> LENGTH: 8
<212> TYPE: PRT
<213> ORGANISM: Artificial Sequence
<220> FEATURE:
<223> OTHER INFORMATION: Recombinant peptide

<400> SEQUENCE: 384

Ala Ser Asp Arg Pro Tyr Leu Leu
1               5

<210> SEQ ID NO 385
<211> LENGTH: 8
<212> TYPE: PRT
<213> ORGANISM: Artificial Sequence
<220> FEATURE:
<223> OTHER INFORMATION: Recombinant peptide

<400> SEQUENCE: 385

Ala Ser Asp Arg Pro Tyr Leu Ile
1               5

<210> SEQ ID NO 386
<211> LENGTH: 8
<212> TYPE: PRT
<213> ORGANISM: Artificial Sequence
<220> FEATURE:
<223> OTHER INFORMATION: Recombinant peptide

<400> SEQUENCE: 386

Ala Ser Asp Arg Pro Tyr Leu Val
1               5

<210> SEQ ID NO 387
<211> LENGTH: 8
<212> TYPE: PRT
<213> ORGANISM: Artificial Sequence
<220> FEATURE:
<223> OTHER INFORMATION: Recombinant peptide

<400> SEQUENCE: 387

Ala Ser Asp Arg Pro Tyr Val Leu
1               5

<210> SEQ ID NO 388
<211> LENGTH: 8
<212> TYPE: PRT
<213> ORGANISM: Artificial Sequence
<220> FEATURE:
<223> OTHER INFORMATION: Recombinant peptide

<400> SEQUENCE: 388

Ala Ser Asp Arg Pro Tyr Val Ile
1               5

<210> SEQ ID NO 389
<211> LENGTH: 8
<212> TYPE: PRT
```

<213> ORGANISM: Artificial Sequence
<220> FEATURE:
<223> OTHER INFORMATION: Recombinant peptide

<400> SEQUENCE: 389

Ala Ser Asp Arg Pro Tyr Val Val
1               5

<210> SEQ ID NO 390
<211> LENGTH: 8
<212> TYPE: PRT
<213> ORGANISM: Artificial Sequence
<220> FEATURE:
<223> OTHER INFORMATION: Recombinant peptide

<400> SEQUENCE: 390

Ala Ser Asp Arg Pro Trp Ile Leu
1               5

<210> SEQ ID NO 391
<211> LENGTH: 8
<212> TYPE: PRT
<213> ORGANISM: Artificial Sequence
<220> FEATURE:
<223> OTHER INFORMATION: Recombinant peptide

<400> SEQUENCE: 391

Ala Ser Asp Arg Pro Trp Ile Ile
1               5

<210> SEQ ID NO 392
<211> LENGTH: 8
<212> TYPE: PRT
<213> ORGANISM: Artificial Sequence
<220> FEATURE:
<223> OTHER INFORMATION: Recombinant peptide

<400> SEQUENCE: 392

Ala Ser Asp Arg Pro Trp Ile Val
1               5

<210> SEQ ID NO 393
<211> LENGTH: 8
<212> TYPE: PRT
<213> ORGANISM: Artificial Sequence
<220> FEATURE:
<223> OTHER INFORMATION: Recombinant peptide

<400> SEQUENCE: 393

Ala Ser Asp Arg Pro Trp Leu Leu
1               5

<210> SEQ ID NO 394
<211> LENGTH: 8
<212> TYPE: PRT
<213> ORGANISM: Artificial Sequence
<220> FEATURE:
<223> OTHER INFORMATION: Recombinant peptide

<400> SEQUENCE: 394

Ala Ser Asp Arg Pro Trp Leu Ile
1               5

<210> SEQ ID NO 395
<211> LENGTH: 8
<212> TYPE: PRT
<213> ORGANISM: Artificial Sequence

```
<220> FEATURE:
<223> OTHER INFORMATION: Recombinant peptide

<400> SEQUENCE: 395

Ala Ser Asp Arg Pro Trp Leu Val
1               5

<210> SEQ ID NO 396
<211> LENGTH: 8
<212> TYPE: PRT
<213> ORGANISM: Artificial Sequence
<220> FEATURE:
<223> OTHER INFORMATION: Recombinant peptide

<400> SEQUENCE: 396

Ala Ser Asp Arg Pro Trp Val Leu
1               5

<210> SEQ ID NO 397
<211> LENGTH: 8
<212> TYPE: PRT
<213> ORGANISM: Artificial Sequence
<220> FEATURE:
<223> OTHER INFORMATION: Recombinant peptide

<400> SEQUENCE: 397

Ala Ser Asp Arg Pro Trp Val Ile
1               5

<210> SEQ ID NO 398
<211> LENGTH: 8
<212> TYPE: PRT
<213> ORGANISM: Artificial Sequence
<220> FEATURE:
<223> OTHER INFORMATION: Recombinant peptide

<400> SEQUENCE: 398

Ala Ser Asp Arg Pro Trp Val Val
1               5

<210> SEQ ID NO 399
<211> LENGTH: 8
<212> TYPE: PRT
<213> ORGANISM: Artificial Sequence
<220> FEATURE:
<223> OTHER INFORMATION: Recombinant peptide

<400> SEQUENCE: 399

Ala Ser Glu Lys Pro Tyr Ile Leu
1               5

<210> SEQ ID NO 400
<211> LENGTH: 8
<212> TYPE: PRT
<213> ORGANISM: Artificial Sequence
<220> FEATURE:
<223> OTHER INFORMATION: Recombinant peptide

<400> SEQUENCE: 400

Ala Ser Glu Lys Pro Tyr Ile Ile
1               5

<210> SEQ ID NO 401
<211> LENGTH: 8
<212> TYPE: PRT
<213> ORGANISM: Artificial Sequence
<220> FEATURE:
```

```
<223> OTHER INFORMATION: Recombinant peptide

<400> SEQUENCE: 401

Ala Ser Glu Lys Pro Tyr Ile Val
1               5

<210> SEQ ID NO 402
<211> LENGTH: 8
<212> TYPE: PRT
<213> ORGANISM: Artificial Sequence
<220> FEATURE:
<223> OTHER INFORMATION: Recombinant peptide

<400> SEQUENCE: 402

Ala Ser Glu Lys Pro Tyr Leu Leu
1               5

<210> SEQ ID NO 403
<211> LENGTH: 8
<212> TYPE: PRT
<213> ORGANISM: Artificial Sequence
<220> FEATURE:
<223> OTHER INFORMATION: Recombinant peptide

<400> SEQUENCE: 403

Ala Ser Glu Lys Pro Tyr Leu Ile
1               5

<210> SEQ ID NO 404
<211> LENGTH: 8
<212> TYPE: PRT
<213> ORGANISM: Artificial Sequence
<220> FEATURE:
<223> OTHER INFORMATION: Recombinant peptide

<400> SEQUENCE: 404

Ala Ser Glu Lys Pro Tyr Leu Val
1               5

<210> SEQ ID NO 405
<211> LENGTH: 8
<212> TYPE: PRT
<213> ORGANISM: Artificial Sequence
<220> FEATURE:
<223> OTHER INFORMATION: Recombinant peptide

<400> SEQUENCE: 405

Ala Ser Glu Lys Pro Tyr Val Leu
1               5

<210> SEQ ID NO 406
<211> LENGTH: 8
<212> TYPE: PRT
<213> ORGANISM: Artificial Sequence
<220> FEATURE:
<223> OTHER INFORMATION: Recombinant peptide

<400> SEQUENCE: 406

Ala Ser Glu Lys Pro Tyr Val Ile
1               5

<210> SEQ ID NO 407
<211> LENGTH: 8
<212> TYPE: PRT
<213> ORGANISM: Artificial Sequence
<220> FEATURE:
<223> OTHER INFORMATION: Recombinant peptide
```

<400> SEQUENCE: 407

Ala Ser Glu Lys Pro Tyr Val Val
1               5

<210> SEQ ID NO 408
<211> LENGTH: 8
<212> TYPE: PRT
<213> ORGANISM: Artificial Sequence
<220> FEATURE:
<223> OTHER INFORMATION: Recombinant peptide

<400> SEQUENCE: 408

Ala Ser Glu Lys Pro Trp Ile Leu
1               5

<210> SEQ ID NO 409
<211> LENGTH: 8
<212> TYPE: PRT
<213> ORGANISM: Artificial Sequence
<220> FEATURE:
<223> OTHER INFORMATION: Recombinant peptide

<400> SEQUENCE: 409

Ala Ser Glu Lys Pro Trp Ile Ile
1               5

<210> SEQ ID NO 410
<211> LENGTH: 8
<212> TYPE: PRT
<213> ORGANISM: Artificial Sequence
<220> FEATURE:
<223> OTHER INFORMATION: Recombinant peptide

<400> SEQUENCE: 410

Ala Ser Glu Lys Pro Trp Ile Val
1               5

<210> SEQ ID NO 411
<211> LENGTH: 8
<212> TYPE: PRT
<213> ORGANISM: Artificial Sequence
<220> FEATURE:
<223> OTHER INFORMATION: Recombinant peptide

<400> SEQUENCE: 411

Ala Ser Glu Lys Pro Trp Leu Leu
1               5

<210> SEQ ID NO 412
<211> LENGTH: 8
<212> TYPE: PRT
<213> ORGANISM: Artificial Sequence
<220> FEATURE:
<223> OTHER INFORMATION: Recombinant peptide

<400> SEQUENCE: 412

Ala Ser Glu Lys Pro Trp Leu Ile
1               5

<210> SEQ ID NO 413
<211> LENGTH: 8
<212> TYPE: PRT
<213> ORGANISM: Artificial Sequence
<220> FEATURE:
<223> OTHER INFORMATION: Recombinant peptide

```
<400> SEQUENCE: 413

Ala Ser Glu Lys Pro Trp Leu Val
1               5

<210> SEQ ID NO 414
<211> LENGTH: 8
<212> TYPE: PRT
<213> ORGANISM: Artificial Sequence
<220> FEATURE:
<223> OTHER INFORMATION: Recombinant peptide

<400> SEQUENCE: 414

Ala Ser Glu Lys Pro Trp Val Leu
1               5

<210> SEQ ID NO 415
<211> LENGTH: 8
<212> TYPE: PRT
<213> ORGANISM: Artificial Sequence
<220> FEATURE:
<223> OTHER INFORMATION: Recombinant peptide

<400> SEQUENCE: 415

Ala Ser Glu Lys Pro Trp Val Ile
1               5

<210> SEQ ID NO 416
<211> LENGTH: 8
<212> TYPE: PRT
<213> ORGANISM: Artificial Sequence
<220> FEATURE:
<223> OTHER INFORMATION: Recombinant peptide

<400> SEQUENCE: 416

Ala Ser Glu Lys Pro Trp Val Val
1               5

<210> SEQ ID NO 417
<211> LENGTH: 8
<212> TYPE: PRT
<213> ORGANISM: Artificial Sequence
<220> FEATURE:
<223> OTHER INFORMATION: Recombinant peptide

<400> SEQUENCE: 417

Ala Ser Glu Arg Pro Tyr Ile Leu
1               5

<210> SEQ ID NO 418
<211> LENGTH: 8
<212> TYPE: PRT
<213> ORGANISM: Artificial Sequence
<220> FEATURE:
<223> OTHER INFORMATION: Recombinant peptide

<400> SEQUENCE: 418

Ala Ser Glu Arg Pro Tyr Ile Ile
1               5

<210> SEQ ID NO 419
<211> LENGTH: 8
<212> TYPE: PRT
<213> ORGANISM: Artificial Sequence
<220> FEATURE:
<223> OTHER INFORMATION: Recombinant peptide

<400> SEQUENCE: 419
```

Ala Ser Glu Arg Pro Tyr Ile Val
1               5

<210> SEQ ID NO 420
<211> LENGTH: 8
<212> TYPE: PRT
<213> ORGANISM: Artificial Sequence
<220> FEATURE:
<223> OTHER INFORMATION: Recombinant peptide

<400> SEQUENCE: 420

Ala Ser Glu Arg Pro Tyr Leu Leu
1               5

<210> SEQ ID NO 421
<211> LENGTH: 8
<212> TYPE: PRT
<213> ORGANISM: Artificial Sequence
<220> FEATURE:
<223> OTHER INFORMATION: Recombinant peptide

<400> SEQUENCE: 421

Ala Ser Glu Arg Pro Tyr Leu Ile
1               5

<210> SEQ ID NO 422
<211> LENGTH: 8
<212> TYPE: PRT
<213> ORGANISM: Artificial Sequence
<220> FEATURE:
<223> OTHER INFORMATION: Recombinant peptide

<400> SEQUENCE: 422

Ala Ser Glu Arg Pro Tyr Leu Val
1               5

<210> SEQ ID NO 423
<211> LENGTH: 8
<212> TYPE: PRT
<213> ORGANISM: Artificial Sequence
<220> FEATURE:
<223> OTHER INFORMATION: Recombinant peptide

<400> SEQUENCE: 423

Ala Ser Glu Arg Pro Tyr Val Leu
1               5

<210> SEQ ID NO 424
<211> LENGTH: 8
<212> TYPE: PRT
<213> ORGANISM: Artificial Sequence
<220> FEATURE:
<223> OTHER INFORMATION: Recombinant peptide

<400> SEQUENCE: 424

Ala Ser Glu Arg Pro Tyr Val Ile
1               5

<210> SEQ ID NO 425
<211> LENGTH: 8
<212> TYPE: PRT
<213> ORGANISM: Artificial Sequence
<220> FEATURE:
<223> OTHER INFORMATION: Recombinant peptide

<400> SEQUENCE: 425

```
Ala Ser Glu Arg Pro Tyr Val Val
1               5

<210> SEQ ID NO 426
<211> LENGTH: 8
<212> TYPE: PRT
<213> ORGANISM: Artificial Sequence
<220> FEATURE:
<223> OTHER INFORMATION: Recombinant peptide

<400> SEQUENCE: 426

Ala Ser Glu Arg Pro Trp Ile Leu
1               5

<210> SEQ ID NO 427
<211> LENGTH: 8
<212> TYPE: PRT
<213> ORGANISM: Artificial Sequence
<220> FEATURE:
<223> OTHER INFORMATION: Recombinant peptide

<400> SEQUENCE: 427

Ala Ser Glu Arg Pro Trp Ile Ile
1               5

<210> SEQ ID NO 428
<211> LENGTH: 8
<212> TYPE: PRT
<213> ORGANISM: Artificial Sequence
<220> FEATURE:
<223> OTHER INFORMATION: Recombinant peptide

<400> SEQUENCE: 428

Ala Ser Glu Arg Pro Trp Ile Val
1               5

<210> SEQ ID NO 429
<211> LENGTH: 8
<212> TYPE: PRT
<213> ORGANISM: Artificial Sequence
<220> FEATURE:
<223> OTHER INFORMATION: Recombinant peptide

<400> SEQUENCE: 429

Ala Ser Glu Arg Pro Trp Leu Leu
1               5

<210> SEQ ID NO 430
<211> LENGTH: 8
<212> TYPE: PRT
<213> ORGANISM: Artificial Sequence
<220> FEATURE:
<223> OTHER INFORMATION: Recombinant peptide

<400> SEQUENCE: 430

Ala Ser Glu Arg Pro Trp Leu Ile
1               5

<210> SEQ ID NO 431
<211> LENGTH: 8
<212> TYPE: PRT
<213> ORGANISM: Artificial Sequence
<220> FEATURE:
<223> OTHER INFORMATION: Recombinant peptide

<400> SEQUENCE: 431

Ala Ser Glu Arg Pro Trp Leu Val
```

```
1               5

<210> SEQ ID NO 432
<211> LENGTH: 8
<212> TYPE: PRT
<213> ORGANISM: Artificial Sequence
<220> FEATURE:
<223> OTHER INFORMATION: Recombinant peptide

<400> SEQUENCE: 432

Ala Ser Glu Arg Pro Trp Val Leu
1               5

<210> SEQ ID NO 433
<211> LENGTH: 8
<212> TYPE: PRT
<213> ORGANISM: Artificial Sequence
<220> FEATURE:
<223> OTHER INFORMATION: Recombinant peptide

<400> SEQUENCE: 433

Ala Ser Glu Arg Pro Trp Val Ile
1               5

<210> SEQ ID NO 434
<211> LENGTH: 8
<212> TYPE: PRT
<213> ORGANISM: Artificial Sequence
<220> FEATURE:
<223> OTHER INFORMATION: Recombinant peptide

<400> SEQUENCE: 434

Ala Ser Glu Arg Pro Trp Val Val
1               5

<210> SEQ ID NO 435
<211> LENGTH: 8
<212> TYPE: PRT
<213> ORGANISM: Artificial Sequence
<220> FEATURE:
<223> OTHER INFORMATION: Recombinant peptide

<400> SEQUENCE: 435

Ala Thr Asp Lys Pro Tyr Ile Leu
1               5

<210> SEQ ID NO 436
<211> LENGTH: 8
<212> TYPE: PRT
<213> ORGANISM: Artificial Sequence
<220> FEATURE:
<223> OTHER INFORMATION: Recombinant peptide

<400> SEQUENCE: 436

Ala Thr Asp Lys Pro Tyr Ile Ile
1               5

<210> SEQ ID NO 437
<211> LENGTH: 8
<212> TYPE: PRT
<213> ORGANISM: Artificial Sequence
<220> FEATURE:
<223> OTHER INFORMATION: Recombinant peptide

<400> SEQUENCE: 437

Ala Thr Asp Lys Pro Tyr Ile Val
1               5
```

```
<210> SEQ ID NO 438
<211> LENGTH: 8
<212> TYPE: PRT
<213> ORGANISM: Artificial Sequence
<220> FEATURE:
<223> OTHER INFORMATION: Recombinant peptide

<400> SEQUENCE: 438

Ala Thr Asp Lys Pro Tyr Leu Leu
1               5

<210> SEQ ID NO 439
<211> LENGTH: 8
<212> TYPE: PRT
<213> ORGANISM: Artificial Sequence
<220> FEATURE:
<223> OTHER INFORMATION: Recombinant peptide

<400> SEQUENCE: 439

Ala Thr Asp Lys Pro Tyr Leu Ile
1               5

<210> SEQ ID NO 440
<211> LENGTH: 8
<212> TYPE: PRT
<213> ORGANISM: Artificial Sequence
<220> FEATURE:
<223> OTHER INFORMATION: Recombinant peptide

<400> SEQUENCE: 440

Ala Thr Asp Lys Pro Tyr Leu Val
1               5

<210> SEQ ID NO 441
<211> LENGTH: 8
<212> TYPE: PRT
<213> ORGANISM: Artificial Sequence
<220> FEATURE:
<223> OTHER INFORMATION: Recombinant peptide

<400> SEQUENCE: 441

Ala Thr Asp Lys Pro Tyr Val Leu
1               5

<210> SEQ ID NO 442
<211> LENGTH: 8
<212> TYPE: PRT
<213> ORGANISM: Artificial Sequence
<220> FEATURE:
<223> OTHER INFORMATION: Recombinant peptide

<400> SEQUENCE: 442

Ala Thr Asp Lys Pro Tyr Val Ile
1               5

<210> SEQ ID NO 443
<211> LENGTH: 8
<212> TYPE: PRT
<213> ORGANISM: Artificial Sequence
<220> FEATURE:
<223> OTHER INFORMATION: Recombinant peptide

<400> SEQUENCE: 443

Ala Thr Asp Lys Pro Tyr Val Val
1               5
```

```
<210> SEQ ID NO 444
<211> LENGTH: 8
<212> TYPE: PRT
<213> ORGANISM: Artificial Sequence
<220> FEATURE:
<223> OTHER INFORMATION: Recombinant peptide

<400> SEQUENCE: 444

Ala Thr Asp Lys Pro Trp Ile Leu
1               5

<210> SEQ ID NO 445
<211> LENGTH: 8
<212> TYPE: PRT
<213> ORGANISM: Artificial Sequence
<220> FEATURE:
<223> OTHER INFORMATION: Recombinant peptide

<400> SEQUENCE: 445

Ala Thr Asp Lys Pro Trp Ile Ile
1               5

<210> SEQ ID NO 446
<211> LENGTH: 8
<212> TYPE: PRT
<213> ORGANISM: Artificial Sequence
<220> FEATURE:
<223> OTHER INFORMATION: Recombinant peptide

<400> SEQUENCE: 446

Ala Thr Asp Lys Pro Trp Ile Val
1               5

<210> SEQ ID NO 447
<211> LENGTH: 8
<212> TYPE: PRT
<213> ORGANISM: Artificial Sequence
<220> FEATURE:
<223> OTHER INFORMATION: Recombinant peptide

<400> SEQUENCE: 447

Ala Thr Asp Lys Pro Trp Leu Leu
1               5

<210> SEQ ID NO 448
<211> LENGTH: 8
<212> TYPE: PRT
<213> ORGANISM: Artificial Sequence
<220> FEATURE:
<223> OTHER INFORMATION: Recombinant peptide

<400> SEQUENCE: 448

Ala Thr Asp Lys Pro Trp Leu Ile
1               5

<210> SEQ ID NO 449
<211> LENGTH: 8
<212> TYPE: PRT
<213> ORGANISM: Artificial Sequence
<220> FEATURE:
<223> OTHER INFORMATION: Recombinant peptide

<400> SEQUENCE: 449

Ala Thr Asp Lys Pro Trp Leu Val
1               5
```

```
<210> SEQ ID NO 450
<211> LENGTH: 8
<212> TYPE: PRT
<213> ORGANISM: Artificial Sequence
<220> FEATURE:
<223> OTHER INFORMATION: Recombinant peptide

<400> SEQUENCE: 450

Ala Thr Asp Lys Pro Trp Val Leu
1               5

<210> SEQ ID NO 451
<211> LENGTH: 8
<212> TYPE: PRT
<213> ORGANISM: Artificial Sequence
<220> FEATURE:
<223> OTHER INFORMATION: Recombinant peptide

<400> SEQUENCE: 451

Ala Thr Asp Lys Pro Trp Val Ile
1               5

<210> SEQ ID NO 452
<211> LENGTH: 8
<212> TYPE: PRT
<213> ORGANISM: Artificial Sequence
<220> FEATURE:
<223> OTHER INFORMATION: Recombinant peptide

<400> SEQUENCE: 452

Ala Thr Asp Lys Pro Trp Val Val
1               5

<210> SEQ ID NO 453
<211> LENGTH: 8
<212> TYPE: PRT
<213> ORGANISM: Artificial Sequence
<220> FEATURE:
<223> OTHER INFORMATION: Recombinant peptide

<400> SEQUENCE: 453

Ala Thr Asp Arg Pro Tyr Ile Leu
1               5

<210> SEQ ID NO 454
<211> LENGTH: 8
<212> TYPE: PRT
<213> ORGANISM: Artificial Sequence
<220> FEATURE:
<223> OTHER INFORMATION: Recombinant peptide

<400> SEQUENCE: 454

Ala Thr Asp Arg Pro Tyr Ile Ile
1               5

<210> SEQ ID NO 455
<211> LENGTH: 8
<212> TYPE: PRT
<213> ORGANISM: Artificial Sequence
<220> FEATURE:
<223> OTHER INFORMATION: Recombinant peptide

<400> SEQUENCE: 455

Ala Thr Asp Arg Pro Tyr Ile Val
1               5

<210> SEQ ID NO 456
```

```
<211> LENGTH: 8
<212> TYPE: PRT
<213> ORGANISM: Artificial Sequence
<220> FEATURE:
<223> OTHER INFORMATION: Recombinant peptide

<400> SEQUENCE: 456

Ala Thr Asp Arg Pro Tyr Leu Leu
1               5

<210> SEQ ID NO 457
<211> LENGTH: 8
<212> TYPE: PRT
<213> ORGANISM: Artificial Sequence
<220> FEATURE:
<223> OTHER INFORMATION: Recombinant peptide

<400> SEQUENCE: 457

Ala Thr Asp Arg Pro Tyr Leu Ile
1               5

<210> SEQ ID NO 458
<211> LENGTH: 8
<212> TYPE: PRT
<213> ORGANISM: Artificial Sequence
<220> FEATURE:
<223> OTHER INFORMATION: Recombinant peptide

<400> SEQUENCE: 458

Ala Thr Asp Arg Pro Tyr Leu Val
1               5

<210> SEQ ID NO 459
<211> LENGTH: 8
<212> TYPE: PRT
<213> ORGANISM: Artificial Sequence
<220> FEATURE:
<223> OTHER INFORMATION: Recombinant peptide

<400> SEQUENCE: 459

Ala Thr Asp Arg Pro Tyr Val Leu
1               5

<210> SEQ ID NO 460
<211> LENGTH: 8
<212> TYPE: PRT
<213> ORGANISM: Artificial Sequence
<220> FEATURE:
<223> OTHER INFORMATION: Recombinant peptide

<400> SEQUENCE: 460

Ala Thr Asp Arg Pro Tyr Val Ile
1               5

<210> SEQ ID NO 461
<211> LENGTH: 8
<212> TYPE: PRT
<213> ORGANISM: Artificial Sequence
<220> FEATURE:
<223> OTHER INFORMATION: Recombinant peptide

<400> SEQUENCE: 461

Ala Thr Asp Arg Pro Tyr Val Val
1               5

<210> SEQ ID NO 462
<211> LENGTH: 8
```

```
<212> TYPE: PRT
<213> ORGANISM: Artificial Sequence
<220> FEATURE:
<223> OTHER INFORMATION: Recombinant peptide

<400> SEQUENCE: 462

Ala Thr Asp Arg Pro Trp Ile Leu
1               5

<210> SEQ ID NO 463
<211> LENGTH: 8
<212> TYPE: PRT
<213> ORGANISM: Artificial Sequence
<220> FEATURE:
<223> OTHER INFORMATION: Recombinant peptide

<400> SEQUENCE: 463

Ala Thr Asp Arg Pro Trp Ile Ile
1               5

<210> SEQ ID NO 464
<211> LENGTH: 8
<212> TYPE: PRT
<213> ORGANISM: Artificial Sequence
<220> FEATURE:
<223> OTHER INFORMATION: Recombinant peptide

<400> SEQUENCE: 464

Ala Thr Asp Arg Pro Trp Ile Val
1               5

<210> SEQ ID NO 465
<211> LENGTH: 8
<212> TYPE: PRT
<213> ORGANISM: Artificial Sequence
<220> FEATURE:
<223> OTHER INFORMATION: Recombinant peptide

<400> SEQUENCE: 465

Ala Thr Asp Arg Pro Trp Leu Leu
1               5

<210> SEQ ID NO 466
<211> LENGTH: 8
<212> TYPE: PRT
<213> ORGANISM: Artificial Sequence
<220> FEATURE:
<223> OTHER INFORMATION: Recombinant peptide

<400> SEQUENCE: 466

Ala Thr Asp Arg Pro Trp Leu Ile
1               5

<210> SEQ ID NO 467
<211> LENGTH: 8
<212> TYPE: PRT
<213> ORGANISM: Artificial Sequence
<220> FEATURE:
<223> OTHER INFORMATION: Recombinant peptide

<400> SEQUENCE: 467

Ala Thr Asp Arg Pro Trp Leu Val
1               5

<210> SEQ ID NO 468
<211> LENGTH: 8
<212> TYPE: PRT
```

```
<213> ORGANISM: Artificial Sequence
<220> FEATURE:
<223> OTHER INFORMATION: Recombinant peptide

<400> SEQUENCE: 468

Ala Thr Asp Arg Pro Trp Val Leu
1               5

<210> SEQ ID NO 469
<211> LENGTH: 8
<212> TYPE: PRT
<213> ORGANISM: Artificial Sequence
<220> FEATURE:
<223> OTHER INFORMATION: Recombinant peptide

<400> SEQUENCE: 469

Ala Thr Asp Arg Pro Trp Val Ile
1               5

<210> SEQ ID NO 470
<211> LENGTH: 8
<212> TYPE: PRT
<213> ORGANISM: Artificial Sequence
<220> FEATURE:
<223> OTHER INFORMATION: Recombinant peptide

<400> SEQUENCE: 470

Ala Thr Asp Arg Pro Trp Val Val
1               5

<210> SEQ ID NO 471
<211> LENGTH: 8
<212> TYPE: PRT
<213> ORGANISM: Artificial Sequence
<220> FEATURE:
<223> OTHER INFORMATION: Recombinant peptide

<400> SEQUENCE: 471

Ala Thr Glu Lys Pro Tyr Ile Leu
1               5

<210> SEQ ID NO 472
<211> LENGTH: 8
<212> TYPE: PRT
<213> ORGANISM: Artificial Sequence
<220> FEATURE:
<223> OTHER INFORMATION: Recombinant peptide

<400> SEQUENCE: 472

Ala Thr Glu Lys Pro Tyr Ile Ile
1               5

<210> SEQ ID NO 473
<211> LENGTH: 8
<212> TYPE: PRT
<213> ORGANISM: Artificial Sequence
<220> FEATURE:
<223> OTHER INFORMATION: Recombinant peptide

<400> SEQUENCE: 473

Ala Thr Glu Lys Pro Tyr Ile Val
1               5

<210> SEQ ID NO 474
<211> LENGTH: 8
<212> TYPE: PRT
<213> ORGANISM: Artificial Sequence
```

```
<220> FEATURE:
<223> OTHER INFORMATION: Recombinant peptide

<400> SEQUENCE: 474

Ala Thr Glu Lys Pro Tyr Leu Leu
1               5

<210> SEQ ID NO 475
<211> LENGTH: 8
<212> TYPE: PRT
<213> ORGANISM: Artificial Sequence
<220> FEATURE:
<223> OTHER INFORMATION: Recombinant peptide

<400> SEQUENCE: 475

Ala Thr Glu Lys Pro Tyr Leu Ile
1               5

<210> SEQ ID NO 476
<211> LENGTH: 8
<212> TYPE: PRT
<213> ORGANISM: Artificial Sequence
<220> FEATURE:
<223> OTHER INFORMATION: Recombinant peptide

<400> SEQUENCE: 476

Ala Thr Glu Lys Pro Tyr Leu Val
1               5

<210> SEQ ID NO 477
<211> LENGTH: 8
<212> TYPE: PRT
<213> ORGANISM: Artificial Sequence
<220> FEATURE:
<223> OTHER INFORMATION: Recombinant peptide

<400> SEQUENCE: 477

Ala Thr Glu Lys Pro Tyr Val Leu
1               5

<210> SEQ ID NO 478
<211> LENGTH: 8
<212> TYPE: PRT
<213> ORGANISM: Artificial Sequence
<220> FEATURE:
<223> OTHER INFORMATION: Recombinant peptide

<400> SEQUENCE: 478

Ala Thr Glu Lys Pro Tyr Val Ile
1               5

<210> SEQ ID NO 479
<211> LENGTH: 8
<212> TYPE: PRT
<213> ORGANISM: Artificial Sequence
<220> FEATURE:
<223> OTHER INFORMATION: Recombinant peptide

<400> SEQUENCE: 479

Ala Thr Glu Lys Pro Tyr Val Val
1               5

<210> SEQ ID NO 480
<211> LENGTH: 8
<212> TYPE: PRT
<213> ORGANISM: Artificial Sequence
<220> FEATURE:
```

```
<223> OTHER INFORMATION: Recombinant peptide

<400> SEQUENCE: 480

Ala Thr Glu Lys Pro Trp Ile Leu
1               5

<210> SEQ ID NO 481
<211> LENGTH: 8
<212> TYPE: PRT
<213> ORGANISM: Artificial Sequence
<220> FEATURE:
<223> OTHER INFORMATION: Recombinant peptide

<400> SEQUENCE: 481

Ala Thr Glu Lys Pro Trp Ile Ile
1               5

<210> SEQ ID NO 482
<211> LENGTH: 8
<212> TYPE: PRT
<213> ORGANISM: Artificial Sequence
<220> FEATURE:
<223> OTHER INFORMATION: Recombinant peptide

<400> SEQUENCE: 482

Ala Thr Glu Lys Pro Trp Ile Val
1               5

<210> SEQ ID NO 483
<211> LENGTH: 8
<212> TYPE: PRT
<213> ORGANISM: Artificial Sequence
<220> FEATURE:
<223> OTHER INFORMATION: Recombinant peptide

<400> SEQUENCE: 483

Ala Thr Glu Lys Pro Trp Leu Leu
1               5

<210> SEQ ID NO 484
<211> LENGTH: 8
<212> TYPE: PRT
<213> ORGANISM: Artificial Sequence
<220> FEATURE:
<223> OTHER INFORMATION: Recombinant peptide

<400> SEQUENCE: 484

Ala Thr Glu Lys Pro Trp Leu Ile
1               5

<210> SEQ ID NO 485
<211> LENGTH: 8
<212> TYPE: PRT
<213> ORGANISM: Artificial Sequence
<220> FEATURE:
<223> OTHER INFORMATION: Recombinant peptide

<400> SEQUENCE: 485

Ala Thr Glu Lys Pro Trp Leu Val
1               5

<210> SEQ ID NO 486
<211> LENGTH: 8
<212> TYPE: PRT
<213> ORGANISM: Artificial Sequence
<220> FEATURE:
<223> OTHER INFORMATION: Recombinant peptide
```

```
<400> SEQUENCE: 486

Ala Thr Glu Lys Pro Trp Val Leu
1               5

<210> SEQ ID NO 487
<211> LENGTH: 8
<212> TYPE: PRT
<213> ORGANISM: Artificial Sequence
<220> FEATURE:
<223> OTHER INFORMATION: Recombinant peptide

<400> SEQUENCE: 487

Ala Thr Glu Lys Pro Trp Val Ile
1               5

<210> SEQ ID NO 488
<211> LENGTH: 8
<212> TYPE: PRT
<213> ORGANISM: Artificial Sequence
<220> FEATURE:
<223> OTHER INFORMATION: Recombinant peptide

<400> SEQUENCE: 488

Ala Thr Glu Lys Pro Trp Val Val
1               5

<210> SEQ ID NO 489
<211> LENGTH: 8
<212> TYPE: PRT
<213> ORGANISM: Artificial Sequence
<220> FEATURE:
<223> OTHER INFORMATION: Recombinant peptide

<400> SEQUENCE: 489

Ala Thr Glu Arg Pro Tyr Ile Leu
1               5

<210> SEQ ID NO 490
<211> LENGTH: 8
<212> TYPE: PRT
<213> ORGANISM: Artificial Sequence
<220> FEATURE:
<223> OTHER INFORMATION: Recombinant peptide

<400> SEQUENCE: 490

Ala Thr Glu Arg Pro Tyr Ile Ile
1               5

<210> SEQ ID NO 491
<211> LENGTH: 8
<212> TYPE: PRT
<213> ORGANISM: Artificial Sequence
<220> FEATURE:
<223> OTHER INFORMATION: Recombinant peptide

<400> SEQUENCE: 491

Ala Thr Glu Arg Pro Tyr Ile Val
1               5

<210> SEQ ID NO 492
<211> LENGTH: 8
<212> TYPE: PRT
<213> ORGANISM: Artificial Sequence
<220> FEATURE:
<223> OTHER INFORMATION: Recombinant peptide
```

```
<400> SEQUENCE: 492

Ala Thr Glu Arg Pro Tyr Leu Leu
1               5

<210> SEQ ID NO 493
<211> LENGTH: 8
<212> TYPE: PRT
<213> ORGANISM: Artificial Sequence
<220> FEATURE:
<223> OTHER INFORMATION: Recombinant peptide

<400> SEQUENCE: 493

Ala Thr Glu Arg Pro Tyr Leu Ile
1               5

<210> SEQ ID NO 494
<211> LENGTH: 8
<212> TYPE: PRT
<213> ORGANISM: Artificial Sequence
<220> FEATURE:
<223> OTHER INFORMATION: Recombinant peptide

<400> SEQUENCE: 494

Ala Thr Glu Arg Pro Tyr Leu Val
1               5

<210> SEQ ID NO 495
<211> LENGTH: 8
<212> TYPE: PRT
<213> ORGANISM: Artificial Sequence
<220> FEATURE:
<223> OTHER INFORMATION: Recombinant peptide

<400> SEQUENCE: 495

Ala Thr Glu Arg Pro Tyr Val Leu
1               5

<210> SEQ ID NO 496
<211> LENGTH: 8
<212> TYPE: PRT
<213> ORGANISM: Artificial Sequence
<220> FEATURE:
<223> OTHER INFORMATION: Recombinant peptide

<400> SEQUENCE: 496

Ala Thr Glu Arg Pro Tyr Val Ile
1               5

<210> SEQ ID NO 497
<211> LENGTH: 8
<212> TYPE: PRT
<213> ORGANISM: Artificial Sequence
<220> FEATURE:
<223> OTHER INFORMATION: Recombinant peptide

<400> SEQUENCE: 497

Ala Thr Glu Arg Pro Tyr Val Val
1               5

<210> SEQ ID NO 498
<211> LENGTH: 8
<212> TYPE: PRT
<213> ORGANISM: Artificial Sequence
<220> FEATURE:
<223> OTHER INFORMATION: Recombinant peptide

<400> SEQUENCE: 498
```

Ala Thr Glu Arg Pro Trp Ile Leu
1               5

<210> SEQ ID NO 499
<211> LENGTH: 8
<212> TYPE: PRT
<213> ORGANISM: Artificial Sequence
<220> FEATURE:
<223> OTHER INFORMATION: Recombinant peptide

<400> SEQUENCE: 499

Ala Thr Glu Arg Pro Trp Ile Ile
1               5

<210> SEQ ID NO 500
<211> LENGTH: 8
<212> TYPE: PRT
<213> ORGANISM: Artificial Sequence
<220> FEATURE:
<223> OTHER INFORMATION: Recombinant peptide

<400> SEQUENCE: 500

Ala Thr Glu Arg Pro Trp Ile Val
1               5

<210> SEQ ID NO 501
<211> LENGTH: 8
<212> TYPE: PRT
<213> ORGANISM: Artificial Sequence
<220> FEATURE:
<223> OTHER INFORMATION: Recombinant peptide

<400> SEQUENCE: 501

Ala Thr Glu Arg Pro Trp Leu Leu
1               5

<210> SEQ ID NO 502
<211> LENGTH: 8
<212> TYPE: PRT
<213> ORGANISM: Artificial Sequence
<220> FEATURE:
<223> OTHER INFORMATION: Recombinant peptide

<400> SEQUENCE: 502

Ala Thr Glu Arg Pro Trp Leu Ile
1               5

<210> SEQ ID NO 503
<211> LENGTH: 8
<212> TYPE: PRT
<213> ORGANISM: Artificial Sequence
<220> FEATURE:
<223> OTHER INFORMATION: Recombinant peptide

<400> SEQUENCE: 503

Ala Thr Glu Arg Pro Trp Leu Val
1               5

<210> SEQ ID NO 504
<211> LENGTH: 8
<212> TYPE: PRT
<213> ORGANISM: Artificial Sequence
<220> FEATURE:
<223> OTHER INFORMATION: Recombinant peptide

<400> SEQUENCE: 504

```
Ala Thr Glu Arg Pro Trp Val Leu
1               5

<210> SEQ ID NO 505
<211> LENGTH: 8
<212> TYPE: PRT
<213> ORGANISM: Artificial Sequence
<220> FEATURE:
<223> OTHER INFORMATION: Recombinant peptide

<400> SEQUENCE: 505

Ala Thr Glu Arg Pro Trp Val Ile
1               5

<210> SEQ ID NO 506
<211> LENGTH: 8
<212> TYPE: PRT
<213> ORGANISM: Artificial Sequence
<220> FEATURE:
<223> OTHER INFORMATION: Recombinant peptide

<400> SEQUENCE: 506

Ala Thr Glu Arg Pro Trp Val Val
1               5

<210> SEQ ID NO 507
<211> LENGTH: 8
<212> TYPE: PRT
<213> ORGANISM: Artificial Sequence
<220> FEATURE:
<223> OTHER INFORMATION: Recombinant peptide

<400> SEQUENCE: 507

Leu Ser Asp Lys Pro Tyr Ile Leu
1               5

<210> SEQ ID NO 508
<211> LENGTH: 8
<212> TYPE: PRT
<213> ORGANISM: Artificial Sequence
<220> FEATURE:
<223> OTHER INFORMATION: Recombinant peptide

<400> SEQUENCE: 508

Leu Ser Asp Lys Pro Tyr Ile Ile
1               5

<210> SEQ ID NO 509
<211> LENGTH: 8
<212> TYPE: PRT
<213> ORGANISM: Artificial Sequence
<220> FEATURE:
<223> OTHER INFORMATION: Recombinant peptide

<400> SEQUENCE: 509

Leu Ser Asp Lys Pro Tyr Ile Val
1               5

<210> SEQ ID NO 510
<211> LENGTH: 8
<212> TYPE: PRT
<213> ORGANISM: Artificial Sequence
<220> FEATURE:
<223> OTHER INFORMATION: Recombinant peptide

<400> SEQUENCE: 510

Leu Ser Asp Lys Pro Tyr Leu Leu
```

```
1               5

<210> SEQ ID NO 511
<211> LENGTH: 8
<212> TYPE: PRT
<213> ORGANISM: Artificial Sequence
<220> FEATURE:
<223> OTHER INFORMATION: Recombinant peptide

<400> SEQUENCE: 511

Leu Ser Asp Lys Pro Tyr Leu Ile
1               5

<210> SEQ ID NO 512
<211> LENGTH: 8
<212> TYPE: PRT
<213> ORGANISM: Artificial Sequence
<220> FEATURE:
<223> OTHER INFORMATION: Recombinant peptide

<400> SEQUENCE: 512

Leu Ser Asp Lys Pro Tyr Leu Val
1               5

<210> SEQ ID NO 513
<211> LENGTH: 8
<212> TYPE: PRT
<213> ORGANISM: Artificial Sequence
<220> FEATURE:
<223> OTHER INFORMATION: Recombinant peptide

<400> SEQUENCE: 513

Leu Ser Asp Lys Pro Tyr Val Leu
1               5

<210> SEQ ID NO 514
<211> LENGTH: 8
<212> TYPE: PRT
<213> ORGANISM: Artificial Sequence
<220> FEATURE:
<223> OTHER INFORMATION: Recombinant peptide

<400> SEQUENCE: 514

Leu Ser Asp Lys Pro Tyr Val Ile
1               5

<210> SEQ ID NO 515
<211> LENGTH: 8
<212> TYPE: PRT
<213> ORGANISM: Artificial Sequence
<220> FEATURE:
<223> OTHER INFORMATION: Recombinant peptide

<400> SEQUENCE: 515

Leu Ser Asp Lys Pro Tyr Val Val
1               5

<210> SEQ ID NO 516
<211> LENGTH: 8
<212> TYPE: PRT
<213> ORGANISM: Artificial Sequence
<220> FEATURE:
<223> OTHER INFORMATION: Recombinant peptide

<400> SEQUENCE: 516

Leu Ser Asp Lys Pro Trp Ile Leu
1               5
```

```
<210> SEQ ID NO 517
<211> LENGTH: 8
<212> TYPE: PRT
<213> ORGANISM: Artificial Sequence
<220> FEATURE:
<223> OTHER INFORMATION: Recombinant peptide

<400> SEQUENCE: 517

Leu Ser Asp Lys Pro Trp Ile Ile
1               5

<210> SEQ ID NO 518
<211> LENGTH: 8
<212> TYPE: PRT
<213> ORGANISM: Artificial Sequence
<220> FEATURE:
<223> OTHER INFORMATION: Recombinant peptide

<400> SEQUENCE: 518

Leu Ser Asp Lys Pro Trp Ile Val
1               5

<210> SEQ ID NO 519
<211> LENGTH: 8
<212> TYPE: PRT
<213> ORGANISM: Artificial Sequence
<220> FEATURE:
<223> OTHER INFORMATION: Recombinant peptide

<400> SEQUENCE: 519

Leu Ser Asp Lys Pro Trp Leu Leu
1               5

<210> SEQ ID NO 520
<211> LENGTH: 8
<212> TYPE: PRT
<213> ORGANISM: Artificial Sequence
<220> FEATURE:
<223> OTHER INFORMATION: Recombinant peptide

<400> SEQUENCE: 520

Leu Ser Asp Lys Pro Trp Leu Ile
1               5

<210> SEQ ID NO 521
<211> LENGTH: 8
<212> TYPE: PRT
<213> ORGANISM: Artificial Sequence
<220> FEATURE:
<223> OTHER INFORMATION: Recombinant peptide

<400> SEQUENCE: 521

Leu Ser Asp Lys Pro Trp Leu Val
1               5

<210> SEQ ID NO 522
<211> LENGTH: 8
<212> TYPE: PRT
<213> ORGANISM: Artificial Sequence
<220> FEATURE:
<223> OTHER INFORMATION: Recombinant peptide

<400> SEQUENCE: 522

Leu Ser Asp Lys Pro Trp Val Leu
1               5
```

```
<210> SEQ ID NO 523
<211> LENGTH: 8
<212> TYPE: PRT
<213> ORGANISM: Artificial Sequence
<220> FEATURE:
<223> OTHER INFORMATION: Recombinant peptide

<400> SEQUENCE: 523

Leu Ser Asp Lys Pro Trp Val Ile
1               5

<210> SEQ ID NO 524
<211> LENGTH: 8
<212> TYPE: PRT
<213> ORGANISM: Artificial Sequence
<220> FEATURE:
<223> OTHER INFORMATION: Recombinant peptide

<400> SEQUENCE: 524

Leu Ser Asp Lys Pro Trp Val Val
1               5

<210> SEQ ID NO 525
<211> LENGTH: 8
<212> TYPE: PRT
<213> ORGANISM: Artificial Sequence
<220> FEATURE:
<223> OTHER INFORMATION: Recombinant peptide

<400> SEQUENCE: 525

Leu Ser Asp Arg Pro Tyr Ile Leu
1               5

<210> SEQ ID NO 526
<211> LENGTH: 8
<212> TYPE: PRT
<213> ORGANISM: Artificial Sequence
<220> FEATURE:
<223> OTHER INFORMATION: Recombinant peptide

<400> SEQUENCE: 526

Leu Ser Asp Arg Pro Tyr Ile Ile
1               5

<210> SEQ ID NO 527
<211> LENGTH: 8
<212> TYPE: PRT
<213> ORGANISM: Artificial Sequence
<220> FEATURE:
<223> OTHER INFORMATION: Recombinant peptide

<400> SEQUENCE: 527

Leu Ser Asp Arg Pro Tyr Ile Val
1               5

<210> SEQ ID NO 528
<211> LENGTH: 8
<212> TYPE: PRT
<213> ORGANISM: Artificial Sequence
<220> FEATURE:
<223> OTHER INFORMATION: Recombinant peptide

<400> SEQUENCE: 528

Leu Ser Asp Arg Pro Tyr Leu Leu
1               5
```

```
<210> SEQ ID NO 529
<211> LENGTH: 8
<212> TYPE: PRT
<213> ORGANISM: Artificial Sequence
<220> FEATURE:
<223> OTHER INFORMATION: Recombinant peptide

<400> SEQUENCE: 529

Leu Ser Asp Arg Pro Tyr Leu Ile
1               5

<210> SEQ ID NO 530
<211> LENGTH: 8
<212> TYPE: PRT
<213> ORGANISM: Artificial Sequence
<220> FEATURE:
<223> OTHER INFORMATION: Recombinant peptide

<400> SEQUENCE: 530

Leu Ser Asp Arg Pro Tyr Leu Val
1               5

<210> SEQ ID NO 531
<211> LENGTH: 8
<212> TYPE: PRT
<213> ORGANISM: Artificial Sequence
<220> FEATURE:
<223> OTHER INFORMATION: Recombinant peptide

<400> SEQUENCE: 531

Leu Ser Asp Arg Pro Tyr Val Leu
1               5

<210> SEQ ID NO 532
<211> LENGTH: 8
<212> TYPE: PRT
<213> ORGANISM: Artificial Sequence
<220> FEATURE:
<223> OTHER INFORMATION: Recombinant peptide

<400> SEQUENCE: 532

Leu Ser Asp Arg Pro Tyr Val Ile
1               5

<210> SEQ ID NO 533
<211> LENGTH: 8
<212> TYPE: PRT
<213> ORGANISM: Artificial Sequence
<220> FEATURE:
<223> OTHER INFORMATION: Recombinant peptide

<400> SEQUENCE: 533

Leu Ser Asp Arg Pro Tyr Val Val
1               5

<210> SEQ ID NO 534
<211> LENGTH: 8
<212> TYPE: PRT
<213> ORGANISM: Artificial Sequence
<220> FEATURE:
<223> OTHER INFORMATION: Recombinant peptide

<400> SEQUENCE: 534

Leu Ser Asp Arg Pro Trp Ile Leu
1               5

<210> SEQ ID NO 535
```

```
<211> LENGTH: 8
<212> TYPE: PRT
<213> ORGANISM: Artificial Sequence
<220> FEATURE:
<223> OTHER INFORMATION: Recombinant peptide

<400> SEQUENCE: 535

Leu Ser Asp Arg Pro Trp Ile Ile
1               5

<210> SEQ ID NO 536
<211> LENGTH: 8
<212> TYPE: PRT
<213> ORGANISM: Artificial Sequence
<220> FEATURE:
<223> OTHER INFORMATION: Recombinant peptide

<400> SEQUENCE: 536

Leu Ser Asp Arg Pro Trp Ile Val
1               5

<210> SEQ ID NO 537
<211> LENGTH: 8
<212> TYPE: PRT
<213> ORGANISM: Artificial Sequence
<220> FEATURE:
<223> OTHER INFORMATION: Recombinant peptide

<400> SEQUENCE: 537

Leu Ser Asp Arg Pro Trp Leu Leu
1               5

<210> SEQ ID NO 538
<211> LENGTH: 8
<212> TYPE: PRT
<213> ORGANISM: Artificial Sequence
<220> FEATURE:
<223> OTHER INFORMATION: Recombinant peptide

<400> SEQUENCE: 538

Leu Ser Asp Arg Pro Trp Leu Ile
1               5

<210> SEQ ID NO 539
<211> LENGTH: 8
<212> TYPE: PRT
<213> ORGANISM: Artificial Sequence
<220> FEATURE:
<223> OTHER INFORMATION: Recombinant peptide

<400> SEQUENCE: 539

Leu Ser Asp Arg Pro Trp Leu Val
1               5

<210> SEQ ID NO 540
<211> LENGTH: 8
<212> TYPE: PRT
<213> ORGANISM: Artificial Sequence
<220> FEATURE:
<223> OTHER INFORMATION: Recombinant peptide

<400> SEQUENCE: 540

Leu Ser Asp Arg Pro Trp Val Leu
1               5

<210> SEQ ID NO 541
<211> LENGTH: 8
```

```
<212> TYPE: PRT
<213> ORGANISM: Artificial Sequence
<220> FEATURE:
<223> OTHER INFORMATION: Recombinant peptide

<400> SEQUENCE: 541

Leu Ser Asp Arg Pro Trp Val Ile
1               5

<210> SEQ ID NO 542
<211> LENGTH: 8
<212> TYPE: PRT
<213> ORGANISM: Artificial Sequence
<220> FEATURE:
<223> OTHER INFORMATION: Recombinant peptide

<400> SEQUENCE: 542

Leu Ser Asp Arg Pro Trp Val Val
1               5

<210> SEQ ID NO 543
<211> LENGTH: 8
<212> TYPE: PRT
<213> ORGANISM: Artificial Sequence
<220> FEATURE:
<223> OTHER INFORMATION: Recombinant peptide

<400> SEQUENCE: 543

Leu Ser Glu Lys Pro Tyr Ile Leu
1               5

<210> SEQ ID NO 544
<211> LENGTH: 8
<212> TYPE: PRT
<213> ORGANISM: Artificial Sequence
<220> FEATURE:
<223> OTHER INFORMATION: Recombinant peptide

<400> SEQUENCE: 544

Leu Ser Glu Lys Pro Tyr Ile Ile
1               5

<210> SEQ ID NO 545
<211> LENGTH: 8
<212> TYPE: PRT
<213> ORGANISM: Artificial Sequence
<220> FEATURE:
<223> OTHER INFORMATION: Recombinant peptide

<400> SEQUENCE: 545

Leu Ser Glu Lys Pro Tyr Ile Val
1               5

<210> SEQ ID NO 546
<211> LENGTH: 8
<212> TYPE: PRT
<213> ORGANISM: Artificial Sequence
<220> FEATURE:
<223> OTHER INFORMATION: Recombinant peptide

<400> SEQUENCE: 546

Leu Ser Glu Lys Pro Tyr Leu Leu
1               5

<210> SEQ ID NO 547
<211> LENGTH: 8
<212> TYPE: PRT
```

```
<213> ORGANISM: Artificial Sequence
<220> FEATURE:
<223> OTHER INFORMATION: Recombinant peptide

<400> SEQUENCE: 547

Leu Ser Glu Lys Pro Tyr Leu Ile
1               5

<210> SEQ ID NO 548
<211> LENGTH: 8
<212> TYPE: PRT
<213> ORGANISM: Artificial Sequence
<220> FEATURE:
<223> OTHER INFORMATION: Recombinant peptide

<400> SEQUENCE: 548

Leu Ser Glu Lys Pro Tyr Leu Val
1               5

<210> SEQ ID NO 549
<211> LENGTH: 8
<212> TYPE: PRT
<213> ORGANISM: Artificial Sequence
<220> FEATURE:
<223> OTHER INFORMATION: Recombinant peptide

<400> SEQUENCE: 549

Leu Ser Glu Lys Pro Tyr Val Leu
1               5

<210> SEQ ID NO 550
<211> LENGTH: 8
<212> TYPE: PRT
<213> ORGANISM: Artificial Sequence
<220> FEATURE:
<223> OTHER INFORMATION: Recombinant peptide

<400> SEQUENCE: 550

Leu Ser Glu Lys Pro Tyr Val Ile
1               5

<210> SEQ ID NO 551
<211> LENGTH: 8
<212> TYPE: PRT
<213> ORGANISM: Artificial Sequence
<220> FEATURE:
<223> OTHER INFORMATION: Recombinant peptide

<400> SEQUENCE: 551

Leu Ser Glu Lys Pro Tyr Val Val
1               5

<210> SEQ ID NO 552
<211> LENGTH: 8
<212> TYPE: PRT
<213> ORGANISM: Artificial Sequence
<220> FEATURE:
<223> OTHER INFORMATION: Recombinant peptide

<400> SEQUENCE: 552

Leu Ser Glu Lys Pro Trp Ile Leu
1               5

<210> SEQ ID NO 553
<211> LENGTH: 8
<212> TYPE: PRT
<213> ORGANISM: Artificial Sequence
```

```
<220> FEATURE:
<223> OTHER INFORMATION: Recombinant peptide

<400> SEQUENCE: 553

Leu Ser Glu Lys Pro Trp Ile Ile
1               5

<210> SEQ ID NO 554
<211> LENGTH: 8
<212> TYPE: PRT
<213> ORGANISM: Artificial Sequence
<220> FEATURE:
<223> OTHER INFORMATION: Recombinant peptide

<400> SEQUENCE: 554

Leu Ser Glu Lys Pro Trp Ile Val
1               5

<210> SEQ ID NO 555
<211> LENGTH: 8
<212> TYPE: PRT
<213> ORGANISM: Artificial Sequence
<220> FEATURE:
<223> OTHER INFORMATION: Recombinant peptide

<400> SEQUENCE: 555

Leu Ser Glu Lys Pro Trp Leu Leu
1               5

<210> SEQ ID NO 556
<211> LENGTH: 8
<212> TYPE: PRT
<213> ORGANISM: Artificial Sequence
<220> FEATURE:
<223> OTHER INFORMATION: Recombinant peptide

<400> SEQUENCE: 556

Leu Ser Glu Lys Pro Trp Leu Ile
1               5

<210> SEQ ID NO 557
<211> LENGTH: 8
<212> TYPE: PRT
<213> ORGANISM: Artificial Sequence
<220> FEATURE:
<223> OTHER INFORMATION: Recombinant peptide

<400> SEQUENCE: 557

Leu Ser Glu Lys Pro Trp Leu Val
1               5

<210> SEQ ID NO 558
<211> LENGTH: 8
<212> TYPE: PRT
<213> ORGANISM: Artificial Sequence
<220> FEATURE:
<223> OTHER INFORMATION: Recombinant peptide

<400> SEQUENCE: 558

Leu Ser Glu Lys Pro Trp Val Leu
1               5

<210> SEQ ID NO 559
<211> LENGTH: 8
<212> TYPE: PRT
<213> ORGANISM: Artificial Sequence
<220> FEATURE:
```

```
<223> OTHER INFORMATION: Recombinant peptide

<400> SEQUENCE: 559

Leu Ser Glu Lys Pro Trp Val Ile
1               5

<210> SEQ ID NO 560
<211> LENGTH: 8
<212> TYPE: PRT
<213> ORGANISM: Artificial Sequence
<220> FEATURE:
<223> OTHER INFORMATION: Recombinant peptide

<400> SEQUENCE: 560

Leu Ser Glu Lys Pro Trp Val Val
1               5

<210> SEQ ID NO 561
<211> LENGTH: 8
<212> TYPE: PRT
<213> ORGANISM: Artificial Sequence
<220> FEATURE:
<223> OTHER INFORMATION: Recombinant peptide

<400> SEQUENCE: 561

Leu Ser Glu Arg Pro Tyr Ile Leu
1               5

<210> SEQ ID NO 562
<211> LENGTH: 8
<212> TYPE: PRT
<213> ORGANISM: Artificial Sequence
<220> FEATURE:
<223> OTHER INFORMATION: Recombinant peptide

<400> SEQUENCE: 562

Leu Ser Glu Arg Pro Tyr Ile Ile
1               5

<210> SEQ ID NO 563
<211> LENGTH: 8
<212> TYPE: PRT
<213> ORGANISM: Artificial Sequence
<220> FEATURE:
<223> OTHER INFORMATION: Recombinant peptide

<400> SEQUENCE: 563

Leu Ser Glu Arg Pro Tyr Ile Val
1               5

<210> SEQ ID NO 564
<211> LENGTH: 8
<212> TYPE: PRT
<213> ORGANISM: Artificial Sequence
<220> FEATURE:
<223> OTHER INFORMATION: Recombinant peptide

<400> SEQUENCE: 564

Leu Ser Glu Arg Pro Tyr Leu Leu
1               5

<210> SEQ ID NO 565
<211> LENGTH: 8
<212> TYPE: PRT
<213> ORGANISM: Artificial Sequence
<220> FEATURE:
<223> OTHER INFORMATION: Recombinant peptide
```

<400> SEQUENCE: 565

Leu Ser Glu Arg Pro Tyr Leu Ile
1               5

<210> SEQ ID NO 566
<211> LENGTH: 8
<212> TYPE: PRT
<213> ORGANISM: Artificial Sequence
<220> FEATURE:
<223> OTHER INFORMATION: Recombinant peptide

<400> SEQUENCE: 566

Leu Ser Glu Arg Pro Tyr Leu Val
1               5

<210> SEQ ID NO 567
<211> LENGTH: 8
<212> TYPE: PRT
<213> ORGANISM: Artificial Sequence
<220> FEATURE:
<223> OTHER INFORMATION: Recombinant peptide

<400> SEQUENCE: 567

Leu Ser Glu Arg Pro Tyr Val Leu
1               5

<210> SEQ ID NO 568
<211> LENGTH: 8
<212> TYPE: PRT
<213> ORGANISM: Artificial Sequence
<220> FEATURE:
<223> OTHER INFORMATION: Recombinant peptide

<400> SEQUENCE: 568

Leu Ser Glu Arg Pro Tyr Val Ile
1               5

<210> SEQ ID NO 569
<211> LENGTH: 8
<212> TYPE: PRT
<213> ORGANISM: Artificial Sequence
<220> FEATURE:
<223> OTHER INFORMATION: Recombinant peptide

<400> SEQUENCE: 569

Leu Ser Glu Arg Pro Tyr Val Val
1               5

<210> SEQ ID NO 570
<211> LENGTH: 8
<212> TYPE: PRT
<213> ORGANISM: Artificial Sequence
<220> FEATURE:
<223> OTHER INFORMATION: Recombinant peptide

<400> SEQUENCE: 570

Leu Ser Glu Arg Pro Trp Ile Leu
1               5

<210> SEQ ID NO 571
<211> LENGTH: 8
<212> TYPE: PRT
<213> ORGANISM: Artificial Sequence
<220> FEATURE:
<223> OTHER INFORMATION: Recombinant peptide

```
<400> SEQUENCE: 571

Leu Ser Glu Arg Pro Trp Ile Ile
1               5

<210> SEQ ID NO 572
<211> LENGTH: 8
<212> TYPE: PRT
<213> ORGANISM: Artificial Sequence
<220> FEATURE:
<223> OTHER INFORMATION: Recombinant peptide

<400> SEQUENCE: 572

Leu Ser Glu Arg Pro Trp Ile Val
1               5

<210> SEQ ID NO 573
<211> LENGTH: 8
<212> TYPE: PRT
<213> ORGANISM: Artificial Sequence
<220> FEATURE:
<223> OTHER INFORMATION: Recombinant peptide

<400> SEQUENCE: 573

Leu Ser Glu Arg Pro Trp Leu Leu
1               5

<210> SEQ ID NO 574
<211> LENGTH: 8
<212> TYPE: PRT
<213> ORGANISM: Artificial Sequence
<220> FEATURE:
<223> OTHER INFORMATION: Recombinant peptide

<400> SEQUENCE: 574

Leu Ser Glu Arg Pro Trp Leu Ile
1               5

<210> SEQ ID NO 575
<211> LENGTH: 8
<212> TYPE: PRT
<213> ORGANISM: Artificial Sequence
<220> FEATURE:
<223> OTHER INFORMATION: Recombinant peptide

<400> SEQUENCE: 575

Leu Ser Glu Arg Pro Trp Leu Val
1               5

<210> SEQ ID NO 576
<211> LENGTH: 8
<212> TYPE: PRT
<213> ORGANISM: Artificial Sequence
<220> FEATURE:
<223> OTHER INFORMATION: Recombinant peptide

<400> SEQUENCE: 576

Leu Ser Glu Arg Pro Trp Val Leu
1               5

<210> SEQ ID NO 577
<211> LENGTH: 8
<212> TYPE: PRT
<213> ORGANISM: Artificial Sequence
<220> FEATURE:
<223> OTHER INFORMATION: Recombinant peptide

<400> SEQUENCE: 577
```

Leu Ser Glu Arg Pro Trp Val Ile
1               5

<210> SEQ ID NO 578
<211> LENGTH: 8
<212> TYPE: PRT
<213> ORGANISM: Artificial Sequence
<220> FEATURE:
<223> OTHER INFORMATION: Recombinant peptide

<400> SEQUENCE: 578

Leu Ser Glu Arg Pro Trp Val Val
1               5

<210> SEQ ID NO 579
<211> LENGTH: 8
<212> TYPE: PRT
<213> ORGANISM: Artificial Sequence
<220> FEATURE:
<223> OTHER INFORMATION: Recombinant peptide

<400> SEQUENCE: 579

Leu Thr Asp Lys Pro Tyr Ile Leu
1               5

<210> SEQ ID NO 580
<211> LENGTH: 8
<212> TYPE: PRT
<213> ORGANISM: Artificial Sequence
<220> FEATURE:
<223> OTHER INFORMATION: Recombinant peptide

<400> SEQUENCE: 580

Leu Thr Asp Lys Pro Tyr Ile Ile
1               5

<210> SEQ ID NO 581
<211> LENGTH: 8
<212> TYPE: PRT
<213> ORGANISM: Artificial Sequence
<220> FEATURE:
<223> OTHER INFORMATION: Recombinant peptide

<400> SEQUENCE: 581

Leu Thr Asp Lys Pro Tyr Ile Val
1               5

<210> SEQ ID NO 582
<211> LENGTH: 8
<212> TYPE: PRT
<213> ORGANISM: Artificial Sequence
<220> FEATURE:
<223> OTHER INFORMATION: Recombinant peptide

<400> SEQUENCE: 582

Leu Thr Asp Lys Pro Tyr Leu Leu
1               5

<210> SEQ ID NO 583
<211> LENGTH: 8
<212> TYPE: PRT
<213> ORGANISM: Artificial Sequence
<220> FEATURE:
<223> OTHER INFORMATION: Recombinant peptide

<400> SEQUENCE: 583

```
Leu Thr Asp Lys Pro Tyr Leu Ile
1               5

<210> SEQ ID NO 584
<211> LENGTH: 8
<212> TYPE: PRT
<213> ORGANISM: Artificial Sequence
<220> FEATURE:
<223> OTHER INFORMATION: Recombinant peptide

<400> SEQUENCE: 584

Leu Thr Asp Lys Pro Tyr Leu Val
1               5

<210> SEQ ID NO 585
<211> LENGTH: 8
<212> TYPE: PRT
<213> ORGANISM: Artificial Sequence
<220> FEATURE:
<223> OTHER INFORMATION: Recombinant peptide

<400> SEQUENCE: 585

Leu Thr Asp Lys Pro Tyr Val Leu
1               5

<210> SEQ ID NO 586
<211> LENGTH: 8
<212> TYPE: PRT
<213> ORGANISM: Artificial Sequence
<220> FEATURE:
<223> OTHER INFORMATION: Recombinant peptide

<400> SEQUENCE: 586

Leu Thr Asp Lys Pro Tyr Val Ile
1               5

<210> SEQ ID NO 587
<211> LENGTH: 8
<212> TYPE: PRT
<213> ORGANISM: Artificial Sequence
<220> FEATURE:
<223> OTHER INFORMATION: Recombinant peptide

<400> SEQUENCE: 587

Leu Thr Asp Lys Pro Tyr Val Val
1               5

<210> SEQ ID NO 588
<211> LENGTH: 8
<212> TYPE: PRT
<213> ORGANISM: Artificial Sequence
<220> FEATURE:
<223> OTHER INFORMATION: Recombinant peptide

<400> SEQUENCE: 588

Leu Thr Asp Lys Pro Trp Ile Leu
1               5

<210> SEQ ID NO 589
<211> LENGTH: 8
<212> TYPE: PRT
<213> ORGANISM: Artificial Sequence
<220> FEATURE:
<223> OTHER INFORMATION: Recombinant peptide

<400> SEQUENCE: 589

Leu Thr Asp Lys Pro Trp Ile Ile
```

```
<210> SEQ ID NO 590
<211> LENGTH: 8
<212> TYPE: PRT
<213> ORGANISM: Artificial Sequence
<220> FEATURE:
<223> OTHER INFORMATION: Recombinant peptide

<400> SEQUENCE: 590

Leu Thr Asp Lys Pro Trp Ile Val
1               5

<210> SEQ ID NO 591
<211> LENGTH: 8
<212> TYPE: PRT
<213> ORGANISM: Artificial Sequence
<220> FEATURE:
<223> OTHER INFORMATION: Recombinant peptide

<400> SEQUENCE: 591

Leu Thr Asp Lys Pro Trp Leu Leu
1               5

<210> SEQ ID NO 592
<211> LENGTH: 8
<212> TYPE: PRT
<213> ORGANISM: Artificial Sequence
<220> FEATURE:
<223> OTHER INFORMATION: Recombinant peptide

<400> SEQUENCE: 592

Leu Thr Asp Lys Pro Trp Leu Ile
1               5

<210> SEQ ID NO 593
<211> LENGTH: 8
<212> TYPE: PRT
<213> ORGANISM: Artificial Sequence
<220> FEATURE:
<223> OTHER INFORMATION: Recombinant peptide

<400> SEQUENCE: 593

Leu Thr Asp Lys Pro Trp Leu Val
1               5

<210> SEQ ID NO 594
<211> LENGTH: 8
<212> TYPE: PRT
<213> ORGANISM: Artificial Sequence
<220> FEATURE:
<223> OTHER INFORMATION: Recombinant peptide

<400> SEQUENCE: 594

Leu Thr Asp Lys Pro Trp Val Leu
1               5

<210> SEQ ID NO 595
<211> LENGTH: 8
<212> TYPE: PRT
<213> ORGANISM: Artificial Sequence
<220> FEATURE:
<223> OTHER INFORMATION: Recombinant peptide

<400> SEQUENCE: 595

Leu Thr Asp Lys Pro Trp Val Ile
1               5
```

```
<210> SEQ ID NO 596
<211> LENGTH: 8
<212> TYPE: PRT
<213> ORGANISM: Artificial Sequence
<220> FEATURE:
<223> OTHER INFORMATION: Recombinant peptide

<400> SEQUENCE: 596

Leu Thr Asp Lys Pro Trp Val Val
1               5

<210> SEQ ID NO 597
<211> LENGTH: 8
<212> TYPE: PRT
<213> ORGANISM: Artificial Sequence
<220> FEATURE:
<223> OTHER INFORMATION: Recombinant peptide

<400> SEQUENCE: 597

Leu Thr Asp Arg Pro Tyr Ile Leu
1               5

<210> SEQ ID NO 598
<211> LENGTH: 8
<212> TYPE: PRT
<213> ORGANISM: Artificial Sequence
<220> FEATURE:
<223> OTHER INFORMATION: Recombinant peptide

<400> SEQUENCE: 598

Leu Thr Asp Arg Pro Tyr Ile Ile
1               5

<210> SEQ ID NO 599
<211> LENGTH: 8
<212> TYPE: PRT
<213> ORGANISM: Artificial Sequence
<220> FEATURE:
<223> OTHER INFORMATION: Recombinant peptide

<400> SEQUENCE: 599

Leu Thr Asp Arg Pro Tyr Ile Val
1               5

<210> SEQ ID NO 600
<211> LENGTH: 8
<212> TYPE: PRT
<213> ORGANISM: Artificial Sequence
<220> FEATURE:
<223> OTHER INFORMATION: Recombinant peptide

<400> SEQUENCE: 600

Leu Thr Asp Arg Pro Tyr Leu Leu
1               5

<210> SEQ ID NO 601
<211> LENGTH: 8
<212> TYPE: PRT
<213> ORGANISM: Artificial Sequence
<220> FEATURE:
<223> OTHER INFORMATION: Recombinant peptide

<400> SEQUENCE: 601

Leu Thr Asp Arg Pro Tyr Leu Ile
1               5
```

```
<210> SEQ ID NO 602
<211> LENGTH: 8
<212> TYPE: PRT
<213> ORGANISM: Artificial Sequence
<220> FEATURE:
<223> OTHER INFORMATION: Recombinant peptide

<400> SEQUENCE: 602

Leu Thr Asp Arg Pro Tyr Leu Val
1               5

<210> SEQ ID NO 603
<211> LENGTH: 8
<212> TYPE: PRT
<213> ORGANISM: Artificial Sequence
<220> FEATURE:
<223> OTHER INFORMATION: Recombinant peptide

<400> SEQUENCE: 603

Leu Thr Asp Arg Pro Tyr Val Leu
1               5

<210> SEQ ID NO 604
<211> LENGTH: 8
<212> TYPE: PRT
<213> ORGANISM: Artificial Sequence
<220> FEATURE:
<223> OTHER INFORMATION: Recombinant peptide

<400> SEQUENCE: 604

Leu Thr Asp Arg Pro Tyr Val Ile
1               5

<210> SEQ ID NO 605
<211> LENGTH: 8
<212> TYPE: PRT
<213> ORGANISM: Artificial Sequence
<220> FEATURE:
<223> OTHER INFORMATION: Recombinant peptide

<400> SEQUENCE: 605

Leu Thr Asp Arg Pro Tyr Val Val
1               5

<210> SEQ ID NO 606
<211> LENGTH: 8
<212> TYPE: PRT
<213> ORGANISM: Artificial Sequence
<220> FEATURE:
<223> OTHER INFORMATION: Recombinant peptide

<400> SEQUENCE: 606

Leu Thr Asp Arg Pro Trp Ile Leu
1               5

<210> SEQ ID NO 607
<211> LENGTH: 8
<212> TYPE: PRT
<213> ORGANISM: Artificial Sequence
<220> FEATURE:
<223> OTHER INFORMATION: Recombinant peptide

<400> SEQUENCE: 607

Leu Thr Asp Arg Pro Trp Ile Ile
1               5
```

```
<210> SEQ ID NO 608
<211> LENGTH: 8
<212> TYPE: PRT
<213> ORGANISM: Artificial Sequence
<220> FEATURE:
<223> OTHER INFORMATION: Recombinant peptide

<400> SEQUENCE: 608

Leu Thr Asp Arg Pro Trp Ile Val
1               5

<210> SEQ ID NO 609
<211> LENGTH: 8
<212> TYPE: PRT
<213> ORGANISM: Artificial Sequence
<220> FEATURE:
<223> OTHER INFORMATION: Recombinant peptide

<400> SEQUENCE: 609

Leu Thr Asp Arg Pro Trp Leu Leu
1               5

<210> SEQ ID NO 610
<211> LENGTH: 8
<212> TYPE: PRT
<213> ORGANISM: Artificial Sequence
<220> FEATURE:
<223> OTHER INFORMATION: Recombinant peptide

<400> SEQUENCE: 610

Leu Thr Asp Arg Pro Trp Leu Ile
1               5

<210> SEQ ID NO 611
<211> LENGTH: 8
<212> TYPE: PRT
<213> ORGANISM: Artificial Sequence
<220> FEATURE:
<223> OTHER INFORMATION: Recombinant peptide

<400> SEQUENCE: 611

Leu Thr Asp Arg Pro Trp Leu Val
1               5

<210> SEQ ID NO 612
<211> LENGTH: 8
<212> TYPE: PRT
<213> ORGANISM: Artificial Sequence
<220> FEATURE:
<223> OTHER INFORMATION: Recombinant peptide

<400> SEQUENCE: 612

Leu Thr Asp Arg Pro Trp Val Leu
1               5

<210> SEQ ID NO 613
<211> LENGTH: 8
<212> TYPE: PRT
<213> ORGANISM: Artificial Sequence
<220> FEATURE:
<223> OTHER INFORMATION: Recombinant peptide

<400> SEQUENCE: 613

Leu Thr Asp Arg Pro Trp Val Ile
1               5

<210> SEQ ID NO 614
```

```
<211> LENGTH: 8
<212> TYPE: PRT
<213> ORGANISM: Artificial Sequence
<220> FEATURE:
<223> OTHER INFORMATION: Recombinant peptide

<400> SEQUENCE: 614

Leu Thr Asp Arg Pro Trp Val Val
1               5

<210> SEQ ID NO 615
<211> LENGTH: 8
<212> TYPE: PRT
<213> ORGANISM: Artificial Sequence
<220> FEATURE:
<223> OTHER INFORMATION: Recombinant peptide

<400> SEQUENCE: 615

Leu Thr Glu Lys Pro Tyr Ile Leu
1               5

<210> SEQ ID NO 616
<211> LENGTH: 8
<212> TYPE: PRT
<213> ORGANISM: Artificial Sequence
<220> FEATURE:
<223> OTHER INFORMATION: Recombinant peptide

<400> SEQUENCE: 616

Leu Thr Glu Lys Pro Tyr Ile Ile
1               5

<210> SEQ ID NO 617
<211> LENGTH: 8
<212> TYPE: PRT
<213> ORGANISM: Artificial Sequence
<220> FEATURE:
<223> OTHER INFORMATION: Recombinant peptide

<400> SEQUENCE: 617

Leu Thr Glu Lys Pro Tyr Ile Val
1               5

<210> SEQ ID NO 618
<211> LENGTH: 8
<212> TYPE: PRT
<213> ORGANISM: Artificial Sequence
<220> FEATURE:
<223> OTHER INFORMATION: Recombinant peptide

<400> SEQUENCE: 618

Leu Thr Glu Lys Pro Tyr Leu Leu
1               5

<210> SEQ ID NO 619
<211> LENGTH: 8
<212> TYPE: PRT
<213> ORGANISM: Artificial Sequence
<220> FEATURE:
<223> OTHER INFORMATION: Recombinant peptide

<400> SEQUENCE: 619

Leu Thr Glu Lys Pro Tyr Leu Ile
1               5

<210> SEQ ID NO 620
<211> LENGTH: 8
```

```
<212> TYPE: PRT
<213> ORGANISM: Artificial Sequence
<220> FEATURE:
<223> OTHER INFORMATION: Recombinant peptide

<400> SEQUENCE: 620

Leu Thr Glu Lys Pro Tyr Leu Val
1               5

<210> SEQ ID NO 621
<211> LENGTH: 8
<212> TYPE: PRT
<213> ORGANISM: Artificial Sequence
<220> FEATURE:
<223> OTHER INFORMATION: Recombinant peptide

<400> SEQUENCE: 621

Leu Thr Glu Lys Pro Tyr Val Leu
1               5

<210> SEQ ID NO 622
<211> LENGTH: 8
<212> TYPE: PRT
<213> ORGANISM: Artificial Sequence
<220> FEATURE:
<223> OTHER INFORMATION: Recombinant peptide

<400> SEQUENCE: 622

Leu Thr Glu Lys Pro Tyr Val Ile
1               5

<210> SEQ ID NO 623
<211> LENGTH: 8
<212> TYPE: PRT
<213> ORGANISM: Artificial Sequence
<220> FEATURE:
<223> OTHER INFORMATION: Recombinant peptide

<400> SEQUENCE: 623

Leu Thr Glu Lys Pro Tyr Val Val
1               5

<210> SEQ ID NO 624
<211> LENGTH: 8
<212> TYPE: PRT
<213> ORGANISM: Artificial Sequence
<220> FEATURE:
<223> OTHER INFORMATION: Recombinant peptide

<400> SEQUENCE: 624

Leu Thr Glu Lys Pro Trp Ile Leu
1               5

<210> SEQ ID NO 625
<211> LENGTH: 8
<212> TYPE: PRT
<213> ORGANISM: Artificial Sequence
<220> FEATURE:
<223> OTHER INFORMATION: Recombinant peptide

<400> SEQUENCE: 625

Leu Thr Glu Lys Pro Trp Ile Ile
1               5

<210> SEQ ID NO 626
<211> LENGTH: 8
<212> TYPE: PRT
```

```
<213> ORGANISM: Artificial Sequence
<220> FEATURE:
<223> OTHER INFORMATION: Recombinant peptide

<400> SEQUENCE: 626

Leu Thr Glu Lys Pro Trp Ile Val
1               5

<210> SEQ ID NO 627
<211> LENGTH: 8
<212> TYPE: PRT
<213> ORGANISM: Artificial Sequence
<220> FEATURE:
<223> OTHER INFORMATION: Recombinant peptide

<400> SEQUENCE: 627

Leu Thr Glu Lys Pro Trp Leu Leu
1               5

<210> SEQ ID NO 628
<211> LENGTH: 8
<212> TYPE: PRT
<213> ORGANISM: Artificial Sequence
<220> FEATURE:
<223> OTHER INFORMATION: Recombinant peptide

<400> SEQUENCE: 628

Leu Thr Glu Lys Pro Trp Leu Ile
1               5

<210> SEQ ID NO 629
<211> LENGTH: 8
<212> TYPE: PRT
<213> ORGANISM: Artificial Sequence
<220> FEATURE:
<223> OTHER INFORMATION: Recombinant peptide

<400> SEQUENCE: 629

Leu Thr Glu Lys Pro Trp Leu Val
1               5

<210> SEQ ID NO 630
<211> LENGTH: 8
<212> TYPE: PRT
<213> ORGANISM: Artificial Sequence
<220> FEATURE:
<223> OTHER INFORMATION: Recombinant peptide

<400> SEQUENCE: 630

Leu Thr Glu Lys Pro Trp Val Leu
1               5

<210> SEQ ID NO 631
<211> LENGTH: 8
<212> TYPE: PRT
<213> ORGANISM: Artificial Sequence
<220> FEATURE:
<223> OTHER INFORMATION: Recombinant peptide

<400> SEQUENCE: 631

Leu Thr Glu Lys Pro Trp Val Ile
1               5

<210> SEQ ID NO 632
<211> LENGTH: 8
<212> TYPE: PRT
<213> ORGANISM: Artificial Sequence
```

```
<220> FEATURE:
<223> OTHER INFORMATION: Recombinant peptide

<400> SEQUENCE: 632

Leu Thr Glu Lys Pro Trp Val Val
1               5

<210> SEQ ID NO 633
<211> LENGTH: 8
<212> TYPE: PRT
<213> ORGANISM: Artificial Sequence
<220> FEATURE:
<223> OTHER INFORMATION: Recombinant peptide

<400> SEQUENCE: 633

Leu Thr Glu Arg Pro Tyr Ile Leu
1               5

<210> SEQ ID NO 634
<211> LENGTH: 8
<212> TYPE: PRT
<213> ORGANISM: Artificial Sequence
<220> FEATURE:
<223> OTHER INFORMATION: Recombinant peptide

<400> SEQUENCE: 634

Leu Thr Glu Arg Pro Tyr Ile Ile
1               5

<210> SEQ ID NO 635
<211> LENGTH: 8
<212> TYPE: PRT
<213> ORGANISM: Artificial Sequence
<220> FEATURE:
<223> OTHER INFORMATION: Recombinant peptide

<400> SEQUENCE: 635

Leu Thr Glu Arg Pro Tyr Ile Val
1               5

<210> SEQ ID NO 636
<211> LENGTH: 8
<212> TYPE: PRT
<213> ORGANISM: Artificial Sequence
<220> FEATURE:
<223> OTHER INFORMATION: Recombinant peptide

<400> SEQUENCE: 636

Leu Thr Glu Arg Pro Tyr Leu Leu
1               5

<210> SEQ ID NO 637
<211> LENGTH: 8
<212> TYPE: PRT
<213> ORGANISM: Artificial Sequence
<220> FEATURE:
<223> OTHER INFORMATION: Recombinant peptide

<400> SEQUENCE: 637

Leu Thr Glu Arg Pro Tyr Leu Ile
1               5

<210> SEQ ID NO 638
<211> LENGTH: 8
<212> TYPE: PRT
<213> ORGANISM: Artificial Sequence
<220> FEATURE:
```

```
<223> OTHER INFORMATION: Recombinant peptide

<400> SEQUENCE: 638

Leu Thr Glu Arg Pro Tyr Leu Val
1               5

<210> SEQ ID NO 639
<211> LENGTH: 8
<212> TYPE: PRT
<213> ORGANISM: Artificial Sequence
<220> FEATURE:
<223> OTHER INFORMATION: Recombinant peptide

<400> SEQUENCE: 639

Leu Thr Glu Arg Pro Tyr Val Leu
1               5

<210> SEQ ID NO 640
<211> LENGTH: 8
<212> TYPE: PRT
<213> ORGANISM: Artificial Sequence
<220> FEATURE:
<223> OTHER INFORMATION: Recombinant peptide

<400> SEQUENCE: 640

Leu Thr Glu Arg Pro Tyr Val Ile
1               5

<210> SEQ ID NO 641
<211> LENGTH: 8
<212> TYPE: PRT
<213> ORGANISM: Artificial Sequence
<220> FEATURE:
<223> OTHER INFORMATION: Recombinant peptide

<400> SEQUENCE: 641

Leu Thr Glu Arg Pro Tyr Val Val
1               5

<210> SEQ ID NO 642
<211> LENGTH: 8
<212> TYPE: PRT
<213> ORGANISM: Artificial Sequence
<220> FEATURE:
<223> OTHER INFORMATION: Recombinant peptide

<400> SEQUENCE: 642

Leu Thr Glu Arg Pro Trp Ile Leu
1               5

<210> SEQ ID NO 643
<211> LENGTH: 8
<212> TYPE: PRT
<213> ORGANISM: Artificial Sequence
<220> FEATURE:
<223> OTHER INFORMATION: Recombinant peptide

<400> SEQUENCE: 643

Leu Thr Glu Arg Pro Trp Ile Ile
1               5

<210> SEQ ID NO 644
<211> LENGTH: 8
<212> TYPE: PRT
<213> ORGANISM: Artificial Sequence
<220> FEATURE:
<223> OTHER INFORMATION: Recombinant peptide
```

```
<400> SEQUENCE: 644

Leu Thr Glu Arg Pro Trp Ile Val
1               5

<210> SEQ ID NO 645
<211> LENGTH: 8
<212> TYPE: PRT
<213> ORGANISM: Artificial Sequence
<220> FEATURE:
<223> OTHER INFORMATION: Recombinant peptide

<400> SEQUENCE: 645

Leu Thr Glu Arg Pro Trp Leu Leu
1               5

<210> SEQ ID NO 646
<211> LENGTH: 8
<212> TYPE: PRT
<213> ORGANISM: Artificial Sequence
<220> FEATURE:
<223> OTHER INFORMATION: Recombinant peptide

<400> SEQUENCE: 646

Leu Thr Glu Arg Pro Trp Leu Ile
1               5

<210> SEQ ID NO 647
<211> LENGTH: 8
<212> TYPE: PRT
<213> ORGANISM: Artificial Sequence
<220> FEATURE:
<223> OTHER INFORMATION: Recombinant peptide

<400> SEQUENCE: 647

Leu Thr Glu Arg Pro Trp Leu Val
1               5

<210> SEQ ID NO 648
<211> LENGTH: 8
<212> TYPE: PRT
<213> ORGANISM: Artificial Sequence
<220> FEATURE:
<223> OTHER INFORMATION: Recombinant peptide

<400> SEQUENCE: 648

Leu Thr Glu Arg Pro Trp Val Leu
1               5

<210> SEQ ID NO 649
<211> LENGTH: 8
<212> TYPE: PRT
<213> ORGANISM: Artificial Sequence
<220> FEATURE:
<223> OTHER INFORMATION: Recombinant peptide

<400> SEQUENCE: 649

Leu Thr Glu Arg Pro Trp Val Ile
1               5

<210> SEQ ID NO 650
<211> LENGTH: 8
<212> TYPE: PRT
<213> ORGANISM: Artificial Sequence
<220> FEATURE:
<223> OTHER INFORMATION: Recombinant peptide
```

<400> SEQUENCE: 650

Leu Thr Glu Arg Pro Trp Val Val
1               5

<210> SEQ ID NO 651
<211> LENGTH: 8
<212> TYPE: PRT
<213> ORGANISM: Artificial Sequence
<220> FEATURE:
<223> OTHER INFORMATION: Recombinant peptide

<400> SEQUENCE: 651

Ile Ser Asp Lys Pro Tyr Ile Leu
1               5

<210> SEQ ID NO 652
<211> LENGTH: 8
<212> TYPE: PRT
<213> ORGANISM: Artificial Sequence
<220> FEATURE:
<223> OTHER INFORMATION: Recombinant peptide

<400> SEQUENCE: 652

Ile Ser Asp Lys Pro Tyr Ile Ile
1               5

<210> SEQ ID NO 653
<211> LENGTH: 8
<212> TYPE: PRT
<213> ORGANISM: Artificial Sequence
<220> FEATURE:
<223> OTHER INFORMATION: Recombinant peptide

<400> SEQUENCE: 653

Ile Ser Asp Lys Pro Tyr Ile Val
1               5

<210> SEQ ID NO 654
<211> LENGTH: 8
<212> TYPE: PRT
<213> ORGANISM: Artificial Sequence
<220> FEATURE:
<223> OTHER INFORMATION: Recombinant peptide

<400> SEQUENCE: 654

Ile Ser Asp Lys Pro Tyr Leu Leu
1               5

<210> SEQ ID NO 655
<211> LENGTH: 8
<212> TYPE: PRT
<213> ORGANISM: Artificial Sequence
<220> FEATURE:
<223> OTHER INFORMATION: Recombinant peptide

<400> SEQUENCE: 655

Ile Ser Asp Lys Pro Tyr Leu Ile
1               5

<210> SEQ ID NO 656
<211> LENGTH: 8
<212> TYPE: PRT
<213> ORGANISM: Artificial Sequence
<220> FEATURE:
<223> OTHER INFORMATION: Recombinant peptide

<400> SEQUENCE: 656

Ile Ser Asp Lys Pro Tyr Leu Val
1               5

<210> SEQ ID NO 657
<211> LENGTH: 8
<212> TYPE: PRT
<213> ORGANISM: Artificial Sequence
<220> FEATURE:
<223> OTHER INFORMATION: Recombinant peptide

<400> SEQUENCE: 657

Ile Ser Asp Lys Pro Tyr Val Leu
1               5

<210> SEQ ID NO 658
<211> LENGTH: 8
<212> TYPE: PRT
<213> ORGANISM: Artificial Sequence
<220> FEATURE:
<223> OTHER INFORMATION: Recombinant peptide

<400> SEQUENCE: 658

Ile Ser Asp Lys Pro Tyr Val Ile
1               5

<210> SEQ ID NO 659
<211> LENGTH: 8
<212> TYPE: PRT
<213> ORGANISM: Artificial Sequence
<220> FEATURE:
<223> OTHER INFORMATION: Recombinant peptide

<400> SEQUENCE: 659

Ile Ser Asp Lys Pro Tyr Val Val
1               5

<210> SEQ ID NO 660
<211> LENGTH: 8
<212> TYPE: PRT
<213> ORGANISM: Artificial Sequence
<220> FEATURE:
<223> OTHER INFORMATION: Recombinant peptide

<400> SEQUENCE: 660

Ile Ser Asp Lys Pro Trp Ile Leu
1               5

<210> SEQ ID NO 661
<211> LENGTH: 8
<212> TYPE: PRT
<213> ORGANISM: Artificial Sequence
<220> FEATURE:
<223> OTHER INFORMATION: Recombinant peptide

<400> SEQUENCE: 661

Ile Ser Asp Lys Pro Trp Ile Ile
1               5

<210> SEQ ID NO 662
<211> LENGTH: 8
<212> TYPE: PRT
<213> ORGANISM: Artificial Sequence
<220> FEATURE:
<223> OTHER INFORMATION: Recombinant peptide

<400> SEQUENCE: 662

Ile Ser Asp Lys Pro Trp Ile Val
1               5

<210> SEQ ID NO 663
<211> LENGTH: 8
<212> TYPE: PRT
<213> ORGANISM: Artificial Sequence
<220> FEATURE:
<223> OTHER INFORMATION: Recombinant peptide

<400> SEQUENCE: 663

Ile Ser Asp Lys Pro Trp Leu Leu
1               5

<210> SEQ ID NO 664
<211> LENGTH: 8
<212> TYPE: PRT
<213> ORGANISM: Artificial Sequence
<220> FEATURE:
<223> OTHER INFORMATION: Recombinant peptide

<400> SEQUENCE: 664

Ile Ser Asp Lys Pro Trp Leu Ile
1               5

<210> SEQ ID NO 665
<211> LENGTH: 8
<212> TYPE: PRT
<213> ORGANISM: Artificial Sequence
<220> FEATURE:
<223> OTHER INFORMATION: Recombinant peptide

<400> SEQUENCE: 665

Ile Ser Asp Lys Pro Trp Leu Val
1               5

<210> SEQ ID NO 666
<211> LENGTH: 8
<212> TYPE: PRT
<213> ORGANISM: Artificial Sequence
<220> FEATURE:
<223> OTHER INFORMATION: Recombinant peptide

<400> SEQUENCE: 666

Ile Ser Asp Lys Pro Trp Val Leu
1               5

<210> SEQ ID NO 667
<211> LENGTH: 8
<212> TYPE: PRT
<213> ORGANISM: Artificial Sequence
<220> FEATURE:
<223> OTHER INFORMATION: Recombinant peptide

<400> SEQUENCE: 667

Ile Ser Asp Lys Pro Trp Val Ile
1               5

<210> SEQ ID NO 668
<211> LENGTH: 8
<212> TYPE: PRT
<213> ORGANISM: Artificial Sequence
<220> FEATURE:
<223> OTHER INFORMATION: Recombinant peptide

<400> SEQUENCE: 668

Ile Ser Asp Lys Pro Trp Val Val

```
1               5
```

<210> SEQ ID NO 669
<211> LENGTH: 8
<212> TYPE: PRT
<213> ORGANISM: Artificial Sequence
<220> FEATURE:
<223> OTHER INFORMATION: Recombinant peptide

<400> SEQUENCE: 669

```
Ile Ser Asp Arg Pro Tyr Ile Leu
1               5
```

<210> SEQ ID NO 670
<211> LENGTH: 8
<212> TYPE: PRT
<213> ORGANISM: Artificial Sequence
<220> FEATURE:
<223> OTHER INFORMATION: Recombinant peptide

<400> SEQUENCE: 670

```
Ile Ser Asp Arg Pro Tyr Ile Ile
1               5
```

<210> SEQ ID NO 671
<211> LENGTH: 8
<212> TYPE: PRT
<213> ORGANISM: Artificial Sequence
<220> FEATURE:
<223> OTHER INFORMATION: Recombinant peptide

<400> SEQUENCE: 671

```
Ile Ser Asp Arg Pro Tyr Ile Val
1               5
```

<210> SEQ ID NO 672
<211> LENGTH: 8
<212> TYPE: PRT
<213> ORGANISM: Artificial Sequence
<220> FEATURE:
<223> OTHER INFORMATION: Recombinant peptide

<400> SEQUENCE: 672

```
Ile Ser Asp Arg Pro Tyr Leu Leu
1               5
```

<210> SEQ ID NO 673
<211> LENGTH: 8
<212> TYPE: PRT
<213> ORGANISM: Artificial Sequence
<220> FEATURE:
<223> OTHER INFORMATION: Recombinant peptide

<400> SEQUENCE: 673

```
Ile Ser Asp Arg Pro Tyr Leu Ile
1               5
```

<210> SEQ ID NO 674
<211> LENGTH: 8
<212> TYPE: PRT
<213> ORGANISM: Artificial Sequence
<220> FEATURE:
<223> OTHER INFORMATION: Recombinant peptide

<400> SEQUENCE: 674

```
Ile Ser Asp Arg Pro Tyr Leu Val
1               5
```

```
<210> SEQ ID NO 675
<211> LENGTH: 8
<212> TYPE: PRT
<213> ORGANISM: Artificial Sequence
<220> FEATURE:
<223> OTHER INFORMATION: Recombinant peptide

<400> SEQUENCE: 675

Ile Ser Asp Arg Pro Tyr Val Leu
1               5

<210> SEQ ID NO 676
<211> LENGTH: 8
<212> TYPE: PRT
<213> ORGANISM: Artificial Sequence
<220> FEATURE:
<223> OTHER INFORMATION: Recombinant peptide

<400> SEQUENCE: 676

Ile Ser Asp Arg Pro Tyr Val Ile
1               5

<210> SEQ ID NO 677
<211> LENGTH: 8
<212> TYPE: PRT
<213> ORGANISM: Artificial Sequence
<220> FEATURE:
<223> OTHER INFORMATION: Recombinant peptide

<400> SEQUENCE: 677

Ile Ser Asp Arg Pro Tyr Val Val
1               5

<210> SEQ ID NO 678
<211> LENGTH: 8
<212> TYPE: PRT
<213> ORGANISM: Artificial Sequence
<220> FEATURE:
<223> OTHER INFORMATION: Recombinant peptide

<400> SEQUENCE: 678

Ile Ser Asp Arg Pro Trp Ile Leu
1               5

<210> SEQ ID NO 679
<211> LENGTH: 8
<212> TYPE: PRT
<213> ORGANISM: Artificial Sequence
<220> FEATURE:
<223> OTHER INFORMATION: Recombinant peptide

<400> SEQUENCE: 679

Ile Ser Asp Arg Pro Trp Ile Ile
1               5

<210> SEQ ID NO 680
<211> LENGTH: 8
<212> TYPE: PRT
<213> ORGANISM: Artificial Sequence
<220> FEATURE:
<223> OTHER INFORMATION: Recombinant peptide

<400> SEQUENCE: 680

Ile Ser Asp Arg Pro Trp Ile Val
1               5
```

<210> SEQ ID NO 681
<211> LENGTH: 8
<212> TYPE: PRT
<213> ORGANISM: Artificial Sequence
<220> FEATURE:
<223> OTHER INFORMATION: Recombinant peptide

<400> SEQUENCE: 681

Ile Ser Asp Arg Pro Trp Leu Leu
1               5

<210> SEQ ID NO 682
<211> LENGTH: 8
<212> TYPE: PRT
<213> ORGANISM: Artificial Sequence
<220> FEATURE:
<223> OTHER INFORMATION: Recombinant peptide

<400> SEQUENCE: 682

Ile Ser Asp Arg Pro Trp Leu Ile
1               5

<210> SEQ ID NO 683
<211> LENGTH: 8
<212> TYPE: PRT
<213> ORGANISM: Artificial Sequence
<220> FEATURE:
<223> OTHER INFORMATION: Recombinant peptide

<400> SEQUENCE: 683

Ile Ser Asp Arg Pro Trp Leu Val
1               5

<210> SEQ ID NO 684
<211> LENGTH: 8
<212> TYPE: PRT
<213> ORGANISM: Artificial Sequence
<220> FEATURE:
<223> OTHER INFORMATION: Recombinant peptide

<400> SEQUENCE: 684

Ile Ser Asp Arg Pro Trp Val Leu
1               5

<210> SEQ ID NO 685
<211> LENGTH: 8
<212> TYPE: PRT
<213> ORGANISM: Artificial Sequence
<220> FEATURE:
<223> OTHER INFORMATION: Recombinant peptide

<400> SEQUENCE: 685

Ile Ser Asp Arg Pro Trp Val Ile
1               5

<210> SEQ ID NO 686
<211> LENGTH: 8
<212> TYPE: PRT
<213> ORGANISM: Artificial Sequence
<220> FEATURE:
<223> OTHER INFORMATION: Recombinant peptide

<400> SEQUENCE: 686

Ile Ser Asp Arg Pro Trp Val Val
1               5

```
<210> SEQ ID NO 687
<211> LENGTH: 8
<212> TYPE: PRT
<213> ORGANISM: Artificial Sequence
<220> FEATURE:
<223> OTHER INFORMATION: Recombinant peptide

<400> SEQUENCE: 687

Ile Ser Glu Lys Pro Tyr Ile Leu
1               5

<210> SEQ ID NO 688
<211> LENGTH: 8
<212> TYPE: PRT
<213> ORGANISM: Artificial Sequence
<220> FEATURE:
<223> OTHER INFORMATION: Recombinant peptide

<400> SEQUENCE: 688

Ile Ser Glu Lys Pro Tyr Ile Ile
1               5

<210> SEQ ID NO 689
<211> LENGTH: 8
<212> TYPE: PRT
<213> ORGANISM: Artificial Sequence
<220> FEATURE:
<223> OTHER INFORMATION: Recombinant peptide

<400> SEQUENCE: 689

Ile Ser Glu Lys Pro Tyr Ile Val
1               5

<210> SEQ ID NO 690
<211> LENGTH: 8
<212> TYPE: PRT
<213> ORGANISM: Artificial Sequence
<220> FEATURE:
<223> OTHER INFORMATION: Recombinant peptide

<400> SEQUENCE: 690

Ile Ser Glu Lys Pro Tyr Leu Leu
1               5

<210> SEQ ID NO 691
<211> LENGTH: 8
<212> TYPE: PRT
<213> ORGANISM: Artificial Sequence
<220> FEATURE:
<223> OTHER INFORMATION: Recombinant peptide

<400> SEQUENCE: 691

Ile Ser Glu Lys Pro Tyr Leu Ile
1               5

<210> SEQ ID NO 692
<211> LENGTH: 8
<212> TYPE: PRT
<213> ORGANISM: Artificial Sequence
<220> FEATURE:
<223> OTHER INFORMATION: Recombinant peptide

<400> SEQUENCE: 692

Ile Ser Glu Lys Pro Tyr Leu Val
1               5

<210> SEQ ID NO 693
```

```
<211> LENGTH: 8
<212> TYPE: PRT
<213> ORGANISM: Artificial Sequence
<220> FEATURE:
<223> OTHER INFORMATION: Recombinant peptide

<400> SEQUENCE: 693

Ile Ser Glu Lys Pro Tyr Val Leu
1               5

<210> SEQ ID NO 694
<211> LENGTH: 8
<212> TYPE: PRT
<213> ORGANISM: Artificial Sequence
<220> FEATURE:
<223> OTHER INFORMATION: Recombinant peptide

<400> SEQUENCE: 694

Ile Ser Glu Lys Pro Tyr Val Ile
1               5

<210> SEQ ID NO 695
<211> LENGTH: 8
<212> TYPE: PRT
<213> ORGANISM: Artificial Sequence
<220> FEATURE:
<223> OTHER INFORMATION: Recombinant peptide

<400> SEQUENCE: 695

Ile Ser Glu Lys Pro Tyr Val Val
1               5

<210> SEQ ID NO 696
<211> LENGTH: 8
<212> TYPE: PRT
<213> ORGANISM: Artificial Sequence
<220> FEATURE:
<223> OTHER INFORMATION: Recombinant peptide

<400> SEQUENCE: 696

Ile Ser Glu Lys Pro Trp Ile Leu
1               5

<210> SEQ ID NO 697
<211> LENGTH: 8
<212> TYPE: PRT
<213> ORGANISM: Artificial Sequence
<220> FEATURE:
<223> OTHER INFORMATION: Recombinant peptide

<400> SEQUENCE: 697

Ile Ser Glu Lys Pro Trp Ile Ile
1               5

<210> SEQ ID NO 698
<211> LENGTH: 8
<212> TYPE: PRT
<213> ORGANISM: Artificial Sequence
<220> FEATURE:
<223> OTHER INFORMATION: Recombinant peptide

<400> SEQUENCE: 698

Ile Ser Glu Lys Pro Trp Ile Val
1               5

<210> SEQ ID NO 699
<211> LENGTH: 8
```

```
<212> TYPE: PRT
<213> ORGANISM: Artificial Sequence
<220> FEATURE:
<223> OTHER INFORMATION: Recombinant peptide

<400> SEQUENCE: 699

Ile Ser Glu Lys Pro Trp Leu Leu
1               5

<210> SEQ ID NO 700
<211> LENGTH: 8
<212> TYPE: PRT
<213> ORGANISM: Artificial Sequence
<220> FEATURE:
<223> OTHER INFORMATION: Recombinant peptide

<400> SEQUENCE: 700

Ile Ser Glu Lys Pro Trp Leu Ile
1               5

<210> SEQ ID NO 701
<211> LENGTH: 8
<212> TYPE: PRT
<213> ORGANISM: Artificial Sequence
<220> FEATURE:
<223> OTHER INFORMATION: Recombinant peptide

<400> SEQUENCE: 701

Ile Ser Glu Lys Pro Trp Leu Val
1               5

<210> SEQ ID NO 702
<211> LENGTH: 8
<212> TYPE: PRT
<213> ORGANISM: Artificial Sequence
<220> FEATURE:
<223> OTHER INFORMATION: Recombinant peptide

<400> SEQUENCE: 702

Ile Ser Glu Lys Pro Trp Val Leu
1               5

<210> SEQ ID NO 703
<211> LENGTH: 8
<212> TYPE: PRT
<213> ORGANISM: Artificial Sequence
<220> FEATURE:
<223> OTHER INFORMATION: Recombinant peptide

<400> SEQUENCE: 703

Ile Ser Glu Lys Pro Trp Val Ile
1               5

<210> SEQ ID NO 704
<211> LENGTH: 8
<212> TYPE: PRT
<213> ORGANISM: Artificial Sequence
<220> FEATURE:
<223> OTHER INFORMATION: Recombinant peptide

<400> SEQUENCE: 704

Ile Ser Glu Lys Pro Trp Val Val
1               5

<210> SEQ ID NO 705
<211> LENGTH: 8
<212> TYPE: PRT
```

```
<213> ORGANISM: Artificial Sequence
<220> FEATURE:
<223> OTHER INFORMATION: Recombinant peptide

<400> SEQUENCE: 705

Ile Ser Glu Arg Pro Tyr Ile Leu
1               5

<210> SEQ ID NO 706
<211> LENGTH: 8
<212> TYPE: PRT
<213> ORGANISM: Artificial Sequence
<220> FEATURE:
<223> OTHER INFORMATION: Recombinant peptide

<400> SEQUENCE: 706

Ile Ser Glu Arg Pro Tyr Ile Ile
1               5

<210> SEQ ID NO 707
<211> LENGTH: 8
<212> TYPE: PRT
<213> ORGANISM: Artificial Sequence
<220> FEATURE:
<223> OTHER INFORMATION: Recombinant peptide

<400> SEQUENCE: 707

Ile Ser Glu Arg Pro Tyr Ile Val
1               5

<210> SEQ ID NO 708
<211> LENGTH: 8
<212> TYPE: PRT
<213> ORGANISM: Artificial Sequence
<220> FEATURE:
<223> OTHER INFORMATION: Recombinant peptide

<400> SEQUENCE: 708

Ile Ser Glu Arg Pro Tyr Leu Leu
1               5

<210> SEQ ID NO 709
<211> LENGTH: 8
<212> TYPE: PRT
<213> ORGANISM: Artificial Sequence
<220> FEATURE:
<223> OTHER INFORMATION: Recombinant peptide

<400> SEQUENCE: 709

Ile Ser Glu Arg Pro Tyr Leu Ile
1               5

<210> SEQ ID NO 710
<211> LENGTH: 8
<212> TYPE: PRT
<213> ORGANISM: Artificial Sequence
<220> FEATURE:
<223> OTHER INFORMATION: Recombinant peptide

<400> SEQUENCE: 710

Ile Ser Glu Arg Pro Tyr Leu Val
1               5

<210> SEQ ID NO 711
<211> LENGTH: 8
<212> TYPE: PRT
<213> ORGANISM: Artificial Sequence
```

<220> FEATURE:
<223> OTHER INFORMATION: Recombinant peptide

<400> SEQUENCE: 711

Ile Ser Glu Arg Pro Tyr Val Leu
1               5

<210> SEQ ID NO 712
<211> LENGTH: 8
<212> TYPE: PRT
<213> ORGANISM: Artificial Sequence
<220> FEATURE:
<223> OTHER INFORMATION: Recombinant peptide

<400> SEQUENCE: 712

Ile Ser Glu Arg Pro Tyr Val Ile
1               5

<210> SEQ ID NO 713
<211> LENGTH: 8
<212> TYPE: PRT
<213> ORGANISM: Artificial Sequence
<220> FEATURE:
<223> OTHER INFORMATION: Recombinant peptide

<400> SEQUENCE: 713

Ile Ser Glu Arg Pro Tyr Val Val
1               5

<210> SEQ ID NO 714
<211> LENGTH: 8
<212> TYPE: PRT
<213> ORGANISM: Artificial Sequence
<220> FEATURE:
<223> OTHER INFORMATION: Recombinant peptide

<400> SEQUENCE: 714

Ile Ser Glu Arg Pro Trp Ile Leu
1               5

<210> SEQ ID NO 715
<211> LENGTH: 8
<212> TYPE: PRT
<213> ORGANISM: Artificial Sequence
<220> FEATURE:
<223> OTHER INFORMATION: Recombinant peptide

<400> SEQUENCE: 715

Ile Ser Glu Arg Pro Trp Ile Ile
1               5

<210> SEQ ID NO 716
<211> LENGTH: 8
<212> TYPE: PRT
<213> ORGANISM: Artificial Sequence
<220> FEATURE:
<223> OTHER INFORMATION: Recombinant peptide

<400> SEQUENCE: 716

Ile Ser Glu Arg Pro Trp Ile Val
1               5

<210> SEQ ID NO 717
<211> LENGTH: 8
<212> TYPE: PRT
<213> ORGANISM: Artificial Sequence
<220> FEATURE:

<223> OTHER INFORMATION: Recombinant peptide

<400> SEQUENCE: 717

Ile Ser Glu Arg Pro Trp Leu Leu
1               5

<210> SEQ ID NO 718
<211> LENGTH: 8
<212> TYPE: PRT
<213> ORGANISM: Artificial Sequence
<220> FEATURE:
<223> OTHER INFORMATION: Recombinant peptide

<400> SEQUENCE: 718

Ile Ser Glu Arg Pro Trp Leu Ile
1               5

<210> SEQ ID NO 719
<211> LENGTH: 8
<212> TYPE: PRT
<213> ORGANISM: Artificial Sequence
<220> FEATURE:
<223> OTHER INFORMATION: Recombinant peptide

<400> SEQUENCE: 719

Ile Ser Glu Arg Pro Trp Leu Val
1               5

<210> SEQ ID NO 720
<211> LENGTH: 8
<212> TYPE: PRT
<213> ORGANISM: Artificial Sequence
<220> FEATURE:
<223> OTHER INFORMATION: Recombinant peptide

<400> SEQUENCE: 720

Ile Ser Glu Arg Pro Trp Val Leu
1               5

<210> SEQ ID NO 721
<211> LENGTH: 8
<212> TYPE: PRT
<213> ORGANISM: Artificial Sequence
<220> FEATURE:
<223> OTHER INFORMATION: Recombinant peptide

<400> SEQUENCE: 721

Ile Ser Glu Arg Pro Trp Val Ile
1               5

<210> SEQ ID NO 722
<211> LENGTH: 8
<212> TYPE: PRT
<213> ORGANISM: Artificial Sequence
<220> FEATURE:
<223> OTHER INFORMATION: Recombinant peptide

<400> SEQUENCE: 722

Ile Ser Glu Arg Pro Trp Val Val
1               5

<210> SEQ ID NO 723
<211> LENGTH: 8
<212> TYPE: PRT
<213> ORGANISM: Artificial Sequence
<220> FEATURE:
<223> OTHER INFORMATION: Recombinant peptide

<400> SEQUENCE: 723

Ile Thr Asp Lys Pro Tyr Ile Leu
1               5

<210> SEQ ID NO 724
<211> LENGTH: 8
<212> TYPE: PRT
<213> ORGANISM: Artificial Sequence
<220> FEATURE:
<223> OTHER INFORMATION: Recombinant peptide

<400> SEQUENCE: 724

Ile Thr Asp Lys Pro Tyr Ile Ile
1               5

<210> SEQ ID NO 725
<211> LENGTH: 8
<212> TYPE: PRT
<213> ORGANISM: Artificial Sequence
<220> FEATURE:
<223> OTHER INFORMATION: Recombinant peptide

<400> SEQUENCE: 725

Ile Thr Asp Lys Pro Tyr Ile Val
1               5

<210> SEQ ID NO 726
<211> LENGTH: 8
<212> TYPE: PRT
<213> ORGANISM: Artificial Sequence
<220> FEATURE:
<223> OTHER INFORMATION: Recombinant peptide

<400> SEQUENCE: 726

Ile Thr Asp Lys Pro Tyr Leu Leu
1               5

<210> SEQ ID NO 727
<211> LENGTH: 8
<212> TYPE: PRT
<213> ORGANISM: Artificial Sequence
<220> FEATURE:
<223> OTHER INFORMATION: Recombinant peptide

<400> SEQUENCE: 727

Ile Thr Asp Lys Pro Tyr Leu Ile
1               5

<210> SEQ ID NO 728
<211> LENGTH: 8
<212> TYPE: PRT
<213> ORGANISM: Artificial Sequence
<220> FEATURE:
<223> OTHER INFORMATION: Recombinant peptide

<400> SEQUENCE: 728

Ile Thr Asp Lys Pro Tyr Leu Val
1               5

<210> SEQ ID NO 729
<211> LENGTH: 8
<212> TYPE: PRT
<213> ORGANISM: Artificial Sequence
<220> FEATURE:
<223> OTHER INFORMATION: Recombinant peptide

```
<400> SEQUENCE: 729

Ile Thr Asp Lys Pro Tyr Val Leu
1               5

<210> SEQ ID NO 730
<211> LENGTH: 8
<212> TYPE: PRT
<213> ORGANISM: Artificial Sequence
<220> FEATURE:
<223> OTHER INFORMATION: Recombinant peptide

<400> SEQUENCE: 730

Ile Thr Asp Lys Pro Tyr Val Ile
1               5

<210> SEQ ID NO 731
<211> LENGTH: 8
<212> TYPE: PRT
<213> ORGANISM: Artificial Sequence
<220> FEATURE:
<223> OTHER INFORMATION: Recombinant peptide

<400> SEQUENCE: 731

Ile Thr Asp Lys Pro Tyr Val Val
1               5

<210> SEQ ID NO 732
<211> LENGTH: 8
<212> TYPE: PRT
<213> ORGANISM: Artificial Sequence
<220> FEATURE:
<223> OTHER INFORMATION: Recombinant peptide

<400> SEQUENCE: 732

Ile Thr Asp Lys Pro Trp Ile Leu
1               5

<210> SEQ ID NO 733
<211> LENGTH: 8
<212> TYPE: PRT
<213> ORGANISM: Artificial Sequence
<220> FEATURE:
<223> OTHER INFORMATION: Recombinant peptide

<400> SEQUENCE: 733

Ile Thr Asp Lys Pro Trp Ile Ile
1               5

<210> SEQ ID NO 734
<211> LENGTH: 8
<212> TYPE: PRT
<213> ORGANISM: Artificial Sequence
<220> FEATURE:
<223> OTHER INFORMATION: Recombinant peptide

<400> SEQUENCE: 734

Ile Thr Asp Lys Pro Trp Ile Val
1               5

<210> SEQ ID NO 735
<211> LENGTH: 8
<212> TYPE: PRT
<213> ORGANISM: Artificial Sequence
<220> FEATURE:
<223> OTHER INFORMATION: Recombinant peptide

<400> SEQUENCE: 735
```

```
Ile Thr Asp Lys Pro Trp Leu Leu
1               5

<210> SEQ ID NO 736
<211> LENGTH: 8
<212> TYPE: PRT
<213> ORGANISM: Artificial Sequence
<220> FEATURE:
<223> OTHER INFORMATION: Recombinant peptide

<400> SEQUENCE: 736

Ile Thr Asp Lys Pro Trp Leu Ile
1               5

<210> SEQ ID NO 737
<211> LENGTH: 8
<212> TYPE: PRT
<213> ORGANISM: Artificial Sequence
<220> FEATURE:
<223> OTHER INFORMATION: Recombinant peptide

<400> SEQUENCE: 737

Ile Thr Asp Lys Pro Trp Leu Val
1               5

<210> SEQ ID NO 738
<211> LENGTH: 8
<212> TYPE: PRT
<213> ORGANISM: Artificial Sequence
<220> FEATURE:
<223> OTHER INFORMATION: Recombinant peptide

<400> SEQUENCE: 738

Ile Thr Asp Lys Pro Trp Val Leu
1               5

<210> SEQ ID NO 739
<211> LENGTH: 8
<212> TYPE: PRT
<213> ORGANISM: Artificial Sequence
<220> FEATURE:
<223> OTHER INFORMATION: Recombinant peptide

<400> SEQUENCE: 739

Ile Thr Asp Lys Pro Trp Val Ile
1               5

<210> SEQ ID NO 740
<211> LENGTH: 8
<212> TYPE: PRT
<213> ORGANISM: Artificial Sequence
<220> FEATURE:
<223> OTHER INFORMATION: Recombinant peptide

<400> SEQUENCE: 740

Ile Thr Asp Lys Pro Trp Val Val
1               5

<210> SEQ ID NO 741
<211> LENGTH: 8
<212> TYPE: PRT
<213> ORGANISM: Artificial Sequence
<220> FEATURE:
<223> OTHER INFORMATION: Recombinant peptide

<400> SEQUENCE: 741
```

Ile Thr Asp Arg Pro Tyr Ile Leu
1               5

<210> SEQ ID NO 742
<211> LENGTH: 8
<212> TYPE: PRT
<213> ORGANISM: Artificial Sequence
<220> FEATURE:
<223> OTHER INFORMATION: Recombinant peptide

<400> SEQUENCE: 742

Ile Thr Asp Arg Pro Tyr Ile Ile
1               5

<210> SEQ ID NO 743
<211> LENGTH: 8
<212> TYPE: PRT
<213> ORGANISM: Artificial Sequence
<220> FEATURE:
<223> OTHER INFORMATION: Recombinant peptide

<400> SEQUENCE: 743

Ile Thr Asp Arg Pro Tyr Ile Val
1               5

<210> SEQ ID NO 744
<211> LENGTH: 8
<212> TYPE: PRT
<213> ORGANISM: Artificial Sequence
<220> FEATURE:
<223> OTHER INFORMATION: Recombinant peptide

<400> SEQUENCE: 744

Ile Thr Asp Arg Pro Tyr Leu Leu
1               5

<210> SEQ ID NO 745
<211> LENGTH: 8
<212> TYPE: PRT
<213> ORGANISM: Artificial Sequence
<220> FEATURE:
<223> OTHER INFORMATION: Recombinant peptide

<400> SEQUENCE: 745

Ile Thr Asp Arg Pro Tyr Leu Ile
1               5

<210> SEQ ID NO 746
<211> LENGTH: 8
<212> TYPE: PRT
<213> ORGANISM: Artificial Sequence
<220> FEATURE:
<223> OTHER INFORMATION: Recombinant peptide

<400> SEQUENCE: 746

Ile Thr Asp Arg Pro Tyr Leu Val
1               5

<210> SEQ ID NO 747
<211> LENGTH: 8
<212> TYPE: PRT
<213> ORGANISM: Artificial Sequence
<220> FEATURE:
<223> OTHER INFORMATION: Recombinant peptide

<400> SEQUENCE: 747

Ile Thr Asp Arg Pro Tyr Val Leu

```
1               5
```

<210> SEQ ID NO 748
<211> LENGTH: 8
<212> TYPE: PRT
<213> ORGANISM: Artificial Sequence
<220> FEATURE:
<223> OTHER INFORMATION: Recombinant peptide

<400> SEQUENCE: 748

```
Ile Thr Asp Arg Pro Tyr Val Ile
1               5
```

<210> SEQ ID NO 749
<211> LENGTH: 8
<212> TYPE: PRT
<213> ORGANISM: Artificial Sequence
<220> FEATURE:
<223> OTHER INFORMATION: Recombinant peptide

<400> SEQUENCE: 749

```
Ile Thr Asp Arg Pro Tyr Val Val
1               5
```

<210> SEQ ID NO 750
<211> LENGTH: 8
<212> TYPE: PRT
<213> ORGANISM: Artificial Sequence
<220> FEATURE:
<223> OTHER INFORMATION: Recombinant peptide

<400> SEQUENCE: 750

```
Ile Thr Asp Arg Pro Trp Ile Leu
1               5
```

<210> SEQ ID NO 751
<211> LENGTH: 8
<212> TYPE: PRT
<213> ORGANISM: Artificial Sequence
<220> FEATURE:
<223> OTHER INFORMATION: Recombinant peptide

<400> SEQUENCE: 751

```
Ile Thr Asp Arg Pro Trp Ile Ile
1               5
```

<210> SEQ ID NO 752
<211> LENGTH: 8
<212> TYPE: PRT
<213> ORGANISM: Artificial Sequence
<220> FEATURE:
<223> OTHER INFORMATION: Recombinant peptide

<400> SEQUENCE: 752

```
Ile Thr Asp Arg Pro Trp Ile Val
1               5
```

<210> SEQ ID NO 753
<211> LENGTH: 8
<212> TYPE: PRT
<213> ORGANISM: Artificial Sequence
<220> FEATURE:
<223> OTHER INFORMATION: Recombinant peptide

<400> SEQUENCE: 753

```
Ile Thr Asp Arg Pro Trp Leu Leu
1               5
```

```
<210> SEQ ID NO 754
<211> LENGTH: 8
<212> TYPE: PRT
<213> ORGANISM: Artificial Sequence
<220> FEATURE:
<223> OTHER INFORMATION: Recombinant peptide

<400> SEQUENCE: 754

Ile Thr Asp Arg Pro Trp Leu Ile
1               5

<210> SEQ ID NO 755
<211> LENGTH: 8
<212> TYPE: PRT
<213> ORGANISM: Artificial Sequence
<220> FEATURE:
<223> OTHER INFORMATION: Recombinant peptide

<400> SEQUENCE: 755

Ile Thr Asp Arg Pro Trp Leu Val
1               5

<210> SEQ ID NO 756
<211> LENGTH: 8
<212> TYPE: PRT
<213> ORGANISM: Artificial Sequence
<220> FEATURE:
<223> OTHER INFORMATION: Recombinant peptide

<400> SEQUENCE: 756

Ile Thr Asp Arg Pro Trp Val Leu
1               5

<210> SEQ ID NO 757
<211> LENGTH: 8
<212> TYPE: PRT
<213> ORGANISM: Artificial Sequence
<220> FEATURE:
<223> OTHER INFORMATION: Recombinant peptide

<400> SEQUENCE: 757

Ile Thr Asp Arg Pro Trp Val Ile
1               5

<210> SEQ ID NO 758
<211> LENGTH: 8
<212> TYPE: PRT
<213> ORGANISM: Artificial Sequence
<220> FEATURE:
<223> OTHER INFORMATION: Recombinant peptide

<400> SEQUENCE: 758

Ile Thr Asp Arg Pro Trp Val Val
1               5

<210> SEQ ID NO 759
<211> LENGTH: 8
<212> TYPE: PRT
<213> ORGANISM: Artificial Sequence
<220> FEATURE:
<223> OTHER INFORMATION: Recombinant peptide

<400> SEQUENCE: 759

Ile Thr Glu Lys Pro Tyr Ile Leu
1               5
```

```
<210> SEQ ID NO 760
<211> LENGTH: 8
<212> TYPE: PRT
<213> ORGANISM: Artificial Sequence
<220> FEATURE:
<223> OTHER INFORMATION: Recombinant peptide

<400> SEQUENCE: 760

Ile Thr Glu Lys Pro Tyr Ile Ile
1               5

<210> SEQ ID NO 761
<211> LENGTH: 8
<212> TYPE: PRT
<213> ORGANISM: Artificial Sequence
<220> FEATURE:
<223> OTHER INFORMATION: Recombinant peptide

<400> SEQUENCE: 761

Ile Thr Glu Lys Pro Tyr Ile Val
1               5

<210> SEQ ID NO 762
<211> LENGTH: 8
<212> TYPE: PRT
<213> ORGANISM: Artificial Sequence
<220> FEATURE:
<223> OTHER INFORMATION: Recombinant peptide

<400> SEQUENCE: 762

Ile Thr Glu Lys Pro Tyr Leu Leu
1               5

<210> SEQ ID NO 763
<211> LENGTH: 8
<212> TYPE: PRT
<213> ORGANISM: Artificial Sequence
<220> FEATURE:
<223> OTHER INFORMATION: Recombinant peptide

<400> SEQUENCE: 763

Ile Thr Glu Lys Pro Tyr Leu Ile
1               5

<210> SEQ ID NO 764
<211> LENGTH: 8
<212> TYPE: PRT
<213> ORGANISM: Artificial Sequence
<220> FEATURE:
<223> OTHER INFORMATION: Recombinant peptide

<400> SEQUENCE: 764

Ile Thr Glu Lys Pro Tyr Leu Val
1               5

<210> SEQ ID NO 765
<211> LENGTH: 8
<212> TYPE: PRT
<213> ORGANISM: Artificial Sequence
<220> FEATURE:
<223> OTHER INFORMATION: Recombinant peptide

<400> SEQUENCE: 765

Ile Thr Glu Lys Pro Tyr Val Leu
1               5
```

-continued

```
<210> SEQ ID NO 766
<211> LENGTH: 8
<212> TYPE: PRT
<213> ORGANISM: Artificial Sequence
<220> FEATURE:
<223> OTHER INFORMATION: Recombinant peptide

<400> SEQUENCE: 766

Ile Thr Glu Lys Pro Tyr Val Ile
1               5

<210> SEQ ID NO 767
<211> LENGTH: 8
<212> TYPE: PRT
<213> ORGANISM: Artificial Sequence
<220> FEATURE:
<223> OTHER INFORMATION: Recombinant peptide

<400> SEQUENCE: 767

Ile Thr Glu Lys Pro Tyr Val Val
1               5

<210> SEQ ID NO 768
<211> LENGTH: 8
<212> TYPE: PRT
<213> ORGANISM: Artificial Sequence
<220> FEATURE:
<223> OTHER INFORMATION: Recombinant peptide

<400> SEQUENCE: 768

Ile Thr Glu Lys Pro Trp Ile Leu
1               5

<210> SEQ ID NO 769
<211> LENGTH: 8
<212> TYPE: PRT
<213> ORGANISM: Artificial Sequence
<220> FEATURE:
<223> OTHER INFORMATION: Recombinant peptide

<400> SEQUENCE: 769

Ile Thr Glu Lys Pro Trp Ile Ile
1               5

<210> SEQ ID NO 770
<211> LENGTH: 8
<212> TYPE: PRT
<213> ORGANISM: Artificial Sequence
<220> FEATURE:
<223> OTHER INFORMATION: Recombinant peptide

<400> SEQUENCE: 770

Ile Thr Glu Lys Pro Trp Ile Val
1               5

<210> SEQ ID NO 771
<211> LENGTH: 8
<212> TYPE: PRT
<213> ORGANISM: Artificial Sequence
<220> FEATURE:
<223> OTHER INFORMATION: Recombinant peptide

<400> SEQUENCE: 771

Ile Thr Glu Lys Pro Trp Leu Leu
1               5

<210> SEQ ID NO 772
```

```
<211> LENGTH: 8
<212> TYPE: PRT
<213> ORGANISM: Artificial Sequence
<220> FEATURE:
<223> OTHER INFORMATION: Recombinant peptide

<400> SEQUENCE: 772

Ile Thr Glu Lys Pro Trp Leu Ile
1               5

<210> SEQ ID NO 773
<211> LENGTH: 8
<212> TYPE: PRT
<213> ORGANISM: Artificial Sequence
<220> FEATURE:
<223> OTHER INFORMATION: Recombinant peptide

<400> SEQUENCE: 773

Ile Thr Glu Lys Pro Trp Leu Val
1               5

<210> SEQ ID NO 774
<211> LENGTH: 8
<212> TYPE: PRT
<213> ORGANISM: Artificial Sequence
<220> FEATURE:
<223> OTHER INFORMATION: Recombinant peptide

<400> SEQUENCE: 774

Ile Thr Glu Lys Pro Trp Val Leu
1               5

<210> SEQ ID NO 775
<211> LENGTH: 8
<212> TYPE: PRT
<213> ORGANISM: Artificial Sequence
<220> FEATURE:
<223> OTHER INFORMATION: Recombinant peptide

<400> SEQUENCE: 775

Ile Thr Glu Lys Pro Trp Val Ile
1               5

<210> SEQ ID NO 776
<211> LENGTH: 8
<212> TYPE: PRT
<213> ORGANISM: Artificial Sequence
<220> FEATURE:
<223> OTHER INFORMATION: Recombinant peptide

<400> SEQUENCE: 776

Ile Thr Glu Lys Pro Trp Val Val
1               5

<210> SEQ ID NO 777
<211> LENGTH: 8
<212> TYPE: PRT
<213> ORGANISM: Artificial Sequence
<220> FEATURE:
<223> OTHER INFORMATION: Recombinant peptide

<400> SEQUENCE: 777

Ile Thr Glu Arg Pro Tyr Ile Leu
1               5

<210> SEQ ID NO 778
<211> LENGTH: 8
```

```
<212> TYPE: PRT
<213> ORGANISM: Artificial Sequence
<220> FEATURE:
<223> OTHER INFORMATION: Recombinant peptide

<400> SEQUENCE: 778

Ile Thr Glu Arg Pro Tyr Ile Ile
1               5

<210> SEQ ID NO 779
<211> LENGTH: 8
<212> TYPE: PRT
<213> ORGANISM: Artificial Sequence
<220> FEATURE:
<223> OTHER INFORMATION: Recombinant peptide

<400> SEQUENCE: 779

Ile Thr Glu Arg Pro Tyr Ile Val
1               5

<210> SEQ ID NO 780
<211> LENGTH: 8
<212> TYPE: PRT
<213> ORGANISM: Artificial Sequence
<220> FEATURE:
<223> OTHER INFORMATION: Recombinant peptide

<400> SEQUENCE: 780

Ile Thr Glu Arg Pro Tyr Leu Leu
1               5

<210> SEQ ID NO 781
<211> LENGTH: 8
<212> TYPE: PRT
<213> ORGANISM: Artificial Sequence
<220> FEATURE:
<223> OTHER INFORMATION: Recombinant peptide

<400> SEQUENCE: 781

Ile Thr Glu Arg Pro Tyr Leu Ile
1               5

<210> SEQ ID NO 782
<211> LENGTH: 8
<212> TYPE: PRT
<213> ORGANISM: Artificial Sequence
<220> FEATURE:
<223> OTHER INFORMATION: Recombinant peptide

<400> SEQUENCE: 782

Ile Thr Glu Arg Pro Tyr Leu Val
1               5

<210> SEQ ID NO 783
<211> LENGTH: 8
<212> TYPE: PRT
<213> ORGANISM: Artificial Sequence
<220> FEATURE:
<223> OTHER INFORMATION: Recombinant peptide

<400> SEQUENCE: 783

Ile Thr Glu Arg Pro Tyr Val Leu
1               5

<210> SEQ ID NO 784
<211> LENGTH: 8
<212> TYPE: PRT
```

```
<213> ORGANISM: Artificial Sequence
<220> FEATURE:
<223> OTHER INFORMATION: Recombinant peptide

<400> SEQUENCE: 784

Ile Thr Glu Arg Pro Tyr Val Ile
1               5

<210> SEQ ID NO 785
<211> LENGTH: 8
<212> TYPE: PRT
<213> ORGANISM: Artificial Sequence
<220> FEATURE:
<223> OTHER INFORMATION: Recombinant peptide

<400> SEQUENCE: 785

Ile Thr Glu Arg Pro Tyr Val Val
1               5

<210> SEQ ID NO 786
<211> LENGTH: 8
<212> TYPE: PRT
<213> ORGANISM: Artificial Sequence
<220> FEATURE:
<223> OTHER INFORMATION: Recombinant peptide

<400> SEQUENCE: 786

Ile Thr Glu Arg Pro Trp Ile Leu
1               5

<210> SEQ ID NO 787
<211> LENGTH: 8
<212> TYPE: PRT
<213> ORGANISM: Artificial Sequence
<220> FEATURE:
<223> OTHER INFORMATION: Recombinant peptide

<400> SEQUENCE: 787

Ile Thr Glu Arg Pro Trp Ile Ile
1               5

<210> SEQ ID NO 788
<211> LENGTH: 8
<212> TYPE: PRT
<213> ORGANISM: Artificial Sequence
<220> FEATURE:
<223> OTHER INFORMATION: Recombinant peptide

<400> SEQUENCE: 788

Ile Thr Glu Arg Pro Trp Ile Val
1               5

<210> SEQ ID NO 789
<211> LENGTH: 8
<212> TYPE: PRT
<213> ORGANISM: Artificial Sequence
<220> FEATURE:
<223> OTHER INFORMATION: Recombinant peptide

<400> SEQUENCE: 789

Ile Thr Glu Arg Pro Trp Leu Leu
1               5

<210> SEQ ID NO 790
<211> LENGTH: 8
<212> TYPE: PRT
<213> ORGANISM: Artificial Sequence
```

```
<220> FEATURE:
<223> OTHER INFORMATION: Recombinant peptide

<400> SEQUENCE: 790

Ile Thr Glu Arg Pro Trp Leu Ile
1               5

<210> SEQ ID NO 791
<211> LENGTH: 8
<212> TYPE: PRT
<213> ORGANISM: Artificial Sequence
<220> FEATURE:
<223> OTHER INFORMATION: Recombinant peptide

<400> SEQUENCE: 791

Ile Thr Glu Arg Pro Trp Leu Val
1               5

<210> SEQ ID NO 792
<211> LENGTH: 8
<212> TYPE: PRT
<213> ORGANISM: Artificial Sequence
<220> FEATURE:
<223> OTHER INFORMATION: Recombinant peptide

<400> SEQUENCE: 792

Ile Thr Glu Arg Pro Trp Val Leu
1               5

<210> SEQ ID NO 793
<211> LENGTH: 8
<212> TYPE: PRT
<213> ORGANISM: Artificial Sequence
<220> FEATURE:
<223> OTHER INFORMATION: Recombinant peptide

<400> SEQUENCE: 793

Ile Thr Glu Arg Pro Trp Val Ile
1               5

<210> SEQ ID NO 794
<211> LENGTH: 8
<212> TYPE: PRT
<213> ORGANISM: Artificial Sequence
<220> FEATURE:
<223> OTHER INFORMATION: Recombinant peptide

<400> SEQUENCE: 794

Ile Thr Glu Arg Pro Trp Val Val
1               5

<210> SEQ ID NO 795
<211> LENGTH: 8
<212> TYPE: PRT
<213> ORGANISM: Artificial Sequence
<220> FEATURE:
<223> OTHER INFORMATION: Recombinant peptide

<400> SEQUENCE: 795

Val Ser Asp Lys Pro Tyr Ile Leu
1               5

<210> SEQ ID NO 796
<211> LENGTH: 8
<212> TYPE: PRT
<213> ORGANISM: Artificial Sequence
<220> FEATURE:
```

<223> OTHER INFORMATION: Recombinant peptide

<400> SEQUENCE: 796

Val Ser Asp Lys Pro Tyr Ile Ile
1               5

<210> SEQ ID NO 797
<211> LENGTH: 8
<212> TYPE: PRT
<213> ORGANISM: Artificial Sequence
<220> FEATURE:
<223> OTHER INFORMATION: Recombinant peptide

<400> SEQUENCE: 797

Val Ser Asp Lys Pro Tyr Ile Val
1               5

<210> SEQ ID NO 798
<211> LENGTH: 8
<212> TYPE: PRT
<213> ORGANISM: Artificial Sequence
<220> FEATURE:
<223> OTHER INFORMATION: Recombinant peptide

<400> SEQUENCE: 798

Val Ser Asp Lys Pro Tyr Leu Leu
1               5

<210> SEQ ID NO 799
<211> LENGTH: 8
<212> TYPE: PRT
<213> ORGANISM: Artificial Sequence
<220> FEATURE:
<223> OTHER INFORMATION: Recombinant peptide

<400> SEQUENCE: 799

Val Ser Asp Lys Pro Tyr Leu Ile
1               5

<210> SEQ ID NO 800
<211> LENGTH: 8
<212> TYPE: PRT
<213> ORGANISM: Artificial Sequence
<220> FEATURE:
<223> OTHER INFORMATION: Recombinant peptide

<400> SEQUENCE: 800

Val Ser Asp Lys Pro Tyr Leu Val
1               5

<210> SEQ ID NO 801
<211> LENGTH: 8
<212> TYPE: PRT
<213> ORGANISM: Artificial Sequence
<220> FEATURE:
<223> OTHER INFORMATION: Recombinant peptide

<400> SEQUENCE: 801

Val Ser Asp Lys Pro Tyr Val Leu
1               5

<210> SEQ ID NO 802
<211> LENGTH: 8
<212> TYPE: PRT
<213> ORGANISM: Artificial Sequence
<220> FEATURE:
<223> OTHER INFORMATION: Recombinant peptide

<400> SEQUENCE: 802

Val Ser Asp Lys Pro Tyr Val Ile
1               5

<210> SEQ ID NO 803
<211> LENGTH: 8
<212> TYPE: PRT
<213> ORGANISM: Artificial Sequence
<220> FEATURE:
<223> OTHER INFORMATION: Recombinant peptide

<400> SEQUENCE: 803

Val Ser Asp Lys Pro Tyr Val Val
1               5

<210> SEQ ID NO 804
<211> LENGTH: 8
<212> TYPE: PRT
<213> ORGANISM: Artificial Sequence
<220> FEATURE:
<223> OTHER INFORMATION: Recombinant peptide

<400> SEQUENCE: 804

Val Ser Asp Lys Pro Trp Ile Leu
1               5

<210> SEQ ID NO 805
<211> LENGTH: 8
<212> TYPE: PRT
<213> ORGANISM: Artificial Sequence
<220> FEATURE:
<223> OTHER INFORMATION: Recombinant peptide

<400> SEQUENCE: 805

Val Ser Asp Lys Pro Trp Ile Ile
1               5

<210> SEQ ID NO 806
<211> LENGTH: 8
<212> TYPE: PRT
<213> ORGANISM: Artificial Sequence
<220> FEATURE:
<223> OTHER INFORMATION: Recombinant peptide

<400> SEQUENCE: 806

Val Ser Asp Lys Pro Trp Ile Val
1               5

<210> SEQ ID NO 807
<211> LENGTH: 8
<212> TYPE: PRT
<213> ORGANISM: Artificial Sequence
<220> FEATURE:
<223> OTHER INFORMATION: Recombinant peptide

<400> SEQUENCE: 807

Val Ser Asp Lys Pro Trp Leu Leu
1               5

<210> SEQ ID NO 808
<211> LENGTH: 8
<212> TYPE: PRT
<213> ORGANISM: Artificial Sequence
<220> FEATURE:
<223> OTHER INFORMATION: Recombinant peptide

```
<400> SEQUENCE: 808

Val Ser Asp Lys Pro Trp Leu Ile
1               5

<210> SEQ ID NO 809
<211> LENGTH: 8
<212> TYPE: PRT
<213> ORGANISM: Artificial Sequence
<220> FEATURE:
<223> OTHER INFORMATION: Recombinant peptide

<400> SEQUENCE: 809

Val Ser Asp Lys Pro Trp Leu Val
1               5

<210> SEQ ID NO 810
<211> LENGTH: 8
<212> TYPE: PRT
<213> ORGANISM: Artificial Sequence
<220> FEATURE:
<223> OTHER INFORMATION: Recombinant peptide

<400> SEQUENCE: 810

Val Ser Asp Lys Pro Trp Val Leu
1               5

<210> SEQ ID NO 811
<211> LENGTH: 8
<212> TYPE: PRT
<213> ORGANISM: Artificial Sequence
<220> FEATURE:
<223> OTHER INFORMATION: Recombinant peptide

<400> SEQUENCE: 811

Val Ser Asp Lys Pro Trp Val Ile
1               5

<210> SEQ ID NO 812
<211> LENGTH: 8
<212> TYPE: PRT
<213> ORGANISM: Artificial Sequence
<220> FEATURE:
<223> OTHER INFORMATION: Recombinant peptide

<400> SEQUENCE: 812

Val Ser Asp Lys Pro Trp Val Val
1               5

<210> SEQ ID NO 813
<211> LENGTH: 8
<212> TYPE: PRT
<213> ORGANISM: Artificial Sequence
<220> FEATURE:
<223> OTHER INFORMATION: Recombinant peptide

<400> SEQUENCE: 813

Val Ser Asp Arg Pro Tyr Ile Leu
1               5

<210> SEQ ID NO 814
<211> LENGTH: 8
<212> TYPE: PRT
<213> ORGANISM: Artificial Sequence
<220> FEATURE:
<223> OTHER INFORMATION: Recombinant peptide

<400> SEQUENCE: 814
```

```
Val Ser Asp Arg Pro Tyr Ile Ile
1               5

<210> SEQ ID NO 815
<211> LENGTH: 8
<212> TYPE: PRT
<213> ORGANISM: Artificial Sequence
<220> FEATURE:
<223> OTHER INFORMATION: Recombinant peptide

<400> SEQUENCE: 815

Val Ser Asp Arg Pro Tyr Ile Val
1               5

<210> SEQ ID NO 816
<211> LENGTH: 8
<212> TYPE: PRT
<213> ORGANISM: Artificial Sequence
<220> FEATURE:
<223> OTHER INFORMATION: Recombinant peptide

<400> SEQUENCE: 816

Val Ser Asp Arg Pro Tyr Leu Leu
1               5

<210> SEQ ID NO 817
<211> LENGTH: 8
<212> TYPE: PRT
<213> ORGANISM: Artificial Sequence
<220> FEATURE:
<223> OTHER INFORMATION: Recombinant peptide

<400> SEQUENCE: 817

Val Ser Asp Arg Pro Tyr Leu Ile
1               5

<210> SEQ ID NO 818
<211> LENGTH: 8
<212> TYPE: PRT
<213> ORGANISM: Artificial Sequence
<220> FEATURE:
<223> OTHER INFORMATION: Recombinant peptide

<400> SEQUENCE: 818

Val Ser Asp Arg Pro Tyr Leu Val
1               5

<210> SEQ ID NO 819
<211> LENGTH: 8
<212> TYPE: PRT
<213> ORGANISM: Artificial Sequence
<220> FEATURE:
<223> OTHER INFORMATION: Recombinant peptide

<400> SEQUENCE: 819

Val Ser Asp Arg Pro Tyr Val Leu
1               5

<210> SEQ ID NO 820
<211> LENGTH: 8
<212> TYPE: PRT
<213> ORGANISM: Artificial Sequence
<220> FEATURE:
<223> OTHER INFORMATION: Recombinant peptide

<400> SEQUENCE: 820
```

Val Ser Asp Arg Pro Tyr Val Ile
1               5

<210> SEQ ID NO 821
<211> LENGTH: 8
<212> TYPE: PRT
<213> ORGANISM: Artificial Sequence
<220> FEATURE:
<223> OTHER INFORMATION: Recombinant peptide

<400> SEQUENCE: 821

Val Ser Asp Arg Pro Tyr Val Val
1               5

<210> SEQ ID NO 822
<211> LENGTH: 8
<212> TYPE: PRT
<213> ORGANISM: Artificial Sequence
<220> FEATURE:
<223> OTHER INFORMATION: Recombinant peptide

<400> SEQUENCE: 822

Val Ser Asp Arg Pro Trp Ile Leu
1               5

<210> SEQ ID NO 823
<211> LENGTH: 8
<212> TYPE: PRT
<213> ORGANISM: Artificial Sequence
<220> FEATURE:
<223> OTHER INFORMATION: Recombinant peptide

<400> SEQUENCE: 823

Val Ser Asp Arg Pro Trp Ile Ile
1               5

<210> SEQ ID NO 824
<211> LENGTH: 8
<212> TYPE: PRT
<213> ORGANISM: Artificial Sequence
<220> FEATURE:
<223> OTHER INFORMATION: Recombinant peptide

<400> SEQUENCE: 824

Val Ser Asp Arg Pro Trp Ile Val
1               5

<210> SEQ ID NO 825
<211> LENGTH: 8
<212> TYPE: PRT
<213> ORGANISM: Artificial Sequence
<220> FEATURE:
<223> OTHER INFORMATION: Recombinant peptide

<400> SEQUENCE: 825

Val Ser Asp Arg Pro Trp Leu Leu
1               5

<210> SEQ ID NO 826
<211> LENGTH: 8
<212> TYPE: PRT
<213> ORGANISM: Artificial Sequence
<220> FEATURE:
<223> OTHER INFORMATION: Recombinant peptide

<400> SEQUENCE: 826

Val Ser Asp Arg Pro Trp Leu Ile

```
1               5

<210> SEQ ID NO 827
<211> LENGTH: 8
<212> TYPE: PRT
<213> ORGANISM: Artificial Sequence
<220> FEATURE:
<223> OTHER INFORMATION: Recombinant peptide

<400> SEQUENCE: 827

Val Ser Asp Arg Pro Trp Leu Val
1               5

<210> SEQ ID NO 828
<211> LENGTH: 8
<212> TYPE: PRT
<213> ORGANISM: Artificial Sequence
<220> FEATURE:
<223> OTHER INFORMATION: Recombinant peptide

<400> SEQUENCE: 828

Val Ser Asp Arg Pro Trp Val Leu
1               5

<210> SEQ ID NO 829
<211> LENGTH: 8
<212> TYPE: PRT
<213> ORGANISM: Artificial Sequence
<220> FEATURE:
<223> OTHER INFORMATION: Recombinant peptide

<400> SEQUENCE: 829

Val Ser Asp Arg Pro Trp Val Ile
1               5

<210> SEQ ID NO 830
<211> LENGTH: 8
<212> TYPE: PRT
<213> ORGANISM: Artificial Sequence
<220> FEATURE:
<223> OTHER INFORMATION: Recombinant peptide

<400> SEQUENCE: 830

Val Ser Asp Arg Pro Trp Val Val
1               5

<210> SEQ ID NO 831
<211> LENGTH: 8
<212> TYPE: PRT
<213> ORGANISM: Artificial Sequence
<220> FEATURE:
<223> OTHER INFORMATION: Recombinant peptide

<400> SEQUENCE: 831

Val Ser Glu Lys Pro Tyr Ile Leu
1               5

<210> SEQ ID NO 832
<211> LENGTH: 8
<212> TYPE: PRT
<213> ORGANISM: Artificial Sequence
<220> FEATURE:
<223> OTHER INFORMATION: Recombinant peptide

<400> SEQUENCE: 832

Val Ser Glu Lys Pro Tyr Ile Ile
1               5
```

```
<210> SEQ ID NO 833
<211> LENGTH: 8
<212> TYPE: PRT
<213> ORGANISM: Artificial Sequence
<220> FEATURE:
<223> OTHER INFORMATION: Recombinant peptide

<400> SEQUENCE: 833

Val Ser Glu Lys Pro Tyr Ile Val
1               5

<210> SEQ ID NO 834
<211> LENGTH: 8
<212> TYPE: PRT
<213> ORGANISM: Artificial Sequence
<220> FEATURE:
<223> OTHER INFORMATION: Recombinant peptide

<400> SEQUENCE: 834

Val Ser Glu Lys Pro Tyr Leu Leu
1               5

<210> SEQ ID NO 835
<211> LENGTH: 8
<212> TYPE: PRT
<213> ORGANISM: Artificial Sequence
<220> FEATURE:
<223> OTHER INFORMATION: Recombinant peptide

<400> SEQUENCE: 835

Val Ser Glu Lys Pro Tyr Leu Ile
1               5

<210> SEQ ID NO 836
<211> LENGTH: 8
<212> TYPE: PRT
<213> ORGANISM: Artificial Sequence
<220> FEATURE:
<223> OTHER INFORMATION: Recombinant peptide

<400> SEQUENCE: 836

Val Ser Glu Lys Pro Tyr Leu Val
1               5

<210> SEQ ID NO 837
<211> LENGTH: 8
<212> TYPE: PRT
<213> ORGANISM: Artificial Sequence
<220> FEATURE:
<223> OTHER INFORMATION: Recombinant peptide

<400> SEQUENCE: 837

Val Ser Glu Lys Pro Tyr Val Leu
1               5

<210> SEQ ID NO 838
<211> LENGTH: 8
<212> TYPE: PRT
<213> ORGANISM: Artificial Sequence
<220> FEATURE:
<223> OTHER INFORMATION: Recombinant peptide

<400> SEQUENCE: 838

Val Ser Glu Lys Pro Tyr Val Ile
1               5
```

<210> SEQ ID NO 839
<211> LENGTH: 8
<212> TYPE: PRT
<213> ORGANISM: Artificial Sequence
<220> FEATURE:
<223> OTHER INFORMATION: Recombinant peptide

<400> SEQUENCE: 839

Val Ser Glu Lys Pro Tyr Val Val
1               5

<210> SEQ ID NO 840
<211> LENGTH: 8
<212> TYPE: PRT
<213> ORGANISM: Artificial Sequence
<220> FEATURE:
<223> OTHER INFORMATION: Recombinant peptide

<400> SEQUENCE: 840

Val Ser Glu Lys Pro Trp Ile Leu
1               5

<210> SEQ ID NO 841
<211> LENGTH: 8
<212> TYPE: PRT
<213> ORGANISM: Artificial Sequence
<220> FEATURE:
<223> OTHER INFORMATION: Recombinant peptide

<400> SEQUENCE: 841

Val Ser Glu Lys Pro Trp Ile Ile
1               5

<210> SEQ ID NO 842
<211> LENGTH: 8
<212> TYPE: PRT
<213> ORGANISM: Artificial Sequence
<220> FEATURE:
<223> OTHER INFORMATION: Recombinant peptide

<400> SEQUENCE: 842

Val Ser Glu Lys Pro Trp Ile Val
1               5

<210> SEQ ID NO 843
<211> LENGTH: 8
<212> TYPE: PRT
<213> ORGANISM: Artificial Sequence
<220> FEATURE:
<223> OTHER INFORMATION: Recombinant peptide

<400> SEQUENCE: 843

Val Ser Glu Lys Pro Trp Leu Leu
1               5

<210> SEQ ID NO 844
<211> LENGTH: 8
<212> TYPE: PRT
<213> ORGANISM: Artificial Sequence
<220> FEATURE:
<223> OTHER INFORMATION: Recombinant peptide

<400> SEQUENCE: 844

Val Ser Glu Lys Pro Trp Leu Ile
1               5

```
<210> SEQ ID NO 845
<211> LENGTH: 8
<212> TYPE: PRT
<213> ORGANISM: Artificial Sequence
<220> FEATURE:
<223> OTHER INFORMATION: Recombinant peptide

<400> SEQUENCE: 845

Val Ser Glu Lys Pro Trp Leu Val
1               5

<210> SEQ ID NO 846
<211> LENGTH: 8
<212> TYPE: PRT
<213> ORGANISM: Artificial Sequence
<220> FEATURE:
<223> OTHER INFORMATION: Recombinant peptide

<400> SEQUENCE: 846

Val Ser Glu Lys Pro Trp Val Leu
1               5

<210> SEQ ID NO 847
<211> LENGTH: 8
<212> TYPE: PRT
<213> ORGANISM: Artificial Sequence
<220> FEATURE:
<223> OTHER INFORMATION: Recombinant peptide

<400> SEQUENCE: 847

Val Ser Glu Lys Pro Trp Val Ile
1               5

<210> SEQ ID NO 848
<211> LENGTH: 8
<212> TYPE: PRT
<213> ORGANISM: Artificial Sequence
<220> FEATURE:
<223> OTHER INFORMATION: Recombinant peptide

<400> SEQUENCE: 848

Val Ser Glu Lys Pro Trp Val Val
1               5

<210> SEQ ID NO 849
<211> LENGTH: 8
<212> TYPE: PRT
<213> ORGANISM: Artificial Sequence
<220> FEATURE:
<223> OTHER INFORMATION: Recombinant peptide

<400> SEQUENCE: 849

Val Ser Glu Arg Pro Tyr Ile Leu
1               5

<210> SEQ ID NO 850
<211> LENGTH: 8
<212> TYPE: PRT
<213> ORGANISM: Artificial Sequence
<220> FEATURE:
<223> OTHER INFORMATION: Recombinant peptide

<400> SEQUENCE: 850

Val Ser Glu Arg Pro Tyr Ile Ile
1               5

<210> SEQ ID NO 851
```

```
<211> LENGTH: 8
<212> TYPE: PRT
<213> ORGANISM: Artificial Sequence
<220> FEATURE:
<223> OTHER INFORMATION: Recombinant peptide

<400> SEQUENCE: 851

Val Ser Glu Arg Pro Tyr Ile Val
1               5

<210> SEQ ID NO 852
<211> LENGTH: 8
<212> TYPE: PRT
<213> ORGANISM: Artificial Sequence
<220> FEATURE:
<223> OTHER INFORMATION: Recombinant peptide

<400> SEQUENCE: 852

Val Ser Glu Arg Pro Tyr Leu Leu
1               5

<210> SEQ ID NO 853
<211> LENGTH: 8
<212> TYPE: PRT
<213> ORGANISM: Artificial Sequence
<220> FEATURE:
<223> OTHER INFORMATION: Recombinant peptide

<400> SEQUENCE: 853

Val Ser Glu Arg Pro Tyr Leu Ile
1               5

<210> SEQ ID NO 854
<211> LENGTH: 8
<212> TYPE: PRT
<213> ORGANISM: Artificial Sequence
<220> FEATURE:
<223> OTHER INFORMATION: Recombinant peptide

<400> SEQUENCE: 854

Val Ser Glu Arg Pro Tyr Leu Val
1               5

<210> SEQ ID NO 855
<211> LENGTH: 8
<212> TYPE: PRT
<213> ORGANISM: Artificial Sequence
<220> FEATURE:
<223> OTHER INFORMATION: Recombinant peptide

<400> SEQUENCE: 855

Val Ser Glu Arg Pro Tyr Val Leu
1               5

<210> SEQ ID NO 856
<211> LENGTH: 8
<212> TYPE: PRT
<213> ORGANISM: Artificial Sequence
<220> FEATURE:
<223> OTHER INFORMATION: Recombinant peptide

<400> SEQUENCE: 856

Val Ser Glu Arg Pro Tyr Val Ile
1               5

<210> SEQ ID NO 857
<211> LENGTH: 8
```

```
<212> TYPE: PRT
<213> ORGANISM: Artificial Sequence
<220> FEATURE:
<223> OTHER INFORMATION: Recombinant peptide

<400> SEQUENCE: 857

Val Ser Glu Arg Pro Tyr Val Val
1               5

<210> SEQ ID NO 858
<211> LENGTH: 8
<212> TYPE: PRT
<213> ORGANISM: Artificial Sequence
<220> FEATURE:
<223> OTHER INFORMATION: Recombinant peptide

<400> SEQUENCE: 858

Val Ser Glu Arg Pro Trp Ile Leu
1               5

<210> SEQ ID NO 859
<211> LENGTH: 8
<212> TYPE: PRT
<213> ORGANISM: Artificial Sequence
<220> FEATURE:
<223> OTHER INFORMATION: Recombinant peptide

<400> SEQUENCE: 859

Val Ser Glu Arg Pro Trp Ile Ile
1               5

<210> SEQ ID NO 860
<211> LENGTH: 8
<212> TYPE: PRT
<213> ORGANISM: Artificial Sequence
<220> FEATURE:
<223> OTHER INFORMATION: Recombinant peptide

<400> SEQUENCE: 860

Val Ser Glu Arg Pro Trp Ile Val
1               5

<210> SEQ ID NO 861
<211> LENGTH: 8
<212> TYPE: PRT
<213> ORGANISM: Artificial Sequence
<220> FEATURE:
<223> OTHER INFORMATION: Recombinant peptide

<400> SEQUENCE: 861

Val Ser Glu Arg Pro Trp Leu Leu
1               5

<210> SEQ ID NO 862
<211> LENGTH: 8
<212> TYPE: PRT
<213> ORGANISM: Artificial Sequence
<220> FEATURE:
<223> OTHER INFORMATION: Recombinant peptide

<400> SEQUENCE: 862

Val Ser Glu Arg Pro Trp Leu Ile
1               5

<210> SEQ ID NO 863
<211> LENGTH: 8
<212> TYPE: PRT
```

```
<213> ORGANISM: Artificial Sequence
<220> FEATURE:
<223> OTHER INFORMATION: Recombinant peptide

<400> SEQUENCE: 863

Val Ser Glu Arg Pro Trp Leu Val
1               5

<210> SEQ ID NO 864
<211> LENGTH: 8
<212> TYPE: PRT
<213> ORGANISM: Artificial Sequence
<220> FEATURE:
<223> OTHER INFORMATION: Recombinant peptide

<400> SEQUENCE: 864

Val Ser Glu Arg Pro Trp Val Leu
1               5

<210> SEQ ID NO 865
<211> LENGTH: 8
<212> TYPE: PRT
<213> ORGANISM: Artificial Sequence
<220> FEATURE:
<223> OTHER INFORMATION: Recombinant peptide

<400> SEQUENCE: 865

Val Ser Glu Arg Pro Trp Val Ile
1               5

<210> SEQ ID NO 866
<211> LENGTH: 8
<212> TYPE: PRT
<213> ORGANISM: Artificial Sequence
<220> FEATURE:
<223> OTHER INFORMATION: Recombinant peptide

<400> SEQUENCE: 866

Val Ser Glu Arg Pro Trp Val Val
1               5

<210> SEQ ID NO 867
<211> LENGTH: 8
<212> TYPE: PRT
<213> ORGANISM: Artificial Sequence
<220> FEATURE:
<223> OTHER INFORMATION: Recombinant peptide

<400> SEQUENCE: 867

Val Thr Asp Lys Pro Tyr Ile Leu
1               5

<210> SEQ ID NO 868
<211> LENGTH: 8
<212> TYPE: PRT
<213> ORGANISM: Artificial Sequence
<220> FEATURE:
<223> OTHER INFORMATION: Recombinant peptide

<400> SEQUENCE: 868

Val Thr Asp Lys Pro Tyr Ile Ile
1               5

<210> SEQ ID NO 869
<211> LENGTH: 8
<212> TYPE: PRT
<213> ORGANISM: Artificial Sequence
```

```
<220> FEATURE:
<223> OTHER INFORMATION: Recombinant peptide

<400> SEQUENCE: 869

Val Thr Asp Lys Pro Tyr Ile Val
1               5

<210> SEQ ID NO 870
<211> LENGTH: 8
<212> TYPE: PRT
<213> ORGANISM: Artificial Sequence
<220> FEATURE:
<223> OTHER INFORMATION: Recombinant peptide

<400> SEQUENCE: 870

Val Thr Asp Lys Pro Tyr Leu Leu
1               5

<210> SEQ ID NO 871
<211> LENGTH: 8
<212> TYPE: PRT
<213> ORGANISM: Artificial Sequence
<220> FEATURE:
<223> OTHER INFORMATION: Recombinant peptide

<400> SEQUENCE: 871

Val Thr Asp Lys Pro Tyr Leu Ile
1               5

<210> SEQ ID NO 872
<211> LENGTH: 8
<212> TYPE: PRT
<213> ORGANISM: Artificial Sequence
<220> FEATURE:
<223> OTHER INFORMATION: Recombinant peptide

<400> SEQUENCE: 872

Val Thr Asp Lys Pro Tyr Leu Val
1               5

<210> SEQ ID NO 873
<211> LENGTH: 8
<212> TYPE: PRT
<213> ORGANISM: Artificial Sequence
<220> FEATURE:
<223> OTHER INFORMATION: Recombinant peptide

<400> SEQUENCE: 873

Val Thr Asp Lys Pro Tyr Val Leu
1               5

<210> SEQ ID NO 874
<211> LENGTH: 8
<212> TYPE: PRT
<213> ORGANISM: Artificial Sequence
<220> FEATURE:
<223> OTHER INFORMATION: Recombinant peptide

<400> SEQUENCE: 874

Val Thr Asp Lys Pro Tyr Val Ile
1               5

<210> SEQ ID NO 875
<211> LENGTH: 8
<212> TYPE: PRT
<213> ORGANISM: Artificial Sequence
<220> FEATURE:
```

<223> OTHER INFORMATION: Recombinant peptide

<400> SEQUENCE: 875

Val Thr Asp Lys Pro Tyr Val Val
1               5

<210> SEQ ID NO 876
<211> LENGTH: 8
<212> TYPE: PRT
<213> ORGANISM: Artificial Sequence
<220> FEATURE:
<223> OTHER INFORMATION: Recombinant peptide

<400> SEQUENCE: 876

Val Thr Asp Lys Pro Trp Ile Leu
1               5

<210> SEQ ID NO 877
<211> LENGTH: 8
<212> TYPE: PRT
<213> ORGANISM: Artificial Sequence
<220> FEATURE:
<223> OTHER INFORMATION: Recombinant peptide

<400> SEQUENCE: 877

Val Thr Asp Lys Pro Trp Ile Ile
1               5

<210> SEQ ID NO 878
<211> LENGTH: 8
<212> TYPE: PRT
<213> ORGANISM: Artificial Sequence
<220> FEATURE:
<223> OTHER INFORMATION: Recombinant peptide

<400> SEQUENCE: 878

Val Thr Asp Lys Pro Trp Ile Val
1               5

<210> SEQ ID NO 879
<211> LENGTH: 8
<212> TYPE: PRT
<213> ORGANISM: Artificial Sequence
<220> FEATURE:
<223> OTHER INFORMATION: Recombinant peptide

<400> SEQUENCE: 879

Val Thr Asp Lys Pro Trp Leu Leu
1               5

<210> SEQ ID NO 880
<211> LENGTH: 8
<212> TYPE: PRT
<213> ORGANISM: Artificial Sequence
<220> FEATURE:
<223> OTHER INFORMATION: Recombinant peptide

<400> SEQUENCE: 880

Val Thr Asp Lys Pro Trp Leu Ile
1               5

<210> SEQ ID NO 881
<211> LENGTH: 8
<212> TYPE: PRT
<213> ORGANISM: Artificial Sequence
<220> FEATURE:
<223> OTHER INFORMATION: Recombinant peptide

<400> SEQUENCE: 881

Val Thr Asp Lys Pro Trp Leu Val
1               5

<210> SEQ ID NO 882
<211> LENGTH: 8
<212> TYPE: PRT
<213> ORGANISM: Artificial Sequence
<220> FEATURE:
<223> OTHER INFORMATION: Recombinant peptide

<400> SEQUENCE: 882

Val Thr Asp Lys Pro Trp Val Leu
1               5

<210> SEQ ID NO 883
<211> LENGTH: 8
<212> TYPE: PRT
<213> ORGANISM: Artificial Sequence
<220> FEATURE:
<223> OTHER INFORMATION: Recombinant peptide

<400> SEQUENCE: 883

Val Thr Asp Lys Pro Trp Val Ile
1               5

<210> SEQ ID NO 884
<211> LENGTH: 8
<212> TYPE: PRT
<213> ORGANISM: Artificial Sequence
<220> FEATURE:
<223> OTHER INFORMATION: Recombinant peptide

<400> SEQUENCE: 884

Val Thr Asp Lys Pro Trp Val Val
1               5

<210> SEQ ID NO 885
<211> LENGTH: 8
<212> TYPE: PRT
<213> ORGANISM: Artificial Sequence
<220> FEATURE:
<223> OTHER INFORMATION: Recombinant peptide

<400> SEQUENCE: 885

Val Thr Asp Arg Pro Tyr Ile Leu
1               5

<210> SEQ ID NO 886
<211> LENGTH: 8
<212> TYPE: PRT
<213> ORGANISM: Artificial Sequence
<220> FEATURE:
<223> OTHER INFORMATION: Recombinant peptide

<400> SEQUENCE: 886

Val Thr Asp Arg Pro Tyr Ile Ile
1               5

<210> SEQ ID NO 887
<211> LENGTH: 8
<212> TYPE: PRT
<213> ORGANISM: Artificial Sequence
<220> FEATURE:
<223> OTHER INFORMATION: Recombinant peptide

```
<400> SEQUENCE: 887

Val Thr Asp Arg Pro Tyr Ile Val
1               5

<210> SEQ ID NO 888
<211> LENGTH: 8
<212> TYPE: PRT
<213> ORGANISM: Artificial Sequence
<220> FEATURE:
<223> OTHER INFORMATION: Recombinant peptide

<400> SEQUENCE: 888

Val Thr Asp Arg Pro Tyr Leu Leu
1               5

<210> SEQ ID NO 889
<211> LENGTH: 8
<212> TYPE: PRT
<213> ORGANISM: Artificial Sequence
<220> FEATURE:
<223> OTHER INFORMATION: Recombinant peptide

<400> SEQUENCE: 889

Val Thr Asp Arg Pro Tyr Leu Ile
1               5

<210> SEQ ID NO 890
<211> LENGTH: 8
<212> TYPE: PRT
<213> ORGANISM: Artificial Sequence
<220> FEATURE:
<223> OTHER INFORMATION: Recombinant peptide

<400> SEQUENCE: 890

Val Thr Asp Arg Pro Tyr Leu Val
1               5

<210> SEQ ID NO 891
<211> LENGTH: 8
<212> TYPE: PRT
<213> ORGANISM: Artificial Sequence
<220> FEATURE:
<223> OTHER INFORMATION: Recombinant peptide

<400> SEQUENCE: 891

Val Thr Asp Arg Pro Tyr Val Leu
1               5

<210> SEQ ID NO 892
<211> LENGTH: 8
<212> TYPE: PRT
<213> ORGANISM: Artificial Sequence
<220> FEATURE:
<223> OTHER INFORMATION: Recombinant peptide

<400> SEQUENCE: 892

Val Thr Asp Arg Pro Tyr Val Ile
1               5

<210> SEQ ID NO 893
<211> LENGTH: 8
<212> TYPE: PRT
<213> ORGANISM: Artificial Sequence
<220> FEATURE:
<223> OTHER INFORMATION: Recombinant peptide

<400> SEQUENCE: 893
```

Val Thr Asp Arg Pro Tyr Val Val
1               5

<210> SEQ ID NO 894
<211> LENGTH: 8
<212> TYPE: PRT
<213> ORGANISM: Artificial Sequence
<220> FEATURE:
<223> OTHER INFORMATION: Recombinant peptide

<400> SEQUENCE: 894

Val Thr Asp Arg Pro Trp Ile Leu
1               5

<210> SEQ ID NO 895
<211> LENGTH: 8
<212> TYPE: PRT
<213> ORGANISM: Artificial Sequence
<220> FEATURE:
<223> OTHER INFORMATION: Recombinant peptide

<400> SEQUENCE: 895

Val Thr Asp Arg Pro Trp Ile Ile
1               5

<210> SEQ ID NO 896
<211> LENGTH: 8
<212> TYPE: PRT
<213> ORGANISM: Artificial Sequence
<220> FEATURE:
<223> OTHER INFORMATION: Recombinant peptide

<400> SEQUENCE: 896

Val Thr Asp Arg Pro Trp Ile Val
1               5

<210> SEQ ID NO 897
<211> LENGTH: 8
<212> TYPE: PRT
<213> ORGANISM: Artificial Sequence
<220> FEATURE:
<223> OTHER INFORMATION: Recombinant peptide

<400> SEQUENCE: 897

Val Thr Asp Arg Pro Trp Leu Leu
1               5

<210> SEQ ID NO 898
<211> LENGTH: 8
<212> TYPE: PRT
<213> ORGANISM: Artificial Sequence
<220> FEATURE:
<223> OTHER INFORMATION: Recombinant peptide

<400> SEQUENCE: 898

Val Thr Asp Arg Pro Trp Leu Ile
1               5

<210> SEQ ID NO 899
<211> LENGTH: 8
<212> TYPE: PRT
<213> ORGANISM: Artificial Sequence
<220> FEATURE:
<223> OTHER INFORMATION: Recombinant peptide

<400> SEQUENCE: 899

```
Val Thr Asp Arg Pro Trp Leu Val
1               5

<210> SEQ ID NO 900
<211> LENGTH: 8
<212> TYPE: PRT
<213> ORGANISM: Artificial Sequence
<220> FEATURE:
<223> OTHER INFORMATION: Recombinant peptide

<400> SEQUENCE: 900

Val Thr Asp Arg Pro Trp Val Leu
1               5

<210> SEQ ID NO 901
<211> LENGTH: 8
<212> TYPE: PRT
<213> ORGANISM: Artificial Sequence
<220> FEATURE:
<223> OTHER INFORMATION: Recombinant peptide

<400> SEQUENCE: 901

Val Thr Asp Arg Pro Trp Val Ile
1               5

<210> SEQ ID NO 902
<211> LENGTH: 8
<212> TYPE: PRT
<213> ORGANISM: Artificial Sequence
<220> FEATURE:
<223> OTHER INFORMATION: Recombinant peptide

<400> SEQUENCE: 902

Val Thr Asp Arg Pro Trp Val Val
1               5

<210> SEQ ID NO 903
<211> LENGTH: 8
<212> TYPE: PRT
<213> ORGANISM: Artificial Sequence
<220> FEATURE:
<223> OTHER INFORMATION: Recombinant peptide

<400> SEQUENCE: 903

Val Thr Glu Lys Pro Tyr Ile Leu
1               5

<210> SEQ ID NO 904
<211> LENGTH: 8
<212> TYPE: PRT
<213> ORGANISM: Artificial Sequence
<220> FEATURE:
<223> OTHER INFORMATION: Recombinant peptide

<400> SEQUENCE: 904

Val Thr Glu Lys Pro Tyr Ile Ile
1               5

<210> SEQ ID NO 905
<211> LENGTH: 8
<212> TYPE: PRT
<213> ORGANISM: Artificial Sequence
<220> FEATURE:
<223> OTHER INFORMATION: Recombinant peptide

<400> SEQUENCE: 905

Val Thr Glu Lys Pro Tyr Ile Val
```

```
1               5

<210> SEQ ID NO 906
<211> LENGTH: 8
<212> TYPE: PRT
<213> ORGANISM: Artificial Sequence
<220> FEATURE:
<223> OTHER INFORMATION: Recombinant peptide

<400> SEQUENCE: 906

Val Thr Glu Lys Pro Tyr Leu Leu
1               5

<210> SEQ ID NO 907
<211> LENGTH: 8
<212> TYPE: PRT
<213> ORGANISM: Artificial Sequence
<220> FEATURE:
<223> OTHER INFORMATION: Recombinant peptide

<400> SEQUENCE: 907

Val Thr Glu Lys Pro Tyr Leu Ile
1               5

<210> SEQ ID NO 908
<211> LENGTH: 8
<212> TYPE: PRT
<213> ORGANISM: Artificial Sequence
<220> FEATURE:
<223> OTHER INFORMATION: Recombinant peptide

<400> SEQUENCE: 908

Val Thr Glu Lys Pro Tyr Leu Val
1               5

<210> SEQ ID NO 909
<211> LENGTH: 8
<212> TYPE: PRT
<213> ORGANISM: Artificial Sequence
<220> FEATURE:
<223> OTHER INFORMATION: Recombinant peptide

<400> SEQUENCE: 909

Val Thr Glu Lys Pro Tyr Val Leu
1               5

<210> SEQ ID NO 910
<211> LENGTH: 8
<212> TYPE: PRT
<213> ORGANISM: Artificial Sequence
<220> FEATURE:
<223> OTHER INFORMATION: Recombinant peptide

<400> SEQUENCE: 910

Val Thr Glu Lys Pro Tyr Val Ile
1               5

<210> SEQ ID NO 911
<211> LENGTH: 8
<212> TYPE: PRT
<213> ORGANISM: Artificial Sequence
<220> FEATURE:
<223> OTHER INFORMATION: Recombinant peptide

<400> SEQUENCE: 911

Val Thr Glu Lys Pro Tyr Val Val
1               5
```

<210> SEQ ID NO 912
<211> LENGTH: 8
<212> TYPE: PRT
<213> ORGANISM: Artificial Sequence
<220> FEATURE:
<223> OTHER INFORMATION: Recombinant peptide

<400> SEQUENCE: 912

Val Thr Glu Lys Pro Trp Ile Leu
1               5

<210> SEQ ID NO 913
<211> LENGTH: 8
<212> TYPE: PRT
<213> ORGANISM: Artificial Sequence
<220> FEATURE:
<223> OTHER INFORMATION: Recombinant peptide

<400> SEQUENCE: 913

Val Thr Glu Lys Pro Trp Ile Ile
1               5

<210> SEQ ID NO 914
<211> LENGTH: 8
<212> TYPE: PRT
<213> ORGANISM: Artificial Sequence
<220> FEATURE:
<223> OTHER INFORMATION: Recombinant peptide

<400> SEQUENCE: 914

Val Thr Glu Lys Pro Trp Ile Val
1               5

<210> SEQ ID NO 915
<211> LENGTH: 8
<212> TYPE: PRT
<213> ORGANISM: Artificial Sequence
<220> FEATURE:
<223> OTHER INFORMATION: Recombinant peptide

<400> SEQUENCE: 915

Val Thr Glu Lys Pro Trp Leu Leu
1               5

<210> SEQ ID NO 916
<211> LENGTH: 8
<212> TYPE: PRT
<213> ORGANISM: Artificial Sequence
<220> FEATURE:
<223> OTHER INFORMATION: Recombinant peptide

<400> SEQUENCE: 916

Val Thr Glu Lys Pro Trp Leu Ile
1               5

<210> SEQ ID NO 917
<211> LENGTH: 8
<212> TYPE: PRT
<213> ORGANISM: Artificial Sequence
<220> FEATURE:
<223> OTHER INFORMATION: Recombinant peptide

<400> SEQUENCE: 917

Val Thr Glu Lys Pro Trp Leu Val
1               5

<210> SEQ ID NO 918
<211> LENGTH: 8
<212> TYPE: PRT
<213> ORGANISM: Artificial Sequence
<220> FEATURE:
<223> OTHER INFORMATION: Recombinant peptide

<400> SEQUENCE: 918

Val Thr Glu Lys Pro Trp Val Leu
1               5

<210> SEQ ID NO 919
<211> LENGTH: 8
<212> TYPE: PRT
<213> ORGANISM: Artificial Sequence
<220> FEATURE:
<223> OTHER INFORMATION: Recombinant peptide

<400> SEQUENCE: 919

Val Thr Glu Lys Pro Trp Val Ile
1               5

<210> SEQ ID NO 920
<211> LENGTH: 8
<212> TYPE: PRT
<213> ORGANISM: Artificial Sequence
<220> FEATURE:
<223> OTHER INFORMATION: Recombinant peptide

<400> SEQUENCE: 920

Val Thr Glu Lys Pro Trp Val Val
1               5

<210> SEQ ID NO 921
<211> LENGTH: 8
<212> TYPE: PRT
<213> ORGANISM: Artificial Sequence
<220> FEATURE:
<223> OTHER INFORMATION: Recombinant peptide

<400> SEQUENCE: 921

Val Thr Glu Arg Pro Tyr Ile Leu
1               5

<210> SEQ ID NO 922
<211> LENGTH: 8
<212> TYPE: PRT
<213> ORGANISM: Artificial Sequence
<220> FEATURE:
<223> OTHER INFORMATION: Recombinant peptide

<400> SEQUENCE: 922

Val Thr Glu Arg Pro Tyr Ile Ile
1               5

<210> SEQ ID NO 923
<211> LENGTH: 8
<212> TYPE: PRT
<213> ORGANISM: Artificial Sequence
<220> FEATURE:
<223> OTHER INFORMATION: Recombinant peptide

<400> SEQUENCE: 923

Val Thr Glu Arg Pro Tyr Ile Val
1               5

```
<210> SEQ ID NO 924
<211> LENGTH: 8
<212> TYPE: PRT
<213> ORGANISM: Artificial Sequence
<220> FEATURE:
<223> OTHER INFORMATION: Recombinant peptide

<400> SEQUENCE: 924

Val Thr Glu Arg Pro Tyr Leu Leu
1               5

<210> SEQ ID NO 925
<211> LENGTH: 8
<212> TYPE: PRT
<213> ORGANISM: Artificial Sequence
<220> FEATURE:
<223> OTHER INFORMATION: Recombinant peptide

<400> SEQUENCE: 925

Val Thr Glu Arg Pro Tyr Leu Ile
1               5

<210> SEQ ID NO 926
<211> LENGTH: 8
<212> TYPE: PRT
<213> ORGANISM: Artificial Sequence
<220> FEATURE:
<223> OTHER INFORMATION: Recombinant peptide

<400> SEQUENCE: 926

Val Thr Glu Arg Pro Tyr Leu Val
1               5

<210> SEQ ID NO 927
<211> LENGTH: 8
<212> TYPE: PRT
<213> ORGANISM: Artificial Sequence
<220> FEATURE:
<223> OTHER INFORMATION: Recombinant peptide

<400> SEQUENCE: 927

Val Thr Glu Arg Pro Tyr Val Leu
1               5

<210> SEQ ID NO 928
<211> LENGTH: 8
<212> TYPE: PRT
<213> ORGANISM: Artificial Sequence
<220> FEATURE:
<223> OTHER INFORMATION: Recombinant peptide

<400> SEQUENCE: 928

Val Thr Glu Arg Pro Tyr Val Ile
1               5

<210> SEQ ID NO 929
<211> LENGTH: 8
<212> TYPE: PRT
<213> ORGANISM: Artificial Sequence
<220> FEATURE:
<223> OTHER INFORMATION: Recombinant peptide

<400> SEQUENCE: 929

Val Thr Glu Arg Pro Tyr Val Val
1               5

<210> SEQ ID NO 930
```

```
<211> LENGTH: 8
<212> TYPE: PRT
<213> ORGANISM: Artificial Sequence
<220> FEATURE:
<223> OTHER INFORMATION: Recombinant peptide

<400> SEQUENCE: 930

Val Thr Glu Arg Pro Trp Ile Leu
1               5

<210> SEQ ID NO 931
<211> LENGTH: 8
<212> TYPE: PRT
<213> ORGANISM: Artificial Sequence
<220> FEATURE:
<223> OTHER INFORMATION: Recombinant peptide

<400> SEQUENCE: 931

Val Thr Glu Arg Pro Trp Ile Ile
1               5

<210> SEQ ID NO 932
<211> LENGTH: 8
<212> TYPE: PRT
<213> ORGANISM: Artificial Sequence
<220> FEATURE:
<223> OTHER INFORMATION: Recombinant peptide

<400> SEQUENCE: 932

Val Thr Glu Arg Pro Trp Ile Val
1               5

<210> SEQ ID NO 933
<211> LENGTH: 8
<212> TYPE: PRT
<213> ORGANISM: Artificial Sequence
<220> FEATURE:
<223> OTHER INFORMATION: Recombinant peptide

<400> SEQUENCE: 933

Val Thr Glu Arg Pro Trp Leu Leu
1               5

<210> SEQ ID NO 934
<211> LENGTH: 8
<212> TYPE: PRT
<213> ORGANISM: Artificial Sequence
<220> FEATURE:
<223> OTHER INFORMATION: Recombinant peptide

<400> SEQUENCE: 934

Val Thr Glu Arg Pro Trp Leu Ile
1               5

<210> SEQ ID NO 935
<211> LENGTH: 8
<212> TYPE: PRT
<213> ORGANISM: Artificial Sequence
<220> FEATURE:
<223> OTHER INFORMATION: Recombinant peptide

<400> SEQUENCE: 935

Val Thr Glu Arg Pro Trp Leu Val
1               5

<210> SEQ ID NO 936
<211> LENGTH: 8
```

```
<212> TYPE: PRT
<213> ORGANISM: Artificial Sequence
<220> FEATURE:
<223> OTHER INFORMATION: Recombinant peptide

<400> SEQUENCE: 936

Val Thr Glu Arg Pro Trp Val Leu
1               5

<210> SEQ ID NO 937
<211> LENGTH: 8
<212> TYPE: PRT
<213> ORGANISM: Artificial Sequence
<220> FEATURE:
<223> OTHER INFORMATION: Recombinant peptide

<400> SEQUENCE: 937

Val Thr Glu Arg Pro Trp Val Ile
1               5

<210> SEQ ID NO 938
<211> LENGTH: 8
<212> TYPE: PRT
<213> ORGANISM: Artificial Sequence
<220> FEATURE:
<223> OTHER INFORMATION: Recombinant peptide

<400> SEQUENCE: 938

Val Thr Glu Arg Pro Trp Val Val
1               5

<210> SEQ ID NO 939
<211> LENGTH: 8
<212> TYPE: PRT
<213> ORGANISM: Artificial Sequence
<220> FEATURE:
<223> OTHER INFORMATION: Recombinant peptide

<400> SEQUENCE: 939

Tyr Ser Asp Lys Pro Tyr Ile Leu
1               5

<210> SEQ ID NO 940
<211> LENGTH: 8
<212> TYPE: PRT
<213> ORGANISM: Artificial Sequence
<220> FEATURE:
<223> OTHER INFORMATION: Recombinant peptide

<400> SEQUENCE: 940

Trp Ser Asp Lys Pro Tyr Ile Leu
1               5

<210> SEQ ID NO 941
<211> LENGTH: 8
<212> TYPE: PRT
<213> ORGANISM: Artificial Sequence
<220> FEATURE:
<223> OTHER INFORMATION: Recombinant peptide

<400> SEQUENCE: 941

Thr Ser Asp Lys Pro Tyr Ile Leu
1               5

<210> SEQ ID NO 942
<211> LENGTH: 8
<212> TYPE: PRT
```

```
<213> ORGANISM: Artificial Sequence
<220> FEATURE:
<223> OTHER INFORMATION: Recombinant peptide

<400> SEQUENCE: 942

Ser Ser Asp Lys Pro Tyr Ile Leu
1               5

<210> SEQ ID NO 943
<211> LENGTH: 8
<212> TYPE: PRT
<213> ORGANISM: Artificial Sequence
<220> FEATURE:
<223> OTHER INFORMATION: Recombinant peptide

<400> SEQUENCE: 943

Arg Ser Asp Lys Pro Tyr Ile Leu
1               5

<210> SEQ ID NO 944
<211> LENGTH: 8
<212> TYPE: PRT
<213> ORGANISM: Artificial Sequence
<220> FEATURE:
<223> OTHER INFORMATION: Recombinant peptide

<400> SEQUENCE: 944

Gln Ser Asp Lys Pro Tyr Ile Leu
1               5

<210> SEQ ID NO 945
<211> LENGTH: 8
<212> TYPE: PRT
<213> ORGANISM: Artificial Sequence
<220> FEATURE:
<223> OTHER INFORMATION: Recombinant peptide

<400> SEQUENCE: 945

Pro Ser Asp Lys Pro Tyr Ile Leu
1               5

<210> SEQ ID NO 946
<211> LENGTH: 8
<212> TYPE: PRT
<213> ORGANISM: Artificial Sequence
<220> FEATURE:
<223> OTHER INFORMATION: Recombinant peptide

<400> SEQUENCE: 946

Asn Ser Asp Lys Pro Tyr Ile Leu
1               5

<210> SEQ ID NO 947
<211> LENGTH: 8
<212> TYPE: PRT
<213> ORGANISM: Artificial Sequence
<220> FEATURE:
<223> OTHER INFORMATION: Recombinant peptide

<400> SEQUENCE: 947

Met Ser Asp Lys Pro Tyr Ile Leu
1               5

<210> SEQ ID NO 948
<211> LENGTH: 8
<212> TYPE: PRT
<213> ORGANISM: Artificial Sequence
```

```
<220> FEATURE:
<223> OTHER INFORMATION: Recombinant peptide

<400> SEQUENCE: 948

Lys Ser Asp Lys Pro Tyr Ile Leu
1               5

<210> SEQ ID NO 949
<211> LENGTH: 8
<212> TYPE: PRT
<213> ORGANISM: Artificial Sequence
<220> FEATURE:
<223> OTHER INFORMATION: Recombinant peptide

<400> SEQUENCE: 949

His Ser Asp Lys Pro Tyr Ile Leu
1               5

<210> SEQ ID NO 950
<211> LENGTH: 8
<212> TYPE: PRT
<213> ORGANISM: Artificial Sequence
<220> FEATURE:
<223> OTHER INFORMATION: Recombinant peptide

<400> SEQUENCE: 950

Gly Ser Asp Lys Pro Tyr Ile Leu
1               5

<210> SEQ ID NO 951
<211> LENGTH: 8
<212> TYPE: PRT
<213> ORGANISM: Artificial Sequence
<220> FEATURE:
<223> OTHER INFORMATION: Recombinant peptide

<400> SEQUENCE: 951

Phe Ser Asp Lys Pro Tyr Ile Leu
1               5

<210> SEQ ID NO 952
<211> LENGTH: 8
<212> TYPE: PRT
<213> ORGANISM: Artificial Sequence
<220> FEATURE:
<223> OTHER INFORMATION: Recombinant peptide

<400> SEQUENCE: 952

Glu Ser Asp Lys Pro Tyr Ile Leu
1               5

<210> SEQ ID NO 953
<211> LENGTH: 8
<212> TYPE: PRT
<213> ORGANISM: Artificial Sequence
<220> FEATURE:
<223> OTHER INFORMATION: Recombinant peptide

<400> SEQUENCE: 953

Asp Ser Asp Lys Pro Tyr Ile Leu
1               5

<210> SEQ ID NO 954
<211> LENGTH: 8
<212> TYPE: PRT
<213> ORGANISM: Artificial Sequence
<220> FEATURE:
```

<223> OTHER INFORMATION: Recombinant peptide

<400> SEQUENCE: 954

Cys Ser Asp Lys Pro Tyr Ile Leu
1               5

<210> SEQ ID NO 955
<211> LENGTH: 7
<212> TYPE: PRT
<213> ORGANISM: Artificial Sequence
<220> FEATURE:
<223> OTHER INFORMATION: Recombinant peptide

<400> SEQUENCE: 955

Tyr Asp Lys Pro Tyr Ile Leu
1               5

<210> SEQ ID NO 956
<211> LENGTH: 7
<212> TYPE: PRT
<213> ORGANISM: Artificial Sequence
<220> FEATURE:
<223> OTHER INFORMATION: Recombinant peptide

<400> SEQUENCE: 956

Trp Asp Lys Pro Tyr Ile Leu
1               5

<210> SEQ ID NO 957
<211> LENGTH: 7
<212> TYPE: PRT
<213> ORGANISM: Artificial Sequence
<220> FEATURE:
<223> OTHER INFORMATION: Recombinant peptide

<400> SEQUENCE: 957

Val Asp Lys Pro Tyr Ile Leu
1               5

<210> SEQ ID NO 958
<211> LENGTH: 7
<212> TYPE: PRT
<213> ORGANISM: Artificial Sequence
<220> FEATURE:
<223> OTHER INFORMATION: Recombinant peptide

<400> SEQUENCE: 958

Arg Asp Lys Pro Tyr Ile Leu
1               5

<210> SEQ ID NO 959
<211> LENGTH: 7
<212> TYPE: PRT
<213> ORGANISM: Artificial Sequence
<220> FEATURE:
<223> OTHER INFORMATION: Recombinant peptide

<400> SEQUENCE: 959

Gln Asp Lys Pro Tyr Ile Leu
1               5

<210> SEQ ID NO 960
<211> LENGTH: 7
<212> TYPE: PRT
<213> ORGANISM: Artificial Sequence
<220> FEATURE:
<223> OTHER INFORMATION: Recombinant peptide

```
<400> SEQUENCE: 960

Pro Asp Lys Pro Tyr Ile Leu
1               5

<210> SEQ ID NO 961
<211> LENGTH: 7
<212> TYPE: PRT
<213> ORGANISM: Artificial Sequence
<220> FEATURE:
<223> OTHER INFORMATION: Recombinant peptide

<400> SEQUENCE: 961

Asn Asp Lys Pro Tyr Ile Leu
1               5

<210> SEQ ID NO 962
<211> LENGTH: 7
<212> TYPE: PRT
<213> ORGANISM: Artificial Sequence
<220> FEATURE:
<223> OTHER INFORMATION: Recombinant peptide

<400> SEQUENCE: 962

Met Asp Lys Pro Tyr Ile Leu
1               5

<210> SEQ ID NO 963
<211> LENGTH: 7
<212> TYPE: PRT
<213> ORGANISM: Artificial Sequence
<220> FEATURE:
<223> OTHER INFORMATION: Recombinant peptide

<400> SEQUENCE: 963

Leu Asp Lys Pro Tyr Ile Leu
1               5

<210> SEQ ID NO 964
<211> LENGTH: 7
<212> TYPE: PRT
<213> ORGANISM: Artificial Sequence
<220> FEATURE:
<223> OTHER INFORMATION: Recombinant peptide

<400> SEQUENCE: 964

Lys Asp Lys Pro Tyr Ile Leu
1               5

<210> SEQ ID NO 965
<211> LENGTH: 7
<212> TYPE: PRT
<213> ORGANISM: Artificial Sequence
<220> FEATURE:
<223> OTHER INFORMATION: Recombinant peptide

<400> SEQUENCE: 965

Ile Asp Lys Pro Tyr Ile Leu
1               5

<210> SEQ ID NO 966
<211> LENGTH: 7
<212> TYPE: PRT
<213> ORGANISM: Artificial Sequence
<220> FEATURE:
<223> OTHER INFORMATION: Recombinant peptide
```

```
<400> SEQUENCE: 966

His Asp Lys Pro Tyr Ile Leu
1               5

<210> SEQ ID NO 967
<211> LENGTH: 7
<212> TYPE: PRT
<213> ORGANISM: Artificial Sequence
<220> FEATURE:
<223> OTHER INFORMATION: Recombinant peptide

<400> SEQUENCE: 967

Gly Asp Lys Pro Tyr Ile Leu
1               5

<210> SEQ ID NO 968
<211> LENGTH: 7
<212> TYPE: PRT
<213> ORGANISM: Artificial Sequence
<220> FEATURE:
<223> OTHER INFORMATION: Recombinant peptide

<400> SEQUENCE: 968

Phe Asp Lys Pro Tyr Ile Leu
1               5

<210> SEQ ID NO 969
<211> LENGTH: 7
<212> TYPE: PRT
<213> ORGANISM: Artificial Sequence
<220> FEATURE:
<223> OTHER INFORMATION: Recombinant peptide

<400> SEQUENCE: 969

Glu Asp Lys Pro Tyr Ile Leu
1               5

<210> SEQ ID NO 970
<211> LENGTH: 7
<212> TYPE: PRT
<213> ORGANISM: Artificial Sequence
<220> FEATURE:
<223> OTHER INFORMATION: Recombinant peptide

<400> SEQUENCE: 970

Asp Asp Lys Pro Tyr Ile Leu
1               5

<210> SEQ ID NO 971
<211> LENGTH: 7
<212> TYPE: PRT
<213> ORGANISM: Artificial Sequence
<220> FEATURE:
<223> OTHER INFORMATION: Recombinant peptide

<400> SEQUENCE: 971

Cys Asp Lys Pro Tyr Ile Leu
1               5

<210> SEQ ID NO 972
<211> LENGTH: 7
<212> TYPE: PRT
<213> ORGANISM: Artificial Sequence
<220> FEATURE:
<223> OTHER INFORMATION: Recombinant peptide

<400> SEQUENCE: 972
```

```
Ala Asp Lys Pro Tyr Ile Leu
1               5

<210> SEQ ID NO 973
<211> LENGTH: 6
<212> TYPE: PRT
<213> ORGANISM: Artificial Sequence
<220> FEATURE:
<223> OTHER INFORMATION: Recombinant peptide

<400> SEQUENCE: 973

Tyr Lys Pro Tyr Ile Leu
1               5

<210> SEQ ID NO 974
<211> LENGTH: 6
<212> TYPE: PRT
<213> ORGANISM: Artificial Sequence
<220> FEATURE:
<223> OTHER INFORMATION: Recombinant peptide

<400> SEQUENCE: 974

Trp Lys Pro Tyr Ile Leu
1               5

<210> SEQ ID NO 975
<211> LENGTH: 6
<212> TYPE: PRT
<213> ORGANISM: Artificial Sequence
<220> FEATURE:
<223> OTHER INFORMATION: Recombinant peptide

<400> SEQUENCE: 975

Val Lys Pro Tyr Ile Leu
1               5

<210> SEQ ID NO 976
<211> LENGTH: 6
<212> TYPE: PRT
<213> ORGANISM: Artificial Sequence
<220> FEATURE:
<223> OTHER INFORMATION: Recombinant peptide

<400> SEQUENCE: 976

Thr Lys Pro Tyr Ile Leu
1               5

<210> SEQ ID NO 977
<211> LENGTH: 6
<212> TYPE: PRT
<213> ORGANISM: Artificial Sequence
<220> FEATURE:
<223> OTHER INFORMATION: Recombinant peptide

<400> SEQUENCE: 977

Ser Lys Pro Tyr Ile Leu
1               5

<210> SEQ ID NO 978
<211> LENGTH: 6
<212> TYPE: PRT
<213> ORGANISM: Artificial Sequence
<220> FEATURE:
<223> OTHER INFORMATION: Recombinant peptide

<400> SEQUENCE: 978
```

```
Gln Lys Pro Tyr Ile Leu
1               5

<210> SEQ ID NO 979
<211> LENGTH: 6
<212> TYPE: PRT
<213> ORGANISM: Artificial Sequence
<220> FEATURE:
<223> OTHER INFORMATION: Recombinant peptide

<400> SEQUENCE: 979

Pro Lys Pro Tyr Ile Leu
1               5

<210> SEQ ID NO 980
<211> LENGTH: 6
<212> TYPE: PRT
<213> ORGANISM: Artificial Sequence
<220> FEATURE:
<223> OTHER INFORMATION: Recombinant peptide

<400> SEQUENCE: 980

Asn Lys Pro Tyr Ile Leu
1               5

<210> SEQ ID NO 981
<211> LENGTH: 6
<212> TYPE: PRT
<213> ORGANISM: Artificial Sequence
<220> FEATURE:
<223> OTHER INFORMATION: Recombinant peptide

<400> SEQUENCE: 981

Met Lys Pro Tyr Ile Leu
1               5

<210> SEQ ID NO 982
<211> LENGTH: 6
<212> TYPE: PRT
<213> ORGANISM: Artificial Sequence
<220> FEATURE:
<223> OTHER INFORMATION: Recombinant peptide

<400> SEQUENCE: 982

Leu Lys Pro Tyr Ile Leu
1               5

<210> SEQ ID NO 983
<211> LENGTH: 6
<212> TYPE: PRT
<213> ORGANISM: Artificial Sequence
<220> FEATURE:
<223> OTHER INFORMATION: Recombinant peptide

<400> SEQUENCE: 983

Ile Lys Pro Tyr Ile Leu
1               5

<210> SEQ ID NO 984
<211> LENGTH: 6
<212> TYPE: PRT
<213> ORGANISM: Artificial Sequence
<220> FEATURE:
<223> OTHER INFORMATION: Recombinant peptide

<400> SEQUENCE: 984

His Lys Pro Tyr Ile Leu
```

-continued

```
1               5

<210> SEQ ID NO 985
<211> LENGTH: 6
<212> TYPE: PRT
<213> ORGANISM: Artificial Sequence
<220> FEATURE:
<223> OTHER INFORMATION: Recombinant peptide

<400> SEQUENCE: 985

Phe Lys Pro Tyr Ile Leu
1               5

<210> SEQ ID NO 986
<211> LENGTH: 6
<212> TYPE: PRT
<213> ORGANISM: Artificial Sequence
<220> FEATURE:
<223> OTHER INFORMATION: Recombinant peptide

<400> SEQUENCE: 986

Cys Lys Pro Tyr Ile Leu
1               5

<210> SEQ ID NO 987
<211> LENGTH: 6
<212> TYPE: PRT
<213> ORGANISM: Artificial Sequence
<220> FEATURE:
<223> OTHER INFORMATION: Recombinant peptide

<400> SEQUENCE: 987

Ala Lys Pro Tyr Ile Leu
1               5

<210> SEQ ID NO 988
<211> LENGTH: 5
<212> TYPE: PRT
<213> ORGANISM: Artificial Sequence
<220> FEATURE:
<223> OTHER INFORMATION: Recombinant peptide

<400> SEQUENCE: 988

Tyr Pro Tyr Ile Leu
1               5

<210> SEQ ID NO 989
<211> LENGTH: 5
<212> TYPE: PRT
<213> ORGANISM: Artificial Sequence
<220> FEATURE:
<223> OTHER INFORMATION: Recombinant peptide

<400> SEQUENCE: 989

Trp Pro Tyr Ile Leu
1               5

<210> SEQ ID NO 990
<211> LENGTH: 5
<212> TYPE: PRT
<213> ORGANISM: Artificial Sequence
<220> FEATURE:
<223> OTHER INFORMATION: Recombinant peptide

<400> SEQUENCE: 990

Val Pro Tyr Ile Leu
1               5
```

```
<210> SEQ ID NO 991
<211> LENGTH: 5
<212> TYPE: PRT
<213> ORGANISM: Artificial Sequence
<220> FEATURE:
<223> OTHER INFORMATION: Recombinant peptide

<400> SEQUENCE: 991

Thr Pro Tyr Ile Leu
1               5

<210> SEQ ID NO 992
<211> LENGTH: 5
<212> TYPE: PRT
<213> ORGANISM: Artificial Sequence
<220> FEATURE:
<223> OTHER INFORMATION: Recombinant peptide

<400> SEQUENCE: 992

Ser Pro Tyr Ile Leu
1               5

<210> SEQ ID NO 993
<211> LENGTH: 5
<212> TYPE: PRT
<213> ORGANISM: Artificial Sequence
<220> FEATURE:
<223> OTHER INFORMATION: Recombinant peptide

<400> SEQUENCE: 993

Gln Pro Tyr Ile Leu
1               5

<210> SEQ ID NO 994
<211> LENGTH: 5
<212> TYPE: PRT
<213> ORGANISM: Artificial Sequence
<220> FEATURE:
<223> OTHER INFORMATION: Recombinant peptide

<400> SEQUENCE: 994

Pro Pro Tyr Ile Leu
1               5

<210> SEQ ID NO 995
<211> LENGTH: 5
<212> TYPE: PRT
<213> ORGANISM: Artificial Sequence
<220> FEATURE:
<223> OTHER INFORMATION: Recombinant peptide

<400> SEQUENCE: 995

Asn Pro Tyr Ile Leu
1               5

<210> SEQ ID NO 996
<211> LENGTH: 5
<212> TYPE: PRT
<213> ORGANISM: Artificial Sequence
<220> FEATURE:
<223> OTHER INFORMATION: Recombinant peptide

<400> SEQUENCE: 996

Met Pro Tyr Ile Leu
1               5
```

```
<210> SEQ ID NO 997
<211> LENGTH: 5
<212> TYPE: PRT
<213> ORGANISM: Artificial Sequence
<220> FEATURE:
<223> OTHER INFORMATION: Recombinant peptide

<400> SEQUENCE: 997

Leu Pro Tyr Ile Leu
1               5

<210> SEQ ID NO 998
<211> LENGTH: 5
<212> TYPE: PRT
<213> ORGANISM: Artificial Sequence
<220> FEATURE:
<223> OTHER INFORMATION: Recombinant peptide

<400> SEQUENCE: 998

Ile Pro Tyr Ile Leu
1               5

<210> SEQ ID NO 999
<211> LENGTH: 5
<212> TYPE: PRT
<213> ORGANISM: Artificial Sequence
<220> FEATURE:
<223> OTHER INFORMATION: Recombinant peptide

<400> SEQUENCE: 999

His Pro Tyr Ile Leu
1               5

<210> SEQ ID NO 1000
<211> LENGTH: 5
<212> TYPE: PRT
<213> ORGANISM: Artificial Sequence
<220> FEATURE:
<223> OTHER INFORMATION: Recombinant peptide

<400> SEQUENCE: 1000

Gly Pro Tyr Ile Leu
1               5

<210> SEQ ID NO 1001
<211> LENGTH: 5
<212> TYPE: PRT
<213> ORGANISM: Artificial Sequence
<220> FEATURE:
<223> OTHER INFORMATION: Recombinant peptide

<400> SEQUENCE: 1001

Phe Pro Tyr Ile Leu
1               5

<210> SEQ ID NO 1002
<211> LENGTH: 5
<212> TYPE: PRT
<213> ORGANISM: Artificial Sequence
<220> FEATURE:
<223> OTHER INFORMATION: Recombinant peptide

<400> SEQUENCE: 1002

Glu Pro Tyr Ile Leu
1               5
```

```
<210> SEQ ID NO 1003
<211> LENGTH: 5
<212> TYPE: PRT
<213> ORGANISM: Artificial Sequence
<220> FEATURE:
<223> OTHER INFORMATION: Recombinant peptide

<400> SEQUENCE: 1003

Asp Pro Tyr Ile Leu
1               5

<210> SEQ ID NO 1004
<211> LENGTH: 5
<212> TYPE: PRT
<213> ORGANISM: Artificial Sequence
<220> FEATURE:
<223> OTHER INFORMATION: Recombinant peptide

<400> SEQUENCE: 1004

Cys Pro Tyr Ile Leu
1               5

<210> SEQ ID NO 1005
<211> LENGTH: 5
<212> TYPE: PRT
<213> ORGANISM: Artificial Sequence
<220> FEATURE:
<223> OTHER INFORMATION: Recombinant peptide

<400> SEQUENCE: 1005

Ala Pro Tyr Ile Leu
1               5

<210> SEQ ID NO 1006
<211> LENGTH: 8
<212> TYPE: PRT
<213> ORGANISM: Artificial Sequence
<220> FEATURE:
<223> OTHER INFORMATION: Recombinant peptide

<400> SEQUENCE: 1006

Ala Ser Gly Lys Thr Phe Ile Thr
1               5

<210> SEQ ID NO 1007
<211> LENGTH: 8
<212> TYPE: PRT
<213> ORGANISM: Artificial Sequence
<220> FEATURE:
<223> OTHER INFORMATION: Recombinant peptide

<400> SEQUENCE: 1007

Ala Asp Gly Lys Ser Tyr Val Thr
1               5

<210> SEQ ID NO 1008
<211> LENGTH: 7
<212> TYPE: PRT
<213> ORGANISM: Artificial Sequence
<220> FEATURE:
<223> OTHER INFORMATION: Recombinant peptide

<400> SEQUENCE: 1008

Arg Arg Lys Pro Tyr Ile Leu
1               5

<210> SEQ ID NO 1009
```

```
<211> LENGTH: 13
<212> TYPE: PRT
<213> ORGANISM: Artificial Sequence
<220> FEATURE:
<223> OTHER INFORMATION: Recombinant peptide

<400> SEQUENCE: 1009

Gln Leu Tyr Glu Asn Lys Pro Arg Arg Pro Tyr Ile Leu
1               5                   10

<210> SEQ ID NO 1010
<211> LENGTH: 169
<212> TYPE: PRT
<213> ORGANISM: Artificial Sequence
<220> FEATURE:
<223> OTHER INFORMATION: Recombinant peptide

<400> SEQUENCE: 1010

Met Arg Gly Met Asn Leu Gln Leu Val Cys Leu Thr Leu Leu Ala Phe
1               5                   10                  15

Ser Ser Trp Ser Leu Cys Ser Asp Ser Glu Glu Asp Val Arg Ala Leu
            20                  25                  30

Glu Ala Asp Leu Leu Thr Asn Met His Thr Ser Lys Ile Ser Lys Ala
        35                  40                  45

Ser Pro Pro Ser Trp Lys Met Thr Leu Leu Asn Val Cys Ser Leu Ile
    50                  55                  60

Asn Asn Val Asn Ser Pro Ala Glu Glu Ala Gly Asp Met His Asp Asp
65                  70                  75                  80

Asp Leu Val Gly Lys Arg Lys Leu Pro Leu Val Leu Asp Gly Phe Ser
                85                  90                  95

Leu Glu Ala Met Leu Thr Ile Phe Gln Leu Gln Lys Ile Cys Arg Ser
            100                 105                 110

Arg Ala Phe Gln His Trp Glu Ile Ile Gln Glu Asp Ile Leu Asp Asn
        115                 120                 125

Val Asn Asp Lys Asn Glu Lys Glu Val Ile Lys Arg Lys Ile Pro
    130                 135                 140

Tyr Ile Leu Lys Arg Gln Leu Tyr Glu Asn Lys Pro Arg Arg Pro Tyr
145                 150                 155                 160

Ile Leu Lys Arg Gly Ser Tyr Tyr Tyr
                165

<210> SEQ ID NO 1011
<211> LENGTH: 25
<212> TYPE: PRT
<213> ORGANISM: Artificial Sequence
<220> FEATURE:
<223> OTHER INFORMATION: Recombinant peptide

<400> SEQUENCE: 1011

Met Leu Thr Lys Phe Glu Thr Lys Ser Ala Arg Val Lys Gly Leu Ser
1               5                   10                  15

Phe His Pro Lys Arg Pro Trp Ile Leu
            20                  25

<210> SEQ ID NO 1012
<211> LENGTH: 64
<212> TYPE: PRT
<213> ORGANISM: Homo sapiens

<400> SEQUENCE: 1012

Val Met Ala Ser Phe Lys Ile Leu Ala Gly Asp Lys Asn Tyr Ile Thr
```

```
                1               5                   10                  15
            Met Asp Glu Leu Arg Arg Glu Leu Pro Pro Asp Gln Ala Glu Tyr Cys
                                20                  25                  30
            Ile Ala Arg Met Ala Pro Tyr Thr Gly Pro Asp Ser Val Pro Gly Ala
                        35                  40                  45
            Leu Asp Tyr Met Ser Phe Ser Thr Ala Leu Tyr Gly Glu Ser Asp Leu
                    50                  55                  60

<210> SEQ ID NO 1013
<211> LENGTH: 64
<212> TYPE: PRT
<213> ORGANISM: Homo sapiens

<400> SEQUENCE: 1013

Val Ile Ala Ser Phe Arg Ile Leu Ala Ser Asp Lys Pro Tyr Ile Leu
            1               5                   10                  15
            Ala Glu Glu Leu Arg Arg Glu Leu Pro Pro Asp Gln Ala Gln Tyr Cys
                                20                  25                  30
            Ile Lys Arg Met Pro Ala Tyr Ser Gly Pro Gly Ser Val Pro Gly Ala
                        35                  40                  45
            Leu Asp Tyr Ala Ala Phe Ser Ser Ala Leu Tyr Gly Glu Ser Asp Leu
                    50                  55                  60

<210> SEQ ID NO 1014
<211> LENGTH: 64
<212> TYPE: PRT
<213> ORGANISM: Homo sapiens

<400> SEQUENCE: 1014

Val Val Ala Ser Phe Lys Ile Leu Ala Gly Asp Lys Asn Tyr Ile Thr
            1               5                   10                  15
            Pro Glu Glu Leu Arg Arg Glu Leu Pro Ala Lys Gln Ala Glu Tyr Cys
                                20                  25                  30
            Ile Arg Arg Met Val Pro Tyr Lys Gly Ser Gly Ala Pro Ala Gly Ala
                        35                  40                  45
            Leu Asp Tyr Val Ala Phe Ser Ser Ala Leu Tyr Gly Glu Ser Asp Leu
                    50                  55                  60

<210> SEQ ID NO 1015
<211> LENGTH: 64
<212> TYPE: PRT
<213> ORGANISM: Homo sapiens

<400> SEQUENCE: 1015

Val Ile Ala Ser Phe Lys Val Leu Ala Gly Asp Lys Asn Phe Ile Thr
            1               5                   10                  15
            Ala Glu Glu Leu Arg Arg Glu Leu Pro Pro Asp Gln Ala Glu Tyr Cys
                                20                  25                  30
            Ile Ala Arg Met Ala Pro Tyr Gln Gly Pro Asp Ala Val Pro Gly Ala
                        35                  40                  45
            Leu Asp Tyr Lys Ser Phe Ser Thr Ala Leu Tyr Gly Glu Ser Asp Leu
                    50                  55                  60

<210> SEQ ID NO 1016
<211> LENGTH: 64
<212> TYPE: PRT
<213> ORGANISM: Drosophila melanogaster

<400> SEQUENCE: 1016
```

Val Ile Asp Ser Phe Arg Ile Leu Ala Ala Asp Lys Pro Tyr Ile Leu
1               5                   10                  15

Pro Asp Glu Leu Arg Arg Glu Leu Pro Pro Gln Ala Glu Tyr Cys
            20                  25                  30

Ile Gln Arg Met Pro Pro Tyr Lys Gly Pro Asn Gly Val Pro Gly Ala
                35                  40                  45

Leu Asp Tyr Met Ser Phe Ser Thr Ala Leu Tyr Gly Glu Thr Asp Leu
    50                  55                  60

<210> SEQ ID NO 1017
<211> LENGTH: 61
<212> TYPE: PRT
<213> ORGANISM: Caenorhabditis elegans

<400> SEQUENCE: 1017

Met Ile Asp Ser Phe Arg Ile Leu Ala Ser Gly Lys Thr Phe Ile Thr
1               5                   10                  15

Ala Asp Glu Leu Glu Arg Glu Leu Pro Arg Asp Gln Ala Ala Tyr Cys
            20                  25                  30

Met Ala Arg Met Ala Pro Ser Arg Glu Pro Gly Ala Pro Pro Arg Ser
                35                  40                  45

Phe Asp Tyr Val Thr Phe Ser Arg Ser Leu Tyr Ser Gln
    50                  55                  60

<210> SEQ ID NO 1018
<211> LENGTH: 55
<212> TYPE: PRT
<213> ORGANISM: Dictyostelium discoideum

<400> SEQUENCE: 1018

Thr Lys Ala Ala Phe Lys Val Met Ala Glu Asp Lys Asp Phe Ile Thr
1               5                   10                  15

Glu Ala Gln Ile Arg Ala Ala Ile Ser Asp Ser Lys Gln Ile Asp Tyr
            20                  25                  30

Leu Leu Ala Ser Met Pro Ala Val Glu Gly Gly Phe Asp Tyr Asn Ser
                35                  40                  45

Phe Ala Glu Lys Leu Tyr Gln
    50                  55

<210> SEQ ID NO 1019
<211> LENGTH: 61
<212> TYPE: PRT
<213> ORGANISM: Schizosaccharomyces pombe

<400> SEQUENCE: 1019

Val Leu Tyr Ala Phe Cys Asp Val Ala Asp Gly Lys Ser Tyr Val Thr
1               5                   10                  15

Ser Asp Asp Leu Leu Arg Ser Gln Val Arg Pro Asn Ile Val Lys Phe
            20                  25                  30

Leu Glu Cys Asn Met Asn Lys His Ser Glu Gly Leu Asp Tyr Leu Thr
                35                  40                  45

Trp Ile Lys Gln Leu Leu Ala Glu Asp Lys Glu Ile Val
    50                  55                  60

<210> SEQ ID NO 1020
<211> LENGTH: 6
<212> TYPE: PRT
<213> ORGANISM: Artificial Sequence
<220> FEATURE:
<223> OTHER INFORMATION: Recombinant peptide

```
<220> FEATURE:
<221> NAME/KEY: MISC_FEATURE
<222> LOCATION: (1)..(1)
<223> OTHER INFORMATION: Xaa in position 1 is D, E, G, Q, T, S, C, P, or
      N

<400> SEQUENCE: 1020

Xaa Lys Pro Tyr Ile Leu
1               5

<210> SEQ ID NO 1021
<211> LENGTH: 8
<212> TYPE: PRT
<213> ORGANISM: Artificial Sequence
<220> FEATURE:
<223> OTHER INFORMATION: Recombinant peptide
<220> FEATURE:
<221> NAME/KEY: MISC_FEATURE
<222> LOCATION: (1)..(1)
<223> OTHER INFORMATION: Xaa in position 1 is A, L, I, or V
<220> FEATURE:
<221> NAME/KEY: MISC_FEATURE
<222> LOCATION: (2)..(2)
<223> OTHER INFORMATION: Xaa in position 2 is S, T, G, A, N, E, or D

<400> SEQUENCE: 1021

Xaa Xaa Asp Arg Pro Tyr Ile Leu
1               5

<210> SEQ ID NO 1022
<211> LENGTH: 8
<212> TYPE: PRT
<213> ORGANISM: Artificial Sequence
<220> FEATURE:
<223> OTHER INFORMATION: Recombinant peptide
<220> FEATURE:
<221> NAME/KEY: MISC_FEATURE
<222> LOCATION: (1)..(1)
<223> OTHER INFORMATION: Xaa in position 1 is A, L, I, or V
<220> FEATURE:
<221> NAME/KEY: MISC_FEATURE
<222> LOCATION: (2)..(2)
<223> OTHER INFORMATION: Xaa in position 2 is S, T, G, A, N, E, or D

<400> SEQUENCE: 1022

Xaa Xaa Glu Arg Pro Tyr Ile Leu
1               5

<210> SEQ ID NO 1023
<211> LENGTH: 8
<212> TYPE: PRT
<213> ORGANISM: Artificial Sequence
<220> FEATURE:
<223> OTHER INFORMATION: Recombinant peptide
<220> FEATURE:
<221> NAME/KEY: MISC_FEATURE
<222> LOCATION: (1)..(1)
<223> OTHER INFORMATION: Xaa in position 1 is A, L, I, or V
<220> FEATURE:
<221> NAME/KEY: MISC_FEATURE
<222> LOCATION: (2)..(2)
<223> OTHER INFORMATION: Xaa in position 2 is S, T, G, A, N, E, or D

<400> SEQUENCE: 1023

Xaa Xaa Gly Arg Pro Tyr Ile Leu
1               5

<210> SEQ ID NO 1024
<211> LENGTH: 8
<212> TYPE: PRT
<213> ORGANISM: Artificial Sequence
```

-continued

```
<220> FEATURE:
<223> OTHER INFORMATION: Recombinant peptide
<220> FEATURE:
<221> NAME/KEY: MISC_FEATURE
<222> LOCATION: (1)..(1)
<223> OTHER INFORMATION: Xaa in position 1 is A, L, I, or V
<220> FEATURE:
<221> NAME/KEY: MISC_FEATURE
<222> LOCATION: (2)..(2)
<223> OTHER INFORMATION: Xaa in position 2 is S, T, G, A, N, E, or D
<220> FEATURE:
<221> NAME/KEY: MISC_FEATURE
<222> LOCATION: (3)..(3)
<223> OTHER INFORMATION: Xaa in position 3 is D, E, or G

<400> SEQUENCE: 1024

Xaa Xaa Xaa Lys Pro Tyr Ile Leu
1               5

<210> SEQ ID NO 1025
<211> LENGTH: 8
<212> TYPE: PRT
<213> ORGANISM: Artificial Sequence
<220> FEATURE:
<223> OTHER INFORMATION: Recombinant peptide
<220> FEATURE:
<221> NAME/KEY: MISC_FEATURE
<222> LOCATION: (1)..(1)
<223> OTHER INFORMATION: Xaa in position 1 is A, L, I, or V
<220> FEATURE:
<221> NAME/KEY: MISC_FEATURE
<222> LOCATION: (2)..(2)
<223> OTHER INFORMATION: Xaa in position 2 is S, T, G, A, N, E, or D
<220> FEATURE:
<221> NAME/KEY: MISC_FEATURE
<222> LOCATION: (3)..(3)
<223> OTHER INFORMATION: Xaa in position 3 is D, E, or G

<400> SEQUENCE: 1025

Xaa Xaa Xaa Arg Pro Tyr Ile Leu
1               5

<210> SEQ ID NO 1026
<211> LENGTH: 7
<212> TYPE: PRT
<213> ORGANISM: Artificial Sequence
<220> FEATURE:
<223> OTHER INFORMATION: Recombinant peptide
<220> FEATURE:
<221> NAME/KEY: MISC_FEATURE
<222> LOCATION: (1)..(1)
<223> OTHER INFORMATION: Xaa in position 1 is S, T, G, A, N, E, or D
<220> FEATURE:
<221> NAME/KEY: MISC_FEATURE
<222> LOCATION: (2)..(2)
<223> OTHER INFORMATION: Xaa in position 2 is D or E

<400> SEQUENCE: 1026

Xaa Xaa Lys Pro Tyr Ile Leu
1               5

<210> SEQ ID NO 1027
<211> LENGTH: 8
<212> TYPE: PRT
<213> ORGANISM: Artificial Sequence
<220> FEATURE:
<223> OTHER INFORMATION: Recombinant peptide
<220> FEATURE:
<221> NAME/KEY: MISC_FEATURE
<222> LOCATION: (1)..(1)
<223> OTHER INFORMATION: Xaa in position 1 is A, L, I, or V
<220> FEATURE:
<221> NAME/KEY: MISC_FEATURE
```

```
<222> LOCATION: (2)..(2)
<223> OTHER INFORMATION: Xaa in position 2 is S, T, G, A, N, E, or D
<220> FEATURE:
<221> NAME/KEY: MISC_FEATURE
<222> LOCATION: (3)..(3)
<223> OTHER INFORMATION: Xaa in position 3 is D or E

<400> SEQUENCE: 1027

Xaa Xaa Xaa Lys Pro Tyr Ile Leu
1               5

<210> SEQ ID NO 1028
<211> LENGTH: 6
<212> TYPE: PRT
<213> ORGANISM: Artificial Sequence
<220> FEATURE:
<223> OTHER INFORMATION: Recombinant peptide
<220> FEATURE:
<221> NAME/KEY: MISC_FEATURE
<222> LOCATION: (1)..(1)
<223> OTHER INFORMATION: Xaa in position 1 is D or E

<400> SEQUENCE: 1028

Xaa Lys Pro Tyr Ile Leu
1               5

<210> SEQ ID NO 1029
<211> LENGTH: 8
<212> TYPE: PRT
<213> ORGANISM: Artificial Sequence
<220> FEATURE:
<223> OTHER INFORMATION: Artificial peptide sequence
<220> FEATURE:
<221> NAME/KEY: MISC_FEATURE
<222> LOCATION: (1)..(1)
<223> OTHER INFORMATION: Xaa in position 1 is A, L, I, or V
<220> FEATURE:
<221> NAME/KEY: MISC_FEATURE
<222> LOCATION: (2)..(2)
<223> OTHER INFORMATION: Xaa in position 2 is S, T, G, A, N, E or D
<220> FEATURE:
<221> NAME/KEY: MISC_FEATURE
<222> LOCATION: (3)..(3)
<223> OTHER INFORMATION: Xaa in position 3 is D, E, G, Q, T, S, C, P, or
      N

<400> SEQUENCE: 1029

Xaa Xaa Xaa Lys Pro Tyr Ile Leu
1               5
```

DIETARY PEPTIDES

CROSS-REFERENCE TO RELATED APPLICATIONS

This application is a divisional of U.S. application Ser. No. 16/062,429, filed Jun. 14, 2018, which is a national stage filing under 35 U.S.C. 371 of PCT/EP2016/081572, filed Dec. 16, 2016 which claims priority from European Application No. 15200440.4, filed Dec. 16, 2015, which applications are hereby incorporated in their entirety by reference in this application.

FIELD OF THE INVENTION

The present invention relates to novel peptides, composition comprising such peptides including nutritional supplements and methods for inducing satiation and satiety, for preventing or reducing the incidence of metabolic syndrome comprising overweight and obesity, cardiovascular diseases, atherosclerosis, hypertension, hepatosteatosis, diabetes and/or cancer.

REFERENCE TO AN ELECTRONIC SEQUENCE LISTING

The instant application contains an electronic Sequence Listing which has been submitted in ASCII format via USPTO Patent Center and is hereby incorporated by reference in its entirety. Said ASCII copy, created on Jul. 26, 2021, is named "20549US00_July_2021_ST25" and is 196,493 bytes in size.

BACKGROUND OF THE INVENTION

Obesity is a common medical condition affecting numerous humans throughout the world and is associated with, induces or increases the risk of developing conditions such as cardiovascular diseases, atherosclerosis, hypertension, hepatosteatosis, cancer and/or diabetes.

Some regulators of obesity have been identified. However, despite intensive study, the regulation of obesity is still poorly understood.

Protein is more satiating than carbohydrate and fat, and its effect on food intake is more than can be accounted for by its energy content alone. The mechanism by which proteins trigger food intake regulatory systems is unclear. However, it seems likely that satiety signals arising from protein ingestion begin in the gastrointestinal tract upon proteolytic digestion.

Accordingly, dietary proteolytic products (peptides and amino acids) induce signalling in enteroendocrine cells of the intestine, which leads to secretion of various gut hormones, e.g. glucagon-like peptide-1 (GLP-1) (FIG. 1) with neuronal, local (auto- and paracrine) and systemic (endocrine) effects (FIG. 2), ultimately leading to satiation (amount of food ingested as a meal) and satiety (length of time between meals). It is well-known that (some) enteroendocrine cells respond to free amino acids and small peptides (di- and tripeptides), which are readily taken up by the enterocytes and metabolized and/or transported into systemic circulation. Rate of digestion, i.e. transit time in the GI tract, secretion of digestive enzymes, etc, is a highly regulated process, where cellular responses to undigested proteins and/or increases in amino acids and peptides in the gut leads to secretion of gut hormones, e.g. GLP-1, peptide tyrosine-tyrosine (PYY), neurotensin (NT), which induces satiation. If these signals persist in the gut because of slow and prolonged release, satiety is enhanced. One such mechanism is the ileal brake, where unknown components in partly digested food reaches the distal small intestine and invokes a response in the form of secretion of the gut hormones GLP-1, PYY, NT and possibly others, as yet unknown hormones. However, the precise mechanism behind the ileal brake is unknown.

The specific peptide(s) responsible for this satiety inducing signal(s) is largely unknown and it would be of great importance if any of these peptides could be identified.

OBJECT OF THE INVENTION

It is an object of embodiments of the invention to provide new polypeptides that induce or signals satiety in a subject.

The polypeptides of the invention may be used to treat conditions associated with a wide variety of metabolic diseases, for use in weight management, and/or for preventing or reducing the incidence of overweight and/or obesity, or for preventing or reducing cardiovascular diseases, atherosclerosis, hypertension, hepatosteatosis, cancer and/or diabetes.

SUMMARY OF THE INVENTION

Dietary proteolytic products (peptides and amino acids) induce signalling in enteroendocrine cells of the intestine, which leads to secretion of various gut hormones, e.g. GLP-1 (FIG. 1) with both central (CNS), local (auto- and paracrine) and systemic (endocrine) effects (FIG. 2), ultimately leading to satiation and satiety.

Figure 3:
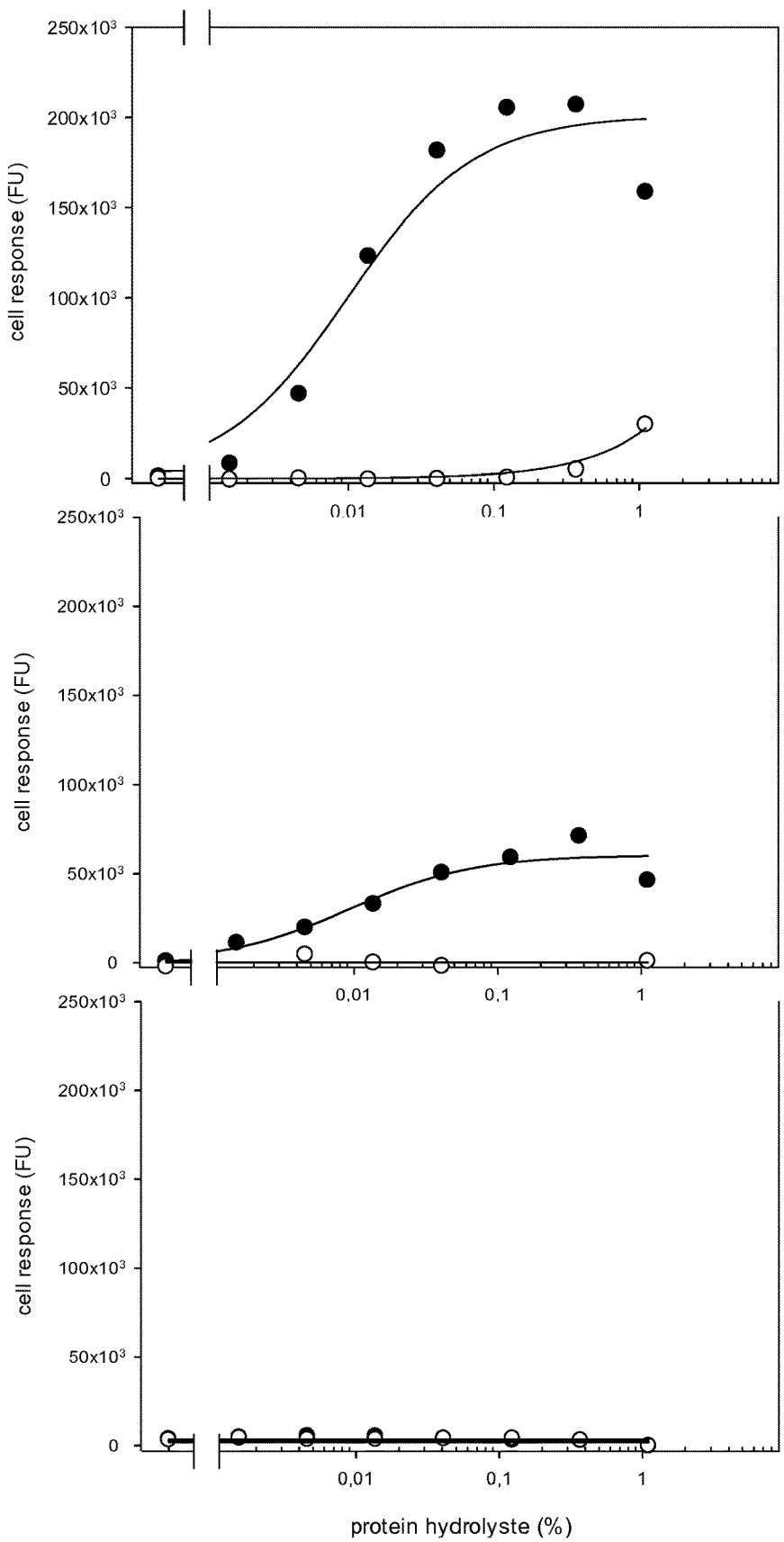
Figure 4:
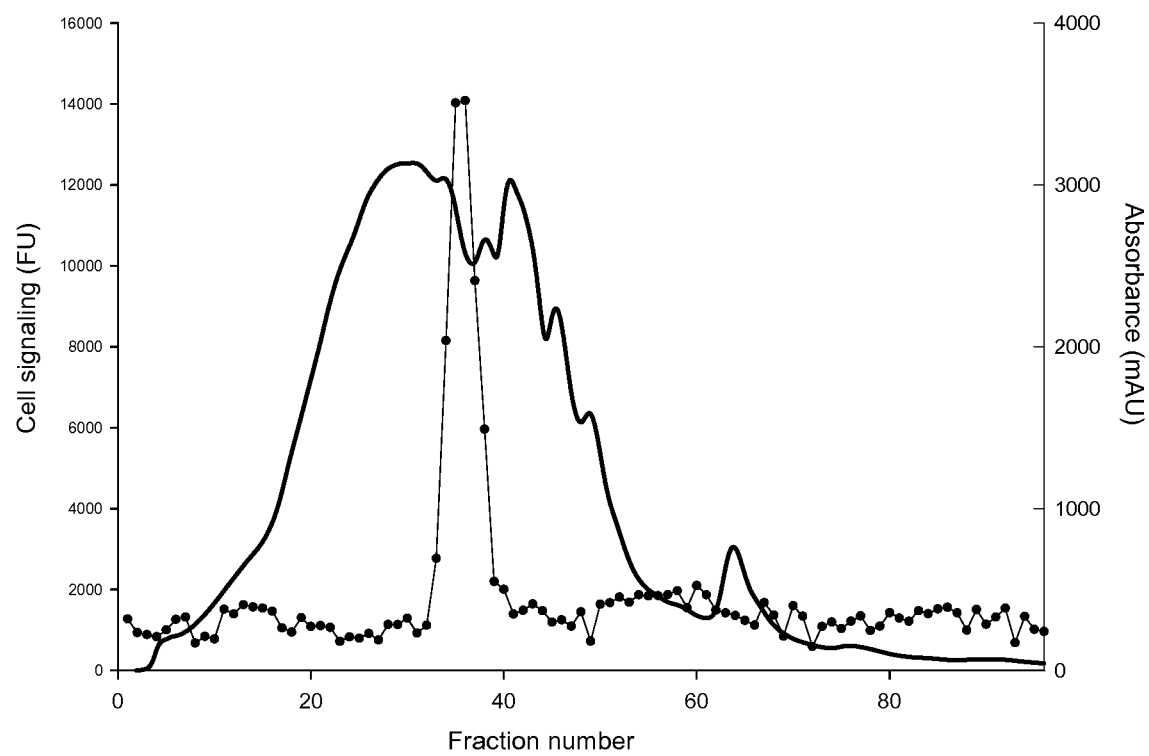

It has been found by the present inventor(s) that novel meat-derived polypeptides are superior in signalling of intestinal cell lines (FIG. 3) and that only very specific peptides are capable of signalling (FIG. 4). The inventors of the present invention have identified polypeptides including an octapeptide (ASDKPYIL, SEQ ID NO:6) present in proteolytic digests (FIG. 5) and resistant to pepsin degradation, of which a pentapeptide (KPYIL, SEQ ID NO:9) is the minimal sequence with significant biologic activity (FIG. 6). The octapeptide sequence is unique for the muscle-specific alpha-actinin-2 protein, and the sequence is conserved between all animal species. This peptide would be applicable as a novel, but natural nutritional supplement to induce satiation and satiety.

So, in a first aspect the present invention relates to an isolated polypeptide comprising the amino acid sequence AA1-AA2-AA3-K-AA5-AA6-AA7-AA8 (formula I, SEQ ID NO:1), wherein AA1 is an optional amino acid selected from A, L, I, and V; AA2 is an optional amino acid selected from S, T, G, A, N, E and D; AA3 is an optional amino acid selected from D, E, and G; AA5 is selected from P, N, S, D, A, T, K, and G; AA6 is selected from Y, N, I, W, and F; AA7 is selected from I, L, R, and V; AA8 is selected from L, I, V, S, M, and T; which polypeptide is not more than 50 amino acids in length; or a variant thereof with a sequence identity of at least 80%.

In a second aspect the present invention relates to an isolated polypeptide consisting of the amino acid sequence R1-AA1-AA2-AA3-K-AA5-AA6-AA7-AA8-R2 (formula II, SEQ ID NO:2), wherein AA1 is an optional amino acid selected from A, L, I, and V; AA2 is an optional amino acid selected from S, T, G, A, N, E and D; AA3 is an optional amino acid selected from D, E, and G; AA5 is selected from P, N, S, D, A, T, K, and G; AA6 is selected from Y, N, I, W, and F; AA7 is selected from I, L, R, and V; AA8 is selected from L, I, V, S, M, and T; R1 defines the N-term (—NH2) or a protection group; R2 defines the C-term (—COOH).

In a third aspect the present invention relates to a polypeptide having or comprising a sequence selected from ASDKPYIL (SEQ ID NO:6), SDKPYIL (SEQ ID NO:7), DKPYIL (SEQ ID NO:8), KPYIL (SEQ ID NO:9), AGDKNYIL (SEQ ID NO:10), AGDKNYIT (SEQ ID NO:11), AGDKSYIT (SEQ ID NO:12), ADGKPYIV (SEQ ID NO:13), AEDKDFIT (SEQ ID NO:14), AADKPYIL (SEQ ID NO:15), ATDKPYIL (SEQ ID NO:16), AGDKPYIT (SEQ ID NO:17), ASEKPYIL (SEQ ID NO:18), ADGKPYVT (SEQ ID NO:19), AGDKPYIL (SEQ ID NO:20), ASDKPNIL (SEQ ID NO:21), ASDKPYIT (SEQ ID NO:22), AADKPFIL (SEQ ID NO:23), ASDKAYIT (SEQ ID NO:24), AGDKAYIT (SEQ ID NO:25), ANGKPFIT (SEQ ID NO:26), AGDKNFIT (SEQ ID NO:27), ASDKSYIT (SEQ ID NO:28), ASDKTYIT (SEQ ID NO:29), ASDKNYIT (SEQ ID NO:30), AGDKKYIT (SEQ ID NO:31), AGDKNYIS (SEQ ID NO:32), AADKNYIT (SEQ ID NO:33), AGDKNYIM (SEQ ID NO:34), AADKNFIM (SEQ ID NO:35), AADKNFIT (SEQ ID NO:36), and AGDKGIRS (SEQ ID NO:37).

In a fourth aspect the present invention relates to a composition comprising a polypeptide of the invention.

In a further aspect the present invention relates to a polypeptide according to the invention for use in promoting satiety in a subject, for use in weight management, and/or for preventing or reducing the incidence of overweight and/or obesity in a subject, or for preventing or reducing cardiovascular diseases, atherosclerosis, hypertension, hepatosteatosis, cancer and/or diabetes.

In a further aspect the present invention relates to a method of preventing or reducing the incidence of obesity in a subject, and/or of promoting satiety in a subject, and/or to reduce or treat cardiovascular diseases, atherosclerosis, hypertension, hepatosteatosis, cancer and/or diabetes comprising enteral administering to a subject in need thereof a polypeptide comprising or consisting of the amino acid sequence AA1-AA2-AA3-AA4-AA5-AA6-AA7-AA8 (formula III, SEQ ID NO:3), wherein AA1 is an optional amino acid selected from A, L, I, and V; AA2 is an optional amino acid selected from S, T, G, A, N, E and D; AA3 is an optional amino acid selected from D, R, K, E, and G; AA4 is an amino acid selected from K and R; AA5 is selected from P, N, S, D, A, T, K, and G; AA6 is selected from Y, N, I, W, and F; AA7 is selected from I, L, R, and V; AA8 is selected from L, I, V, S, M, and T; which polypeptide is not more than 50 amino acids in length; or a variant thereof with a sequence identity of at least 80%.

In a further aspect the present invention relates to a composition according to the invention for use in promoting satiety in a subject, and/or for use in weight management, and/or for preventing or reducing the incidence of obesity in a subject and/or for use in preventing or reducing cardiovascular diseases, atherosclerosis, hypertension, cardiovascular diseases, high blood pressure, cancer and/or diabetes.

In a further aspect the present invention relates to a method of promoting satiety in a subject, and/or of preventing or reducing the incidence of obesity in a subject, and/or to reduce or treat cardiovascular diseases, atherosclerosis, hypertension, cardiovascular diseases, high blood pressure, cancer and/or diabetes, comprising administering to a subject in need thereof a composition according to the invention.

LEGENDS TO THE FIGURES

FIG. 1. Dose-response curve for effect of protein hydrolysate on release of GLP-1 from GLUTag cells (open circles) or a control cell line (closed symbols) that does not produce GLP-1. Cells (~5×10^5 per sample) were incubated for up to 90 min in Dulbeccos Modified Eagle Medium (DMEM) containing 5.56 mM glucose in absence or presence of different amounts (weight/volume) of meat protein hydrolysate. Supernatant was filtered through 0.45 micron filters and assayed for content of GLP-1 as described in ELISA protocol. Data are mean+SEM from quadruplicate samples.

Figure 2:
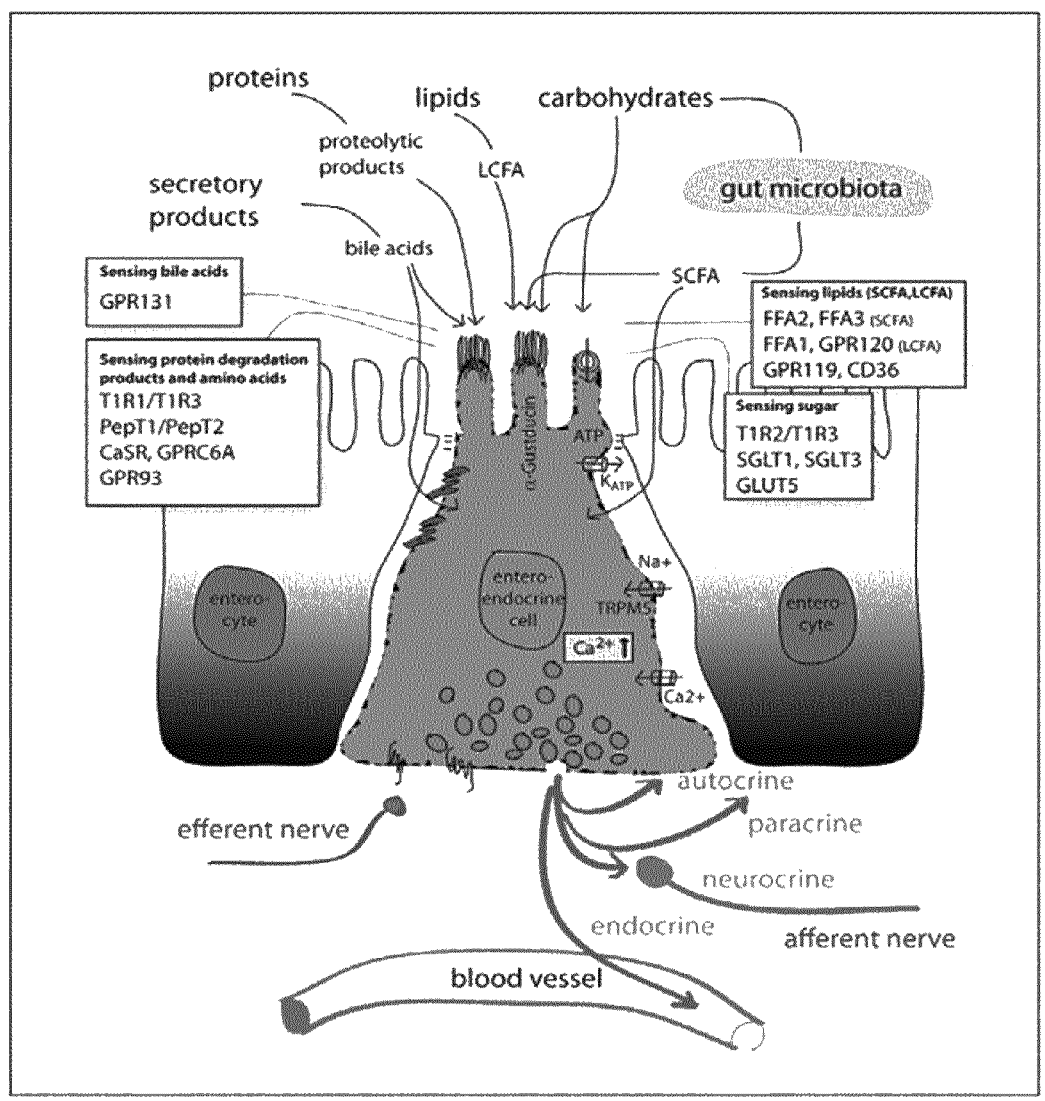

FIG. 2. Signaling by dietary nutrients in enteroendocrine cells. Illustration from Horm Res Paediatr. 2015; 83(1):1-10.

FIG. 3. Stimulation of cell signaling (measured as increase in intracellular fluorescence) by meat protein hydrolysates (filled symbols) or whey protein hydrolysates (open symbols) in three different intestinal cell lines: Top) a murine intestinal cell line; middle) GLUTag cells; bottom) CaCo2 cells.

FIG. 4. Size exclusion fractionation of protein hydrolysate and test of biologic activity. Absorbance at 280 nm shown by thick, solid line, activity of fractions by filled circles.

Figure 5:
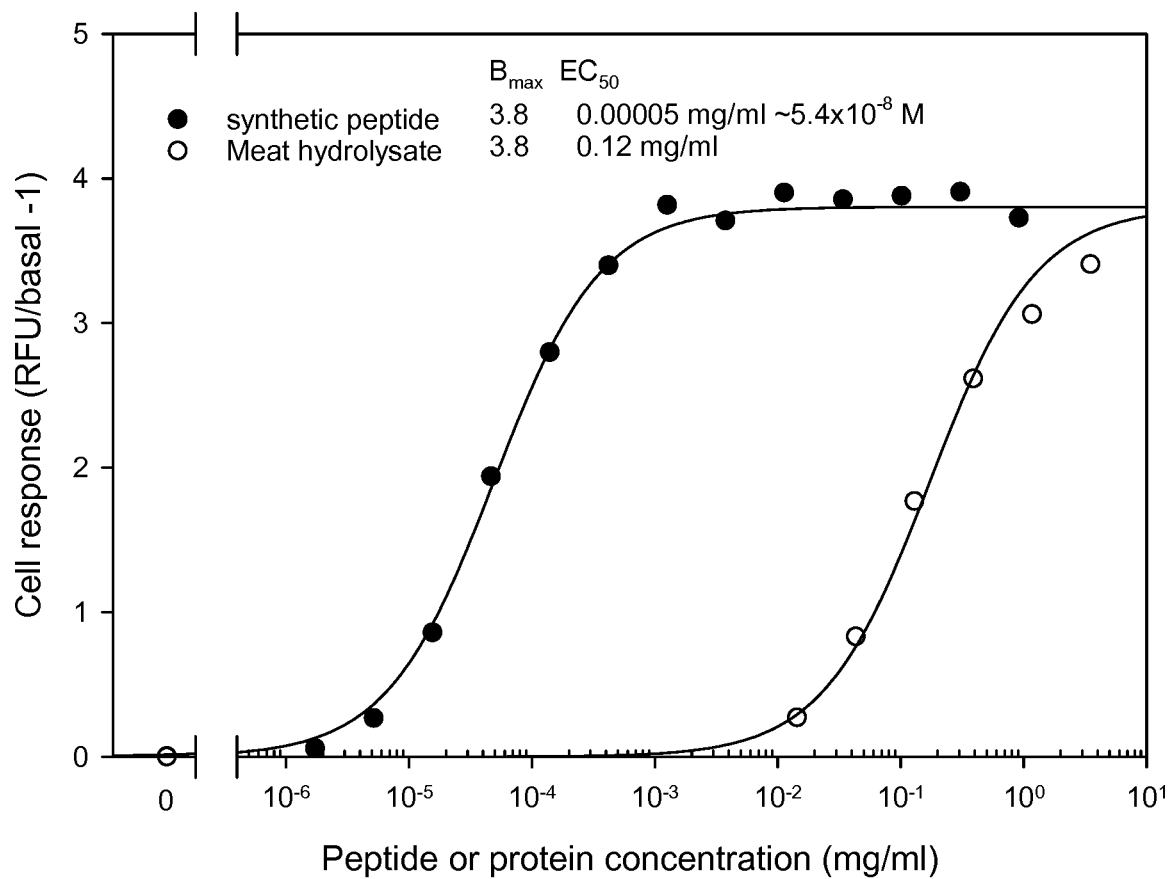
Figure 6:
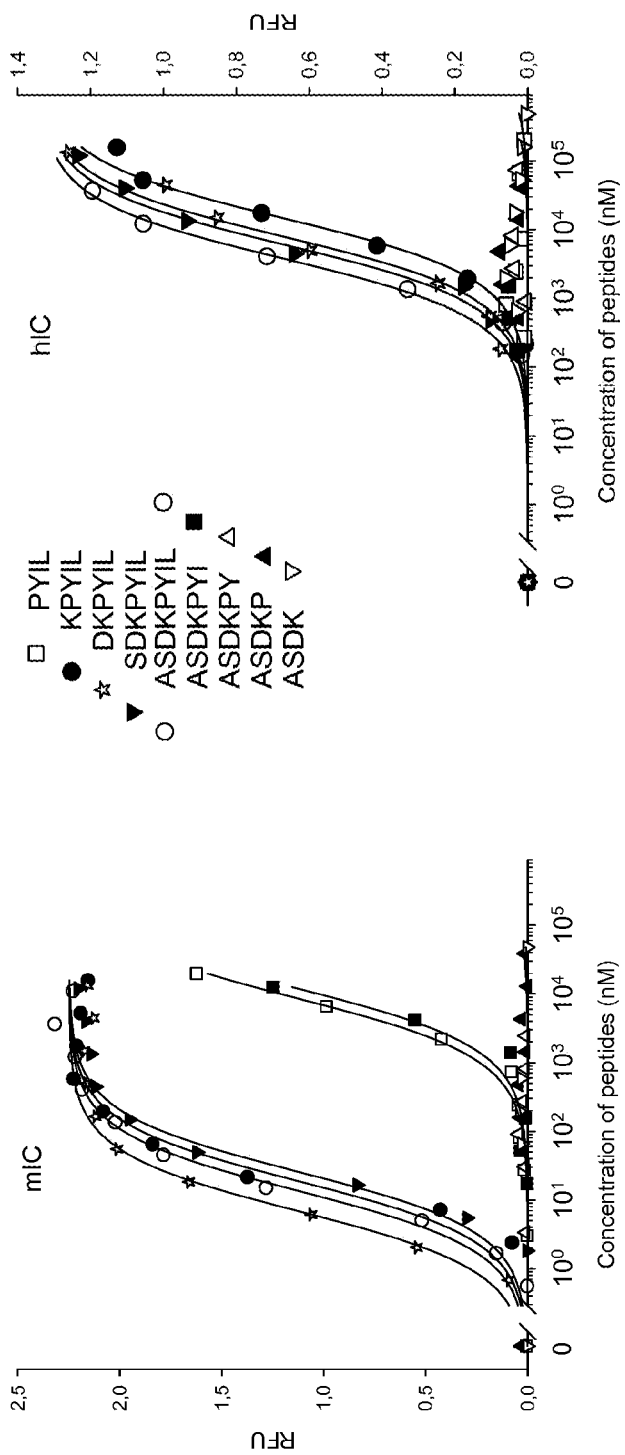

FIG. 5. Verification of identified sequence ASDKPYIL by synthetic peptide. Comparison of dose-response relationship of meat hydrolysate and pure, synthetic peptide identified by sequencing of purified fractions.

FIG. 6. Identification of minimal active sequence in ASDKPYIL (SEQ ID NO: 6) in murine (mIC) and human (hIC) intestinal cells.

Truncation from the amino-terminal or from the carboxy-terminal end of ASDKPYIL (SEQ ID NO: 6) has different consequences. Deleting the carboxy-terminal leucine reduces potency more than two orders of magnitude in mIC cells and abrogates activity in hIC. Peptides with further deletions of 2, 3 or 4 amino acids from the carboxy-terminus are without activity. Deleting the first three amino acids from the amino-terminus has no big impact on activity.

However, the fourth amino acid, lysine, is critical, since PYIL (SEQ ID NO: 4) has two orders of magnitude lower activity compared with the full sequence in mIC and no activity in hIC. The following peptides are represented in FIG. 6: PYIL (SEQ ID NO: 4), KPYIL (SEQ ID NO: 9), DKPYIL (SEQ ID NO: 8), SDKPYIL (SEQ ID NO: 7), ASDKPYIL (SEQ ID NO: 6), ASDKPYI (residues 1-7 of SEQ ID NO: 6), ASDKPYI (residues 1-6 of SEQ ID NO: 6), ASDKPY (residues 1-5 of SEQ ID NO: 6), ASDKP (residues 1-5 of SEQ ID NO: 6), ASDK (residues 1-4 of SEQ ID NO: 6).

Figure 7:
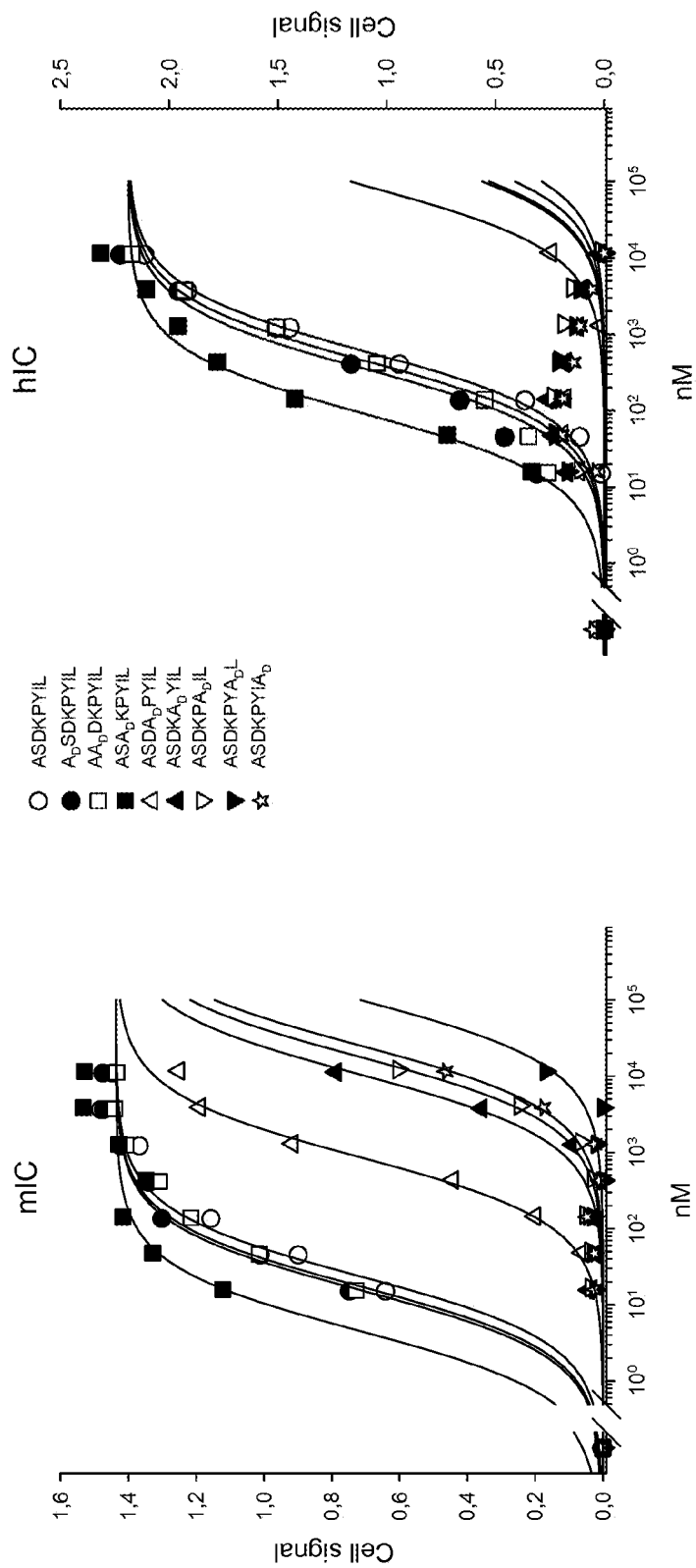

FIG. 7. Identification of critical residues in ASDKPYIL (SEQ ID NO: 6) (d-Ala ($A_D$) scan). Systematic replacement of all residues in ASDKPYIL (SEQ ID NO: 6) with the d-isomer of alanine and corresponding biological activity. Results show that 1) the last four amino acids (PYIL, SEQ ID NO:4) are critical, 2) replacing K reduces potency more than 30-fold, 3) replacing the aspartic residue improves potency almost 10-fold, and 4) alanine and serine on the first two positions are without importance.

Figure 8:
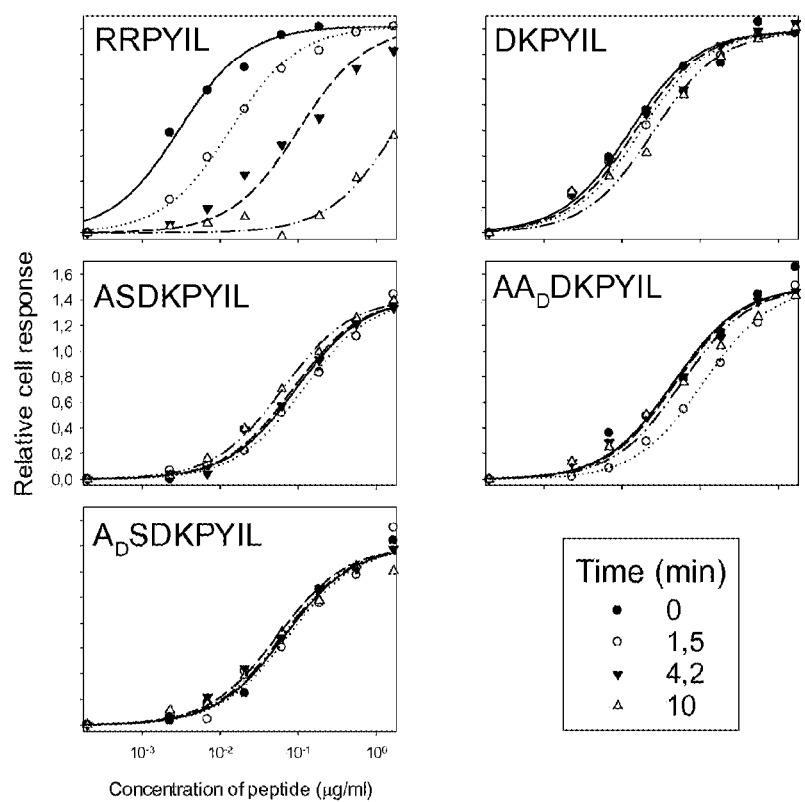

FIG. 8. Stability of peptides in rodent intestine.

0.001 mg/ml of the indicated peptides were incubated with pieces of rodent intestine (mouse and rat intestine gave similar results) for up to 10 minutes at 37° C. Recovery of activity was tested with dose-response curves as indicated.

The following peptides are represented in FIG. 8: RRPYIL (SEQ ID NO: 39), DKPYIL (SEQ ID NO: 8), ASDKPYIL (SEQ ID NO: 6), AADKPYIL (SEQ ID NO: 15).

Figure 9:
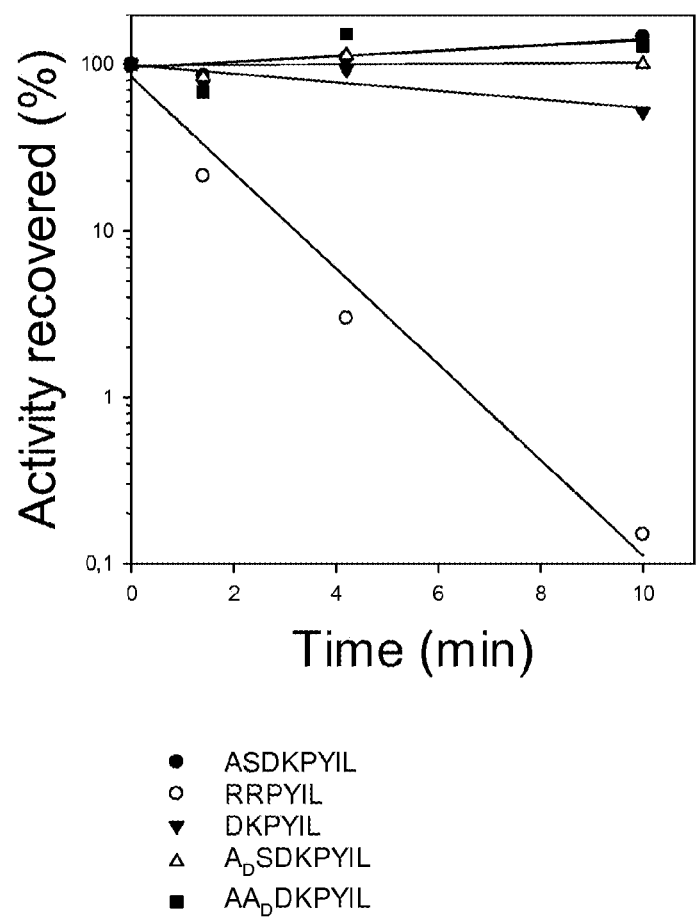

FIG. 9. Stability of peptides in rodent intestine. $EC_{50}$ values for different peptides and different incubation times were calculated from FIG. 8 and recovered activity plotted as a function of time. The following peptides are represented in FIG. 9: ASDKPYIL (SEQ ID NO: 6), RRPYIL (SEQ ID NO: 39), DKPYIL (SEQ ID NO: 8), AADKPYIL (SEQ ID NO: 15).

FIG. 10. Comparison of the sequences of three known gut hormones, neurotensin, neuromedin N (SEQ ID NO: 1010) and xenin (SEQ ID NO: 1011) with that of DC7-2 (ASDKPYIL, SEQ ID NO: 6). The PYIL (SEQ ID NO: 4) sequence is conserved, although Y is replaced by W in xenin.

Figure 11:
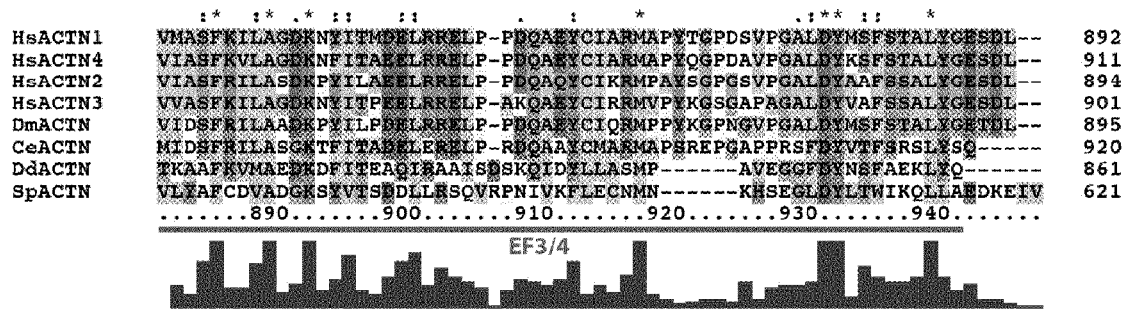

FIG. 11. Comparison of the DC7-2 sequence (aa 891-898) in isoforms of a-actinin 2 (Hs: *Homo sapiens* ACTN1 (SEQ ID NO: 1012); ACTN2 (SEQ ID NO: 1013); ACTN3 (SEQ ID NO: 1014); ACTN4 (SEQ ID NO: 1015)) and conservation between species (Dm: *Drosophila melanogaster* (DmACTN, SEQ ID NO: 1016); Ce: *Caenorhabditis elegans* (CeACTN, SEQ ID NO: 1017); Dd: Dictyostelium discoideum (DdACTN, SEQ ID NO: 1018); Sp: *Schizosaccharomyces pombe* (SpACTN, SEQ ID NO: 1019); Dr: *Danio rerio*). The following peptides are represented in FIG. 11: AGDKNYIT (SEQ ID NO: 11), AGDKNFIT (SEQ ID NO: 27), ASDKPYIL (SEQ ID NO: 6), AADKPYIL (SEQ ID NO: 15), ASGKTFIT (SEQ ID NO: 1006), AEDKDFIT (SEQ ID NO: 14), ADGKSYVT (SEQ ID NO: 1007).

Figure 12:
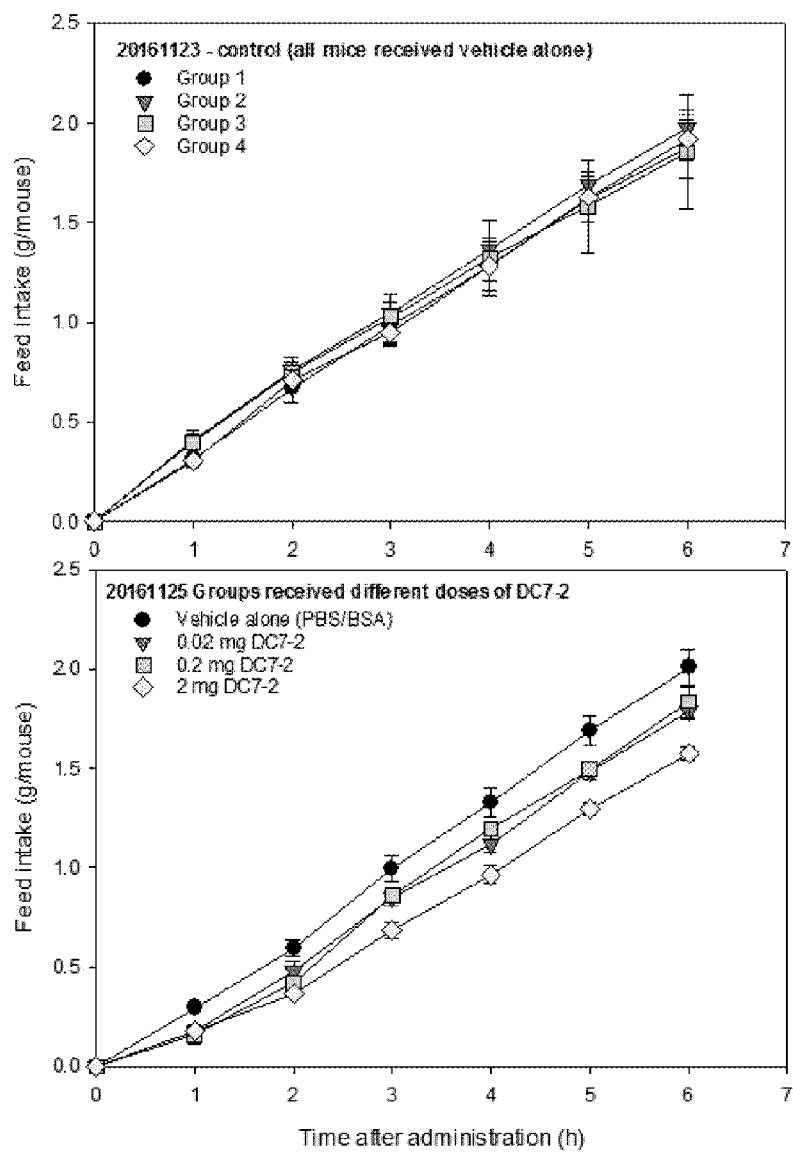

FIG. 12. 24 Balb/c female mice, 10-11 weeks, 20-22 g, were acclimatized to 12 h dark light cycle and placed single-housed in metabolic cages. Following administration of the indicated doses of DC7-2, feed and water intake was monitored for 6 h.

Figure 13:
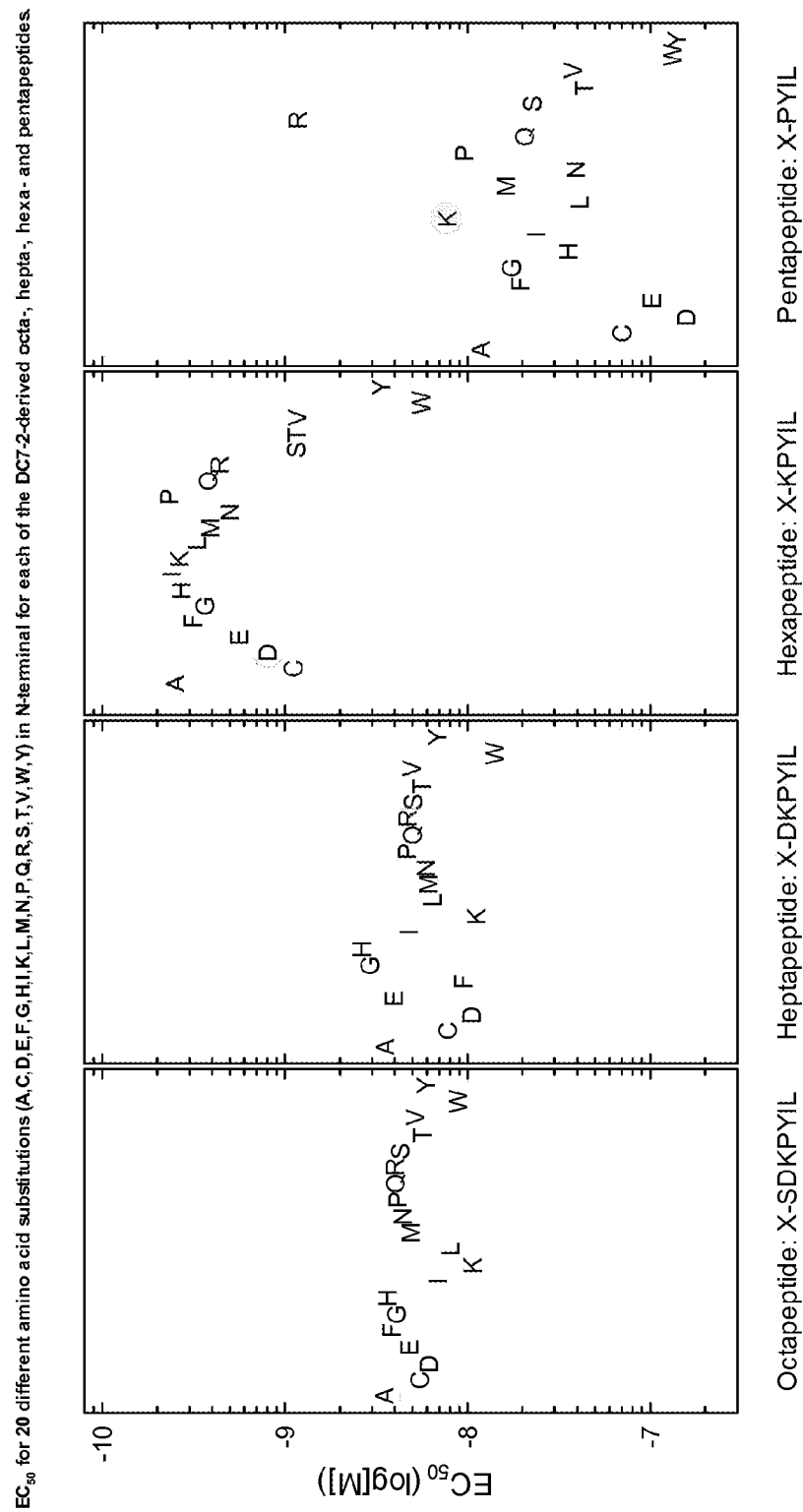

FIG. 13. Summary of cell signaling activities of N-terminal substitutions in octa-, hepta-, hexa- and pentapeptides based on the sequence of DC7-2. Single-letter abbreviations for the 20 amino acids are shown on the plot centered at the corresponding EC50. The native amino acid in DC7-2 is marked with a grey circle for each of the peptides. The following peptides are represented in FIG. 13: SDKPYIL (SEQ ID NO: 7), DKPYIL (SEQ ID NO: 8), KPYIL (SEQ ID NO: 9), PYIL (SEQ ID NO: 4).

Figure 14:
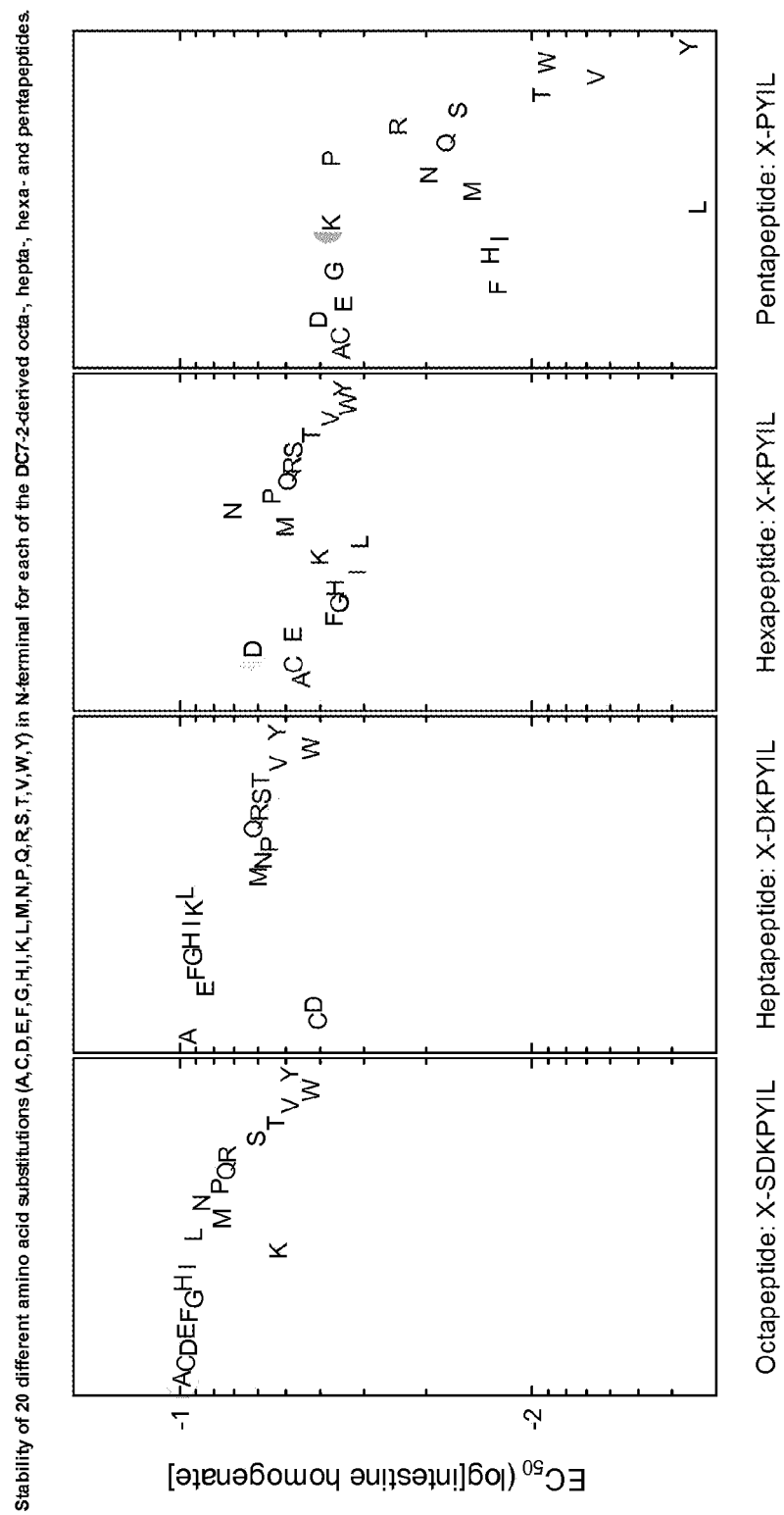

FIG. 14. Stability of DC7-2 families of peptides in intestine homogenates. Single-letter abbreviations for the 20 amino acids are shown on the plot with the corresponding stability expressed as the logarithm to the concentration of intestine homogenate that degrades half of the activity of peptide. All peptides were incubated at 10-5 M with various dilutions of a homogenate of the entire small intestine (pool from 20 mice). After incubation for 90 min at 37° C., degradation was stopped by addition of 1 M phosphoric acid (final 0.4 M, pH ~1.2). Each peptide incubation mix was neutralized with NaOH and immediately tested for activity in intestinal cells. Control for zero degradation, i.e. addition of phosphoric acid before addition of intestine homogenate, was included for each peptide. The native amino acid in DC7-2 is marked with a grey circle for each of the peptides. The following peptides are represented in FIG. 14: SDKPYIL (SEQ ID NO: 7), DKPYIL (SEQ ID NO: 8), KPYIL (SEQ ID NO: 9), PYIL (SEQ ID NO: 4).

Figure 15:
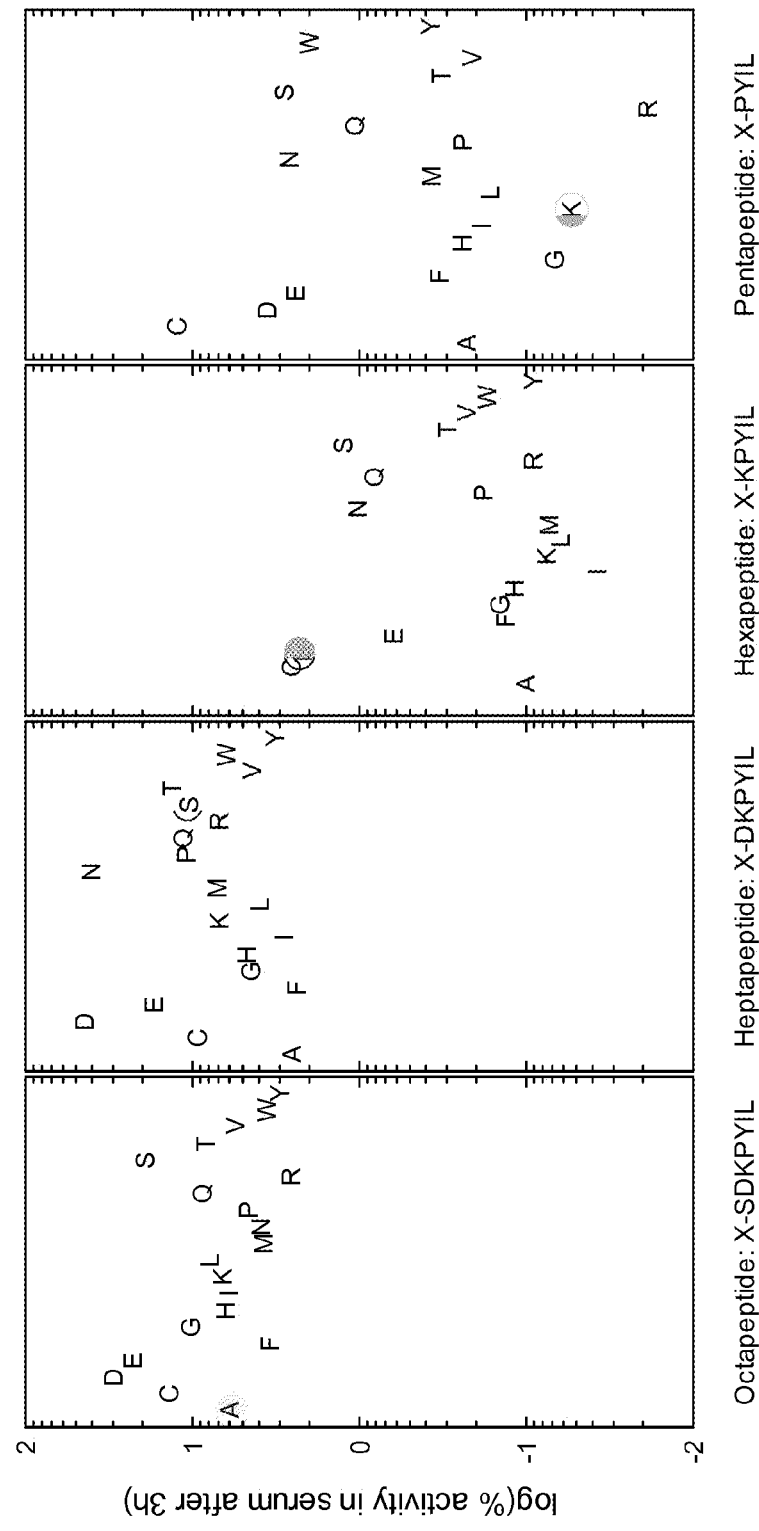

FIG. 15. Stability of DC7-2 families of peptides in serum. The following peptides are represented in FIG. 15: SDKPYIL (SEQ ID NO: 7), DKPYIL (SEQ ID NO: 8), KPYIL (SEQ ID NO: 9), PYIL (SEQ ID NO: 4).

Figure 16:
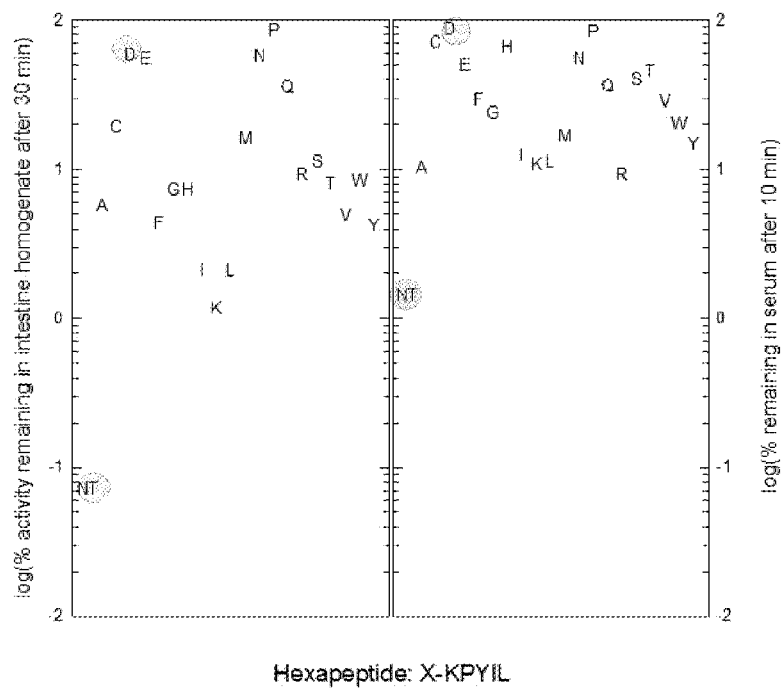

FIG. 16. Stability of X-KPYIL hexapeptides in intestine homogenate and serum. The following peptides are represented in FIG. 16: KPYIL (SEQ ID NO: 9).

Figure 17:
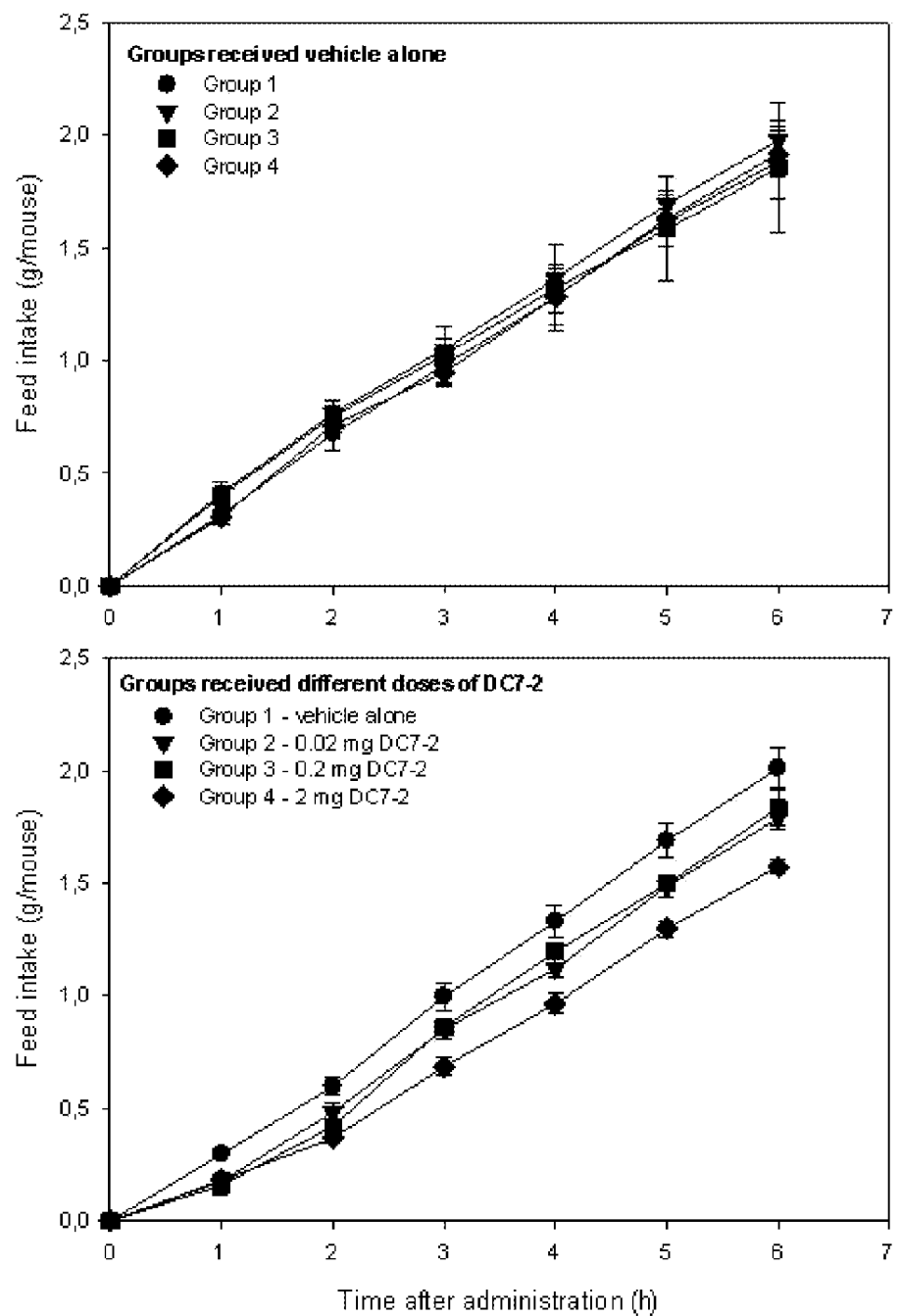

FIG. 17. 24 Balb/c female mice, 10-11 weeks, 20-22 g, were acclimatized to 12 h dark light cycle. Mice were divided into four groups each of six mice and placed single-housed in metabolic cages. Mice were then administered vehicle alone (day 1) for monitoring of feed and water intake for 6 h. On day 3, the same groups received the indicated doses of DC7-2, and feed and water intake was monitored for 6 h.

Figure 18:
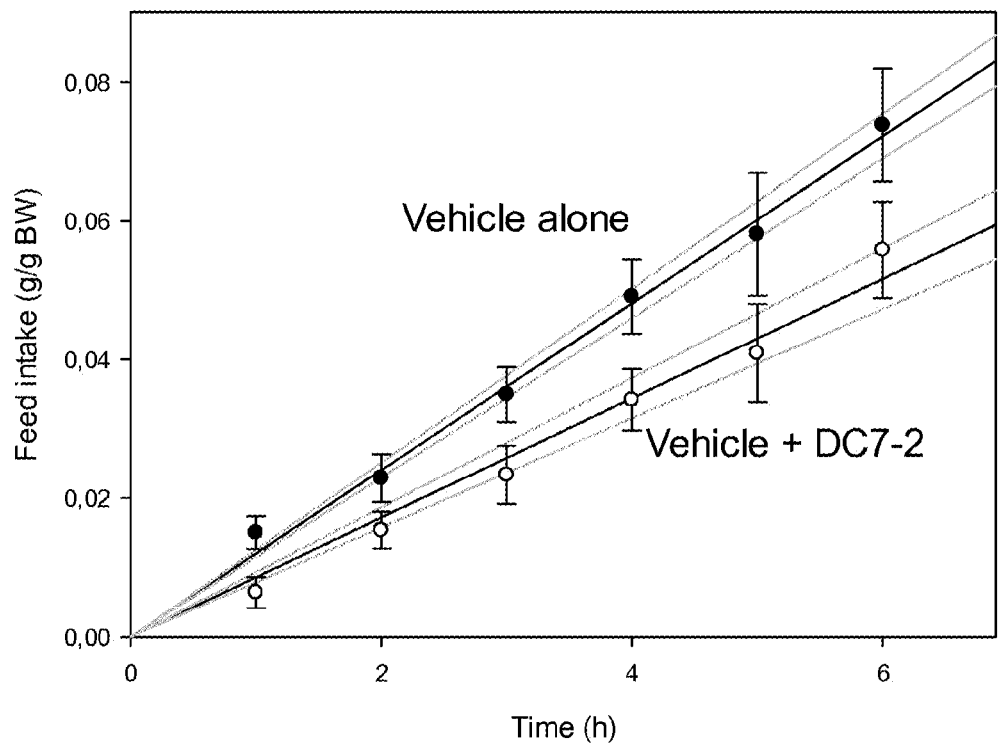

FIG. 18. Swiss Webster male mice, 25-30 g, were acclimatized to 12 h dark/light cycle and placed single-housed in cages. Following administration just prior to onset of dark cycle of vehicle alone (0.5 ml of PBS w 1% of BSA) or vehicle+DC7-2, feed intake was monitored every hour for 6 h (during dark cycle). Mean and SEM from four experiments, each with 6-8 mice per treatment. Data were fitted with linear regression (R2>0.99) and 95% confidence intervals are shown as grey lines. Accumulated feed intake for treatment with DC7-2 was 64%+/−5% compared with control for these four experiments.

Figure 19:
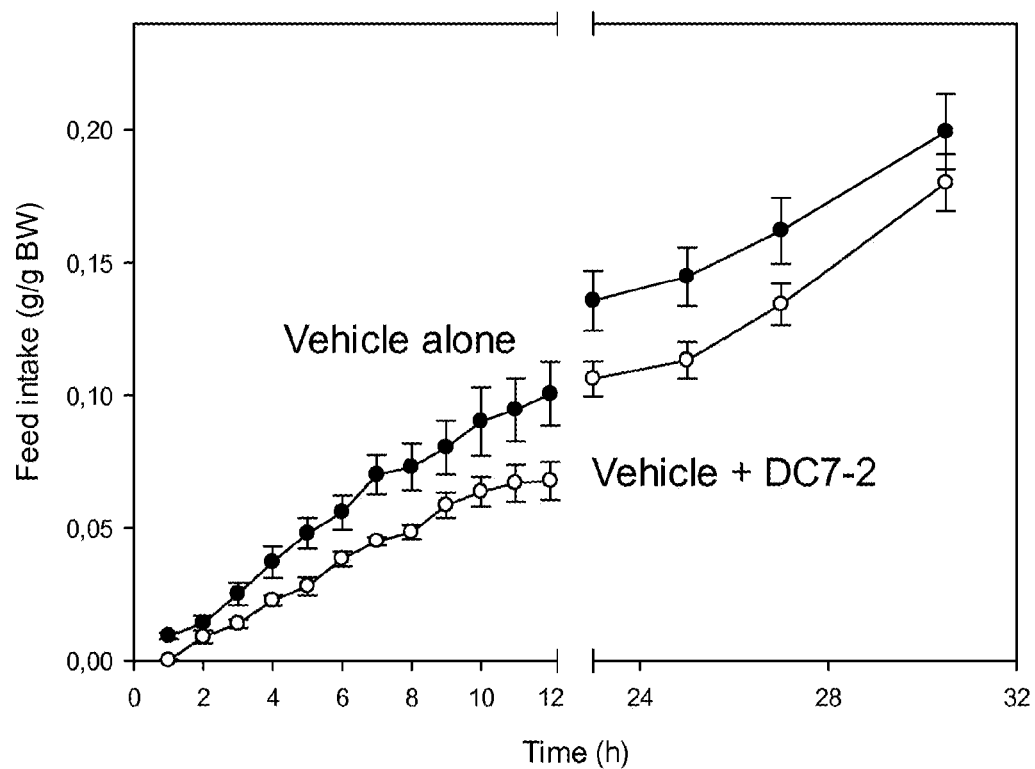

FIG. 19. Swiss Webster male mice, 25-30 g, were acclimatized to 12 h dark/light cycle and placed single-housed in cages. Following administration just prior to onset of dark cycle of vehicle alone (0.5 ml of PBS w 1% of BSA) or vehicle+DC7-2, feed intake was monitored every hour for 12 h (during dark cycle) and then intermittently up to 30 h.

Figure 20:
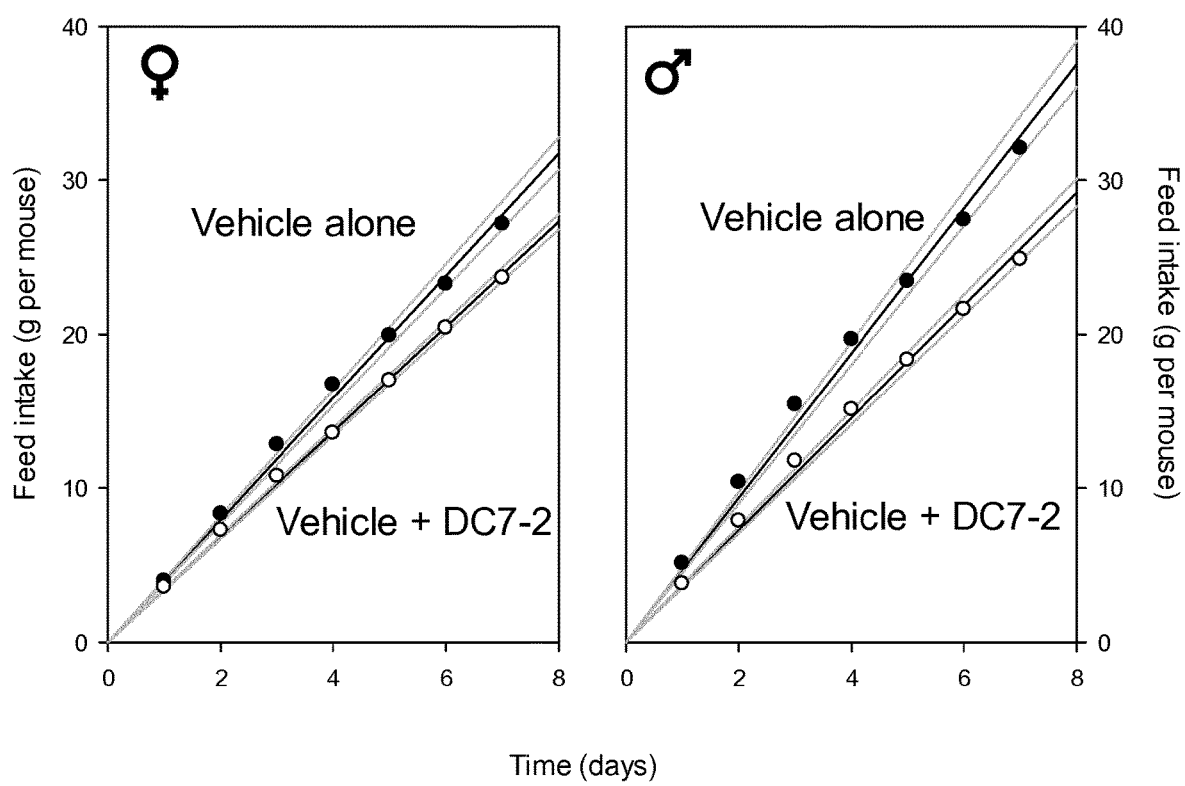

FIG. 20. Swiss Webster male (25-30 g) or female (20-25 g) mice were acclimatized to 12 h dark/light cycle and placed in groups of 6-8 mice per cage. Vehicle (0.5 ml of PBS w 1% of BSA) alone or vehicle+DC7-2 was administered three times per day (08:00; 16:00; 24:00), and feed intake was monitored daily for a week. Data were fitted with linear regression (R2>0.99) and 95% confidence intervals (grey lines).

DETAILED DISCLOSURE OF THE INVENTION

The inventors of the present invention have found novel polypeptides that may be used to induce signalling in intestinal cells and may consequently induce satiety. Although a specific peptide has been identified from a proteolytic digest of muscle-specific alpha-actinin-2 protein, it is envisioned that similar polypeptides will bind the same receptors in the intestine and provide the same biological activity, i.e. signal to induce satiation and satiety. Similar peptides may contain e.g. conservative substitutions or be truncated. The rationale for using the polypeptides of the invention is that the energy content due to the relatively small length of the peptide is low as compared to the effect on satiety.

Definitions

When terms such as "one", "a" or "an" are used in this disclosure they mean "at least one", or "one or more" unless otherwise indicated. Further, the term "comprising" is intended to mean "including" and thus allows for the presence of other constituents, features, conditions, or steps than those explicitly recited.

In some specific embodiments, the first 1, 2, or 3 amino acids in the N-terminal of the amino acid sequences according to the invention are in the D-form. It is assumed that the N-terminal trimming and thereby degradation of the peptides are somewhat delayed by having amino acids of the D-form in the N-terminal of these polypeptides. Alternatively and in some embodiments, the first 1, 2, or 3 amino acids in the N-terminal of the amino acid sequences according to the invention are amino acids in beta or gamma forms. Beta amino acids have their amino group bonded to the beta carbon rather than the alpha carbon as in the 20 standard natural amino acids. A capital D-letter subscript after the letter representing the amino acid residue designate herein amino acids specified to be in D-form, such as $W_D$ referring to a tryptophan in D-form. A capital L-letter subscript after the letter representing the amino acid residue designate herein amino acids specified to be in L-form, such as $W_L$ referring to a tryptophan in L-form. If not otherwise indicated, an amino acid is in its natural L-form.

Alternatively, the first 1, 2, or 3 amino acids in the N-terminal of the amino acid sequences according to the invention may be modified by incorporation of protective groups, e.g. fluorine, or alternatively cyclic amino acids or other suitable non-natural amino acids are used.

A "variant" or "analogue" of a peptide refers to a peptide having an amino acid sequence that is substantially identical to a reference peptide, typically a native or "parent" polypeptide, or a polypeptide of formula I or II. The peptide variant may possess one or more amino acid substitutions, deletions, and/or insertions at certain positions within the native amino acid sequence. The "variant" within this definition still has functional activity. In some embodiment a variant has at least 80% sequence identity with the reference polypeptide. In some embodiments a variant has at least 85% sequence identity with the reference polypeptide. In other embodiments a variant has at least 90% sequence identity with the reference polypeptide. In a further embodiment a variant has at least 95% sequence identity with the reference polypeptide.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). A particular form of conservative amino acid substitutions include those with amino acids, which are not among the normal 20 amino acids encoded by the genetic code. Since preferred embodiments of the present invention entail use of synthetic peptides, it is unproblematic to provide such "non-naturally occurring" amino acid residues in the peptides disclosed herein, and thereby it is possible to exchange the natural saturated carbon chains in the side chains of amino acid residues with shorter or longer saturated carbon chains—for instance, lysine may be substituted with an amino acid having a side chain—$(CH2)nNH3$, where n is different from 4, and arginine may be substituted with an amino acid having the side chain $(CH2)nNHC(=NH2)NH2$, where n is different from 3, etc. Similarly, the acidic amino acids aspartic acid and glutamic acid may be substituted with amino acid residues having the side chains—$(CH2)nCOOH$, where $n>2$.

The polypeptides of this invention may in some embodiments benefit from having higher stability than polypeptides containing only naturally occurring amino acids, and its modification enables to have much higher stability, such as a modification in the N-terminal of the polypeptide.

Accordingly and in some embodiments, the polypeptides of this invention have at their N-terminal a protection group, such as a protection group selected from the group consisting of acetyl group, fluorenyl methoxy carbonyl group, formyl group, palmitoyl group, myristyl group, stearyl group and polyethylene glycol (PEG).

The active peptide may also be di- or multimerized, e.g. through cross-linking with suitable di- or multivalent chemical cross-linkers, e.g. disuccinimidyl suberate, containing spacers of different length, e.g. 10-100 Å, and different functionality, e.g. homo- or heterofunctional, for coupling through non-critical amino or other reactive groups. Alternatively, photoactivation or enzymatic cross-linking may be used to increase stability and potency in vivo.

The modifications of peptides described above greatly increase the stability of the peptides of this invention. The term used herein "stability" refers to in vivo stability, such as the stability in the gut of a subject receiving such polypeptide. The protection group described above protects the peptides from the attack of protease in vivo.

The polypeptides according to the invention may be derived from a proteolytic digests of meat and be resistant to pepsin degradation. Accordingly, in some embodiments a polypeptide according to the invention may only contain naturally occurring amino acids.

In other embodiments, a polypeptide according to the invention is more stable towards degradation in the gastrointestinal tract, e.g. as measured in a stability assay described in the examples of the present invention, as compared to a control peptide. In some embodiments, a polypeptide according to the invention is more stable towards degradation in the gastrointestinal tract, e.g. measured in a stability assay described in the examples of the present invention as compared to a control peptide with the sequence RRPYIL, (SEQ ID NO:39).

In some embodiments, a polypeptide according to the invention has an half-life (T½) of degradation in vivo in the gut or in vitro, e.g. measured in a stability assay described in the example 2 of the present invention, which is higher than 2 min, such as higher than 4 min, such as higher than 6 min, such as higher than 8 min, such as higher than 10 min, such as higher than 15 min, such as higher than 20 min, such as higher than 25 min, such as higher than 30 min, such as higher than 35 min, such as higher than 40 min, such as higher than 45 min, such as higher than 50 min, such as higher than 55 min, such as higher than 60 min.

The term "substantially identical" in the context of two amino acid sequences means that the sequences, when optimally aligned, such as by the programs GAP or BESTFIT using default gap weights, share at least about 50, at least about 60, at least about 70, at least about 80, at least about 90, at least about 95, at least about 98, or at least about 99 percent sequence identity. In some embodiments, when measuring the sequence identity between two different peptide sequences, a gap of one or two amino acids is allowed when the two peptide sequences are aligned without having any influence on the value of sequence identity. In some embodiments, a residue position that is not identical differ by only a conservative amino acid substitution. Sequence identity is typically measured using sequence analysis software. Protein analysis software matches similar sequences using measures of similarity assigned to various substitutions, deletions and other modifications, including conservative amino acid substitutions. For instance, the publicly available GCG software contains programs such as "Gap"

and "BestFit" which can be used with default parameters to determine sequence homology or sequence identity between closely related polypeptides, such as homologous polypeptides from different species of organisms or between a wild-type protein and a mutein thereof. See, e.g., GCG Version 6.1. Polypeptide sequences can also be compared using FASTA or ClustalW, applying default or recommended parameters. A program in GCG Version 6.1., FASTA (e.g., FASTA2 and FASTA3) provides alignments and percent sequence identity of the regions of the best overlap between the query and search sequences (Pearson, Methods Enzymol. 1990; 183:63-98; Pearson, Methods Mol. Biol. 2000; 132:185-219). Another preferred algorithm when comparing a sequence to a database containing a large number of sequences from various organisms is the computer program BLAST, especially blastp, using default parameters. See, e.g., Altschul et al., J. Mol. Biol. 1990; 215:403-410; Altschul et al., Nucleic Acids Res. 1997; 25:3389-402 (1997); each herein incorporated by reference. "Corresponding" amino acid positions in two substantially identical amino acid sequences are those aligned by any of the protein analysis software mentioned herein, typically using default parameters.

The term "functional activity" as used herein refers to a polypeptide that stimulates cell signalling measured as fluorescence by elevated intracellular calcium or cellular release of gut hormones, such as measured in the signalling assays described in the examples. The functional activity of a variant may exhibit at least about 25%, such as at least about 50%, such as at least about 75%, such as at least about 90% of the specific activity of a reference polypeptide, such as the octapeptide ASDKPYIL (SEQ ID NO: 6), when tested in the assays as described herein. Alternatively, the functional activity of a variant may exhibit higher activity than a reference polypeptide, such as the octapeptide ASDKPYIL (SEQ ID NO: 6), when tested in the assays as described herein.

An "isolated" molecule is a molecule that is the predominant species in the composition wherein it is found with respect to the class of molecules to which it belongs (i.e., it makes up at least about 5% of the type of molecule in the composition and typically will make up at least about 10%, at least about 20%, at least about 30%, at least about 40%, at least about 50%, at least about 60%, at least about 70%, at least about 80%, at least about 85%, at least about 90%, at least about 95%, or more of the species of molecules, e.g., peptides, in the composition). Commonly, a composition of a specific peptide sequence may exhibit 90%-99% homogeneity for peptides in the context of all present peptide species in the composition or at least with respect to substantially active peptide species in the context of proposed use. If produced synthetically, a composition of a specific peptide sequence will exhibit 98%-99%, or even higher and close to 100% homogeneity for peptides in the context of all present peptide species in the composition or at least with respect to substantially active peptide species in the context of proposed use.

Unless otherwise indicated the polypeptides within the present invention is a linear sequence of amino acids. The term "linear sequence" as used herein refers to the specific sequence of amino acids connected by standard peptide bonds in standard N- to C-terminal direction. The peptide may contain only peptide bonds. In some embodiments however, a second part of a peptide sequence may be bound to and continue from the side chain of a terminal amino acid in a first part of an amino acid sequence. Also the term does not exclude that an amino acid within a sequence, such as within AA1-AA8, may be connected, such as through the side chains, with another amino acid at a distant location within the peptide sequence, such as a distant location within AA1-AA8.

In the context of the present invention, "treatment" or "treating" refers to preventing, alleviating, managing, curing or reducing one or more symptoms or clinically relevant manifestations of a disease or disorder, unless contradicted by context. For example, "treatment" of a patient in whom no symptoms or clinically relevant manifestations of a disease or disorder have been identified is preventive or prophylactic therapy, whereas "treatment" of a patient in whom symptoms or clinically relevant manifestations of a disease or disorder have been identified generally does not constitute preventive or prophylactic therapy.

The terms "patient" and "subject" refer to any human or animal that may be treated using the methods of the present invention.

Many aspect of the present invention relates to the use of polypeptides or compositions to promote satiety in a subject. The underlying cause of a metabolic syndrome or disorder that may treated by the polypeptides or compositions according to the invention, is an overconsumption of calories, while still not feeling satiety. By inducing or promoting satiety in a subject, such total amounts of calories, including calories derived from fat and carbohydrates are reduced in the subject. Accordingly, the polypeptides and compositions of the invention may be used in preventing or reducing a metabolic syndrome or disorder, such as obesity, insulin-deficiency or insulin-resistance related disorders, Diabetes Mellitus (such as, for example, Type 2 Diabetes), glucose intolerance, abnormal lipid metabolism, atherosclerosis, hypertension, cardiac pathology, stroke, non-alcoholic fatty liver disease, hyperglycemia, hepatic steatosis, dyslipidemia, dysfunction of the immune system associated with overweight and obesity, cardiovascular diseases, high cholesterol, elevated triglycerides, asthma, sleep apnoea, osteoarthritis, neuro-degeneration, gallbladder disease, syndrome X, inflammatory and immune disorders, atherogenic dyslipidemia and cancer.

Preparation of Polypeptides of the Invention

The invention also relates to a method of preparing polypeptides of the invention as mentioned above. The method of synthesis or preparation thereof includes, but is not limited to recombinant (whether produced from cDNA, genomic DNA, synthetic DNA or other form of nucleic acid), synthetic, and transgenic means.

The polypeptides of the invention described herein may be produced by means of recombinant nucleic acid techniques. In general, a nucleic acid sequence encoding the desired polypeptide is then inserted into an expression vector, which is in turn transformed or transfected into host cells.

As an alternative and also the preferred option, the polypeptides of the invention are produced by synthetic means, i.e. by polypeptide synthesis. In some embodiments, the invention relates to a method of manufacturing an analogue comprising non-natural amino acids from about 5 total residues to about 20 total residues. In some embodiments, an analogue comprises 1, 2, 3, 4, 5, 6, 7, 8, 9, 10, 11, 12, 13, 14, 15, 16, 17, 18, 19, or 20 non-natural amino acids, such as any one of the following non-naturally occurring amino acid residues.

The polypeptides of the present invention can also comprise non-naturally occurring amino acid residues. Non-naturally occurring amino acids include, without limitation, beta-alanine, desaminohistidine, trans-3-methylproline, 2,4- methanoproline, cis-4-hydroxyproline, trans-4-hydroxyproline, N-methylglycine, allo-threonine, methylthreonine, hydroxyethylcys-teine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, nor-valine, 2-azaphenylalanine, 3-azaphenylalanine, 4-azaphenylalanine, and 4-fluorophenylalanine. Several methods are known in the art for incorporating non-naturally occurring amino acid residues into polypeptides. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Polypeptides are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in Xenopus oocytes by microinjection of mutated mRNA and chemically aminoacylated suppressor tRNAs (Turcatti et al., J. Biol. Chem. 271:19991-8, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

As another alternative to synthetic preparation, the polypeptides of the invention may be purified from any natural source containing such polypeptide, such as from the proteolytic hydrolysate of muscle tissue, such as any source containing alpha-actinin-2 protein, such as by the methods described in the example section.

Accordingly, in some embodiments the sequence of the polypeptides of the invention is derived from a sequence found in nature, such as a fragment of alpha-actinin-2 protein.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). They may be purified by affinity chromatography on an antibody column. Additional purification may be achieved by conventional chemical purification means, such as high performance liquid chromatography. Other methods of purification, including barium citrate precipitation, are known in the art, and may be applied to the purification—see, for example, Scopes, R., Protein Purification, Springer-Verlag, N.Y., 1982.

For the methods of the invention including the therapeutic purposes it is not critical to have a high purity of a specific peptide of the invention. However, the higher the concentration of a specific peptide of the invention the higher is the effect in terms of inducing satiation and satiety relative to amount of total protein and total amount of calories consumed by the subject receiving the composition of polypeptides. It is to be understood that the idea of the invention is to administer polypeptides that induce satiation or satiety without administering a lot of calories to the subject.

In some embodiments the compositions of polypeptides of the invention are substantially pure. Thus, in an embodiment of the invention the polypeptides of the invention are purified to at least about 90 to 95% homogeneity, preferably to at least about 98% homogeneity. Purity may be assessed by e.g. HPLC and amino-terminal amino acid sequencing.

Administration and Pharmaceutical Compositions

Administration of the polypeptides according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Some kind of oral administration is preferred since these types of polypeptides are derived from a source that naturally has to pass through the mouth and to the intestinal mucosa. Compositions of the current invention may be administered in several dosage forms, for example, as solutions, suspensions, emulsions, microemulsions, multiple emulsion, foams, salves, pastes, plasters, ointments, tablets, coated tablets, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

One of skill in the art will recognize that the appropriate dosage of the compositions and pharmaceutical compositions may vary depending on the individual being treated and the purpose. For example, the age, body weight, and medical history of the individual patient may affect the therapeutic efficacy of the therapy. Further, a lower dosage of the composition may be needed to produce a transient cessation of symptoms, while a larger dose may be needed to produce a complete cessation of symptoms associated with the disease, disorder, or indication. A competent physician can consider these factors and adjust the dosing regimen to ensure the dose is achieving the desired therapeutic outcome without undue experimentation. It is also noted that the clinician and/or treating physician will know how and when to interrupt, adjust, and/or terminate therapy in conjunction with individual patient response. Dosages may also depend on the strength of the particular polypeptide of the invention chosen for the pharmaceutical composition.

The dose of the composition or pharmaceutical compositions may vary. The dose of the composition may be once per day. In some embodiments, multiple doses may be administered to the subject per day. In some embodiments, the total dosage is administered in at least two application periods, In some embodiments, the period can be an hour, a day, a month, a year, a week, or a two-week period. In an additional embodiment of the invention, the total dosage is administered in two or more separate application periods, or separate doses.

In some embodiments, subjects can be administered the composition in which the composition is provided in a daily dose range of about 0.0001 mg/kg to about 5000 mg/kg of the weight of the subject. The dose administered to the subject can also be measured in terms of total amount of polypeptide of the invention administered per day. In some embodiments, a subject is administered from about 0.001 to about 3000 milligrams of polypeptide of the invention per day. In some embodiments a subject is administered up to about 2000 milligrams of polypeptide of the invention per day. In some embodiments, a subject is administered up to about 1800 milligrams of polypeptide of the invention per day. In some embodiments, a subject is administered up to about 1600 milligrams of polypeptide of the invention per day. In some embodiments, a subject is administered up to about 1400 milligrams of polypeptide of the invention per day. In some embodiments, a subject is administered up to about 1200 milligrams of polypeptide of the invention per day. In some embodiments, a subject is administered up to about 1000 milligrams of polypeptide of the invention per day. In some embodiments, a subject is administered up to about 800 milligrams of polypeptide of the invention per day. In some embodiments, a subject is administered from about 0.001 milligrams to about 700 milligrams of polypeptide of the invention per dose. In some embodiments, a subject is administered up to about 700 milligrams of polypeptide of the invention per dose. In some embodiments, a subject is administered up to about 600 milligrams of polypeptide of the invention per dose. In some embodiments, a subject is administered up to about 500 milligrams of polypeptide of the invention per dose. In some embodiments, a subject is administered up to about 400 milligrams of polypeptide of the invention per dose. In some embodiments, a subject is administered up to about 300 milligrams of polypeptide of the invention per dose. In some embodiments, a subject is administered up to about 200 milligrams of polypeptide of the invention per dose. In some embodiments, a subject is administered up to about 100 milligrams of polypeptide of the invention per dose. In some embodiments, a subject is administered up to about 50 milligrams of polypeptide of the invention per dose.

A composition, wherein a polypeptide of the invention is added may be any food composition, food product, or food ingredient. Here, the term "food" is used in a broad sense—and covers food for humans as well as food for animals (i.e. a feed). In a preferred aspect, the food is for human consumption. The food may be in the form of a solution or as a solid—depending on the use and/or the mode of application and/or the mode of administration.

When used as—or in the preparation of—a food—such as functional food—the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

The composition of the present invention may be used as a food ingredient.

As used herein the term "food ingredient" includes a formulation which is or can be added to functional foods or foodstuffs as a nutritional supplement. The term food ingredient as used here also refers to formulations which can be used at low levels in a wide variety of products that require gelling, texturising, stabilising, suspending, film-forming and structuring, retention of juiciness and improved mouthfeel, without adding viscosity.

The food ingredient may be in the form of a solution or as a solid—depending on the use and/or the mode of application and/or the mode of administration.

The composition of the present invention may be—or may be added to—food supplements.

The composition of the present invention may be—or may be added to—functional foods.

As used herein, the term "functional food" means food which is capable of providing not only a nutritional effect and/or a taste satisfaction, but is also capable of delivering a further beneficial effect to consumer.

Accordingly, functional foods are ordinary foods that have components or ingredients (such as those described herein) incorporated into them that impart to the food a specific functional—e.g. medical or physiological benefit—other than a purely nutritional effect.

Although there is no legal definition of a functional food, most of the parties with an interest in this area agree that they are foods marketed as having specific health effects.

Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Surveys have suggested that consumers place the most emphasis on functional food claims relating to heart disease. Preventing cancer is another aspect of nutrition which interests consumers a great deal, but interestingly this is the area that consumers feel they can exert least control over. In fact, according to the World Health Organization, at least 35% of cancer cases are diet-related. Furthermore claims relating to osteoporosis, gut health and obesity effects are also key factors that are likely to incite functional food purchase and drive market development.

The composition of the present invention can be used in the preparation of or added to food products such as one or more of: jams, marmalades, jellies, dairy products (such as milk or cheese), meat products, poultry products, fish products, vegetable-based soups, and bakery products.

By way of example, the composition of the present invention can be used as ingredients to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, breakfast cereals, instant noodles and cup noodles, instant soups and cup soups, balanced foods and drinks, sweeteners, texture improved snack bars, fibre bars, bake stable fruit fillings, care glaze, chocolate bakery filling, cheese cake flavoured filling, fruit flavoured cake filling, cake and doughnut icing, heat stable bakery filling, instant bakery filling creams, filing for cookies, ready-to-use bakery filling, reduced calorie filling, adult nutritional beverage, acidified soy/juice beverage, aseptic/retorted chocolate drink, bar mixes, beverage powders, calcium fortified soy/plaim and chocolate milk, calcium fortified coffee beverage.

A composition according to the present invention can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped topping, low fat & lite natural cheddar cheese, low fat Swiss style yoghurt, aerated frozen desserts, and novelty bars, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

For certain aspects, preferably the foodstuff is a beverage.

For certain aspects, preferably the foodstuff is a bakery product—such as bread, Danish pastry, biscuits or cookies.

The present invention also provides a method of preparing a food or a food ingredient, the method comprising mixing a polypeptide according to the present invention or the composition according to the present invention with another food ingredient.

SPECIFIC EMBODIMENTS OF THE INVENTION

One aspect of the invention related to an isolated polypeptide comprising the amino acid sequence AA1-AA2-AA3-K-AA5-AA6-AA7-AA8 (formula I, SEQ ID NO:1), wherein AA1 is an optional amino acid selected from A, L, I, and V; AA2 is an optional amino acid selected from S, T, G, A, N, E and D; AA3 is an optional amino acid selected from D, E, and G; AA5 is selected from P, N, S, D, A, T, K, and G; AA6 is selected from Y, N, I, W, and F; AA7 is selected from I, L, R, and V; AA8 is selected from L, I, V, S, M, and T; which polypeptide is not more than 50 amino acids in length; or a variant thereof with a sequence identity of at least 80%.

Another aspect of the invention related to a method of promoting satiety in a subject or to a method of preventing or reducing the incidence of obesity in a subject comprising enteral administering to a subject in need thereof a polypeptide comprising or consisting of the amino acid sequence AA1-AA2-AA3-AA4-AA5-AA6-AA7-AA8 (formula III, SEQ ID NO:3), wherein AA1 is an optional amino acid selected from A, L, I, and V; AA2 is an optional amino acid selected from S, T, G, A, N, E and D; AA3 is an optional amino acid selected from D, R, K, E, and G; AA4 is an amino acid selected from K and R; AA5 is selected from P, N, S, D, A, T, K, and G; AA6 is selected from Y, N, I, W, and F; AA7 is selected from I, L, R, and V; AA8 is selected from L, I, V, S, M, and T; which polypeptide is not more than 50 amino acids in length; or a variant thereof with a sequence identity of at least 80%.

In the following AA1-AA8 may refer to the amino acids of either formula I, II, or III.

In some embodiments AA1 is absent. In some embodiments AA1 is any one natural amino acid selected from Y, W, V, T, S, R, Q, P, N, M, L, K, I, H, G, F, E, D, C, and A. In some embodiments AA2 is absent. In some embodiments AA2 is any one natural amino acid selected from Y, W, V, T, S, R, Q, P, N, M, L, K, I, H, G, F, E, D, C, and A. In some embodiments AA3 is absent. In some embodiments AA1 is present. In some embodiments AA2 is present. In some embodiments AA3 is present. In some embodiments AA1 is A. In some embodiments AA2 is S. In some embodiments AA3 is D. In some embodiments AA3 is selected from any one amino acid C,D,E,N,P, and Q. In some embodiments AA3 is selected from E and G. In some embodiments AA3 is P. In some embodiments AA3 is C. In some embodiments AA4 is K. In some embodiments AA6 is Y. In some embodiments AA7 is I. In some embodiments AA8 is L. In some embodiments the amino acid sequence is not found in nature. In some embodiments AA8 is the C-terminal amino acid. In some embodiments AA5 is P. In some embodiments AA6 is selected from Y and W. In some embodiments AA7 is selected from I and L.

In some embodiments AA2 is an optional amino acid selected from S, T, A, N, E and D. In some embodiments AA5 is selected from P, S, D, A, T, K, and G. In some embodiments AA6 is selected from Y, N, I, and W. In some embodiments AA8 is selected from L, I, V, S, and M.

In some embodiments the polypeptide does not comprise any one of the sequences AVTEKKYILYDFSVTS (SEQ ID NO:5), PRRPYIL (SEQ ID NO:38), RRPYIL (SEQ ID NO:39), RPYIL (SEQ ID NO:40), RRPWIL (SEQ ID NO:41), KRPYIL (SEQ ID NO:42), KKPYIL (SEQ ID NO:43), Adamantoyl-KPYIL (SEQ ID NO:9), H-Lys-psi (CH$_2$NH)Lys-Pro-Tyr-Ile-Leu-OH (SEQ ID NO:44). In some embodiments the polypeptide does not comprise derivatives of Lys.

In some embodiments the polypeptide does not consists of any one of the sequences AVTEKKYILYDFSVTS (SEQ ID NO:5), PRRPYIL (SEQ ID NO:38), RRPYIL (SEQ ID NO:39), RPYIL (SEQ ID NO:40), RRPWIL (SEQ ID NO:41), KRPYIL (SEQ ID NO:42), KKPYIL (SEQ ID NO:43), Adamantoyl-KPYIL(SEQ ID NO:9), H-Lys-psi (CH$_2$NH)Lys-Pro-Tyr-Ile-Leu-OH (SEQ ID NO:44). In some embodiments the polypeptide is not a derivative of KPYIL (SEQ ID NO:9).

In some embodiments the amino acid sequence only contains natural amino acids.

In some embodiments the polypeptide of the invention is 5-50, such as 5-50, 5-49, 5-48, 5-47, 5-46, 5-45, 5-44, 5-43, 5-42, 5-41, 5-40, 5-39, 5-38, 5-37, 5-36, 5-35, 5-34, 5-33, 5-32, 5-31, 5-30, 5-29, 5-28, 5-27, 5-26, 5-25, 5-24, 5-23, 5-22, 5-21, 5-20, 5-19, such as 5-18, such as 5-17, such as 5-16, such as 5-15, such as 5-14, such as 5-13, such as 5-12, such as 5-11, such as 5-10, such as 5-9, such as 5-8, such as 5-7, such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments the polypeptide of the invention is less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, such as 18, such as 17, such as 16, such as 15, such as 14, such as 13, such as 12, such as 11, such as 10, such as 9, such as 8, such as 7 amino acids in length.

In some embodiments the polypeptide of the invention is 5-50, such as 6-50, such as 7-50, such as 8-50, such as 9-50, such as 10-50, such as 11-50, such as 12-50, such as 13-50, such as 14-50, such as 15-50, such as 16-50, such as 17-50, such as 18-50, such as 19-50, such as 20-50, such as 21-50, such as 22-50, such as 23-50, such as 24-50, such as 25-50, such as 26-50, such as 27-50, such as 28-50, such as 29-50, such as 30-50, such as 31-50, such as 32-50, such as 33-50, such as 34-50, such as 35-50, such as 36-50, such as 37-50, such as 38-50, such as 39-50, such as 40-50, such as 41-50, such as 42-50, such as 43-50, such as 44-50, such as 45-50, such as 46-50, such as 47-50, such as 48-50, such as 49-50 amino acids in length.

In some embodiments the polypeptide of the invention is more than 5, such as 6, such as 7, such as 8, such as 9, such as 10, such as 11, such as 12, such as 13, such as 14, such as 15, such as 16, such as 17, such as 18, such as 19, such as 20, such as 21, such as 22, such as 23, such as 24, such as 25, such as 26, such as 27, such as 28, such as 29, such as 30, such as 31, such as 32, such as 33, such as 34, such as 35, such as 36, such as 37, such as 38, such as 39, such as 40, such as 41, such as 42, such as 43, such as 44, such as 45, such as 46, such as 47, such as 48, such as more than 49 amino acids in length.

In some embodiments the polypeptide of the invention is an octapeptide or a heptapeptide In some embodiments the polypeptide of the invention has or comprises a sequence selected from ASDKPYIL (SEQ ID NO: 6), SDKPYIL (SEQ ID NO: 7), DKPYIL (SEQ ID NO: 8), and KPYIL (SEQ ID NO: 9).

In some embodiments the polypeptide of the invention consist of or comprises a sequence selected from ASDKPYIL (SEQ ID NO: 6), AGDKNYIL (SEQ ID NO: 10), AGDKNYIT (SEQ ID NO: 11), AGDKSYIT (SEQ ID NO: 12), ADGKPYIV (SEQ ID NO: 13), AEDKDFIT (SEQ ID NO: 14), AADKPYIL (SEQ ID NO: 15), ATDKPYIL (SEQ ID NO: 16), AGDKPYIT (SEQ ID NO: 17), ASEKPYIL (SEQ ID NO: 18), ADGKPYVT (SEQ ID NO: 19), AGDKPYIL (SEQ ID NO: 20), ASDKPNIL (SEQ ID NO: 21), ASDKPYIT (SEQ ID NO: 22), AADKPFIL (SEQ ID NO: 23), ASDKAYIT (SEQ ID NO: 24), AGDKAYIT (SEQ ID NO: 25), ANGKPFIT (SEQ ID NO: 26), AGDKNFIT (SEQ ID NO: 27), ASDKSYIT (SEQ ID NO: 28), ASDKTYIT (SEQ ID NO: 29), ASDKNYIT (SEQ ID NO: 30), AGDKKYIT (SEQ ID NO: 31), AGDKNYIS (SEQ ID NO: 32), AADKNYIT (SEQ ID NO: 33), AGDKNYIM (SEQ ID NO: 34), AADKNFIM (SEQ ID NO: 35), AADKNFIT (SEQ ID NO: 36), and AGDKGIRS (SEQ ID NO: 37).

In some embodiments the polypeptide of the invention is an isolated polypeptide.

In some embodiments the polypeptide of the invention is synthetically made.

In some embodiments the polypeptide of the invention is a purified fragment.

In some embodiments the polypeptide of the invention is purified from animal sources.

In some embodiments the polypeptide of the invention is generated by enzymatic treatment of proteins from animal sources.

In some embodiments the polypeptide of the invention has been modified by N terminal acylation or other chemical modifications to introduce protection groups.

In some specific embodiments, the polypeptide of the invention consists of or comprises an amino acid sequence selected from the group consisting of KPYIL (SEQ ID NO: 9), KPYII (SEQ ID NO:45), KPYIV (SEQ ID NO:46), KPYLL (SEQ ID NO:47), KPYLI (SEQ ID NO:48), KPYLV (SEQ ID NO:49), KPYVL (SEQ ID NO:50), KPYVI (SEQ ID NO:51), KPYVV (SEQ ID NO:52), KPWIL (SEQ ID NO:53), KPWII (SEQ ID NO:54), KPWIV (SEQ ID NO:55), KPWLL (SEQ ID NO:56), KPWLI (SEQ ID NO:57), KPWLV (SEQ ID NO:58), KPWVL (SEQ ID NO:59), KPWVI (SEQ ID NO:60), KPWVV (SEQ ID NO:61), RPYIL (SEQ ID NO:40), RPYII (SEQ ID NO:62), RPYIV (SEQ ID NO:63), RPYLL (SEQ ID NO:64), RPYLI (SEQ ID NO:65), RPYLV (SEQ ID NO:66), RPYVL (SEQ ID NO:67), RPYVI (SEQ ID NO:68), RPYVV (SEQ ID NO:69), RPWIL (SEQ ID NO:70), RPWII (SEQ ID NO:71), RPWIV (SEQ ID NO:72), RPWLL (SEQ ID NO:73), RPWLI (SEQ ID NO:74), RPWLV (SEQ ID NO:75), RPWVL (SEQ ID NO:76), RPWVI (SEQ ID NO:77), and RPWVV (SEQ ID NO:78).

In some specific embodiments, the polypeptide of the invention consist of or comprises an amino acid sequence selected from the group consisting of DKPYIL (SEQ ID NO:8), DKPYII (SEQ ID NO:79), DKPYIV (SEQ ID NO:80), DKPYLL (SEQ ID NO:81), DKPYLI (SEQ ID NO:82), DKPYLV (SEQ ID NO:83), DKPYVL (SEQ ID NO:84), DKPYVI (SEQ ID NO:85), DKPYVV (SEQ ID NO:86), DKPWIL (SEQ ID NO:87), DKPWII (SEQ ID NO:88), DKPWIV (SEQ ID NO:89), DKPWLL (SEQ ID NO:90), DKPWLI (SEQ ID NO:91), DKPWLV (SEQ ID NO:92), DKPWVL (SEQ ID NO:93), DKPWVI (SEQ ID NO:94), DKPWVV (SEQ ID NO:95), DRPYIL (SEQ ID NO:96), DRPYII (SEQ ID NO:97), DRPYIV (SEQ ID NO:98), DRPYLL (SEQ ID NO:99), DRPYLI (SEQ ID NO:100), DRPYLV (SEQ ID NO:101), DRPYVL (SEQ ID NO:102), DRPYVI (SEQ ID NO:103), DRPYVV (SEQ ID NO:104), DRPWIL (SEQ ID NO:105), DRPWII (SEQ ID NO:106), DRPWIV (SEQ ID NO:107), DRPWLL (SEQ ID NO:108), DRPWLI (SEQ ID NO:109), DRPWLV (SEQ ID NO:110), DRPWVL (SEQ ID NO:111), DRPWVI (SEQ ID NO:112), DRPWVV (SEQ ID NO:113), EKPYIL (SEQ ID NO:114), EKPYII (SEQ ID NO:115), EKPYIV (SEQ ID NO:116), EKPYLL (SEQ ID NO:117), EKPYLI (SEQ ID NO:118), EKPYLV (SEQ ID NO:119), EKPYVL (SEQ ID NO:120), EKPYVI (SEQ ID NO:121), EKPYVV (SEQ ID NO:122), EKPWIL (SEQ ID NO:123), EKPWII (SEQ ID NO:124), EKPWIV (SEQ ID NO:125), EKPWLL (SEQ ID NO:126), EKPWLI (SEQ ID NO:127), EKPWLV (SEQ ID NO:128), EKPWVL (SEQ ID NO:129), EKPWVI (SEQ ID NO:130), EKPWVV (SEQ ID NO:131), ERPYIL (SEQ ID NO:132), ERPYII (SEQ ID NO:133), ERPYIV (SEQ ID NO:134), ERPYLL (SEQ ID NO:135), ERPYLI (SEQ ID NO:136), ERPYLV (SEQ ID NO:137), ERPYVL (SEQ ID NO:138), ERPYVI (SEQ ID NO:139), ERPYVV (SEQ ID NO:140), ERPWIL (SEQ ID NO:141), ERPWII (SEQ ID NO:142), ERPWIV (SEQ ID NO:143), ERPWLL (SEQ ID NO:144), ERPWLI (SEQ ID NO:145), ERPWLV (SEQ ID NO:146), ERPWVL (SEQ ID NO:147), ERPWVI (SEQ ID NO:148), ERPWVV (SEQ ID NO:149), RKPYIL (SEQ ID NO:150), RKPYII (SEQ ID NO:151), RKPYIV (SEQ ID NO:152), RKPYLL (SEQ ID NO:153), RKPYLI (SEQ ID NO:154), RKPYLV (SEQ ID NO:155), RKPYVL (SEQ ID NO:156), RKPYVI (SEQ ID NO:157), RKPYVV (SEQ ID NO:158), RKPWIL (SEQ ID NO:159), RKPWII (SEQ ID NO:160), RKPWIV (SEQ ID NO:161), RKPWLL (SEQ ID NO:162), RKPWLI (SEQ ID NO:163), RKPWLV (SEQ ID NO:164), RKPWVL (SEQ ID NO:165), RKPWVI (SEQ ID NO:166), RKPWVV (SEQ ID NO:167), RRPYIL (SEQ ID NO:39), RRPYII (SEQ ID NO: 168), RRPYIV (SEQ ID NO:169), RRPYLL (SEQ ID NO:170), RRPYLI (SEQ ID NO:171), RRPYLV (SEQ ID NO:172), RRPYVL (SEQ ID NO:173), RRPYVI (SEQ ID NO:174), RRPYVV (SEQ ID NO:175), RRPWIL (SEQ ID NO:41), RRPWII (SEQ ID NO:176), RRPWIV (SEQ ID NO:177), RRPWLL (SEQ ID NO:178), RRPWLI (SEQ ID NO:179), RRPWLV (SEQ ID NO:180), RRPWVL (SEQ ID NO:181), RRPWVI (SEQ ID NO:182), RRPWVV (SEQ ID NO:183), GKPYIL (SEQ ID NO:184), GKPYII (SEQ ID NO:185), GKPYIV (SEQ ID NO:186), GKPYLL (SEQ ID NO:187), GKPYLI (SEQ ID NO:188), GKPYLV (SEQ ID NO:189), GKPYVL (SEQ ID NO:190), GKPYVI (SEQ ID NO:191), GKPYVV (SEQ ID NO:192), GKPWIL (SEQ ID NO:193), GKPWII (SEQ ID NO:194), GKPWIV (SEQ ID NO:195), GKPWLL (SEQ ID NO:196), GKPWLI (SEQ ID NO:197), GKPWLV (SEQ ID NO:198), GKPWVL (SEQ ID NO:199), GKPWVI (SEQ ID NO:200), GKPWVV (SEQ ID NO:201), GRPYIL (SEQ ID NO:202), GRPYII (SEQ ID NO:203), GRPYIV (SEQ ID NO:204), GRPYLL (SEQ ID NO:205), GRPYLI (SEQ ID NO:206), GRPYLV (SEQ ID NO:207), GRPYVL (SEQ ID NO:208), GRPYVI (SEQ ID NO:209), GRPYVV (SEQ ID NO:210), GRPWIL (SEQ ID NO:211), GRPWII (SEQ ID NO:212), GRPWIV (SEQ ID NO:213), GRPWLL (SEQ ID NO:214), GRPWLI (SEQ ID NO:215), GRPWLV (SEQ ID NO:216), GRPWVL (SEQ ID NO:217), GRPWVI (SEQ ID NO:218), and GRPWVV (SEQ ID NO:219).

In some specific embodiments, the polypeptide of the invention consists of or comprises an amino acid sequence selected from the group consisting of SDKPYIL (SEQ ID NO:220), SDKPYII (SEQ ID NO:221), SDKPYIV (SEQ ID NO:222), SDKPYLL (SEQ ID NO:223), SDKPYLI (SEQ ID NO:224), SDKPYLV (SEQ ID NO:225), SDKPYVL (SEQ ID NO:226), SDKPYVI (SEQ ID NO:227), SDKPYVV (SEQ ID NO:228), SDKPWIL (SEQ ID NO:229), SDKPWII (SEQ ID NO:230), SDKPWIV (SEQ ID NO:231), SDKPWLL (SEQ ID NO:232), SDKPWLI (SEQ ID NO:233), SDKPWLV (SEQ ID NO:234), SDKPWVL (SEQ ID NO:235), SDKPWVI (SEQ ID NO:236), SDKPWVV (SEQ ID NO:237), SDRPYIL (SEQ ID NO:238), SDRPYII (SEQ ID NO:239), SDRPYIV (SEQ ID NO:240), SDRPYLL (SEQ ID NO:241), SDRPYLI (SEQ ID NO:242), SDRPYLV (SEQ ID NO:243), SDRPYVL (SEQ ID NO:244), SDRPYVI (SEQ ID NO:245), SDRPYVV (SEQ ID NO:246), SDRPWIL (SEQ ID NO:247), SDRPWII (SEQ ID NO:248), SDRPWIV (SEQ ID NO:249), SDRPWLL (SEQ ID NO:250), SDRPWLI (SEQ ID NO:251), SDRPWLV (SEQ ID NO:252), SDRPWVL (SEQ ID NO:253), SDRPWVI (SEQ ID NO:254), SDRPWVV (SEQ ID NO:255), SEKPYIL (SEQ ID NO:256), SEKPYII (SEQ ID NO:257), SEKPYIV (SEQ ID NO:258), SEKPYLL (SEQ ID NO:259), SEKPYLI (SEQ ID NO:260), SEKPYLV (SEQ ID NO:261), SEKPYVL (SEQ ID NO:262), SEKPYVI (SEQ ID NO:263), SEKPYVV (SEQ ID NO:264), SEKPWIL (SEQ ID NO:265), SEKPWII (SEQ ID NO:266), SEKPWIV (SEQ ID NO:267), SEKPWLL (SEQ ID NO:268), SEKPWLI (SEQ ID NO:269), SEKPWLV (SEQ ID NO:270), SEKPWVL (SEQ ID NO:271), SEKPWVI (SEQ ID NO:272), SEKPWVV (SEQ ID NO:273), SERPYIL (SEQ ID NO:274), SERPYII (SEQ ID NO:275), SERPYIV (SEQ ID NO:276), SERPYLL (SEQ ID NO:277), SERPYLI (SEQ ID NO:278), SERPYLV (SEQ ID NO:279), SERPYVL (SEQ ID NO:280), SERPYVI (SEQ ID NO:281), SERPYVV (SEQ ID NO:282), SERPWIL (SEQ ID NO:283), SERPWII (SEQ ID NO:284), SERPWIV (SEQ ID NO:285), SERPWLL (SEQ ID NO:286), SERPWLI (SEQ ID NO:287), SERPWLV (SEQ ID NO:288), SERPWVL (SEQ ID NO:289), SERPWVI (SEQ ID NO:290), SERPWVV (SEQ ID NO:291), TDKPYIL (SEQ ID NO:292), TDKPYII (SEQ ID NO:293), TDKPYIV (SEQ ID NO:294), TDKPYLL (SEQ ID NO:295), TDKPYLI (SEQ ID NO:296), TDKPYLV (SEQ ID NO:297), TDKPYVL (SEQ ID NO:298), TDKPYVI (SEQ ID NO:299), TDKPYVV (SEQ ID NO:300), TDKPWIL (SEQ ID NO:301), TDKPWII (SEQ ID NO:302), TDKPWIV (SEQ ID NO:303), TDKPWLL (SEQ ID NO:304), TDKPWLI (SEQ ID NO:305), TDKPWLV (SEQ ID NO:306), TDKPWVL (SEQ ID NO:307), TDKPWVI (SEQ ID NO:308), TDKPWVV (SEQ ID NO:309), TDRPYIL (SEQ ID NO:310), TDRPYII (SEQ ID NO:311), TDRPYIV (SEQ ID NO:312), TDRPYLL (SEQ ID NO:313), TDRPYLI (SEQ ID NO:314), TDRPYLV (SEQ ID NO:315), TDRPYVL (SEQ ID NO:316), TDRPYVI (SEQ ID NO:317), TDRPYVV (SEQ ID NO:318), TDRPWIL (SEQ ID NO:319), TDRPWII (SEQ ID NO:320), TDRPWIV (SEQ ID NO:321), TDRPWLL (SEQ ID NO:322), TDRPWLI (SEQ ID NO:323), TDRPWLV (SEQ ID NO:324), TDRPWVL (SEQ ID NO:325), TDRPWVI (SEQ ID NO:326), TDRPWVV (SEQ ID NO:327), TEKPYIL (SEQ ID NO:328), TEKPYII (SEQ ID NO:329), TEKPYIV (SEQ ID NO:330), TEKPYLL (SEQ ID NO:331), TEKPYLI (SEQ ID NO:332), TEKPYLV (SEQ ID NO:333), TEKPYVL (SEQ ID NO:334), TEKPYVI (SEQ ID NO:335), TEKPYVV (SEQ ID NO:336), TEKPWIL (SEQ ID NO:337), TEKPWII (SEQ ID NO:338), TEKPWIV (SEQ ID NO:339), TEKPWLL (SEQ ID NO:340), TEKPWLI (SEQ ID NO:341), TEKPWLV (SEQ ID NO:342), TEKPWVL (SEQ ID NO:343), TEKPWVI (SEQ ID NO:344), TEKPWVV (SEQ ID NO:345), TERPYIL (SEQ ID NO:346), TERPYII (SEQ ID NO:347), TERPYIV (SEQ ID NO:348), TERPYLL (SEQ ID NO:349), TERPYLI (SEQ ID NO:350), TERPYLV (SEQ ID NO:351), TERPYVL (SEQ ID NO:352), TERPYVI (SEQ ID NO:353), TERPYVV (SEQ ID NO:354), TERPWIL (SEQ ID NO:355), TERPWII (SEQ ID NO:356), TERPWIV (SEQ ID NO:357), TERPWLL (SEQ ID NO:358), TERPWLI (SEQ ID NO:359), TERPWLV (SEQ ID NO:360), TERPWVL (SEQ ID NO:361), TERPWVI (SEQ ID NO:362), and TERPWVV (SEQ ID NO:363).

In some specific embodiments, the polypeptide of the invention consists of or comprises an amino acid sequence selected from the group consisting of ASDKPYII (SEQ ID NO:364), ASDKPYIV (SEQ ID NO:365), ASDKPYLL (SEQ ID NO:366), ASDKPYLI (SEQ ID NO:367), ASDKPYLV (SEQ ID NO:368), ASDKPYVL (SEQ ID NO:369), ASDKPYVI (SEQ ID NO:370), ASDKPYVV (SEQ ID NO:371), ASDKPWIL (SEQ ID NO:372), ASDKPWII (SEQ ID NO:373), ASDKPWIV (SEQ ID NO:374), ASDKPWLL (SEQ ID NO:375), ASDKPWLI (SEQ ID NO:376), ASDKPWLV (SEQ ID NO:377), ASDKPWVL (SEQ ID NO:378), ASDKPWVI (SEQ ID NO:379), ASDKPWVV (SEQ ID NO:380), ASDRPYIL (SEQ ID NO:381), ASDRPYII (SEQ ID NO:382), ASDRPYIV (SEQ ID NO:383), ASDRPYLL (SEQ ID NO:384), ASDRPYLI (SEQ ID NO:385), ASDRPYLV (SEQ ID NO:386), ASDRPYVL (SEQ ID NO:387), ASDRPYVI (SEQ ID NO:388), ASDRPYVV (SEQ ID NO:389), ASDRPWIL (SEQ ID NO:390), ASDRPWII (SEQ ID NO:391), ASDRPWIV (SEQ ID NO:392), ASDRPWLL (SEQ ID NO:393), ASDRPWLI (SEQ ID NO:394), ASDRPWLV (SEQ ID NO:395), ASDRPWVL (SEQ ID NO:396), ASDRPWVI (SEQ ID NO:397), ASDRPWVV (SEQ ID NO:398), ASEKPYIL (SEQ ID NO:399), ASEKPYII (SEQ ID NO:400), ASEKPYIV (SEQ ID NO:401), ASEKPYLL (SEQ ID NO:402), ASEKPYLI (SEQ ID NO:403), ASEKPYLV (SEQ ID NO:404), ASEKPYVL (SEQ ID NO:405), ASEKPYVI (SEQ ID NO:406), ASEKPYVV (SEQ ID NO:407), ASEKPWIL (SEQ ID NO:408), ASEKPWII (SEQ ID NO:409), ASEKPWIV (SEQ ID NO:410), ASEKPWLL (SEQ ID NO:411), ASEKPWLI (SEQ ID NO:412), ASEKPWLV (SEQ ID NO:413), ASEKPWVL (SEQ ID NO:414), ASEKPWVI (SEQ ID NO:415), ASEKPWVV (SEQ ID NO:416), ASERPYIL (SEQ ID NO:417), ASERPYII (SEQ ID NO:418), ASERPYIV (SEQ ID NO:419), ASERPYLL (SEQ ID NO:420), ASERPYLI (SEQ ID NO:421), ASERPYLV (SEQ ID NO:422), ASERPYVL (SEQ ID NO:423), ASERPYVI (SEQ ID NO:424), ASERPYVV (SEQ ID NO:425), ASERPWIL (SEQ ID NO:426), ASERPWII (SEQ ID NO:427), ASERPWIV (SEQ ID NO:428), ASERPWLL (SEQ ID NO:429), ASERPWLI (SEQ ID NO:430), ASERPWLV (SEQ ID NO:431), ASERPWVL (SEQ ID NO:432), ASERPWVI (SEQ ID NO:433), ASERPWVV (SEQ ID NO:434), ATDKPYIL (SEQ ID NO:435), ATDKPYII (SEQ ID NO:436), ATDKPYIV (SEQ ID NO:437), ATDKPYLL (SEQ ID NO:438), ATDKPYLI (SEQ ID NO:439), ATDKPYLV (SEQ ID NO:440), ATDKPYVL (SEQ ID NO:441), ATDKPYVI (SEQ ID NO:442), ATDKPYVV (SEQ ID NO:443), ATDKPWIL (SEQ ID NO:444), ATDKPWII (SEQ ID NO:445), ATDKPWIV (SEQ ID NO:446), ATDKPWLL (SEQ ID NO:447), ATDKPWLI (SEQ ID NO:448), ATDKPWLV (SEQ ID NO:449), ATDKPWVL (SEQ ID NO:450), ATDKPWVI (SEQ ID NO:451), ATDKPWVV (SEQ ID NO:452), ATDRPYIL (SEQ ID NO:453), ATDRPYII (SEQ ID NO:454), ATDRPYIV (SEQ ID NO:455), ATDRPYLL (SEQ ID NO:456), ATDRPYLI (SEQ ID NO:457), ATDRPYLV (SEQ ID NO:458), ATDRPYVL (SEQ ID NO:459), ATDRPYVI (SEQ ID NO:460), ATDRPYVV (SEQ ID NO:461), ATDRPWIL (SEQ ID NO:462), ATDRPWII (SEQ ID NO:463), ATDRPWIV (SEQ ID NO:464), ATDRPWLL (SEQ ID NO:465), ATDRPWLI (SEQ ID NO:466), ATDRPWLV (SEQ ID NO:467), ATDRPWVL (SEQ ID NO:468), ATDRPWVI (SEQ ID NO:469), ATDRPWVV (SEQ ID NO:470), ATEKPYIL (SEQ ID NO:471), ATEKPYII (SEQ ID NO:472), ATEKPYIV (SEQ ID NO:473), ATEKPYLL (SEQ ID NO:474), ATEKPYLI (SEQ ID NO:475), ATEKPYLV (SEQ ID NO:476), ATEKPYVL (SEQ ID NO:477), ATEKPYVI (SEQ ID NO:478), ATEKPYVV (SEQ ID NO:479), ATEKPWIL (SEQ ID NO:480), ATEKPWII (SEQ ID NO:481), ATEKPWIV (SEQ ID NO:482), ATEKPWLL (SEQ ID NO:483), ATEKPWLI (SEQ ID NO:484), ATEKPWLV (SEQ ID NO:485), ATEKPWVL (SEQ ID NO:486), ATEKPWVI (SEQ ID NO:487), ATEKPWVV (SEQ ID NO:488), ATERPYIL (SEQ ID NO:489), ATERPYII (SEQ ID NO:490), ATERPYIV (SEQ ID NO:491), ATERPYLL (SEQ ID NO:492), ATERPYLI (SEQ ID NO:493), ATERPYLV (SEQ ID NO:494), ATERPYVL (SEQ ID NO:495), ATERPYVI (SEQ ID NO:496), ATERPYVV (SEQ ID NO:497), ATERPWIL (SEQ ID NO:498), ATERPWII (SEQ ID NO:499), ATERPWIV (SEQ ID NO:500), ATERPWLL (SEQ ID NO:501), ATERPWLI (SEQ ID NO:502), ATERPWLV (SEQ ID NO:503), ATERPWVL (SEQ ID NO:504), ATERPWVI (SEQ ID NO:505), ATERPWVV (SEQ ID NO:506), LSDKPYIL (SEQ ID NO:507), LSDKPYII (SEQ ID NO:508), LSDKPYIV (SEQ ID NO:509), LSDKPYLL (SEQ ID NO:510), LSDKPYLI (SEQ ID NO:511), LSDKPYLV (SEQ ID NO:512), LSDKPYVL (SEQ ID NO:513), LSDKPYVI (SEQ ID NO:514), LSDKPYVV (SEQ ID NO:515), LSDKPWIL (SEQ ID NO:516), LSDKPWII (SEQ ID NO:517), LSDKPWIV (SEQ ID NO:518), LSDKPWLL (SEQ ID NO:519), LSDKPWLI (SEQ ID NO:520), LSDKPWLV (SEQ ID NO:521), LSDKPWVL (SEQ ID NO:522), LSDKPWVI (SEQ ID NO:523), LSDKPWVV (SEQ ID NO:524), LSDRPYIL (SEQ ID NO:525), LSDRPYII (SEQ ID NO:526), LSDRPYIV (SEQ ID NO:527), LSDRPYLL (SEQ ID NO:528), LSDRPYLI (SEQ ID NO:529), LSDRPYLV (SEQ ID NO:530), LSDRPYVL (SEQ ID NO:531), LSDRPYVI (SEQ ID NO:532), LSDRPYVV (SEQ ID NO:533), LSDRPWIL (SEQ ID NO:534), LSDRPWII (SEQ ID NO:535), LSDRPWIV (SEQ ID NO:536), LSDRPWLL (SEQ ID NO:537), LSDRPWLI (SEQ ID NO:538), LSDRPWLV (SEQ ID NO:539), LSDRPWVL (SEQ ID NO:540), LSDRPWVI (SEQ ID NO:541), LSDRPWVV (SEQ ID NO:542), LSEKPYIL (SEQ ID NO:543), LSEKPYII (SEQ ID NO:544), LSEKPYIV (SEQ ID NO:545), LSEKPYLL (SEQ ID NO:546), LSEKPYLI (SEQ ID NO:547), LSEKPYLV (SEQ ID NO:548), LSEKPYVL (SEQ ID NO:549), LSEKPYVI (SEQ ID NO:550), LSEKPYVV (SEQ ID NO:551), LSEKPWIL (SEQ ID NO:552), LSEKPWII (SEQ ID NO:553), LSEKPWIV (SEQ ID NO:554), LSEKPWLL (SEQ ID NO:555), LSEKPWLI (SEQ ID NO:556), LSEKPWLV (SEQ ID NO:557), LSEKPWVL (SEQ ID NO:558), LSEKPWVI (SEQ ID NO:559), LSEKPWVV (SEQ ID NO:560), LSERPYIL (SEQ ID NO:561), LSERPYII (SEQ ID NO:562), LSERPYIV (SEQ ID NO:563), LSERPYLL (SEQ ID NO:564), LSERPYLI (SEQ ID NO:565), LSERPYLV (SEQ ID NO:566), LSERPYVL (SEQ ID NO:567), LSERPYVI (SEQ ID NO:568), LSERPYVV (SEQ ID NO:569), LSERPWIL (SEQ ID NO:570), LSERPWII (SEQ ID NO:571), LSERPWIV (SEQ ID NO:572), LSERPWLL (SEQ ID NO:573), LSERPWLI (SEQ ID NO:574), LSERPWLV (SEQ ID NO:575), LSERPWVL (SEQ ID NO:576), LSERPWVI (SEQ ID NO:577), LSERPWVV (SEQ ID NO:578), LTDKPYIL (SEQ ID NO:579), LTDKPYII (SEQ ID NO:580), LTDKPYIV (SEQ ID NO:581), LTDKPYLL (SEQ ID NO:582), LTDKPYLI (SEQ ID NO:583), LTDKPYLV (SEQ ID NO:584), LTDKPYVL (SEQ ID NO:585), LTDKPYVI (SEQ ID NO:586), LTDKPYVV (SEQ ID NO:587), LTDKPWIL (SEQ ID NO:588), LTDKPWII (SEQ ID NO:589), LTDKPWIV (SEQ ID NO:590), LTDKPWLL (SEQ ID NO:591), LTDKPWLI (SEQ ID NO:592), LTDKPWLV (SEQ ID NO:593), LTDKPWVL (SEQ ID NO:594), LTDKPWVI (SEQ ID NO:595), LTDKPWVV (SEQ ID NO:596), LTDRPYIL (SEQ ID NO:597), LTDRPYII (SEQ ID NO:598), LTDRPYIV (SEQ ID NO:599), LTDRPYLL (SEQ ID NO:600), LTDRPYLI (SEQ ID NO:601), LTDRPYLV (SEQ ID NO:602), LTDRPYVL (SEQ ID NO:603), LTDRPYVI (SEQ ID NO:604), LTDRPYVV (SEQ ID NO:605), LTDRPWIL (SEQ ID NO:606), LTDRPWII (SEQ ID NO:607), LTDRPWIV (SEQ ID NO:608), LTDRPWLL (SEQ ID NO:609), LTDRPWLI (SEQ ID NO:610), LTDRPWLV (SEQ ID NO:611), LTDRPWVL (SEQ ID NO:612), LTDRPWVI (SEQ ID NO:613), LTDRPWVV (SEQ ID NO:614), LTEKPYIL (SEQ ID NO:615), LTEKPYII (SEQ ID NO:616), LTEKPYIV (SEQ ID NO:617), LTEKPYLL (SEQ ID NO:618), LTEKPYLI (SEQ ID NO:619), LTEKPYLV (SEQ ID NO:620), LTEKPYVL (SEQ ID NO:621), LTEKPYVI (SEQ ID NO:622), LTEKPYVV (SEQ ID NO:623), LTEKPWIL (SEQ ID NO:624), LTEKPWII (SEQ ID NO:625), LTEKPWIV (SEQ ID NO:626), LTEKPWLL (SEQ ID NO:627), LTEKPWLI (SEQ ID NO:628), LTEKPWLV (SEQ ID NO:629), LTEKPWVL (SEQ ID NO:630), LTEKPWVI (SEQ ID NO:631), LTEKPWVV (SEQ ID NO:632), LTERPYIL (SEQ ID NO:633), LTERPYII (SEQ ID NO:634), LTERPYIV (SEQ ID NO:635), LTERPYLL (SEQ ID NO:636), LTERPYLI (SEQ ID NO:637), LTERPYLV (SEQ ID NO:638), LTERPYVL (SEQ ID NO:639), LTERPYVI (SEQ ID NO:640), LTERPYVV (SEQ ID NO:641), LTERPWIL (SEQ ID NO:642), LTERPWII (SEQ ID NO:643), LTERPWIV (SEQ ID NO:644), LTERPWLL (SEQ ID NO:645), LTERPWLI (SEQ ID NO:646), LTERPWLV (SEQ ID NO:647), LTERPWVL (SEQ ID NO:648), LTERPWVI (SEQ ID NO:649), LTERPWVV (SEQ ID NO:650), ISDKPYIL (SEQ ID NO:651), ISDKPYII (SEQ ID NO:652), ISDKPYIV (SEQ ID NO:653), ISDKPYLL (SEQ ID NO:654), ISDKPYLI (SEQ ID NO:655), ISDKPYLV (SEQ ID NO:656), ISDKPYVL (SEQ ID NO:657), ISDKPYVI (SEQ ID NO:658), ISDKPYVV (SEQ ID NO:659), ISDKPWIL (SEQ ID NO:660), ISDKPWII (SEQ ID NO:661), ISDKPWIV (SEQ ID NO:662), ISDKPWLL (SEQ ID NO:663), ISDKPWLI (SEQ ID NO:664), ISDKPWLV (SEQ ID NO:665), ISDKPWVL (SEQ ID NO:666), ISDKPWVI (SEQ ID NO:667), ISDKPWVV (SEQ ID NO:668), ISDRPYIL (SEQ ID NO:669), ISDRPYII (SEQ ID NO:670), ISDRPYIV (SEQ ID NO:671), ISDRPYLL (SEQ ID NO:672), ISDRPYLI (SEQ ID NO:673), ISDRPYLV (SEQ ID NO:674), ISDRPYVL (SEQ ID NO:675), ISDRPYVI (SEQ ID NO:676), ISDRPYVV (SEQ ID NO:677), ISDRPWIL (SEQ ID NO:678), ISDRPWII (SEQ ID NO:679), ISDRPWIV (SEQ ID NO:680), ISDRPWLL (SEQ ID NO:681), ISDRPWLI (SEQ ID NO:682), ISDRPWLV (SEQ ID NO:683), ISDRPWVL (SEQ ID NO:684), ISDRPWVI (SEQ ID NO:685), ISDRPWVV (SEQ ID NO:686), ISEKPYIL (SEQ ID NO:687), ISEKPYII (SEQ ID NO:688), ISEKPYIV (SEQ ID NO:689), ISEKPYLL (SEQ ID NO:690), ISEKPYLI (SEQ ID NO:691), ISEKPYLV (SEQ ID NO:692), ISEKPYVL (SEQ ID NO:693), ISEKPYVI (SEQ ID NO:694), ISEKPYVV (SEQ ID NO:695), ISEKPWIL (SEQ ID NO:696), ISEKPWII (SEQ ID NO:697), ISEKPWIV (SEQ ID NO:698), ISEKPWLL (SEQ ID NO:699), ISEKPWLI (SEQ ID NO:700), ISEKPWLV (SEQ ID NO:701), ISEKPWVL (SEQ ID NO:702), ISEKPWVI (SEQ ID NO:703), ISEKPWVV (SEQ ID NO:704), ISERPYIL (SEQ ID NO:705), ISERPYII (SEQ ID NO:706), ISERPYIV (SEQ ID NO:707), ISERPYLL (SEQ ID NO:708), ISERPYLI (SEQ ID NO:709), ISERPYLV (SEQ ID NO:710), ISERPYVL (SEQ ID NO:711), ISERPYVI (SEQ ID NO:712), ISERPYVV (SEQ ID NO:713), ISERPWIL (SEQ ID NO:714), ISERPWII (SEQ ID NO:715), ISERPWIV (SEQ ID NO:716), ISERPWLL (SEQ ID NO:717), ISERPWLI (SEQ ID NO:718), ISERPWLV (SEQ ID NO:719), ISERPWVL (SEQ ID NO:720), ISERPWVI (SEQ ID NO:721), ISERPWVV (SEQ ID NO:722), ITDKPYIL (SEQ ID NO:723), ITDKPYII (SEQ ID NO:724), ITDKPYIV (SEQ ID NO:725), ITDKPYLL (SEQ ID NO:726), ITDKPYLI (SEQ ID NO:727), ITDKPYLV (SEQ ID NO:728), ITDKPYVL (SEQ ID NO:729), ITDKPYVI (SEQ ID NO:730), ITDKPYVV (SEQ ID NO:731), ITDKPWIL (SEQ ID NO:732), ITDKPWII (SEQ ID NO:733), ITDKPWIV (SEQ ID NO:734), ITDKPWLL (SEQ ID NO:735), ITDKPWLI (SEQ ID NO:736), ITDKPWLV (SEQ ID NO:737), ITDKPWVL (SEQ ID NO:738), ITDKPWVI (SEQ ID NO:739), ITDKPWVV (SEQ ID NO:740), ITDRPYIL (SEQ ID NO:741), ITDRPYII (SEQ ID NO:742), ITDRPYIV (SEQ ID NO:743), ITDRPYLL (SEQ ID NO:744), ITDRPYLI (SEQ ID NO:745), ITDRPYLV (SEQ ID NO:746), ITDRPYVL (SEQ ID NO:747), ITDRPYVI (SEQ ID NO:748), ITDRPYVV (SEQ ID NO:749), ITDRPWIL (SEQ ID NO:750), ITDRPWII (SEQ ID NO:751), ITDRPWIV (SEQ ID NO:752), ITDRPWLL (SEQ ID NO:753), ITDRPWLI (SEQ ID NO:754), ITDRPWLV (SEQ ID NO:755), ITDRPWVL (SEQ ID NO:756), ITDRPWVI (SEQ ID NO:757), ITDRPWVV (SEQ ID NO:758), ITEKPYIL (SEQ ID NO:759), ITEKPYII (SEQ ID NO:760), ITEKPYIV (SEQ ID NO:761), ITEKPYLL (SEQ ID NO:762), ITEKPYLI (SEQ ID NO:763), ITEKPYLV (SEQ ID NO:764), ITEKPYVL (SEQ ID NO:765), ITEKPYVI (SEQ ID NO:766), ITEKPYVV (SEQ ID NO:767), ITEKPWIL (SEQ ID NO:768), ITEKPWII (SEQ ID NO:769), ITEKPWIV (SEQ ID NO:770), ITEKPWLL (SEQ ID NO:771), ITEKPWLI (SEQ ID NO:772), ITEKPWLV (SEQ ID NO:773), ITEKPWVL (SEQ ID NO:774), ITEKPWVI (SEQ ID NO:775), ITEKPWVV (SEQ ID NO:776), ITERPYIL (SEQ ID NO:777), ITERPYII (SEQ ID NO:778), ITERPYIV (SEQ ID NO:779), ITERPYLL (SEQ ID NO:780), ITERPYLI (SEQ ID NO:781), ITERPYLV (SEQ ID NO:782), ITERPYVL (SEQ ID NO:783), ITERPYVI (SEQ ID NO:784), ITERPYVV (SEQ ID NO:785), ITERPWIL (SEQ ID NO:786), ITERPWII (SEQ ID NO:787), ITERPWIV (SEQ ID NO:788), ITERPWLL (SEQ ID NO:789), ITERPWLI (SEQ ID NO:790), ITERPWLV (SEQ ID NO:791), ITERPWVL (SEQ ID NO:792), ITERPWVI (SEQ ID NO:793), ITERPWVV (SEQ ID NO:794), VSDKPYIL (SEQ ID NO:795), VSDKPYII (SEQ ID NO:796), VSDKPYIV (SEQ ID NO:797), VSDKPYLL (SEQ ID NO:798), VSDKPYLI (SEQ ID NO:799), VSDKPYLV (SEQ ID NO:800), VSDKPYVL (SEQ ID NO:801), VSDKPYVI (SEQ ID NO:802), VSDKPYVV (SEQ ID NO:803), VSDKPWIL (SEQ ID NO:804), VSDKPWII (SEQ ID NO:805), VSDKPWIV (SEQ ID NO:806), VSDKPWLL (SEQ ID NO:807), VSDKPWLI (SEQ ID NO:808), VSDKPWLV (SEQ ID NO:809), VSDKPWVL (SEQ ID NO:810), VSDKPWVI (SEQ ID NO:811), VSDKPWVV (SEQ ID NO:812), VSDRPYIL (SEQ ID NO:813), VSDRPYII (SEQ ID NO:814), VSDRPYIV (SEQ ID NO:815), VSDRPYLL (SEQ ID NO:816), VSDRPYLI (SEQ ID NO:817), VSDRPYLV (SEQ ID NO:818), VSDRPYVL (SEQ ID NO:819), VSDRPYVI (SEQ ID NO:820), VSDRPYVV (SEQ ID NO:821), VSDRPWIL (SEQ ID NO:822), VSDRPWII (SEQ ID NO:823), VSDRPWIV (SEQ ID NO:824), VSDRPWLL (SEQ ID NO:825), VSDRPWLI (SEQ ID NO:826), VSDRPWLV (SEQ ID NO:827), VSDRPWVL (SEQ ID NO:828), VSDRPWVI (SEQ ID NO:829), VSDRPWVV (SEQ ID NO:830), VSEKPYIL (SEQ ID NO:831), VSEKPYII (SEQ ID NO:832), VSEKPYIV (SEQ ID NO:833), VSEKPYLL (SEQ ID NO:834), VSEKPYLI (SEQ ID NO:835), VSEKPYLV (SEQ ID NO:836), VSEKPYVL (SEQ ID NO:837), VSEKPYVI (SEQ ID NO:838), VSEKPYVV (SEQ ID NO:839), VSEKPWIL (SEQ ID NO:840), VSEKPWII (SEQ ID NO:841), VSEKPWIV (SEQ ID NO:842), VSEKPWLL (SEQ ID NO:843), VSEKPWLI (SEQ ID NO:844), VSEKPWLV (SEQ ID NO:845), VSEKPWVL (SEQ ID NO:846), VSEKPWVI (SEQ ID NO:847), VSEKPWVV (SEQ ID NO:848), VSERPYIL (SEQ ID NO:849), VSERPYII (SEQ ID NO:850), VSERPYIV (SEQ ID NO:851), VSERPYLL (SEQ ID NO:852), VSERPYLI (SEQ ID NO:853), VSERPYLV (SEQ ID NO:854), VSERPYVL (SEQ ID NO:855), VSERPYVI (SEQ ID NO:856), VSERPYVV (SEQ ID NO:857), VSERPWIL (SEQ ID NO:858), VSERPWII (SEQ ID NO:859), VSERPWIV (SEQ ID NO:860), VSERPWLL (SEQ ID NO:861), VSERPWLI (SEQ ID NO:862), VSERPWLV (SEQ ID NO:863), VSERPWVL (SEQ ID NO:864), VSERPWVI (SEQ ID NO:865), VSERPWVV (SEQ ID NO:866), VTDKPYIL (SEQ ID NO:867), VTDKPYII (SEQ ID NO:868), VTDKPYIV (SEQ ID NO:869), VTDKPYLL (SEQ ID NO:870), VTDKPYLI (SEQ ID NO:871), VTDKPYLV (SEQ ID NO:872), VTDKPYVL (SEQ ID NO:873), VTDKPYVI (SEQ ID NO:874), VTDKPYVV (SEQ ID NO:875), VTDKPWIL (SEQ ID NO:876), VTDKPWII (SEQ ID NO:877), VTDKPWIV (SEQ ID NO:878), VTDKPWLL (SEQ ID NO:879), VTDKPWLI (SEQ ID NO:880), VTDKPWLV (SEQ ID NO:881), VTDKPWVL (SEQ ID NO:882), VTDKPWVI (SEQ ID NO:883), VTDKPWVV (SEQ ID NO:884), VTDRPYIL (SEQ ID NO:885), VTDRPYII (SEQ ID NO:886), VTDRPYIV (SEQ ID NO:887), VTDRPYLL (SEQ ID NO:888), VTDRPYLI (SEQ ID NO:889), VTDRPYLV (SEQ ID NO:890), VTDRPYVL (SEQ ID NO:891), VTDRPYVI (SEQ ID NO:892), VTDRPYVV (SEQ ID NO:893), VTDRPWIL (SEQ ID NO:894), VTDRPWII (SEQ ID NO:895), VTDRPWIV (SEQ ID NO:896), VTDRPWLL (SEQ ID NO:897), VTDRPWLI (SEQ ID NO:898), VTDRPWLV (SEQ ID NO:899), VTDRPWVL (SEQ ID NO:900), VTDRPWVI (SEQ ID NO:901), VTDRPWVV (SEQ ID NO:902), VTEKPYIL (SEQ ID NO:903), VTEKPYII (SEQ ID NO:904), VTEKPYIV (SEQ ID NO:905), VTEKPYLL (SEQ ID NO:906), VTEKPYLI (SEQ ID NO:907), VTEKPYLV (SEQ ID NO:908), VTEKPYVL (SEQ ID NO:909), VTEKPYVI (SEQ ID NO:910), VTEKPYVV (SEQ ID NO:911), VTEKPWIL (SEQ ID NO:912), VTEKPWII (SEQ ID NO:913), VTEKPWIV (SEQ ID NO:914), VTEKPWLL (SEQ ID NO:915), VTEKPWLI (SEQ ID NO:916), VTEKPWLV (SEQ ID NO:917), VTEKPWVL (SEQ ID NO:918), VTEKPWVI (SEQ ID NO:919), VTEKPWVV (SEQ ID NO:920), VTERPYIL (SEQ ID NO:921), VTERPYII (SEQ ID NO:922), VTERPYIV (SEQ ID NO:923), VTERPYLL (SEQ ID NO:924), VTERPYLI (SEQ ID NO:925), VTERPYLV (SEQ ID NO:926), VTERPYVL (SEQ ID NO:927), VTERPYVI (SEQ ID NO:928), VTERPYVV (SEQ ID NO:929), VTERPWIL (SEQ ID NO:930), VTERPWII (SEQ ID NO:931), VTERPWIV (SEQ ID NO:932), VTERPWLL (SEQ ID NO:933), VTERPWLI (SEQ ID NO:934), VTERPWLV (SEQ ID NO:935), VTERPWVL (SEQ ID NO:936), VTERPWVI (SEQ ID NO:937), and VTERPWVV (SEQ ID NO:938).

In some specific embodiments, the polypeptide of the invention consists of or comprises an amino acid sequence derived from Alpha-actinin-1, such as a sequence selected from ASDKPYIL (SEQ ID NO: 6), AGDKNYIL (SEQ ID NO: 10), AGDKNYIT (SEQ ID NO: 11), AGDKSYIT (SEQ ID NO: 12), ADGKPYIV (SEQ ID NO: 13), and AEDKDFIT (SEQ ID NO: 14).

In some specific embodiments, the polypeptide of the invention consists of or comprises an amino acid sequence derived from Alpha-actinin-2, such as a sequence selected from ASDKPYIL (SEQ ID NO: 6), AADKPYIL (SEQ ID NO: 15), AGDKNYIT (SEQ ID NO: 11), ATDKPYIL (SEQ ID NO: 16), AGDKPYIT (SEQ ID NO: 17), ASEKPYIL (SEQ ID NO: 18), ADGKPYVT (SEQ ID NO: 19), AGDKPYIL (SEQ ID NO: 20), ASDKPNIL (SEQ ID NO: 21), ASDKPYIT (SEQ ID NO: 22), AADKPFIL (SEQ ID NO: 23), ASDKAYIT (SEQ ID NO: 24), AGDKAYIT (SEQ ID NO: 25), ANGKPFIT (SEQ ID NO: 26), and AGDKNFIT (SEQ ID NO: 27).

In some specific embodiments, the polypeptide of the invention consists of or comprises an amino acid sequence derived from Alpha-actinin-3, such as a sequence selected from ASDKPYIL (SEQ ID NO: 6), AADKPYIL (SEQ ID NO: 15), ASDKAYIT (SEQ ID NO: 24), ASDKSYIT (SEQ ID NO: 28), ASDKTYIT (SEQ ID NO: 29), ASDKNYIT (SEQ ID NO: 30), AGDKNYIL (SEQ ID NO: 10), AGDKSYIT (SEQ ID NO: 12), AGDKNYIT (SEQ ID NO: 11), AGDKKYIT (SEQ ID NO: 31), and AGDKNYIS (SEQ ID NO: 32).

In some specific embodiments, the polypeptide of the invention consists of or comprises an amino acid sequence derived from Alpha-actinin-4, such as a sequence selected from ASDKPYIL (SEQ ID NO: 6), AGDKPYIL (SEQ ID NO: 20), AADKNYIT (SEQ ID NO: 33), AGDKNYIM (SEQ ID NO: 34), AGDKNYIT (SEQ ID NO: 11), AADKNFIM (SEQ ID NO: 35), AADKNFIT (SEQ ID NO: 36), AGDKGIRS (SEQ ID NO: 37), and AGDKNFIT (SEQ ID NO: 27).

The present invention further relates to compositions comprising the polypeptides of the invention. In some embodiments the compositions of the invention is capable of promoting satiety in a subject upon consumption.

In some embodiments in the compositions of the invention the amount of said polypeptide in the composition is less than about 10 g, such as less than 9 g, 8 g, 7 g, 6 g, 5 g, 4 g, 3 g, 2 g, 1 g, 900 mg, 800 mg, 700 mg, 600 mg, 500 mg, 400 mg, 300 mg, 200 mg, 150 mg, 100 mg, 90 mg, 80 mg, 70 mg, 60 mg, 50 mg, 40 mg, 30 mg, 25 mg, 20 mg, 15 mg, 10 mg, or 5 mg.

In some embodiments in the compositions of the invention the amount of said polypeptide in the composition is at least about 5 mg, such as at least about 10 mg, 15 mg, 20 mg, 25 mg, 30 mg, 40 mg, 50 mg, 60 mg, 70 mg, 80 mg, 90 mg, 100 mg, 150 mg, 200 mg, 300 mg, 400 mg, 500 mg, 600 mg, 700 mg, 800 mg, 900 mg, 1 g, 2 g, 3 g, 4 g, 5 g, 6 g, 7 g, 8 g, 9 g, or 10 g.

In some embodiments in the compositions of the invention the energy content derived through the process of cellular respiration is less than 50 kilojoules (kJ), such as less than 40 kJ, such as less than 30 kJ, such as less than 20 kJ, such as less than 10 kJ, such as less than 5000 Joules (J), such as less than 1000 J, such as less than 900 J, such as less than 800 J, such as less than 700 J, such as less than 600 J, such as less than 500 J, such as less than 400 J, such as less than 300 J, such as less than 200 J, such as less than 100 J, such as less than 50 J.

In some embodiments the compositions of the invention is a food composition.

In some embodiments the compositions of the invention is a fermented composition.

In some embodiments the compositions of the invention is a dairy product.

In some embodiments the compositions of the invention is a pharmaceutical composition.

In some embodiments the compositions of the invention is a nutritional composition.

In some embodiments the compositions of the invention is an oral dosage form. In some embodiments the oral dosage form is selected from the group comprising tablets, capsules, caplets, slurries, sachets, suspensions, chewing gum, and powder formulation that may be dissolved in a liquid. In some embodiments the oral dosage form is a suspension. In some embodiments the oral dosage form is a powder formulation that may be dissolved in a liquid. In some embodiments the liquid is water, milk, juice, or yogurt.

Example 1

Assays:

$Ca^{2+}$ Flux Assay:

Elevation of intracellular calcium level was measured using the fluorescent calcium chelating dye Fluo-4 AM (ThermoFischer Scientific, Denmark). Briefly, cells were grown as a monolayer in 96-well tissue culture plates (Sarstedt, Germany) to near confluence in appropriate growth medium as described in the cell culture section. Prior to the start of the assay, the cells were incubated with 1.5 µM Fluo-4 AM in complete culture media mixed 1:1 with Hank's balanced salt solution (HBSS, ThermoFischer Scientific, Denmark) containing 25 mM HEPES (pH 7.4), 1% BSA (Sigma-Aldrich, Denmark), 2% ink (Soluro GMBH, Germany), 0.01% Pluronic F-127 (Sigma-Aldrich, Denmark) and 1 mM Probenecide (Sigma-Aldrich) for 60 minutes at 37° C.

All test compounds were dissolved in water, and then diluted in 1×HBSS containing 25 mM HEPES (pH 7.4), 1% BSA and 2% ink. Without any removal of excess Fluo-4 AM, test compounds were added directly into the wells and fluorescence were measured using instrument settings for excitation at 488 nm and emission at 525 nm in a microtiter plate reader (SpectraMax M5, Molecular Devices, USA).

Cell Culture:

Cell culture media, Dulbecco's phosphate-buffered saline, pH 7.4 (DPBS), glutamine, trypsin-EDTA and antibiotics were obtained from ThermoFischer Scientific (Denmark). Fetal bovine serum and all other chemicals were purchased from Sigma-Aldrich (Denmark), unless otherwise stated.

Murine intestinal enteroendocrine L-cell lines that expresses the proglucagon gene and secretes GLP-1 in vitro were used. Cells were grown in DMEM containing 1 g/L D-glucose, 10% fetal bovine serum, 2 mM glutamine, 1% penicillin/streptomycin/neomycin and cultured in a humidified incubator in 95% air and 5% CO2 at 37° C.

Other murine intestinal cell lines were cultured in Dulbecco's modified Eagle's medium (DMEM) supplemented with 2 mM glutamine, 2.5 g/L glucose, 20 mM HEPES, 60 nM sodium selenite, 5 µg/ml transferrin, 5 µg/ml insulin, 50 nM dexamethasone, 10 nM EGF, 1 nM triiodothyronine, 2% fetal bovine serum and 1% penicillin/streptomycin/neomycin at 37° C. in 5% C02-95% air atmosphere.

Human intestinal cell lines were cultured in McCoy's modified 5A medium supplemented with 10% fetal bovine serum and 1% penicillin/streptomycin/neomycin at 37° C. and 5% CO2 in a humidified incubator.

Cells were routinely sub-cultivated 1:3 and given new media every second day.

Determination of GLP-1 Levels:

GLP-1 levels were determined using a sandwich enzyme-linked immunoabsorbant assay (ELISA). The primary antibody to GLP-1 [2.5 µg/ml mouse monoclonal (HYB 147-06) in 0.05M bicarbonate/carbonate buffer; BioPorto Diagnostics A/S, Gentofte, Denmark) was coated on a flat-bottom 96-well plate (Sarstedt, Numbrecht, Germany) for at least 24 hours at 4° C. This primary antibody is specific for the amidated C-terminus of the peptide and reacts with GLP-1 (7-36), GLP-1 (9-36) and GLP-1 (1-36), but not with GLP-1 (7-37). After blocking the plate using a PBS buffer containing 4% w/v BSA (Sigma-Aldrich, Denmark) and 0.1% v/v Tween 20 (Sigma-Aldrich) for 1 hour at room temperature, the plate was washed four times with PBS buffer containing 0.1% v/v Tween 20. A standard curve with GLP-1 peptide [human GLP-1 (7-36), Sigma-Aldrich, Denmark) concentrations ranging from 0 µg/ml to 1000 µg/ml was prepared in PBS buffer containing 0.5% BSA and 0.05% Tween 20, and samples were diluted if necessary. Samples and standards were added to the microtiter plate and incubated with the primary antibody for two hours at room temperature. Subsequently, the plate was washed four times, and the wells were incubated with a secondary biotinylated antibody to GLP-1 [1 µg/ml; mouse monoclonal (ABS 033-01), Bio-Porto Diagnostics A/S, Gentofte, Denmark) for two hours at room temperature. After another washing step, samples were incubated with streptavidin-horseradish peroxidase (1:200, Dako A/S, Denmark) for 45 minutes followed by an incubation with TMB solution (containing 3,3',5,'5-tetramethylbenzidine and H2O2, SMS-gruppen, Denmark). The reaction was stopped by adding H2SO4 (0.2M), and the absorbance of the yellow end product was measured at 450 nm on a microtiter plate spectrophotometer (SpectraMax M5, Molecular Devices, USA). The concentrations of the samples were determined by interpolation to the concentrations of the standard solutions.

Cells (~5×10^5 per sample) were incubated for up to 90 min in Dulbeccos Modified Eagle Medium (DMEM) containing 5.56 mM glucose in absence or presence of different amounts (weight/volume) of protein hydrolysate (pig heart). Supernatant was filtered through 0.45 micron filters and assayed for content of GLP-1 as described in ELISA protocol. Data are mean+SEM from quadruplicate samples.

Preparation of Bioactive Peptides by Enzymatic Digestion of Meat

Minced meat is diluted 1-10 times with distilled water, adjusted to pH 1-3 with hydrochloric acid, and incubated with 0.01-10% pepsin (w/w) at 4-40° C. for ½-12 h with adequate mixing. Insoluble material is removed by centrifugation at 100-1000×g for 3-30 min, and supernatant is neutralized with NaOH. Using sterile conditions, low molecular weight peptides in supernatant are recovered by tangential ultrafiltration at 4-40° C. for ½-12 h, and excess water is evaporated at 25-50° C. for up to 12 h. The concentrated dialysate is tested for bioactivity with cells and used for further purification by HPLC.

Purification and Identification of Bioactive Peptide ASDKPYIL (SEQ ID NO: 6)

Upconcentrated dialysates were fractionated on preparative C18 columns using buffer B: 20 mM phosphate buffer pH 8.25/10% ACN and a gradient of 0-40% in buffer A: 60% ACN in same buffer. Fractions were tested for bioactivity and further purified by isocratic elution using EVO C18 columns with 4.5% ACN in 0.1% FA isocratic for 30 min. Fractions were subject to MS characterization, where a dominating peak with m/z 453.75 (+2) was observed. Extracted ions chromatograms show this peak to be present in all active fractions. De novo sequencing of 453.75 peak gives [A]SDKPY[I,L][I,L]. N-terminal A (e.g., SEQ ID NO: 6) is calculated from parent ion −A7. I and L are not resolved by MS because of equal molecular weights. Search of protein sequences gives only ASDKPYIL (SEQ ID NO: 6) as match. ASDKPYIL (SEQ ID NO: 6) is only found in alpha-actinin-2, a major muscle protein.

Stability of Peptides Ex Vivo.

Peptides are degraded by proteases in the gastrointestinal tract. However the speed of this degradation depends on the sequence of the peptide. In order to measure stability of the ASDKPYIL (SEQ ID NO: 6) peptide series and to compare with e.g. RRKPYIL (SEQ ID NO: 1008), 10 or 50 mg (wet weight) of mouse or rat intestinal tissue (distal ileum) was equilibrated in V-bottom 24 well plates in 800 µl HBSS, 25 mM HEPES, pH 7.4 at 37° C. with shaking at 350 rpm. Identical amounts of different peptides (final concentration of 1 µg/ml) were added to the intestinal pieces and incubation continued. At various time points, 100 µl aliquots were removed and diluted into whey protein hydrolysate (final concentration of 10 mg/ml) to non-specifically compete protease activity. Peptide solutions were then diluted and tested for bioactivity (FIG. 8). Peptides incubated under same conditions but in absence of intestine served as controls (no degradation). Determination of EC50 for stimulation of cells allowed calculation of recovered peptide (FIG. 9), assuming simple inactivation by the tissue.

Example 2

1) Structure-Activity Relationship and Stability (SAR)
   a. Extended versions
   b. Substituted versions
2) In Vivo Studies in Mice
   c. Acute effects on feed intake (satiety)
   d. Long-term effects on weight may be determined
   Based on structural modelling studies of DC7-2 and NTR-1 interactions, peptides being octapeptides, heptapeptides, hexapeptides, or pentapeptides to exhibit increased potency due to increased binding may be predicted.

Comparison with SAR studies using synthetic peptides, peptides with increased potency and stability may be both predicted and observed.

Assays:

Synthetic Peptides:

Based on the sequence of the natural hormone Neurotensin (QLYENKPRRPYIL, SEQ ID NO: 1009), the bioactive Neurotensin fragment NT(8-13)(RRPYIL, SEQ ID NO: 39) and the identified bioactive octapeptide DC7-2 (ASDKPYIL, SEQ ID NO: 6), synthetic peptides with systematic substitutions of N-terminal amino acids of the octapeptide (X-SDKPYIL, SEQ ID NO: 220), the heptapeptide (X-DKPYIL, SEQ ID NO: 8), the hexapeptide (X-KPYIL, SEQ ID NO: 9) and the pentapeptide (X-PYIL SEQ ID NO: 4) were synthesised using standard techniques (Schafer-N, Denmark). All peptides were dissolved in pure HPLC-grade water and stored at −20° C.

Stability of Peptides:

Concentration Determination:

Protein concentration of synthetic peptides (Schafer-N, Denmark), NT (Sigma-Aldrich, Denmark) and NT (8-13) (Sigma-Aldrich, Denmark) were determined by measuring absorbance at 280 nm in Costar® 96-well UV-transparent plates (Corning, Sigma-Aldrich, Denmark). Each peptide was measured in 4 different concentrations by dilution in Hank's balanced salt solution (HBSS, ThermoFischer Scientific, Denmark) containing 25 mM HEPES (pH 7.4) (Sigma-Aldrich, Denmark). For stability assays, all peptides were diluted to $3\times10^{-5}$ M in HBSS; 25 mM HEPES (Ph 7.4) and stored at +4° C.

Intestine Homogenate:

Small intestines from 20 Swiss-Webster males were homogenized in 350 ml Dulbecco's phosphate-buffered saline (PBS) (pH 7.4) (ThermoFischer Scientific, Denmark) with a IKA® basic 18 Ultra-Turrax tissue homogenizer set a speed 5 followed by filtration using 100 μm nylon mesh filter. Protein concentration was 6 mg/ml using the bicinconinic acid assay (ThermoFischer Scientific, Denmark) and bovine serum albumin as standard. The intestine homogenate was diluted 10 times in HBSS containing 25 mM HEPES (pH 7.4), and further diluted 30×, 90×, 270×, 810× or 2430× before incubation with peptides. All solutions were prewarmed to 37° C. before mixing with peptide solutions.

Peptides were incubated at $10^{-5}$ M with dilutions of small intestine homogenate at 37° C. for 90 minutes with shaking. Reactions were stopped by addition of 1 M phosphoric acid (final 0.4 M, pH ~1.2). Each peptide incubation mix was then neutralized with NaOH to pH 7.2-7.4 and immediately tested for activity in intestinal cells. Control for zero degradation, i.e. addition of 1 M phosphoric acid prior to addition of intestine homogenate, was included for each peptide.

Fetal Bovine Serum:

All peptides were incubated at $10^{-5}$ M with Fetal Bovine Serum (FBS; final concentration of 66.7%) (Sigma Aldrich, Denmark) at 37° C. for 3 hours. The peptide degradation was terminated using 1 M phosphoric acid (final 0.4 M, pH ~1.2) and neutralized to pH 7.2-7.4 with NaOH before testing activity in intestinal cells. As for small intestine homogenates, a zero degradation control was included for each peptide.

Kinetic Studies of Selected Peptides:

DC7-2, NT, DKPYIL (SEQ ID NO: 8) and NT-(8-13) (final concentration of 10-6 M) were incubated either with FBS or with 270× diluted intestinal homogenate at 37° C. for various time points with shaking. Degradation was stopped with 1 M phosphoric acid and the samples were subsequently neutralized and immediately tested with intestinal cells as described above. Control for zero degradation was included for each peptide as above.

Study of Hexapeptides:

The 20 hexapeptides with systematic N-terminal substitutions (X-KPYIL, SEQ ID NO: 9) (Schafer-N, Denmark) and NT (8-13) was incubated at 10-6 M in either FBS for 10 minutes or with 270× diluted intestinal homogenate for 30 minutes at 37° C. with shaking. The degradation was stopped with 1 M phosphoric acid. Peptide solutions were neutralized with NaOH (pH 7.2-7.4), diluted and immediately tested for bioactivity using murine intestinal cells. Determination of EC50 for stimulation of cells allowed calculation of recovered peptide. Systematic substitutions of N-terminal amino acids in octapeptide ASDKPYIL (SEQ ID NO: 6) and their importance for activity and stability. Sequence, activity and stability of DC7-2 is indicated in grey.

| Peptide ID | Sequence | Cell signaling activity (EC50, nM) Mean | Cell signaling activity (EC50, nM) SEM | Stability in serum (activity remaining)[1] | Stability in intestine (activity remaining)[2] |
|---|---|---|---|---|---|
| 36055 | Y SDKPYIL (SEQ ID NO: 939) | 5.92E-09 | 5.53E-10 | 0.0491 | 3.0 |
| 36054 | W SDKPYIL (SEQ ID NO: 940) | 8.87E-09 | 7.94E-10 | 0.0426 | 3.6 |
| 36053 | V SDKPYIL (SEQ ID NO: 795) | 5.15E-09 | 5.32E-10 | 0.0488 | 5.6 |
| 36052 | T SDKPYIL (SEQ ID NO: 941) | 5.63E-09 | 5.67E-10 | 0.0535 | 8.4 |
| 36051 | S SDKPYIL (SEQ ID NO: 942) | 4.27E-09 | 3.92E-10 | 0.0609 | 19.5 |
| 36050 | R SDKPYIL (SEQ ID NO: 943) | 4.01E-09 | 4.43E-10 | 0.0735 | 2.6 |
| 36049 | Q SDKPYIL (SEQ ID NO: 944) | 4.01E-09 | 4.51E-10 | 0.0742 | 8.8 |
| 36048 | P SDKPYIL (SEQ ID NO: 945) | 4.14E-09 | 4.54E-10 | 0.0772 | 4.6 |
| 36047 | N SDKPYIL (SEQ ID NO: 946) | 4.41E-09 | 4.28E-10 | 0.0872 | 3.9 |
| 36046 | M SDKPYIL (SEQ ID NO: 947) | 4.88E-09 | 5.01E-10 | 0.0762 | 3.8 |

-continued

| Peptide ID | Sequence | Cell signaling activity (EC50, nM) Mean | SEM | Stability in serum (activity remaining)[1] | Stability in intestine (activity remaining)[2] |
|---|---|---|---|---|---|
| 36045 | L SDKPYIL (SEQ ID NO: 507) | 8.06E-09 | 8.25E-10 | 0.0917 | 7.9 |
| 36044 | K SDKPYIL (SEQ ID NO: 948) | 1.07E-08 | 1.05E-09 | 0.0527 | 6.6 |
| 36043 | I SDKPYIL (SEQ ID NO: 651) | 6.87E-09 | 7.41E-10 | 0.0956 | 6.0 |
| 36042 | H SDKPYIL (SEQ ID NO: 949) | 3.63E-09 | 3.24E-10 | 0.0980 | 6.4 |
| 36041 | G SDKPYIL (SEQ ID NO: 950) | 4.07E-09 | 5.07E-10 | 0.0912 | 10.3 |
| 36040 | F SDKPYIL (SEQ ID NO: 951) | 3.85E-09 | 4.95E-10 | 0.0944 | 3.4 |
| 36039 | E SDKPYIL (SEQ ID NO: 952) | 4.82E-09 | 5.76E-10 | 0.0964 | 23.0 |
| 36038 | D SDKPYIL (SEQ ID NO: 953) | 6.15E-09 | 6.85E-10 | 0.0947 | 29.9 |
| 36037 | C SDKPYIL (SEQ ID NO: 954) | 5.44E-09 | 6.25E-10 | 0.0963 | 14.0 |
| 36036 | A SDKPYIL (SEQ ID NO: 6) | 3.51E-09 | 4.75E-10 | 0.0988 | 6.0 |

Notes for Tables 1) Stability in serum is expressed as fraction of peptide activity left after 10 min of incubation in serum at 37° C. compared with undigested sample as described in Examples. 2) Stability in intestine is expressed as % activity left after 30 min incubation in intestine homogenate at 37° C. as described in Examples.

Systematic substitutions of N-terminal amino acid in heptapeptide SDKPYIL (SEQ ID NO: 220) and their importance for activity and stability. Sequence, activity and stability of peptide contained in DC7-2 is indicated in grey.

| Peptide ID | Sequence | Cell signaling activity (EC50, nM) Mean | STD | Stability in serum ($t^{1}/_{2}$, min) | Stability in intestine ($t^{1}/_{2}$, min) |
|---|---|---|---|---|---|
| 36035 | Y DKPYIL (SEQ ID NO: 955) | 6.83E-09 | 5.97E-10 | 0.0531 | 3.2 |
| 36034 | W DKPYIL (SEQ ID NO: 956) | 1.41E-08 | 1.18E-09 | 0.0427 | 6.3 |
| 36033 | V DKPYIL (SEQ ID NO: 957) | 4.94E-09 | 4.75E-10 | 0.0528 | 4.4 |
| 36032 | T DKPYIL (SEQ ID NO: 292) | 5.61E-09 | 5.33E-10 | 0.0593 | 13.3 |
| 36031 | S DKPYIL (SEQ ID NO: 7) | 5.00E-09 | 4.88E-10 | 0.0587 | 10.6 |
| 36030 | R DKPYIL (SEQ ID NO: 958) | 4.68E-09 | 4.77E-10 | 0.0597 | 6.9 |
| 36029 | Q DKPYIL (SEQ ID NO: 959) | 4.97E-09 | 4.86E-10 | 0.0620 | 11.5 |
| 36028 | P DKPYIL (SEQ ID NO: 960) | 4.67E-09 | 4.64E-10 | 0.0558 | 10.9 |
| 36027 | N DKPYIL (SEQ ID NO: 961) | 5.92E-09 | 5.21E-10 | 0.0580 | 40.5 |
| 36026 | M DKPYIL (SEQ ID NO: 962) | 6.08E-09 | 5.69E-10 | 0.0601 | 7.1 |
| 36025 | L DKPYIL (SEQ ID NO: 963) | 6.41E-09 | 9.98E-10 | 0.0969 | 3.9 |
| 36024 | K DKPYIL (SEQ ID NO: 964) | 1.12E-08 | 1.61E-09 | 0.0910 | 6.9 |
| 36023 | I DKPYIL (SEQ ID NO: 965) | 4.77E-09 | 8.27E-10 | 0.0928 | 2.8 |
| 36022 | H DKPYIL (SEQ ID NO: 966) | 2.65E-09 | 3.53E-10 | 0.0932 | 4.7 |
| 36021 | G DKPYIL (SEQ ID NO: 967) | 2.91E-09 | 3.86E-10 | 0.0920 | 4.5 |

-continued

| Peptide ID | Sequence | Cell signaling activity (EC50, nM) Mean | STD | Stability in serum (t½, min) | Stability in intestine (t½, min) |
|---|---|---|---|---|---|
| 36020 | F DKPYIL (SEQ ID NO: 968) | 9.52E-09 | 1.38E-09 | 0.0901 | 2.4 |
| 36019 | E DKPYIL (SEQ ID NO: 969) | 3.96E-09 | 6.89E-10 | 0.0846 | 17.2 |
| 36018 | D DKPYIL (SEQ ID NO: 970) | 1.05E-08 | 1.47E-09 | 0.0419 | 44.3 |
| 36017 | C DKPYIL (SEQ ID NO: 971) | 7.72E-09 | 1.17E-09 | 0.0407 | 9.4 |
| 36016 | A DKPYIL (SEQ ID NO: 972) | 3.52E-09 | 6.43E-10 | 0.0952 | 2.5 |

Systematic substitutions of N-terminal amino acid in hexapeptide DKPYTL (SEQ ID NO: 8) and their importance for activity and stability. Sequence, activity and stability of peptide contained in DC7-2 is indicated in grey.

| Peptide ID | Sequence | Cell signaling activity (EC50, nM) Mean | STD | Stability in serum $(t)^{1/2}$, min) | Stability in intestine $(t^{1/2}$, min) |
|---|---|---|---|---|---|
| 35995 | Y KPYIL (SEQ ID NO: 973) | 3.34E-09 | 5.33E-10 | 0.0346 | 0.1 |
| 35994 | W KPYIL (SEQ ID NO: 974) | 5.58E-09 | 8.57E-10 | 0.0334 | 0.2 |
| 35993 | V KPYIL (SEQ ID NO: 975) | 1.17E-09 | 1.73E-10 | 0.0375 | 0.2 |
| 35992 | T KPYIL (SEQ ID NO: 976) | 1.16E-09 | 1.72E-10 | 0.0424 | 0.3 |
| 35991 | S KPYIL (SEQ ID NO: 977) | 1.15E-09 | 1.70E-10 | 0.0477 | 1.3 |
| 35990 | R KPYIL (SEQ ID NO: 150) | 4.40E-10 | 6.59E-11 | 0.0480 | 0.1 |
| 35989 | Q KPYIL (SEQ ID NO: 978) | 3.78E-10 | 5.67E-11 | 0.0495 | 0.8 |
| 35988 | P KPYIL (SEQ ID NO: 979) | 2.32E-10 | 3.53E-11 | 0.0550 | 0.2 |
| 35987 | N KPYIL (SEQ ID NO: 980) | 5.00E-10 | 7.42E-11 | 0.0709 | 1.0 |
| 35986 | M KPYIL (SEQ ID NO: 981) | 3.88E-10 | 5.82E-11 | 0.0504 | 0.1 |
| 35985 | L KPYIL (SEQ ID NO: 982) | 3.30E-10 | 4.60E-11 | 0.0310 | 0.1 |
| 35984 | K KPYIL (SEQ ID NO: 43) | 2.64E-10 | 3.72E-11 | 0.0403 | 0.1 |
| 35983 | I KPYIL (SEQ ID NO: 983) | 2.40E-10 | 3.37E-11 | 0.0315 | 0.0 |
| 35982 | H KPYIL (SEQ ID NO: 984) | 2.71E-10 | 3.82E-11 | 0.0363 | 0.1 |
| 35981 | G KPYIL (SEQ ID NO: 184) | 3.64E-10 | 5.05E-11 | 0.0353 | 0.1 |
| 35980 | F KPYIL (SEQ ID NO: 985) | 3.15E-10 | 4.39E-11 | 0.0365 | 0.1 |
| 35979 | E KPYIL (SEQ ID NO: 114) | 5.65E-10 | 7.80E-11 | 0.0478 | 0.6 |
| 35978 | D KPYIL (SEQ ID NO: 8) | 8.03E-10 | 1.11E-10 | 0.0623 | 2.2 |
| 35977 | C KPYIL (SEQ ID NO: 986) | 1.11E-09 | 1.53E-10 | 0.0477 | 2.6 |
| 35976 | A KPYIL (SEQ ID NO: 987) | 2.51E-10 | 3.50E-11 | 0.0454 | 0.1 |

Systematic substitutions of N-terminal amino acid in pentapeptide KPYIL (SEQ ID NO: 9) and their importance for activity and stability. Sequence, activity and stability of peptide contained in DC7-2 is indicated in grey.

| Peptide ID | Sequence | Cell signaling activity (EC50, nM) Mean | STD | Stability in serum $(t)^{1/2}$, min | Stability in intestine $(t)^{1/2}$, min |
|---|---|---|---|---|---|
| 36015 | Y PYIL (SEQ ID NO: 988) | 1.40E-07 | 1.01E-08 | 0.0091 | 2.0 |
| 36014 | W PYIL (SEQ ID NO: 989) | 1.33E-07 | 1.32E-08 | 0.0066 | 0.2 |
| 36013 | V PYIL (SEQ ID NO: 990) | 3.78E-08 | 2.71E-09 | 0.0094 | 0.3 |
| 36012 | T PYIL (SEQ ID NO: 991) | 4.36E-08 | 3.13E-09 | 0.0163 | 2.9 |
| 36011 | S PYIL (SEQ ID NO: 992) | 2.25E-08 | 1.62E-09 | 0.0241 | 0.0 |
| 36010 | R PYIL (SEQ ID NO: 40) | 1.18E-09 | 1.00E-10 | 0.0176 | 1.1 |
| 36009 | Q PYIL (SEQ ID NO: 993) | 2.05E-08 | 1.47E-09 | 0.0372 | 0.2 |
| 36008 | P PYIL (SEQ ID NO: 994) | 9.61E-09 | 6.98E-10 | 0.0197 | 2.6 |
| 36007 | N PYIL (SEQ ID NO: 995) | 3.93E-08 | 2.81E-09 | 0.0148 | 0.4 |
| 36006 | M PYIL (SEQ ID NO: 996) | 1.62E-08 | 1.17E-09 | 0.0034 | 0.2 |
| 36005 | L PYIL (SEQ ID NO: 997) | 4.10E-08 | 4.52E-09 | 0.0373 | 0.1 |
| 36004 | K PYIL (SEQ ID NO: 9) | 7.71E-09 | 8.77E-10 | 0.0124 | 0.2 |
| 36003 | I PYIL (SEQ ID NO: 998) | 2.38E-08 | 2.63E-09 | 0.0132 | 0.2 |
| 36002 | H PYIL (SEQ ID NO: 999) | 3.56E-08 | 3.94E-09 | 0.0366 | 0.1 |
| 36001 | G PYIL (SEQ ID NO: 1000) | 1.74E-08 | 1.94E-09 | 0.0125 | 0.3 |
| 36000 | F PYIL (SEQ ID NO: 1001) | 1.95E-08 | 2.17E-09 | 0.0343 | 2.4 |
| 35999 | E PYIL (SEQ ID NO: 1002) | 1.02E-07 | 1.12E-08 | 0.0405 | 3.6 |
| 35998 | D PYIL (SEQ ID NO: 1003) | 1.58E-07 | 1.74E-08 | 0.0352 | 12.5 |
| 35997 | C PYIL (SEQ ID NO: 1004) | 6.99E-08 | 7.73E-09 | 0.0349 | 0.2 |
| 35996 | A PYIL (SEQ ID NO: 1005) | 1.18E-08 | 1.31E-09 | 0.0036 | 0.4 |

In conclusion, the results demonstrates that octa- and heptapeptides are more stable, and that the N-terminal aa in the hexapeptide has a significant implication on the stability.

As compared to the hexapeptide of a natural homone, neurotensin (8-13) (NT with the sequence RRPYIL, SEQ ID NO: 39), one specific peptide of the present invention DKPYIL (SEQ ID NO: 8) is nearly 100 times more stable in serum and around 100-1000× more stable in intestine homogenate.

In Vivo Studies

Acute effects of DC7-2 on satiety is shown in FIG. 12, 17-20.

The invention claimed is:

1. A method of, in a subject in need thereof, promoting satiety, comprising enteral administering to the subject in need thereof a polypeptide comprising or consisting of the amino acid sequence AA1-AA2-AA3-AA4-P—Y—I-L (formula III, SEQ ID NO:3), wherein AA1 is an optional amino acid selected from A, L, I, and V; AA2 is an optional amino acid selected from S, T, G, A, N, E and D; AA3 is an optional amino acid selected from D, R, K, E, and G; and AA4 is an amino acid selected from K and R; which polypeptide is not more than 50 amino acids in length; or a variant thereof with a sequence identity of at least 80%, wherein the polypeptide is a linear sequence of amino acids comprising only standard peptide bonds, or administering a composition comprising said polypeptide.

2. The method according to claim 1, wherein AA4 is K.

3. The method according to claim 1, wherein AA1 is absent in said polypeptide.

4. The method according to claim 1, wherein AA2 is absent in said polypeptide.

5. The method according to claim 1, wherein AA3 is absent in said polypeptide.

6. The method according to claim 1, wherein AA1 is present in said polypeptide.

7. The method according to claim 1, wherein AA2 is present in said polypeptide.

8. The method according to claim 1, wherein AA3 is present in said polypeptide.

9. The method according to claim 4, wherein AA1 is A.

10. The method according to claim 5, wherein AA2 is S.

11. The method according to claim 6, wherein AA3 is D.

12. The method according to claim 1, wherein said polypeptide has a length of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids.

13. The method according to claim 1, wherein said polypeptide consists of or comprises a sequence selected from ASDKPYIL (SEQ ID NO: 6), SDKPYIL (SEQ ID NO: 220), DKPYIL (SEQ ID NO: 8), KPYIL (SEQ ID NO: 9), AADKPYIL (SEQ ID NO: 15), ATDKPYIL (SEQ ID NO: 16), ASEKPYIL (SEQ ID NO: 18), and AGDKPYTL (SEQ ID NO: 20).

14. The method according to claim 1, wherein said polypeptide is modified by N terminal acylation or other protection groups.

15. The method according to claim 1, wherein the amount of said polypeptide administered is less than about 10 g.

16. The method according to claim 1, wherein the amount of said polypeptide administered is at least about 5 mg.

17. The method according to claim 1, wherein said composition is a food composition, a fermented composition, a dairy product, a nutritional composition, or a pharmaceutical composition.

18. The method according to claim 1, wherein the enteral administration is nasal or oral administration, and if a composition is administered, said composition is an oral dosage form.

19. The method according to claim 18, wherein said oral dosage form is selected from the group comprising tablets, capsules, caplets, slurries, sachets, suspensions, chewing gum, and powder formulation that may be dissolved in a liquid.

20. The method according to claim 18, wherein the oral dosage form is a powder formulation that may be dissolved in a liquid.

21. The method according to claim 20, wherein said liquid is water, milk, juice, a soft drink, a fruit juice or a beverage comprising whey protein, a cocoa drink, a milk drink, a lactic acid bacteria drink, yoghurt and drinking yoghurt, an adult nutritional beverage, an acidified soy/juice beverage, an aseptic/retorted chocolate drink, a bar mix, calcium fortified soy/plain and chocolate milk, and a calcium fortified coffee beverage.

* * * * *